United States Patent [19]
Albright et al.

[11] Patent Number: 5,686,445
[45] Date of Patent: Nov. 11, 1997

[54] PYRIDOBENZOXAZEPINE AND PYRIDOBENZOTHIAZEPINE VASOPRESSIN ANTAGONISTS

[75] Inventors: Jay Donald Albright, Nanuet; Xuemei Du, Valley Cottage, both of N.Y.

[73] Assignee: American Cyanamid Company, Madison, N.J.

[21] Appl. No.: 637,908

[22] Filed: Apr. 25, 1996

Related U.S. Application Data

[63] Continuation-in-part of Ser. No. 254,823, Jun. 13, 1994, Pat. No. 5,512,563, which is a continuation-in-part of Ser. No. 100,003, Jul. 29, 1993, abandoned.

[51] Int. Cl.$^6$ .................... A61K 31/55; C07D 498/04; C07D 513/04
[52] U.S. Cl. ................ 514/211; 540/542; 540/548
[58] Field of Search ................... 540/542, 548; 514/211

[56] References Cited

FOREIGN PATENT DOCUMENTS

| | | |
|---|---|---|
| 382185 | 8/1990 | European Pat. Off. . |
| 470514 | 2/1992 | European Pat. Off. . |
| 514667 | 11/1992 | European Pat. Off. . |
| 533240 | 3/1993 | European Pat. Off. . |
| 533242 | 3/1993 | European Pat. Off. . |
| 533244 | 3/1993 | European Pat. Off. . |
| 9105549 | 5/1991 | WIPO . |
| 533243 | 3/1993 | WIPO . |

OTHER PUBLICATIONS

Albright, Chemical Abstract 123:313792y (1995) for Canadian Patent 2,128,955 (Jan. 30, 1995).
International Union of Pure and Applied Chemistry (IUPAC), vol. 82,1960, p. 5566.
Drug Evaluations, 6th Ed., 1986, Amer. Medical Assn., pp. 160–162.
Cecil Textbook of Medicine, 19th Ed., 1992, Wynoaarden, M.D., Editor, pp. 2075–2079.
Yamamura, et al., Science, 252, pp. 572–574, (1991).
Yamamura, et al., Br. J. Pharmacol., 105, pp. 787–791 (1992).

*Primary Examiner*—Philip I. Datlow
*Attorney, Agent, or Firm*—Steven R. Eck

[57] ABSTRACT

Tricyclic compounds of the general Formula I:

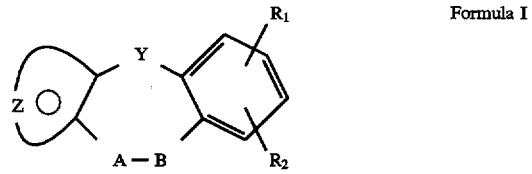

as defined herein which exhibit antagonist activity at $V_1$ and/or $V_2$ receptors and exhibit in vivo vasopressin antagonist activity, methods for using such compounds in treating diseases characterized by excess renal reabsorption of water, and processes for preparing such compounds.

9 Claims, No Drawings

PYRIDOBENZOXAZEPINE AND PYRIDOBENZOTHIAZEPINE VASOPRESSIN ANTAGONISTS

This case is a continuation-in-part of U.S. application Ser. No. 08/254,823, filed Jun. 13, 1994, now U.S. Pat. No. 5,512,563 which, in turn, is a continuation-in-part of Ser. No. 100,003, filed Jul. 29, 1993, now abandoned.

1. FIELD OF THE INVENTION

This invention relates to new tricyclic non-peptide vasopressin antagonists which are useful in treating conditions where decreased vasopressin levels are desired, such as in congestive heart failure, in disease conditions with excess renal water reabsorption and in conditions with increased vascular resistance and coronary vasoconstriction.

2. BACKGROUND OF THE INVENTION

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its actions through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induced increases in total peripheral resistance and altered local blood flow, $V_1$-antagonists may be therapeutic agents. $V_1$ antagonists may decrease blood pressure, induce hypotensive effects and thus be therapeutically useful in treatment of some types of hypertension.

The blockade of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephrotic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone. On the basis of biochemical and pharmacological effects of the hormone, antagonists of vasopressin are expected to be therapeutically useful in the treatment and/or prevention of hypertension, cardiac insufficiency, coronary vasospasm, cardiac ischemia, renal vasospasm, liver cirrhosis, congestive heart failure, nephrotic syndrome, brain edema, cerebral ischemia, cerebral hemorrhage-stroke, thrombosis-bleeding and abnormal states of water rentention.

The following prior art references describe peptide vasopressin antagonists: M. Manning et al., *J. Med. Chem.*, 35, 382(1992); M. Manning et al., *J. Med. Chem.*, 35, 3895 (1992); H. Gavras and B. Lammek, U.S. Pat. No. 5,070,187 (1991); M. Manning and W. H. Sawyer, U.S. Pat. No. 5,055,448(1991); F. E. Ali, U.S. Pat. No. 4,766,108 (1988); R. R. Ruffolo et al., *Drug News and Perspective*, 4(4), 217, (May) (1991). P. D. Williams et al., have reported on potent hexapeptide oxytocin antagonists [*J. Med. Chem.*, 35, 3905 (1992)] which also exhibit weak vasopressin antagonist activity in binding to $V_1$ and $V_2$ receptors. Peptide vasopressin antagonists suffer from a lack of oral activity and many of these peptides are not selective antagonists since they also exhibit partial agonist activity.

Non-peptide vasopressin antagonists have recently been disclosed, Y. Yamamura et al., *Science*, 252, 579(1991); Y. Yamamura et al., *Br. J. Pharmacol*, 105, 787(1992); Ogawa et al., (Otsuka Pharm Co., LTD.) EP 0514667-A1; JP 04154765-A; EPO 382185-A2; and WO9105549. Ogawa et al, (Otsuka Pharm. Co.) EP 470514A disclose carbostyril derivatives and pharmaceutical compositions containing the same. Non-peptide oxytocin and vasopressin antagonist have been disclosed by Merck and Co.; M. G. Bock and P. D. Williams, EP 0533242A; M. G. Bock et al., EP 0533244A; J. M. Erb, D. F. Verber, P. D. Williams, EP 0533240A; K. Gilbert et al., EP 0533243A.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., *J. Med. Chem.* 35, 3919 (1992), *J. Med. Chem.*, 36, 3993 (1993) and references therein. The compounds of this invention are antagonists of the peptide hormone oxytocin and are useful in the control of premature birth.

The present invention relates to novel tricyclic derivatives which exhibit antagonist activity at $V_1$ and/or $V_2$ receptors and exhibit in vivo vasopressin antagonist activity. The compounds also exhibit antagonist activity at oxytocin receptors.

SUMMARY OF THE INVENTION

This invention relates to new compounds selected from those of the general formula I:

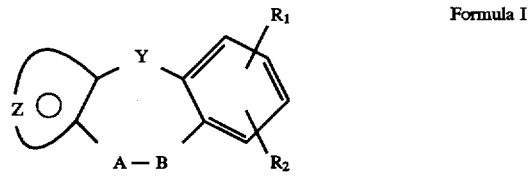

Formula I wherein Y is $(CH_2)_n$, O, S, NH, $NCOCH_3$, N-lower alkyl $(C_1-C_3)$, CH-lower alkyl$(C_1-C_3)$, —CHNH-lower alkyl $(C_1-C_3)$, $CHNH_2$, CHN[lower alkyl $(C_1-C_3)]_2$, CHO-lower alkyl$(C_1-C_3)$, CHS-lower alkyl$(C_1-C_3)$, or the moiety:

wherein n is an integer from 0–2;

A—B is

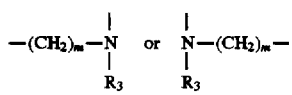

wherein m is an integer from 1–2, provided that when Y is —(CH$_2$)$_n$— and n=2, m may also be zero and when n is zero, m may also be three, provided also that when Y is —(CH$_2$)$_n$— and n is 2, m may not also be two.

R$_1$ is hydrogen, halogen (chlorine, bromine, fluorine, iodine), OH, —S-lower alkyl(C$_1$–C$_3$), —SH, —SO lower alkyl(C$_1$–C$_3$), —SO$_2$-lower alkyl(C$_1$–C$_3$), —CO-lower alkyl(C$_1$–C$_3$), —CF$_3$; lower alkyl(C$_1$–C$_3$); O-lower alkyl (C$_1$–C$_3$), —NO$_2$, —NH$_2$, —NHCO lower alkyl(C$_1$–C$_3$), —N-[lower alkyl(C$_1$–C$_3$)]$_2$, —SO$_2$NH$_2$; —SO$_2$NH lower alkyl (C$_1$–C$_3$) or —SO$_2$N[lower alkyl (C$_1$–C$_3$)]$_2$;

R$_2$ is hydrogen, Cl, Br, F, I, —OH, lower alkyl(C$_1$–C$_3$), O-lower alkyl(C$_1$–C$_3$), or R$_1$ and R$_2$ taken together are methylenedioxy or ethylenedioxy;

R$_3$ is the moiety:

wherein Ar is a moiety selected from the group

and X is O, S, —NCH$_3$, or —N—COCH$_3$;

R$_4$ is hydrogen, lower alkyl(C$_1$–C$_3$); —CO-lower alkyl (C$_1$–C$_3$); phenylCO, phenylSO$_2$; tolylSO$_2$; SO$_2$lower alkyl (C$_1$–C$_3$); or moieties of the formulae:

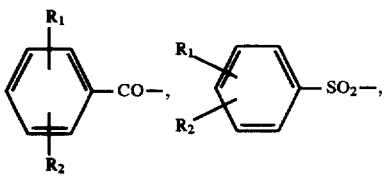

R$_5$ is hydrogen, —CH$_3$, —C$_2$H$_5$, Cl, Br, F, —O—CH$_3$, or —O—C$_2$H$_5$;

R$_6$ is selected from (a) moieties of the formula:

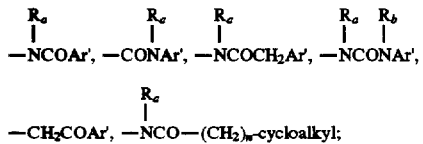

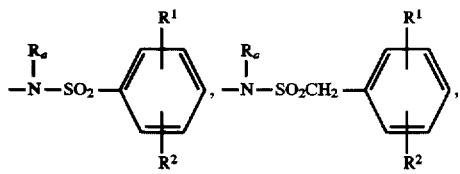

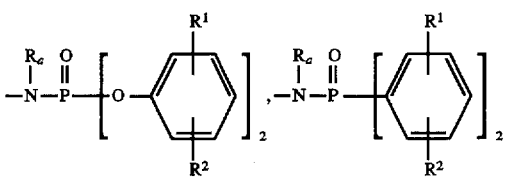

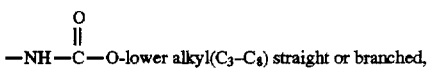

—NH—C(=O)—O-lower alkyl(C$_3$–C$_8$) straight or branched,

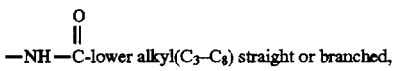

—NH—C(=O)-lower alkyl(C$_3$–C$_8$) straight or branched,

—NHSO$_2$-lower alkyl(C$_3$–C$_8$) straight or branched,

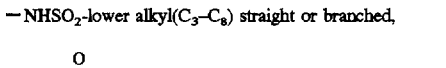

—NH—C(=O)—O-lower alkenyl(C$_3$–C$_8$) straight or branched,

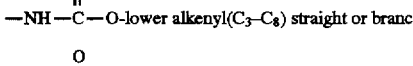

—NH—C(=O)-lower alkenyl(C$_3$–C$_8$) straight or branched,

—NHSO$_2$-lower alkenyl(C$_3$–C$_8$) straight or branched, wherein cycloalkyl is defined as C$_3$ to C$_6$ cycloalkyl, cyclohexenyl or cyclopentenyl; R$_a$ is hydrogen, CH$_3$, C$_2$H$_5$, moieties of the formulae:

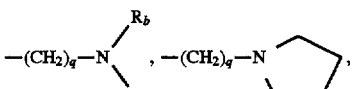

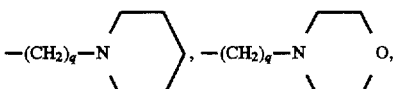

—(CH$_2$)$_2$O-lower alkyl (C$_1$–C$_3$) or —CH$_2$CH$_2$OH; q is one or two; R$_b$ is hydrogen, CH$_3$ or —C$_2$H$_5$;

(b) a moiety of the formula:

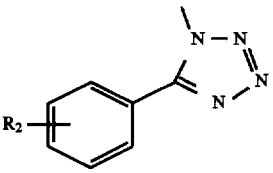

where R$_2$ is as hereinbefore defined;

(c) a moiety of the formula:

wherein J is R$_a$, lower alkyl(C$_1$–Ca) branched or unbranched, lower alkenyl(C$_2$–C$_8$) branched or unbranched, O-lower alkyl(C$_1$–C$_8$) branched or unbranched, —O-lower alkenyl(C$_2$–C$_8$) branched or unbranched, tetrahydrofuran, tetrahydrothiophene, or —CH$_2$—K wherein K is halogen, —OH, tetrahydrofuran, tetrahydrothiophene or the heterocyclic ring moiety:

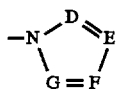

wherein D, E, F and G are selected from carbon or nitrogen and wherein the carbon atoms may be optionally substituted with halogen, ($C_1$–$C_3$)lower alkyl, hydroxy, —CO-lower alkyl($C_1$–$C_3$), CHO, ($C_1$–$C_3$)lower alkoxy, -$CO_2$-lower alkyl($C_1$–$C_3$), and $R_a$ and $R_b$ are as hereinbefore defined;

(d) a moiety selected from those of the formulae:

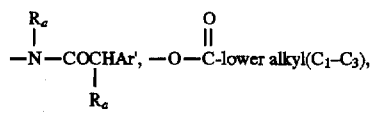

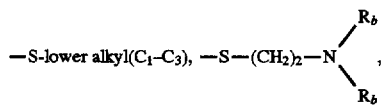

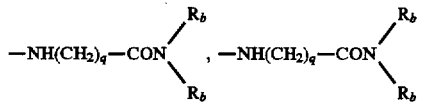

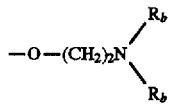

wherein $R_c$ is selected from halogen, ($C_1$–$C_3$)lower alkyl, —O-lower alkyl($C_1$–$C_3$) and OH, $R_b$ is as hereinbefore defined;

Ar' is a moiety selected from the group

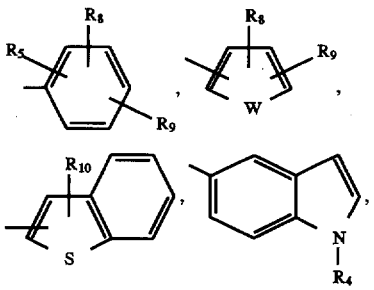

$R_7$ is hydrogen, —$CH_3$, —$C_2H_5$, Cl, Br, F, —$OCH_3$, —$OC_2H_5$, or —$CF_3$;

$R_8$ and $R_9$ are independently hydrogen, lower alkyl ($C_1$–$C_3$); O-lower alkyl($C_1$–$C_3$); S-lower alkyl($C_1$–$C_3$), —$CF_3$, —CN, —OH, —$SCF_3$, —$OCF_3$, halogen, $NO_2$, amino or NH lower alkyl($C_1$–$C_3$);

$R_{10}$ is halogen, hydrogen or lower alkyl($C_1$–$C_3$); W' is O, S, NH, N-lower alkyl($C_1$–$C_3$), NCO-lower alkyl($C_1$–$C_3$) or $NSO_2$-lower alkyl($C_1$–$C_3$).

the moiety Z 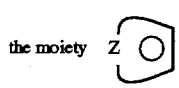

represents: (1) fused phenyl or fused substituted phenyl optionally substituted by one or two substituents selected from ($C_1$–$C_3$) lower alkyl, halogen, amino, ($C_1$–$C_3$) lower alkoxy, or ($C_1$–$C_3$) lower alkylamino; (2) a 5-membered aromatic (unsaturated) heterocyclic ring having one heteroatom selected from O, N or S; (3) a 6-membered aromatic (unsaturated) heterocyclic ring having one nitrogen atom; (4) a 5 or 6-membered aromatic (unsaturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by ($C_1$–$C_3$) lower alkyl, formyl, a moiety of the formula:

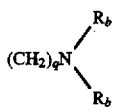

halogen or ($C_1$–$C_3$) lower alkoxy. For example, the fused heterocyclic ring may be represented by furan, pyrrole, pyrazole, thiophene, thiazole, oxazole, imidazole, pyrimidine or pyridine ring which may be substituted or unsubstituted.

DETAILED DESCRIPTION OF THE INVENTION

Within the group of the compounds defined by Formula I, certain subgroups of compounds are broadly preferred. Broadly preferred are those compounds wherein $R_3$ is a moiety:

and Ar is selected from the moiety:

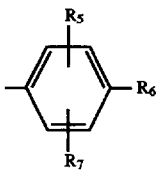

wherein $R_5$, $R_6$ and $R_7$ are as hereinbefore defined.

Especially preferred are compounds wherein $R_3$ is the moiety:

and Ar is selected from the moiety:

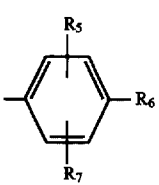

$R_6$ is NHCOAr' and Ar' is

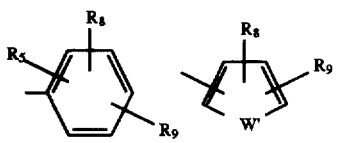

wherein $R_8$, $R_9$ and W' are as hereinbefore defined.

Also especially broadly preferred are compounds wherein Y in Formula I is —$(CH_2)_n$— and n is zero or one; A—B is

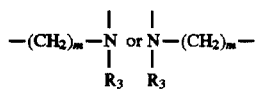

and $R_4$, $R_5$, $R_6$, $R_7$, $R_8$, $R_9$ and $R_{10}$ are as hereinbefore defined; and m is an integer from 1–2.

The most broadly preferred of the compounds of Formula I are those wherein Y is —$(CH_2)_n$— and n is one; A—B is

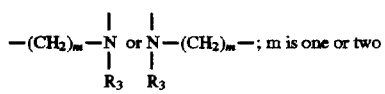

$R_3$ is the moiety:

Ar is

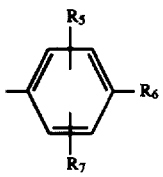

$R_6$ is

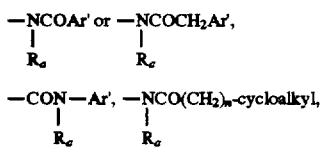

and Ar' is a moiety:

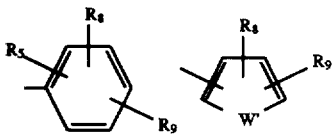

Cycloalkyl and W' are as previously defined and $R_8$ and $R_9$ are preferably ortho $CF_3$, Cl, $OCH_3$, $CH_3$, $SCH_3$ or $OCF_3$ substituents or Ar' is a disubstituted derivative wherein $R_8$ and $R_9$ are independently Cl, $OCH_3$, $CH_3$.

The most highly broadly preferred of the compounds of Formula I are those wherein Y is —$(CH_2)_n$—, n is zero or one and the moiety

represents a fused phenyl, substituted phenyl, thiophene, furan, pyrrole or pyridine ring;

A—B is

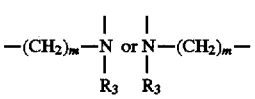

m is one when n is one and m is two when n is zero; $R_3$ is the moiety:

wherein Ar is

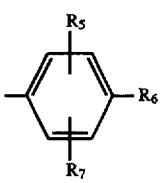

and $R_6$ is selected from the group

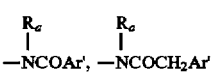

where Ar' is selected from the group

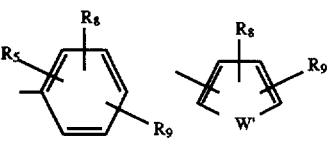

and $R_a$, $R_b$, $R_1$, $R_2$, $R_4$, $R_5$, $R_6$, $R_7$, $R_8$, $R_9$ and W' are as previously defined.

Most particularly preferred are compounds of the formulae:

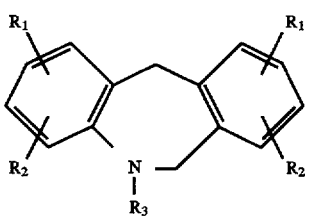

and

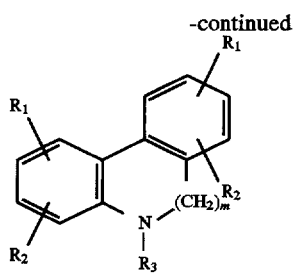

wherein m is an integer one or two; $R_1$ and $R_2$ are as previously defined;

$R_3$ is the moiety:

wherein Ar is selected from moieties of the formulae:

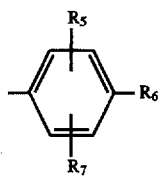

$R_6$ is

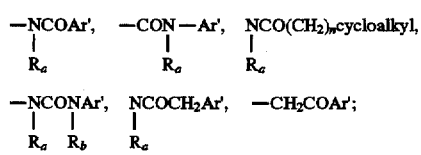

wherein cycloalkyl is defined as $C_3$–$C_6$ cycloalkyl, cyclohexenyl or cyclopentenyl and wherein Ar' is selected from the moieties:

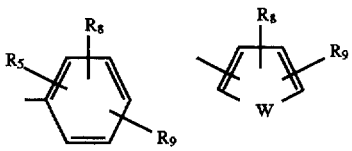

$R_a$ is independently selected from hydrogen, $CH_3$ or —$C_2H_5$; and $R_5$, $R_7$, $R_8$, $R_9$, $R_{10}$ and W' are as hereinbefore defined.

Compounds of this invention may be prepared as shown in Scheme I by reaction of tricyclic derivatives of Formula 3a and 3b with a substituted or unsubstituted 4-nitrobenzoyl chloride 4 to give the intermediates 5a and 5b. Reduction of the nitro group in intermediates 5a and 5b gives the 4-aminobenzoyl derivatives 6a and 6b. The reduction of the nitro group in intermediates 5a and 5b may be carried out under catalytic reduction conditions (hydrogen-Pd/C; Pd/C-hydrazine-ethanol) or under chemical reduction conditions ($SnCl_2$-ethanol; Zn-acetic acid; $TiCl_3$) and related reduction conditions known in the art for converting a nitro group to an amino group. The conditions for conversion of the nitro group to the amino group are chosen on the basis of compatibility with the preservation of other functional groups in the molecule.

Reaction of compounds of Formula 6a and 6b with aroyl chloride or related activated aryl carboxylic acids in solvents such as chloroform, dichloromethane, dioxane, tetrahydrofuran, toluene and the like in the presence of a tertiary base such as triethylamine and diisopropylethylamine or pyridine and the like, affords the compounds 8a and 8b which are vasopressin antagonists.

Scheme 1

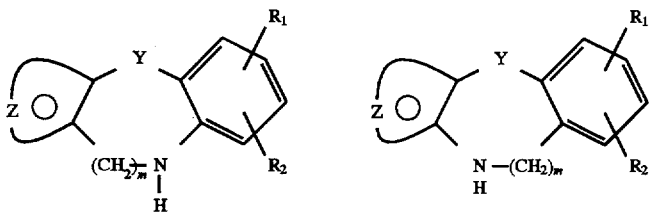

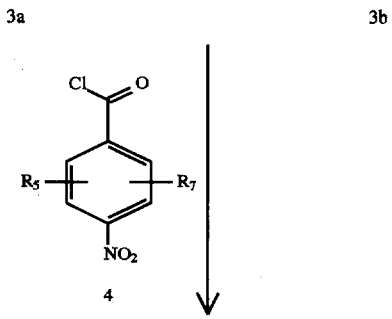

-continued
Scheme 1
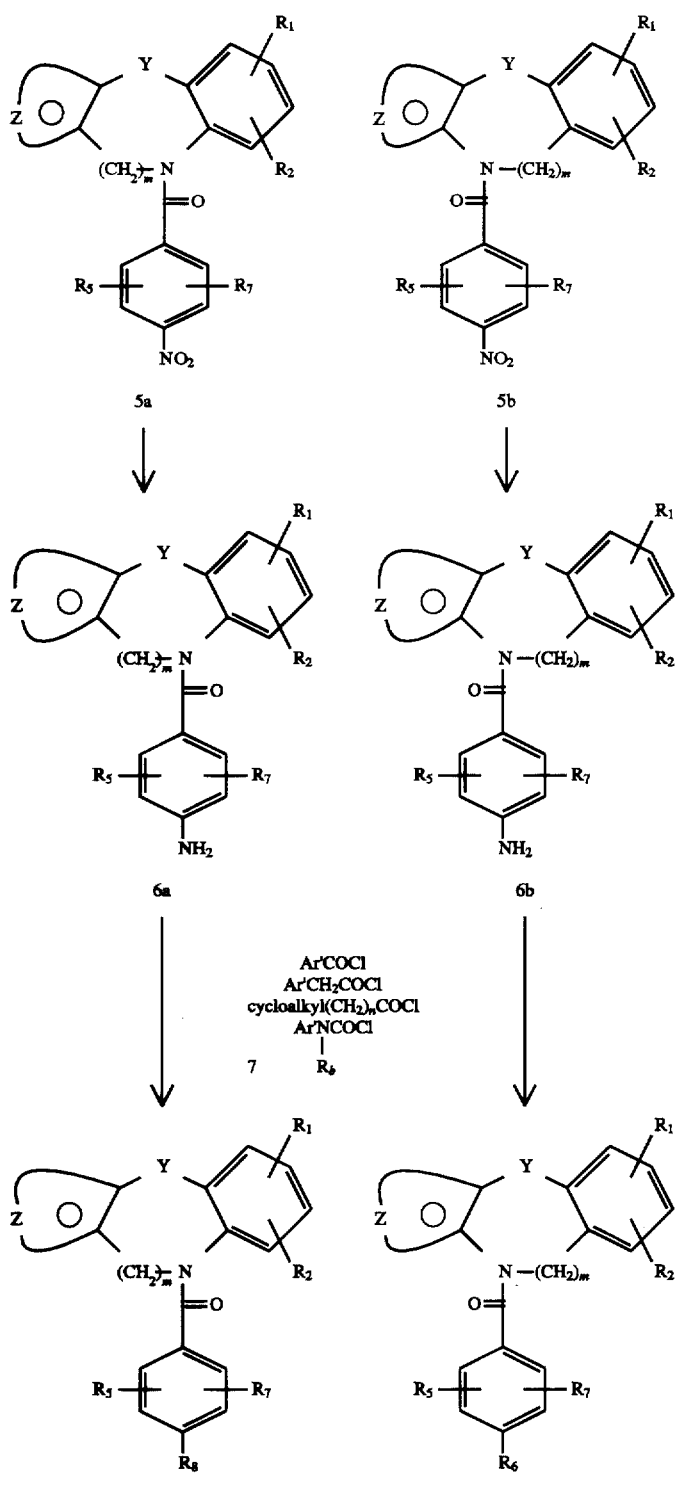
$R_6$= NHCOAr'; —NHCONAr; —NHCO(CH$_2$)$_n$cycloalkyl; —NHCOCH$_2$Ar'
            |
            R$_b$ Reaction of tricyclic derivatives of Formula 6a and 6b with either a carbamoyl derivative 9 or a isocyanate derivative 10 gives compounds (Scheme 2) of Formula 11a and 11b which are vasopressin antagonists of Formula I wherein $R_6$ is —NHCONAr'
   |
   $R_b$ and $R_b$ is H, $CH_3$ or $C_2H_5$.

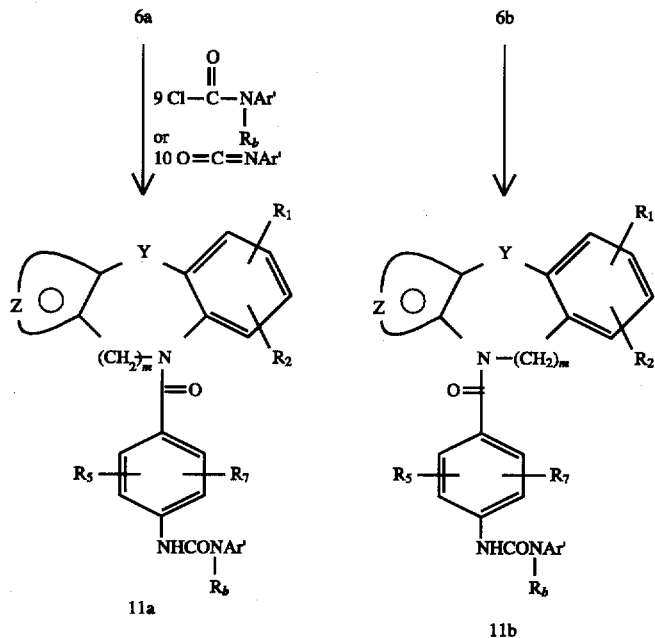

Scheme 2

Reaction of tricyclic derivatives of Formula 6a and 6b with arylacetic acids, activated as the acid chlorides 12, anhydrides, mixed anhydrides or activated with known activating reagents, gives compounds 13a and 13b (Scheme 3).

Scheme 3

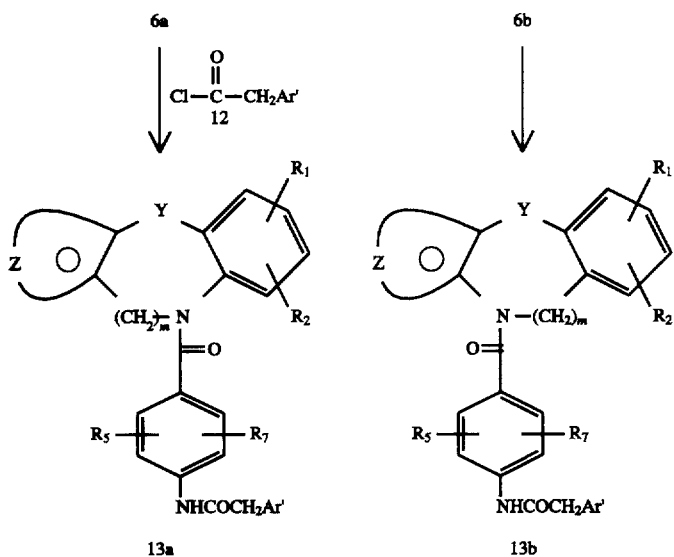

The compounds of Formula I wherein Y, A—B, Z, $R_1$, $R_2$ and $R_3$ are as defined and the aryl of $R_3$ (—COAr) is

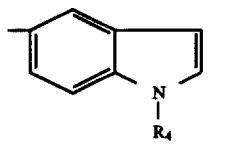

may be prepared, as shown in Scheme 4, by reacting an activated ester of the indole-5-carboxylic acids 14 with tricyclic derivatives 3a and 3b. The indole-5-carboxylic acids 14 may be activated by preparing the anhydride, a mixed anhydride or reacting with diethyl cyanophosphonate, N,N-carbonyldiimidazole or related peptide coupling reagents. As an example, the derivative 15 may be prepared by the reaction of acid 14 and N,N-carbonyldiimidazole in tetrahydrofuran; the solvent is removed and the derivative reacted with 3a or 3b at 100° C. to 120° C. without a solvent. Alternatively, 3a and 3b may be reacted with 15 in a solvent such as toluene or xylene at reflux temperatures. The activating reagent for the indole acids 14 is chosen on the basis of its compatibility with the $R_4$ group and its reactivity with the tricyclic derivatives 3a and 3b to give the vasopressin antagonists 16a and 16b.

Scheme 4

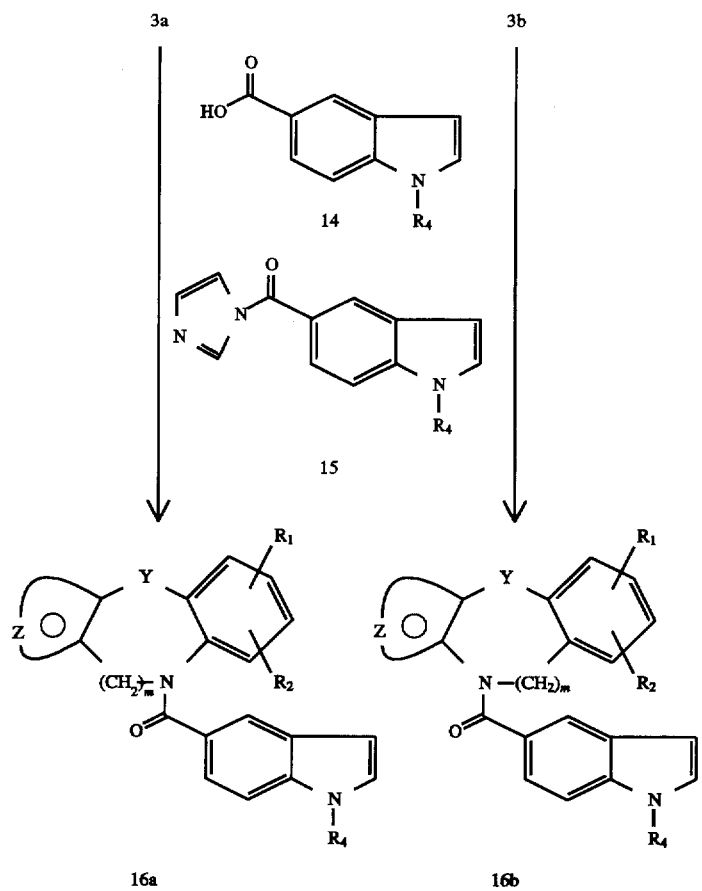

The compounds of Formula I wherein Y, A—B, Z, $R_1$, $R_2$ and $R_3$ are as defined and the $R_3$ (—COAr) aryl group is

wherein $R_6$ is

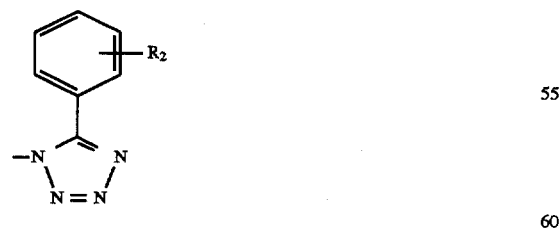

may be prepared as shown in Scheme 5 by first reacting the derivatives 8a and 8b with sodium hydride or similar reagents to form the amide anion and then reacting the anion with a dialkoxyphosphoryl chloride to give the intermediates 17a and 17b. Reaction of these intermediates with sodium or lithium azide gives the products 18a and 18b.

Scheme 5
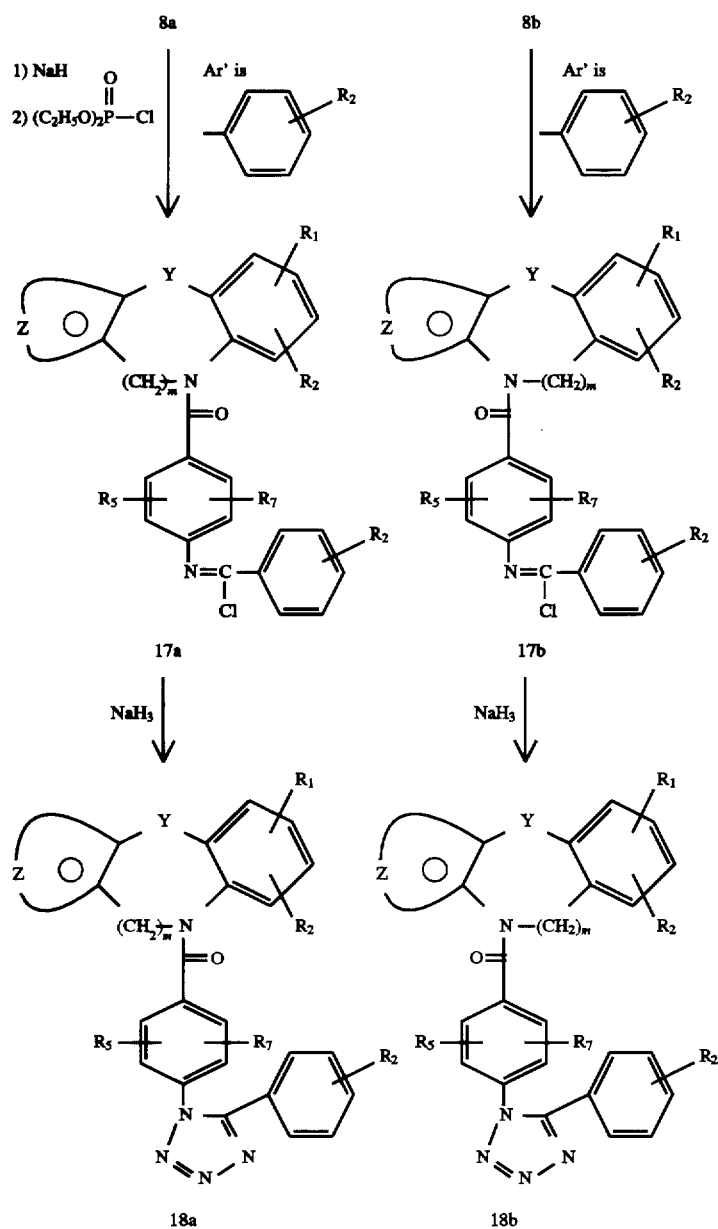
Alternatively, the products 18a and 18b may be prepared by coupling tetrazole derivatives of the Formula 19 with tricyclic derivatives 3a and 3b (Scheme 6). The tetrazole carboxylic acids are activated for coupling to the tricyclic compounds 3a and 3b by reaction with peptide coupling reagents, by conversion to the acid chlorides, anhydrides or mixed anhydrides.

Scheme 6

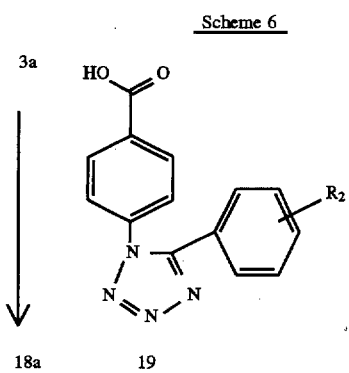

As an alternative method for synthesis of compounds of this invention as depicted in Formula I wherein Y, A—B, $R_1$, $R_2$, and Z are as previously defined and $R_3$ is

is the coupling of aryl carboxylic acids 20a with the tricyclic derivatives 3a and 3b as shown in Scheme 7.

The aryl carboxylic acids are activated for coupling by conversion to an acid chloride, bromide or anhydride or by first reacting with an activating reagent such as N,N-dicyclocarbodiimide, diethyl cyanophosphonate and related "peptide type" activating reagents. The method of activating the acids 20a for coupling to the tricyclic derivatives 3a and 3b is chosen on the basis of compatibility with other substituent groups in the molecule. The method of choice is the conversion of the aryl carboxylic acids 20a to the corresponding aroyl chloride. The aryl acid chlorides 20 may be prepared by standard procedures known in the art, such as reaction with thionyl chloride, oxalyl chloride and the like. The coupling reaction is carried out in solvents such as halogenated hydrocarbons, toluene, xylene, tetrahydrofuran dioxane in the presence of pyridine or tertiary bases such as triethylamine and the like. Alternatively, the aroyl chlorides, prepared from the aryl carboxylic acids 20, may be reacted with derivatives 3a and 3b in pyridine with or without 4-(dimethylamino)pyridine to give derivatives 21a and 21b.

In general, when the aryl carboxylic acids are activated with N,N-carbonyldiimidazole and other "peptide type" activating reagents, higher temperatures are required than when the aroyl chlorides are used. The reaction may be carried out in a higher boiling solvent xylene or without a solvent (100° C. to 150° C.).

Scheme 7

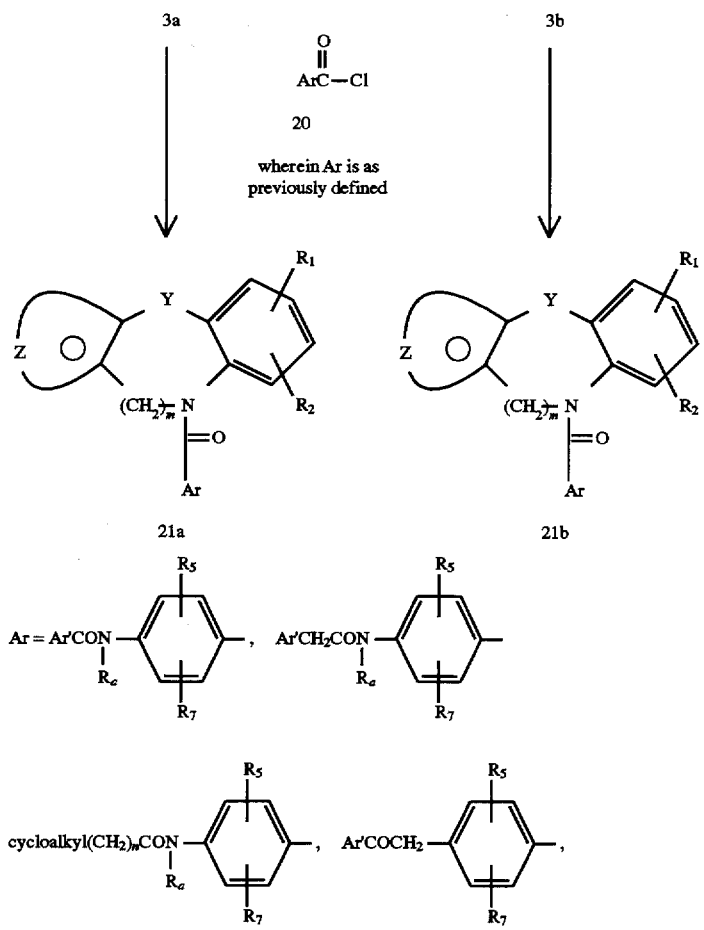

-continued
Scheme 7

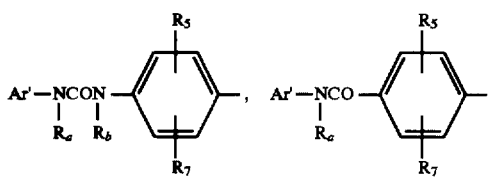

$R_a$ and $R_b$ are H, $CH_3$ or $C_2H_5$

The starting materials 3a and 3b in Scheme 1 can be made by literature methods. For example, intermediate 6,11-dihydro-5H-dibenz[b,e]azepines and substituted derivatives are prepared according to literature procedures: L. H. Werner, et al., *J. Med. Chem.*, 8, 74–80 (1965); A. W. H. Wardrop et al., *J. Chem. Soc. Perkins Trans I*, 1279–1285 (1976).

Substituted 5,11-dihydrodibenz[b,e]azepin-6-one are prepared by literature procedures: J. Schmutz et al., *Helv. Chim. Acta.*, 48, 336 (1965); and reduced to substituted 6,11-dihydro-5H-dibenz[b,e]azepines with lithium aluminum hydride, diborane, diborane-dimethyl-sulfide and agents known to reduce an amide carbonyl to a methylene group. Intermediate 10,11-dihydrodibenz[b,f][1,4]thiazepines are prepared by literature procedures—for example, see K. Brewster et al., *J. Chem. Soc. Perkin I*, 1286 (1976). Reduction of either dibenz[b,f][1,4]oxazepines [A. W. H. Wardrop et al., *J. Chem. Soc. Perkin Trans. I*, 1279 (1976)] and dibenz[b,f][1,4]oxazepin-11(10H)-ones and dibenz[b,f][1,4]thiazepin-11(10H)-ones—J. Schmutz et al., *Helv. Chim. Acta*, 45, 336 (1965); may be carried out with lithium aluminum hydride in inert solvents such as dioxane and the like. The tricyclic 6,7-dihydro-5H-dibenz[b,d]azepine intermediates of Formula 30 may be prepared by the literature procedures: T. Ohta et al., *Tetrahedron Lett.*, 26, 5811 (1985); Wiesner et al., *J. Amer. Chem. Soc.*, 77, 675 (1955); or derivatives may be prepared by coupling procedures illustrated in Scheme 8. The reduction of nitro compounds of structure type 31 followed by ring closure, affords lactams 32 which are reduced to give tricyclic azepines of Formula 33.

5,11-Dihydro-6M-pyrido[3,2-c][1]benzazepines are prepared by literature procedures—J. Firl et. al., *Liebigs Ann. Chem.* 469, (1989). Tricyclic 1,2,3,4-tetrahydropyrazolo[4,3-c][1]benzazepines are synthesized as described in the literature—G. Palazpino et. al., *J. Heterocyclic Chem.*, 26, 71 (1989).

Scheme 8

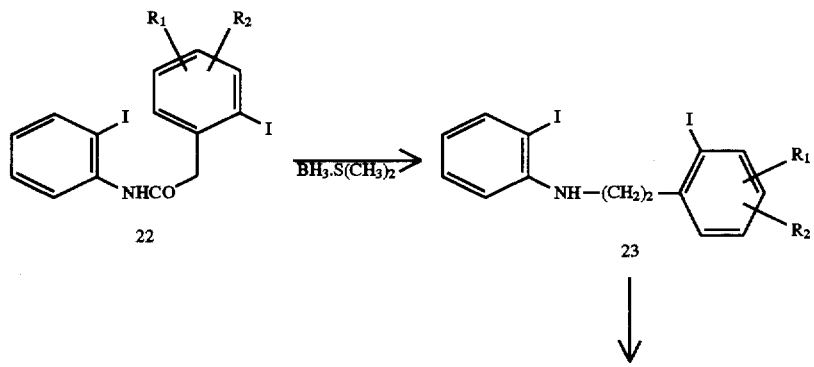

-continued
Scheme 8
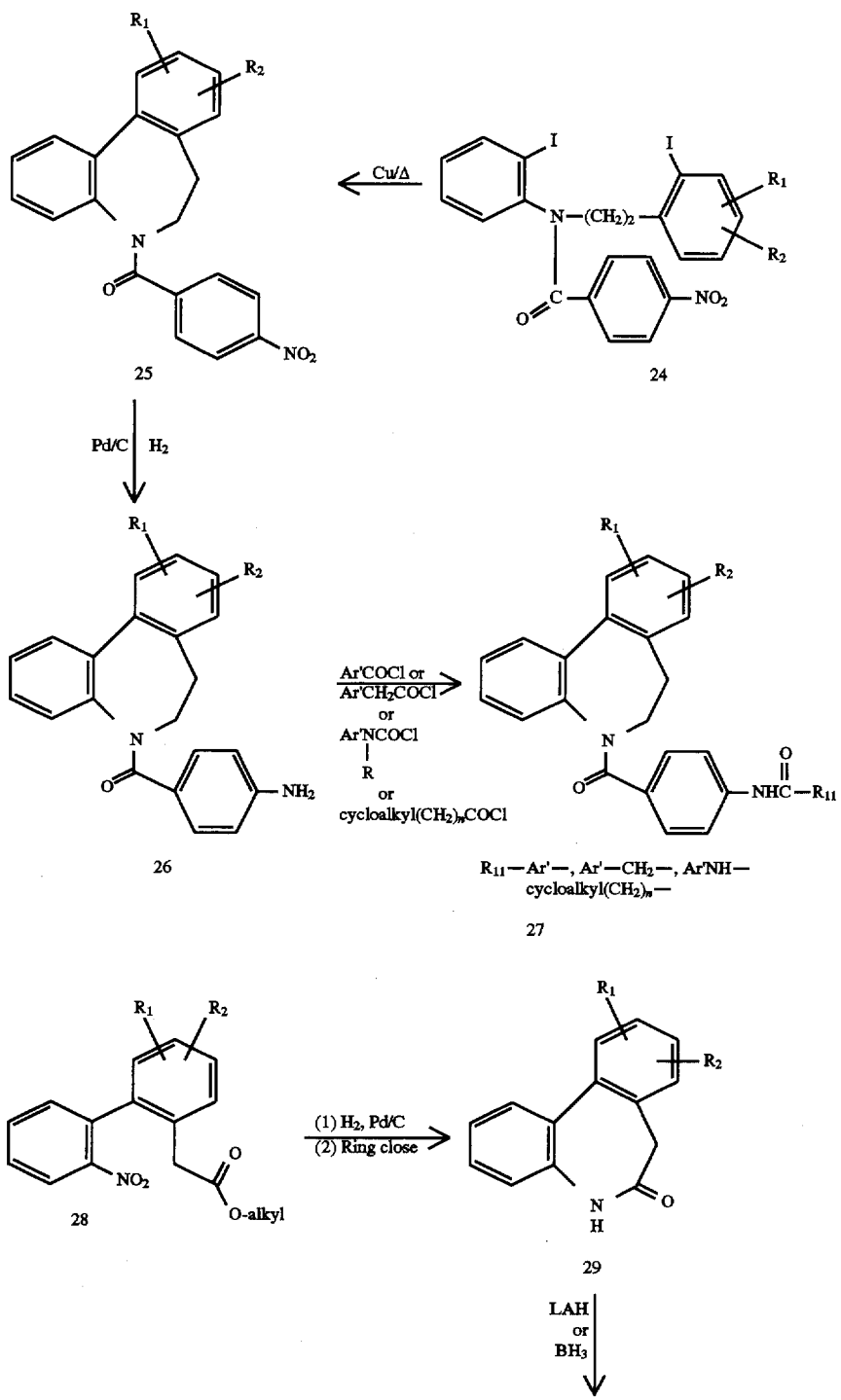

-continued
Scheme 8

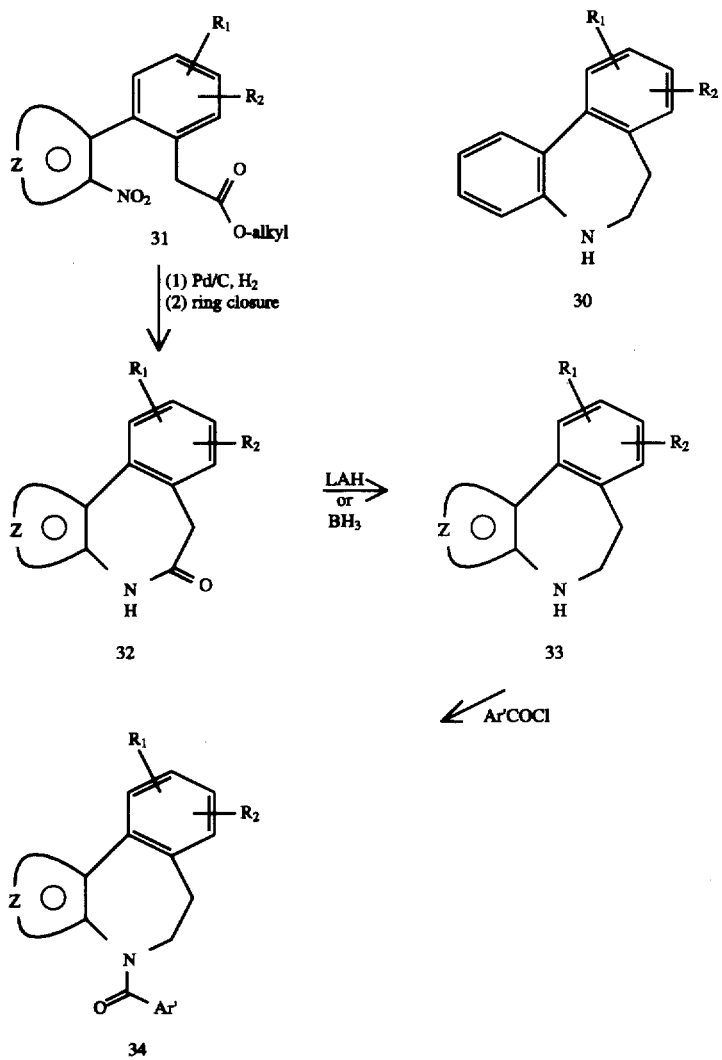

Tricyclic intermediates 42 for the synthesis of selected vasopressin antagonists of this invention wherein Y in Formula I is —CH$_2$— and m is one, may be prepared as shown in Scheme 9. Suitable 1-nitro-2-chloro or 1-nitro-2-bromo heterocycles 35 undergo halogen exchange when reacted with an alkyllithium reagent such as t-butyllithium, s-butyllithium or n-butyllithium to give intermediates 37 which react with anhydrides of Formula 38. R$_{12}$ is tert-butyl, secondary butyl, n-butyl, 2,6-dimethylpiperidine or a hindered non-nucleophilic dialkylamine. The nitro products 39 are reduced with hydrogen and a suitable catalyst or chemically reduced (Zn-acetic acid, TiCl$_3$ etc.) to be amino intermediates 40. Ring closure to the cyclic lactams 41 is conveniently carried out by heating in xylene or an inert solvent at 100° C. to 200° C. The cyclic lactams of structure type 41 are readily reduced by diborane in tetrahydrofuran, diborane-dimethylsulfide in tetrahydrofuran or lithium aluminum hydride in a suitable solvent such as dioxane to give the tricyclic compounds 42.

Scheme 9

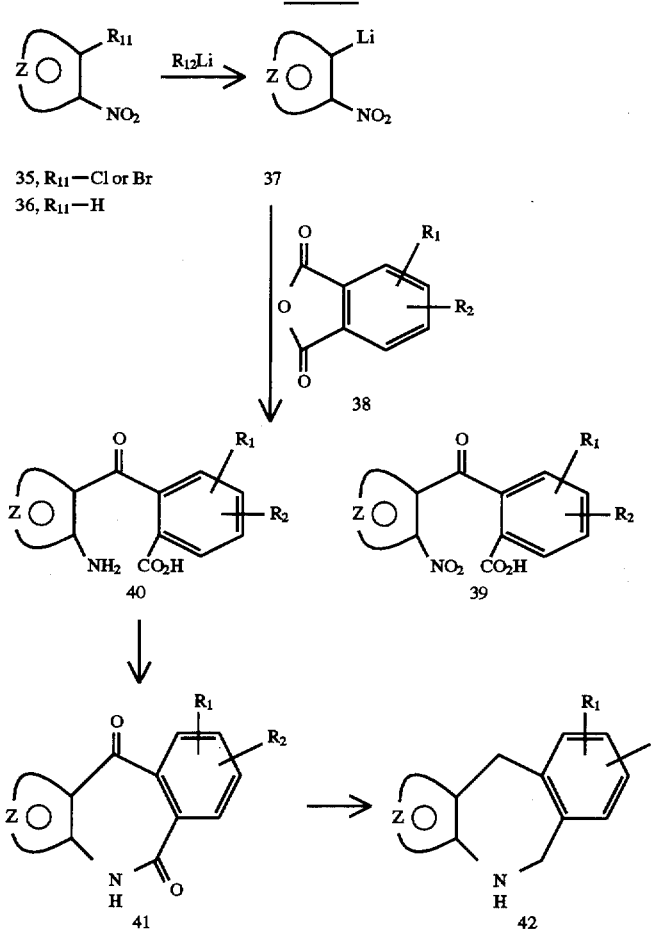

35, $R_{11}$—Cl or Br
36, $R_{11}$—H

Alternatively, as shown in Scheme 10, some of the tricyclic derivatives of structural type 42 may be prepared by "palladium" type coupling or "copper" induced coupling of halogenated derivatives 43 to give tricyclic lactams 44. Reduction of the lactam carbonyl group gives the intermediates 42. Coupling of halogen derivatives 45 to effect ring closure with activated copper or "palladium" type reagents which induce aryl coupling gives lactams 46. Diborane reduction of lactams 46 gives derivatives 47. Ullmann cross-couplings of halogenated heterocycles and 2-bromo-nitrobenzenes and related cross-couplings by low valent palladium species such as [Pd(PPh$_3$)$_4$] and PdCl$_2$(PPh$_3$)$_2$ are known synthetic procedures; N. Shimizu et al., *Tetrahedron Lett*, 34, 3421 (1993) and references therein; N. M. Ali et al., *Tetrahedron*, 37, 8117 (1992) and references therein; J. Stavenuiter et al., *Heterocycles*, 26, 2711 (1987) and references therein.

Scheme 10

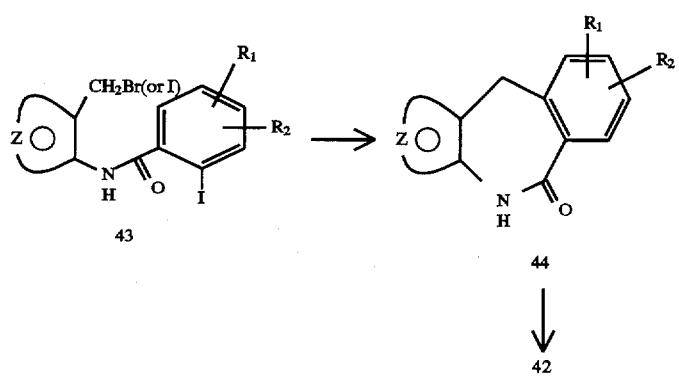

-continued
Scheme 10

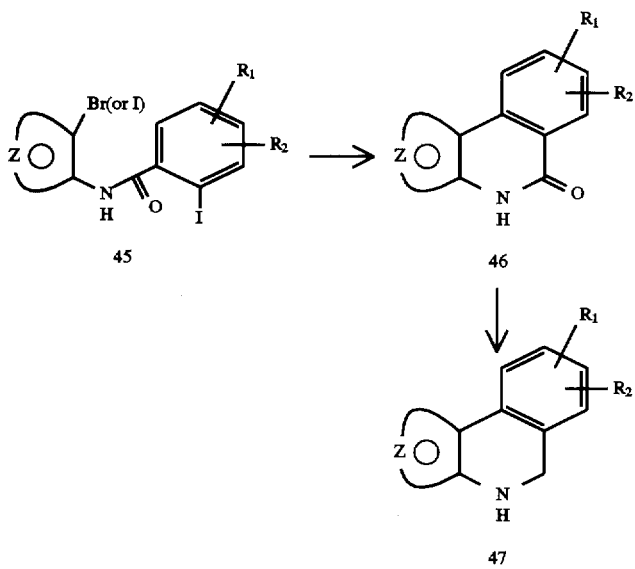

Tetrahydro-1H-1-benzazepin-5-ones 51 and the tetrahydro-1H-1-benzazepin-2,5-diones 52 are useful compounds for the synthesis of intermediate tricyclic heterocyclic structures 53 and 54 (Scheme 11). The tetrahydrobenzazepin-5-ones 51 and 52 may be formylated to give hydroxymethylene derivatives or reacted with either the Vilsmeier reagent or the N,N-dimethylformamide dimethyl acetal to give the dimethylaminomethylene derivatives. The construction of heterocyclic rings from α-hydroxymethyleneketones by reactions with hydrazine N-methylhydrazine, hydroxylamine or formamidine to give pyrazoles, N-methylpyrazoles, oxazoles or pyrimidines respectively, is a standard literature procedure. See Vilsmeier formylation—*Tetrahedron*, 49, 4015–4034 (1993) and references therein and ring formations—*J. Heterocyclic Chem.*, 29, 1214 (1992) and references therein.

Substituted and unsubstituted tetrahydrobenzazepin-2-ones are known compounds which are prepared by reaction of α-tetralones with sodium azide under acidic conditions.

[*J. Chem. Soc.* 456 (1937); *Tetrahedron* 49, 1807 (1993)] (Schmidt reaction). Reduction of tetrahydro-1H-benzazepin-2-ones gives the tetrahydro-1H-benzazepines 48 which on acylation gives compounds 49. Oxidation of N-acyl tetrahydro-1H-benzapines of type 49 to give the 5-one derivatives is a known oxidative procedure; R. L. Augustine and W. G. Pierson, *J. Org. Chem.*, 34, 1070 (1969).

The synthesis of 3,4-dihydro-1H-1-benzazepine-2,5-diones (52:R$_{15}$=H) has been reported as well as the conversion of 3,4-dihydro-1H-1-benzazepine-2,5-diones to 4-[(dimethylamino)methylene]-3,4-dihydro-1H-1-benzazepine-2,5-diones with N,N-dimethylformamide, dimethylacetal:[W.-Y. Chen and N. W. Gilman, *J. Heterocyclic Chem.*, 20, 663 (1983)]. The preceding reference describes the synthesis of 2-methyl-5,7-dihydropyrimido[5,4-d][1]benzazepin-6(6H)-ones which may be reduced to remove the lactam carbonyl group to give tricyclic derivatives of structural type 5 wherein Z is a pyrimidine ring.

Scheme 11

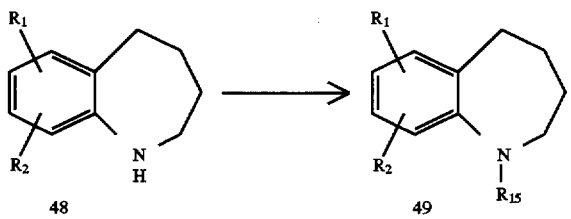

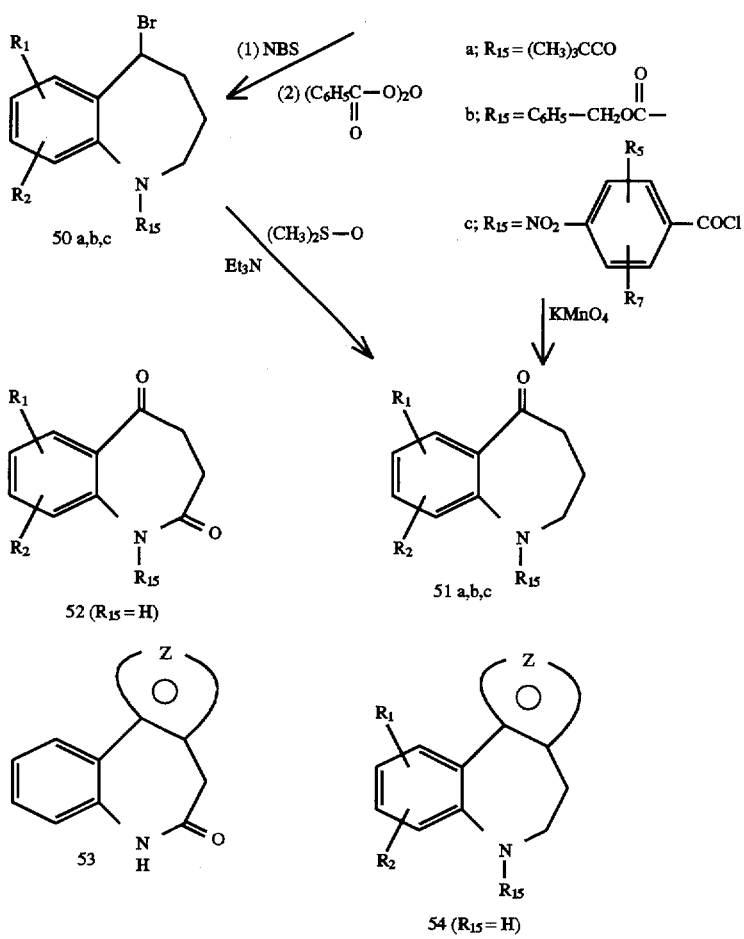

The synthesis of compounds of Formula I wherein $R_3$ is

the Ar group is

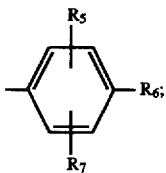

$R_6$ is

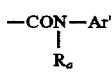

and where Ar' is as previously defined is carried out according to Scheme 12. The tricyclic compounds 3a and 3b are reacted with mono-methyl terephythalyl chloride 55 (prepared from mono-methyl terephthalate and thionyl chloride) in the presence of a tertiary base such as triethylamine in solvents such as dichloromethane, tetrahydrofuran, dioxane, toluene and the like to give derivatives 56a and 56b. These ester intermediates (56a and 56b) are hydrolyzed with two to ten equivalents of an alkaline hydroxide such as potassium or sodium hydroxide in aqueous methanol or ethanol to give the corresponding acids after acidification and workup. The free acids are converted to the acid chlorides with thionyl chloride and these acid chloride intermediates, 57a and 57b, reacted with aminoaryl derivatives of formula:

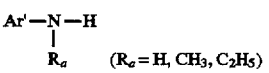

wherein Ar' is as previously defined to give compounds 59a and 59b.

Scheme 12
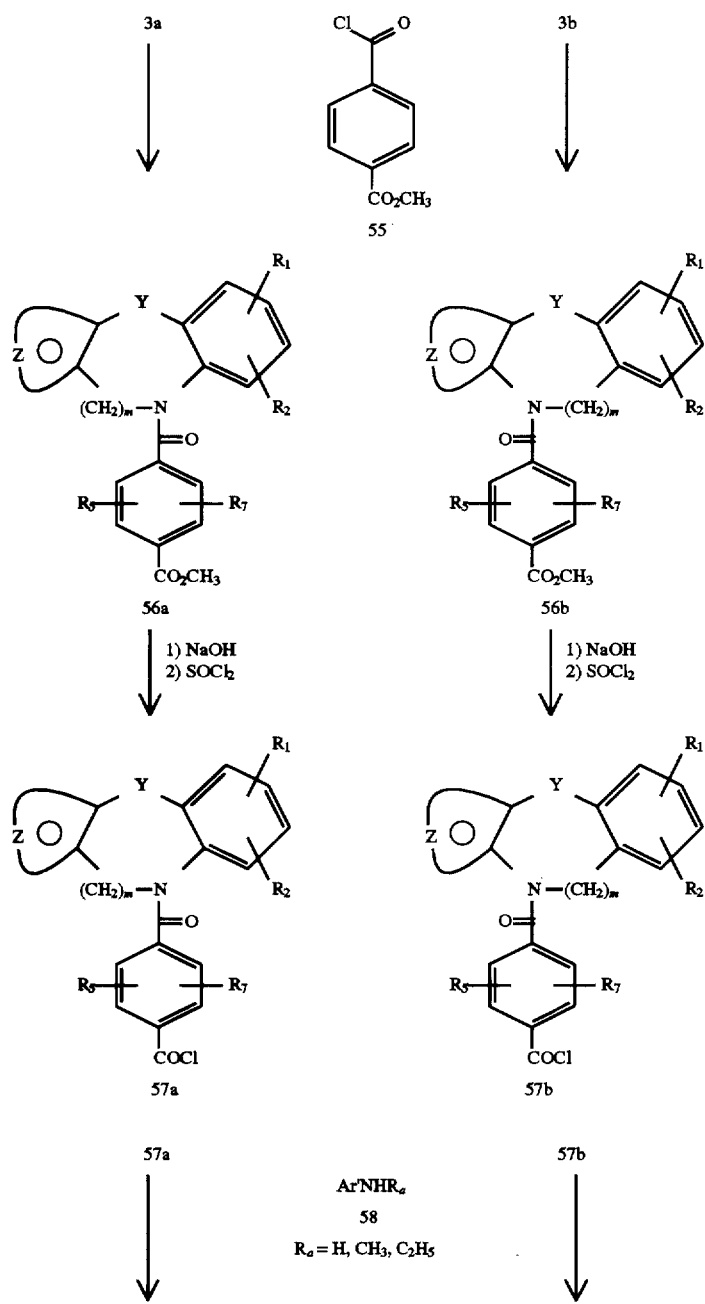

-continued
Scheme 12

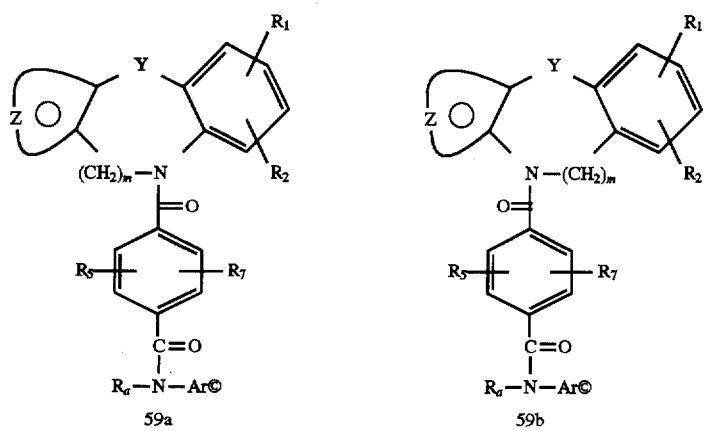

As described in reaction Scheme 1, the following specific tricyclic ring systems of the generic formula 3a and 3b are illustrated to show one of the synthetic methods for the synthesis of the compounds of this invention. These derivatives 60, 63, 66, 69, 72, 75, 78, 81, 84, 87, 90, and 93 when subjected to the reaction conditions in Scheme i which is the acylation of the tricyclic compounds ($R_{16}$=H) with 4-nitrobenzoyl chloride or a substituted 4-nitrobenzoyl chloride in the presence of a trialkylamine such as triethylamine in solvents such as chloroform, dichloromethane, dioxane, tetrahydrofuran, toluene and the like give the intermediates 61, 64, 67, 70, 73, 76, 79, 82, 85, 88, 91, 94. These 4-nitrobenzoyl and substituted 4-nitro-benzoyl derivatives are reduced with hydrogen in the presence of a catalyst such as Pd/C in solvents such as ethanol, ethanol-ethyl acetate, acetic acid or N,N-dimethylformamide to give the 4-aminobenzyl or substituted 4-aminobenzoyl derivatives 62, 65, 68, 71, 74, 77, 80, 83, 86, 89, 92, 95. Alternatively, the 4-nitrobenzoyl and substituted 4-nitrobenzoyl derivatives 61, 64, 67, 70, 73, 76, 79, 82, 85, 88., 91, 94 are reduced with Pd/C and hydrazine in refluxing ethanol.

The 4-aminobenzoyl and substituted 4-aminobenzoyl derivatives 62, 65, 68, 71, 74, 77, 80, 83, 86, 89, 92, 95 are reacted with acid chlorides of the formula:

Ar'COCl,

($R_a$ = H, $CH_3$, $C_2H_5$)

cycloalkyl$(CH_2)_n$COCl, Ar'$CH_2$COCl, to give products as shown in Scheme 1 wherein $R_6$ is as defined.

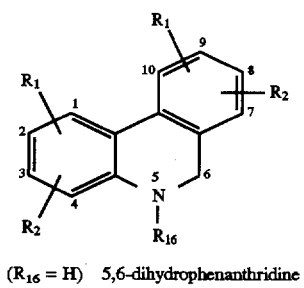

($R_{16}$ = H)  5,6-dihydrophenanthridine  60

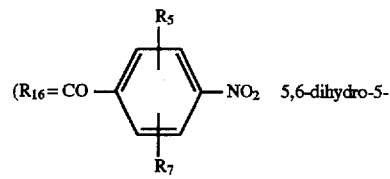

(4-nitrobenzoyl)phenanthridine  61

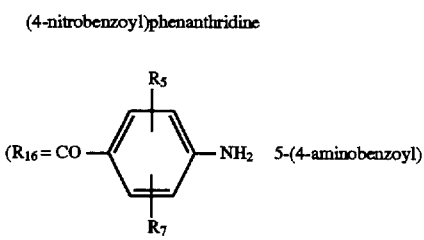

5,6-dihydrophenanthridine  62

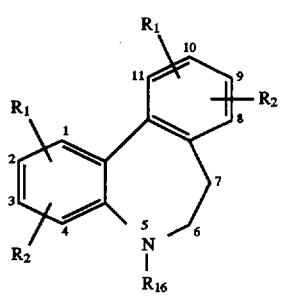

($R_{16}$ = H)  6,7-dihydro-5H-dibenz[b,d]azepine  63

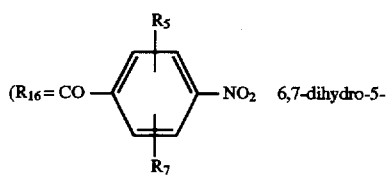

(4-nitrobenzoyl)-5H-dibenz[b,d]azepine  64

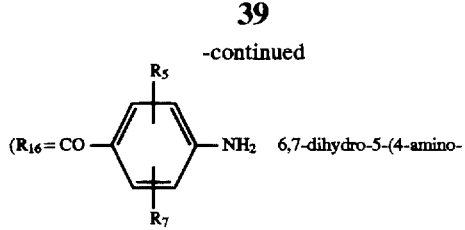

($R_{16}$ = CO) 6,7-dihydro-5-(4-amino-benzoyl)-5H-dibenz[b,d]azepine

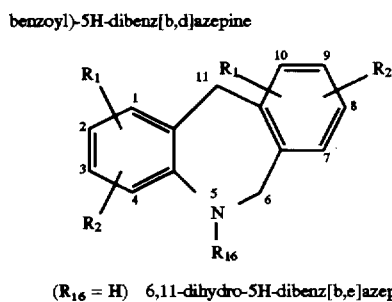

($R_{16}$ = H) 6,11-dihydro-5H-dibenz[b,e]azepine  66

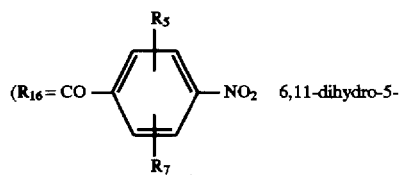

($R_{16}$ = CO) 6,11-dihydro-5-(4-nitrobenzoyl)-5H-dibenz[b,e]azepine  67

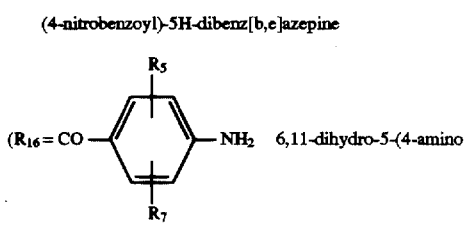

($R_{16}$ = CO) 6,11-dihydro-5-(4-amino benzoyl)-5H-dibenz[b,e]azepine  68

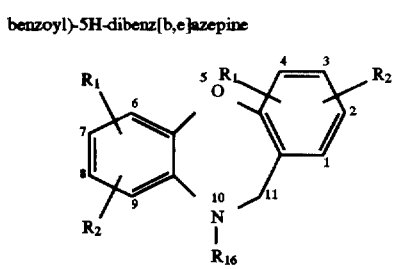

($R_{16}$ = H) 10,11-dihydrodibenz[b,f][1,4]oxazepine  69

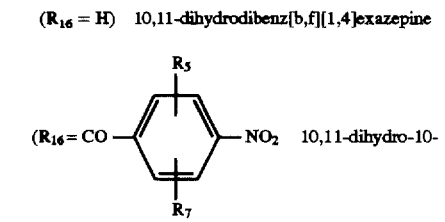

($R_{16}$ = CO) 10,11-dihydro-10-(4-nitrobenzoyl)dibenz[b,f][1,4]oxazepine  70

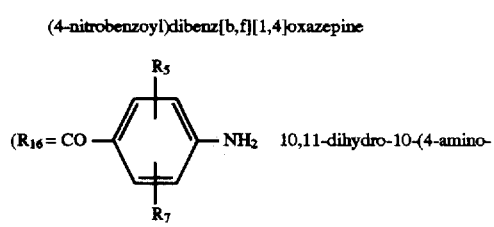

($R_{16}$ = CO) 10,11-dihydro-10-(4-amino-benzoyl)dibenz[b,f][1,4]oxazepine  71

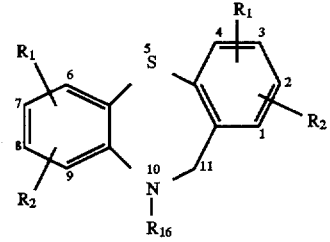

($R_{16}$ = H) 10,11-dihydrodibenz[b,f][1,4]thiazepine  72

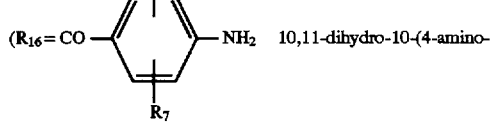

($R_{16}$ = CO) 10,11-dihydro-10-(4-nitrobenzoyl)dibenz[b,f][1,4]thiazepine  73

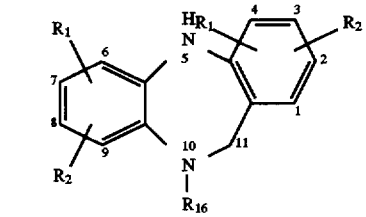

($R_{16}$ = CO) 10,11-dihydro-10-(4-aminobenzoyl)dibenz[b,f][1,4]thiazepine  74

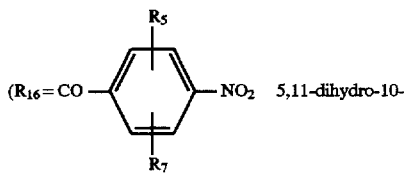

($R_{16}$ = H) 5,11-dihydro-10H-dibenz[b,e][1,4]diazepine  75

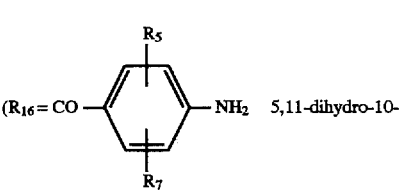

($R_{16}$ = CO) 5,11-dihydro-10-(4-nitrobenzoyl)-10-dibenz[b,e][1,4]diazepine  76

($R_{16}$ = CO) 5,11-dihydro-10-(4-aminobenzoyl)-10H-dibenz[b,e][1,4]diazepine  77

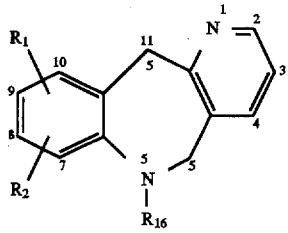

(R₁₆ = H)  5,11-dihydro-6H-pyrido[3,2-c][1]benzazepine  78

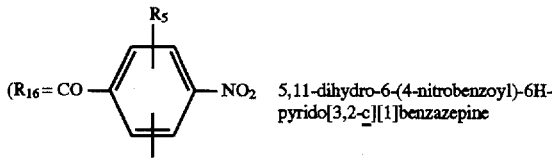

(R₁₆ = CO)  5,11-dihydro-6-(4-nitrobenzoyl)-6H-pyrido[3,2-c][1]benzazepine  79

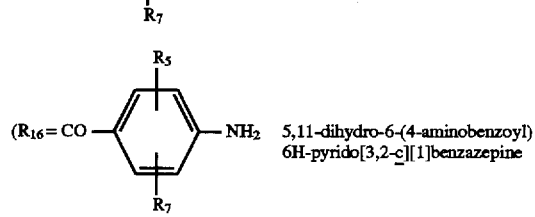

(R₁₆ = CO)  5,11-dihydro-6-(4-aminobenzoyl)-6H-pyrido[3,2-c][1]benzazepine  80

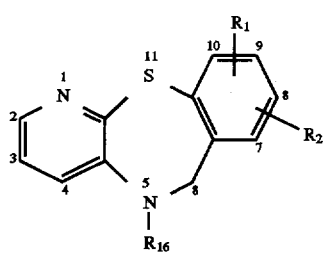

(R₁₆ = H)  5,6-dihydropyrido[2,3-b][1,4]benzothiazepine  81

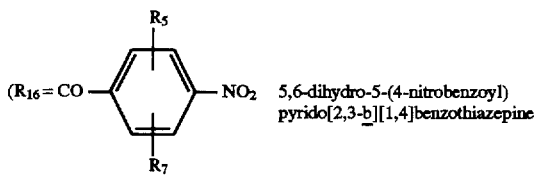

(R₁₆ = CO)  5,6-dihydro-5-(4-nitrobenzoyl)pyrido[2,3-b][1,4]benzothiazepine  82

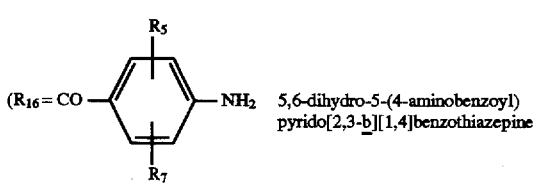

(R₁₆ = CO)  5,6-dihydro-5-(4-aminobenzoyl)pyrido[2,3-b][1,4]benzothiazepine  83

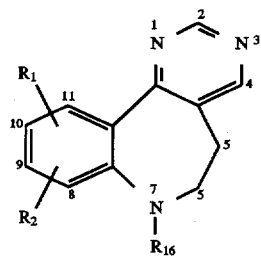

(R₁₆ = H)  6,7-dihydro-5H-pyrimido[5,4-d][1]benzazepine  84

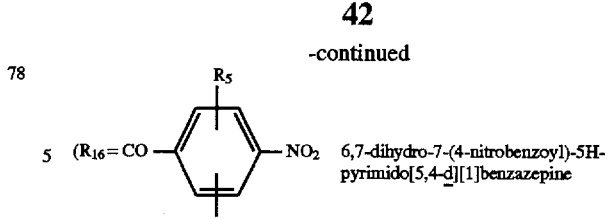

(R₁₆ = CO)  6,7-dihydro-7-(4-nitrobenzoyl)-5H-pyrimido[5,4-d][1]benzazepine  85

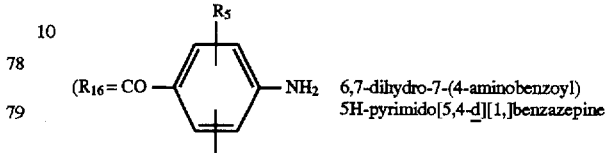

(R₁₆ = CO)  6,7-dihydro-7-(4-aminobenzoyl)-5H-pyrimido[5,4-d][1,]benzazepine  86

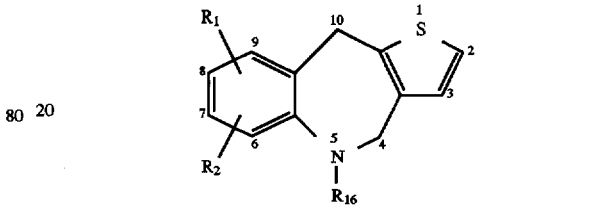

(R₁₆ = H)  4,10-dihydro-5H-thiano[3,2-c][1]benzazepine  87

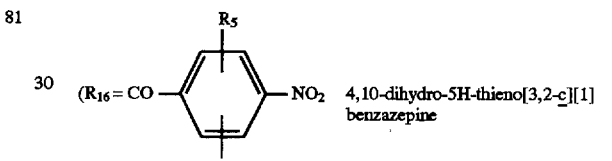

(R₁₆ = CO)  4,10-dihydro-5H-thieno[3,2-c][1]benzazepine  88

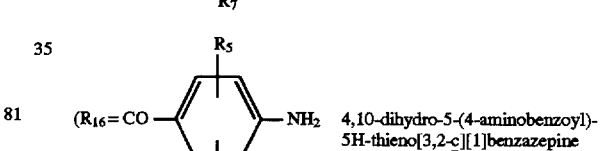

(R₁₆ = CO)  4,10-dihydro-5-(4-aminobenzoyl)-5H-thieno[3,2-c][1]benzazepine  89

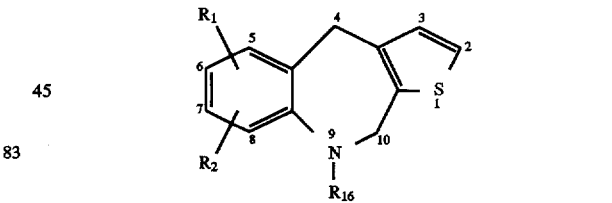

(R₁₆ = H)  4,10-dihydro-9H-thieno[2,3-c][1]benzazepine  90

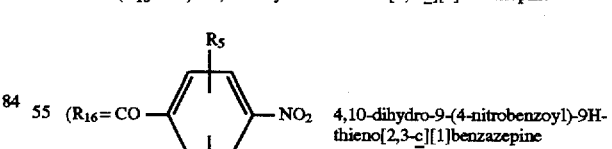

(R₁₆ = CO)  4,10-dihydro-9-(4-nitrobenzoyl)-9H-thieno[2,3-c][1]benzazepine  91

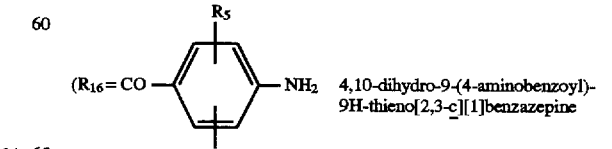

(R₁₆ = CO)  4,10-dihydro-9-(4-aminobenzoyl)-9H-thieno[2,3-c][1]benzazepine  92

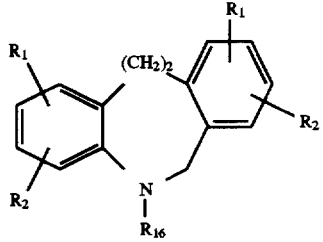

(R$_{16}$ = H)  5,6,11,12-tetrahydrodibenz[b,f]azocine   93

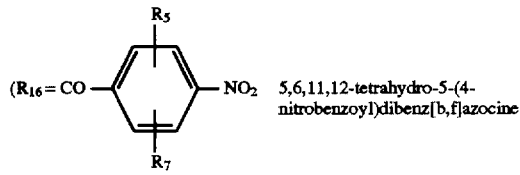

(R$_{16}$ = CO—⟨⟩—NO$_2$)  5,6,11,12-tetrahydro-5-(4-nitrobenzoyl)dibenz[b,f]azocine   94

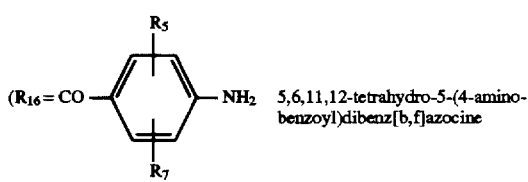

(R$_{16}$ = CO—⟨⟩—NH$_2$)  5,6,11,12-tetrahydro-5-(4-aminobenzoyl)dibenz[b,f]azocine   95

As described in Scheme 2, the tricyclic 4-aminobenzoyl or substituted 4-aminobenzoyl derivatives 62, 65, 68, 71, 74, 77, 80, 83, 86, 89, 92, and 95 are reacted with carbamoyl derivatives

Ar'NCOCl
|
R$_b$ (R$_b$ = H, CH$_3$, C$_2$H$_5$)

or arylisocyanates

Ar'—N=C=O to give specific derivatives wherein R$_6$ is

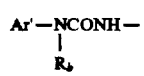

Ar'—NCONH—
|
R$_b$ and R$_b$ is independently selected from H, CH$_3$ or —C$_2$H$_5$.

As described in Scheme 7, the tricyclic derivatives 60, 63, 66, 69, 72, 75, 78, 81, 84, 87, 90, and 93 are reacted in one step with a previously synthesized ArCOCl compound wherein Ar is as previously defined. For example, reaction of the specific tricyclic derivatives 60, 63, 66, 69, 72, 75, 78, 81, 84, 87, 92, 93 with aroyl chlorides of the following structural types:

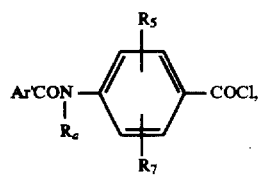

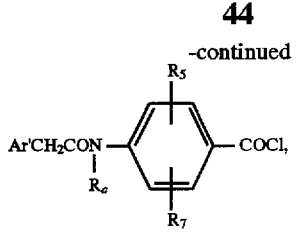

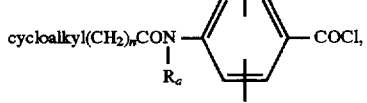

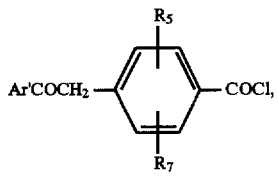

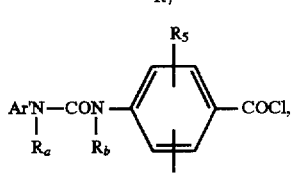

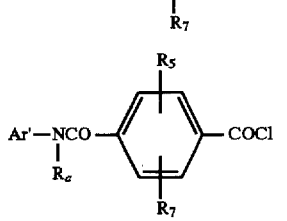

gives in one step derivatives of these delineated tricyclic compounds wherein the Ar group of the moiety:

O
||
—CAr in formula I is

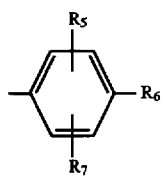

and R$_6$ is

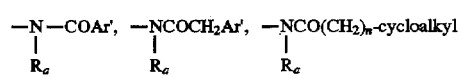

—N—COAr',  —NCOCH$_2$Ar',  —NCO(CH$_2$)$_n$-cycloalkyl
|          |                 |
R$_a$      R$_a$             R$_a$ —CH$_2$COAr',  —N—CON—Ar'  —CON—Ar'
               |    |        |
               R$_a$ R$_b$   R$_a$ wherein cycloalkyl, R$_a$, R$_b$, R$_1$, R$_2$, R$_5$, R$_7$ and Ar' are as hereinbefore described.

Among the more preferred compounds of this invention are those selected from Formula I:

Formula I $$\text{structure showing pyridine with } R_1, R_2 \text{ substituents, N, Y linker to phenyl ring with } R_1, R_2, \text{ and A—B bridge}$$

wherein;

Y is O, S, NH, NCOCH$_3$, N-lower alkyl (C$_1$-C$_3$);

A—B is $$-(CH_2)-\underset{R_3}{N}- \quad \text{or} \quad -\underset{R_3}{N}-(CH_2)-$$

R$_1$ is H, halogen (chlorine, fluorine, bromine, iodine), OH, —S-lower alkyl (C$_1$-C$_3$), —SH, —SO lower alkyl (C$_1$-C$_3$), —SO$_2$ lower alkyl (C$_1$-C$_3$), —CO lower alkyl (C$_1$-C$_3$), —CF$_3$, lower alkyl (C$_1$-C$_3$), —O lower alkyl (C$_1$-C$_3$), —NO$_2$, —NH$_2$, —NHCO lower alkyl (C$_1$-C$_3$), —N-[lower alkyl (C$_1$-C$_3$)]$_2$, SO$_2$NH$_2$, —SO$_2$NH lower alkyl (C$_1$-C$_3$), or —SO$_2$N [lower alkyl (C$_1$-C$_3$)]$_2$;

R$_2$ is H, Cl, Br, I, F, —OH, lower alkyl (C$_1$-C$_3$), —O lower alkyl (C$_1$-C$_3$); or R$_1$ and R$_2$ taken together are methylenedioxy or ethylenedioxy;

R$_3$ is the moiety $$-\overset{O}{\underset{\|}{C}}Ar$$

wherein Ar is a moiety selected from the group (phenyl with R$_5$, R$_6$, R$_7$ substituents), (indole with R$_4$ on N), or (five-membered heterocycle with R$_5$, R$_6$, X)

and X is selected from O, S, —NCH$_3$, or —N—COCH$_3$;

R$_4$ is selected from H, lower alkyl (C$_1$-C$_3$), —CO-lower alkyl (C$_1$-C$_3$), SO$_2$ lower alkyl (C$_1$-C$_3$), and the moieties of the formulae:

(phenyl with R$_1$, R$_2$)—CO—  or  (phenyl with R$_1$, R$_2$)—SO$_2$—;

R$_5$ is H, —CH$_3$, —C$_2$H$_5$, Cl, Br, F, —O—CH$_3$, or —O—C$_2$H$_5$;

R$_6$ is selected from:

(a) moieties of the formula:

$$-\underset{R_a}{N}COAr', \quad -\underset{R_a}{C}ON-Ar', \quad -\underset{R_a}{N}CO\underset{R_a}{N}-Ar',$$

$$-\underset{R_a}{N}CO(CH_2)_n\text{-cycloalkyl}, \quad -\underset{R_a}{N}COCH_2Ar',$$

$$-\underset{R_a}{N}-SO_2-\text{(phenyl with } R_2, R_7\text{)},$$

$$-\underset{R_a}{N}-SO_2CH_2-\text{(phenyl with } R_2, R_7\text{)},$$

$$-\underset{R_a}{N}-\overset{O}{\underset{\|}{P}}\left[-O-\text{(phenyl with } R_2, R_7\text{)}\right]_2,$$

$$-\underset{R_a}{N}-\overset{O}{\underset{\|}{P}}\left[\text{(phenyl with } R_2, R_7\text{)}\right]_2,$$

$-\underset{R_a}{N}SO_2\text{-lower alkyl}(C_1\text{-}C_8), \quad -CH_2COAr',$ or $-\underset{R_a}{N}SO_2\text{-lower alkenyl}(C_1\text{-}C_8),$ wherein cycloalkyl is defined as C$_{3-C6}$ cycloalkyl, cyclohexenyl or cyclopentenyl;

R$_2$ is as hereinbefore defined;

n is 0–2;

R$_7$ is H, —CH$_3$, —CH$_2$H$_5$, Cl, Br, F, —OCH$_3$, —OC$_2$H$_5$, or —CF$_3$;

R$_a$ is hydrogen, CH$_3$, C$_2$H$_5$, moieties of the formulae:

$$-(CH_2)_q-N\underset{R_b}{\overset{R_b}{\diagup}}, \quad -(CH_2)_q-N\text{(pyrrolidine)},$$

$$-(CH_2)_q-N\text{(piperidine)}, \quad \text{or} \quad -(CH_2)_q-N\text{(morpholine)}O,$$

—(CH$_2$)2—O-lower alkyl (C$_1$-C$_3$) or —CH$_2$CH$_2$OH;

q is one or two;

R$_b$ is hydrogen, —CH$_3$ or —C$_2$H$_5$;

Ar' is selected from the group:

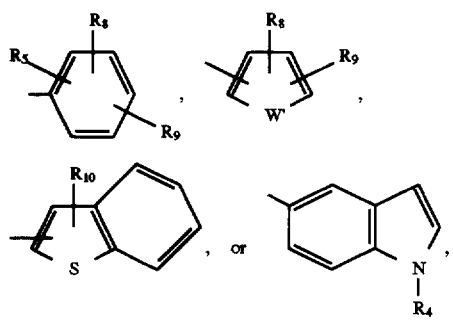

wherein $R_4$, $R_5$ are as hereinbefore defined;

$R_8$ and $R_9$ are independently hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

$R_{10}$ is selected from halogen, hydrogen, or lower alkyl ($C_1$–$C_3$);

W' is selected from O, S, NH, N-lower alkyl ($C_1$–$C_3$), —NCO-lower alkyl ($C_1$–$C_3$), or $NSO_2$-lower alkyl ($C_1$–$C_3$); and (b) a moiety of the formula:

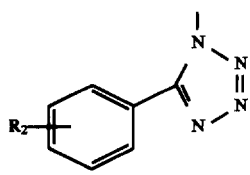

where $R_2$ is as hereinbefore defined;

(c) a moiety of the formula:

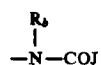

wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —$CH_2$—K wherein K is halogen, —OH, tetrahydrofuran, tetrahydrothiophene or the heterocyclic ring moiety:

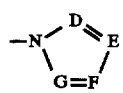

wherein D, E, F and G are selected from carbon or nitrogen and wherein the carbon atoms may be optionally substituted with halogen, ($C_1$–$C_3$)lower alkyl, hydroxy, —CO-lower alkyl ($C_1$–$C_3$), CHO, ($C_1$–$C_3$)lower alkoxy, or —$CO_2$-lower alkyl ($C_1$–$C_3$), and $R_a$ and $R_b$ are as hereinbefore defined;

(d) a moiety selected from those of the formulae:

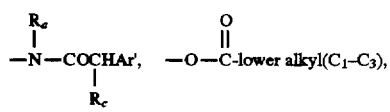

-continued

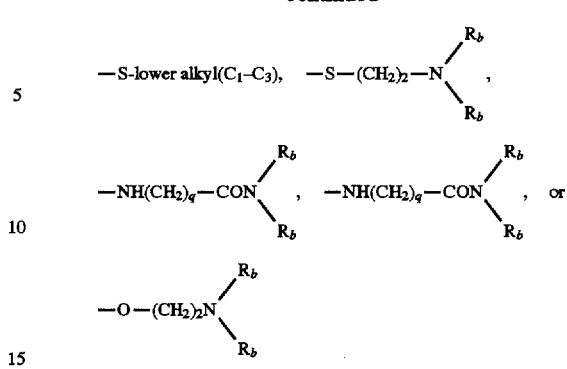

wherein $R_c$ is selected from halogen, ($C_1$–$C_3$) lower alkyl, —O-lower alkyl ($C_1$–$C_3$) or OH;

$R_b$ is as hereinbefore defined;

q is 1 or 2;

wherein Ar' is selected from the group:

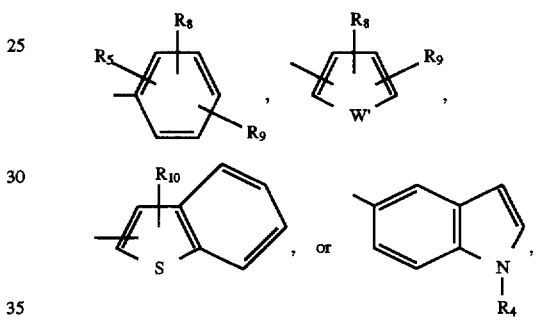

$R_7$ is hydrogen, —$CH_3$, —$C_2H_5$, Cl, Br, F, —$OCH_3$, —$OC_2H_5$, or —$CF_3$;

$R_8$ and $R_9$ are independently hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

$R_{10}$ is selected from the group of halogen, hydrogen, or lower alkyl ($C_1$–$C_3$);

W' is selected from O, S, NH, N-lower alkyl ($C_1$–$C_3$), —NCO-lower alkyl ($C_1$–$C_3$), or $NSO_2$-lower alkyl ($C_1$–$C_3$);

or a pharmaceutically acceptable salt, ester or prodrug thereof.

Within the group above are the following preferred subgroups 1 to 5 of compounds:

1. wherein $R^3$ is the moiety:

wherein Ar is a moiety selected from the group

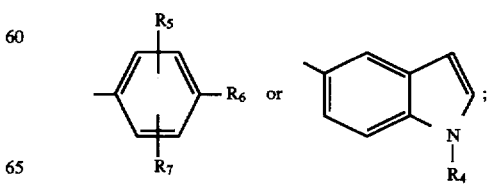

$R_6$ is selected from the group

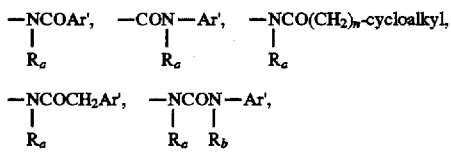

or —CH$_2$COAr';
wherein
n is 0–2;
Ar' is

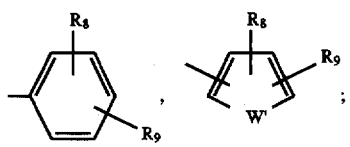

W' is O or S;
A—B, $R_a$, $R_b$, $R_1$, $R_2$, $R_4$, $R_5$, $R_7$, $R_8$, $R_9$, and cycloalkyl are as defined in Claim 1;

or a pharmaceutically acceptable salt, ester or prodrug thereof.

2. compounds of the formula:

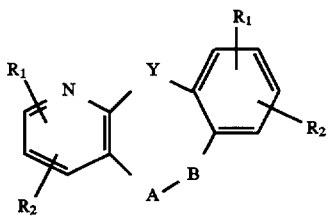

wherein;
Y is O, S, NH, NCOCH$_3$, N-lower alkyl
A—B is

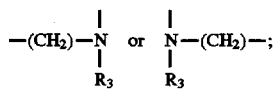

$R_1$ is H, halogen (Cl, F, Br, I), OH, —S-lower alkyl (C$_1$–C$_3$), —SH, —SO lower alkyl (C$_1$–C$_3$), —SO$_2$ lower alkyl (C$_1$–C$_3$), —CO lower alkyl (C$_1$–C$_3$), —CF$_3$, lower alkyl (C$_1$–C$_3$), —O lower alkyl (C$_1$–C$_3$), —NO$_2$, —NH$_2$, —NHCO lower alkyl (C$_1$–C$_3$), —N-[lower alkyl (C$_1$–C$_3$)]$_2$, SO$_2$NH$_2$, —SO$_2$NH lower alkyl (C$_1$–C$_3$), or —SO$_2$N [lower alkyl (C$_1$–C$_3$)]$_2$;

$R_2$ is selected from H, Cl, Br, I, F, —OH, lower alkyl (C$_1$–C$_3$), or —O lower alkyl (C$_1$–C$_3$); or $R_1$ and $R_2$ taken together are methylenedioxy or ethylenedioxy;

$R_3$ is the moiety

wherein Ar is a moiety selected from the group

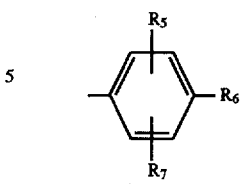

$R_5$ is H, —CH$_3$, —C$_2$H$_5$, Cl, Br, F, —O—CH$_3$, or —O—C$_2$H$_5$;
$R_6$ is selected from:

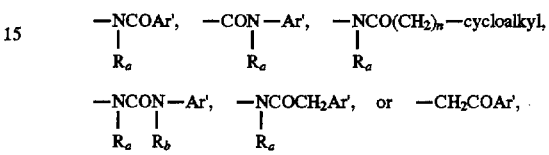

wherein
cycloalkyl is defined as C$_3$–C$_6$ cycloalkyl, cyclohexenyl or cyclopentenyl;
n is 0–2;
and wherein Ar' is selected from the moieties:

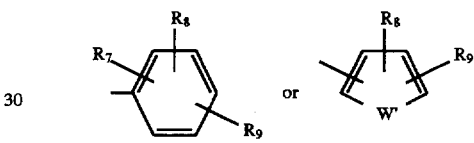

wherein $R_a$ and $R_b$ are independently selected from H, —CH$_3$, or —C$_2$H$_5$;
$R_7$ is H, —CH$_3$, —C$_2$H$_5$, Cl, Br, F, —O—CH$_3$, —O—C$_2$H$_5$ or —CF$_3$;
$R_8$ and $R_9$ are independently selected from hydrogen, lower alkyl (C$_1$–C$_3$), O-lower alkyl (C$_1$–C$_3$), S-lower alkyl (C$_1$–C$_3$), —CF$_3$, —CN, —OH, —SCF$_3$, —OCF$_3$, halogen, NO$_2$, amino, or —NH-lower alkyl (C$_1$–C$_3$);
W' is selected from O, S, NH, N-lower alkyl (C$_1$–C$_3$), —NCO-lower alkyl (C$_1$–C$_3$), or NSO$_2$-lower alkyl (C$_1$–C$_3$);
or a pharmaceutically acceptable salt, ester or prodrug thereof.

3. compounds of the formula:

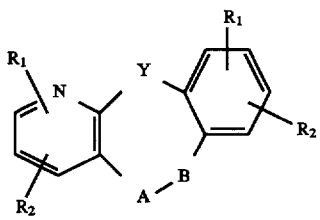

wherein;
Y is O;
A—B is

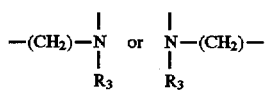

$R_1$ is H, halogen (Cl, F, Br, I), OH, —S-lower alkyl (C$_1$–C$_3$), —SH, —SO lower alkyl (C$_1$–C$_3$), —SO$_2$ lower alkyl (C$_1$–C$_3$), —CO lower alkyl (C$_1$–C$_3$), —CF$_3$, lower alkyl ($C_1$-$C_3$), —O lower alkyl ($C_1$-$C_3$), —$NO_2$, —$NH_2$, —NHCO lower alkyl ($C_1$-$C_3$), —N-[lower alkyl ($C_1$-$C_3$)]$_2$, $SO_2NH_2$, —$SO_2$NH lower alkyl ($C_1$-$C_3$), or —$SO_2$N [lower alkyl ($C_1$-$C_3$)]$_2$;

$R_2$ is selected from H, Cl, Br, I, F, —OH, lower alkyl ($C_1$-$C_3$), or —O lower alkyl ($C_1$-$C_3$); or $R_1$ and $R_2$ taken together are methylenedioxy or ethylenedioxy;

$R_3$ is the moiety

—CAr wherein Ar is a moiety selected from the group

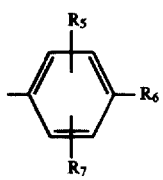

$R_5$ is H, —$CH_3$, —$C_2H_5$, Cl, Br, F, —O—$CH_3$, or —O—$C_2H_5$;

$R_6$ is selected from:

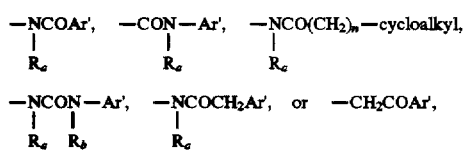

wherein cycloalkyl is defined as $C_3$-$C_6$ cycloalkyl, cyclohexenyl or cyclopentenyl;

n is 0-2;

and wherein Ar' is selected from the moieties:

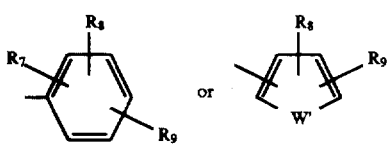

wherein $R_a$ and $R_b$ are independently selected from H, —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$-$C_3$), O-lower alkyl ($C_1$-$C_3$), S-lower alkyl ($C_1$-$C_3$), —$CF_3$, —CN, —OH, —$SCF_3$, —$OCF_3$, halogen, $NO_2$, amino, or —NH-lower alkyl ($C_1$-$C_3$);

W' is selected from O, S, NH, N-lower alkyl ($C_1$-$C_3$), —NCO-lower alkyl ($C_1$-$C_3$), or $NSO_2$-lower alkyl ($C_1$-$C_3$);

or a pharmaceutically acceptable salt, ester or prodrug thereof.

4. compounds of the formula:

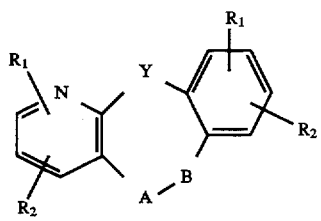

wherein;

Y is S;

A—B is

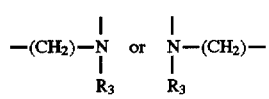

$R_1$ is H, halogen (Cl, F, Br, I), OH, —S-lower alkyl ($C_1$-$C_3$), —SH, —SO lower alkyl ($C_1$-$C_3$), —$SO_2$ lower alkyl ($C_1$-$C_3$), —CO lower alkyl ($C_1$-$C_3$), —$CF_3$, lower alkyl ($C_1$-$C_3$), —O lower alkyl ($C_1$-$C_3$), —$NO_2$, —$NH_2$, —NHCO lower alkyl ($C_1$-$C_3$), —N-[lower alkyl ($C_1$-$C_3$)]$_2$, $SO_2NH_2$, —$SO_2$NH lower alkyl ($C_1$-$C_3$), or —$SO_2$N [lower alkyl ($C_1$-$C_3$)]$_2$;

$R_2$ is selected from H, Cl, Br, I, F, —OH, lower alkyl ($C_1$-$C_3$), or —O lower alkyl ($C_1$-$C_3$); or $R_1$ and $R_2$ taken together are methylenedioxy or ethylenedioxy;

$R_3$ is the moiety

—CAr wherein Ar is a moiety selected from the group

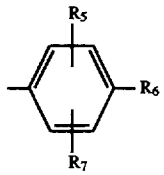

$R_5$ is H, —$CH_3$, —$C_2H_5$, Cl, Br, F, —O—$C_2H_5$;

$R_6$ is selected from:

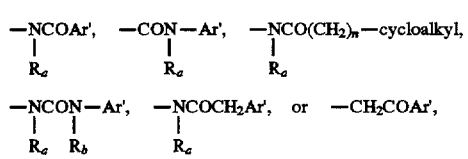

wherein cycloalkyl is defined as $C_3$-$C_6$ cycloalkyl, cyclohexenyl or cyclopentenyl;

n is 0–2;

and wherein Ar' is selected from the moieties:

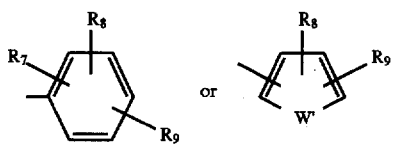

wherein $R_a$ and $R_b$ are independently selected from —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

W' is selected from O, S, NH, N-lower alkyl ($C_1$–$C_3$), —NCO-lower alkyl ($C_1$–$C_3$), or $NSO_2$-lower alkyl ($C_1$–$C_3$);

or a pharmaceutically acceptable salt, ester or prodrug thereof.

5. compounds of the formula:

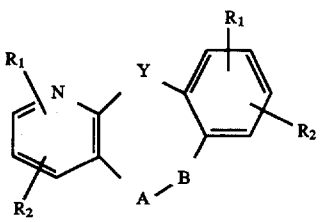

wherein;

Y is NH, —$NHCOCH_3$, —NH-lower alkyl ($C_1$–$C_3$);

A—B is

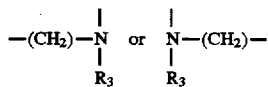

$R_1$ is H, halogen (Cl, F, Br, I), OH, —S-lower alkyl ($C_1$–$C_3$), —SH, —SO lower alkyl ($C_1$–$C_3$), —$SO_2$ lower alkyl ($C_1$–$C_3$), —CO lower alkyl ($C_1$–$C_3$), —$CF_3$, lower alkyl ($C_1$–$C_3$), —O lower alkyl ($C_1$–$C_3$), —$NO_2$, —$NH_2$, —NHCO lower alkyl ($C_1$–$C_3$), —N[lower alkyl ($C_1$–$C_3$)]$_2$, $SO_2NH_2$, —$SO_2NH$ lower alkyl ($C_1$–$C_3$), or —$SO_2N$ [lower alkyl ($C_1$–$C_3$)]$_2$;

$R_2$ is selected from H, Cl, Br, I, F, —OH, lower alkyl ($C_1$–$C_3$), or —O lower alkyl ($C_1$–$C_3$); or $R_1$ and $R_2$ taken together are methylenedioxy or ethylenedioxy;

$R_3$ is the moiety

wherein Ar is a moiety selected from the group

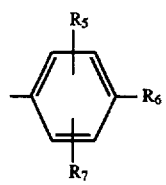

$R_5$ is H, —$CH_3$, —$C_2H_5$, Cl, Br, F, —O—$CH_3$, or —O—$C_2H_5$;

$R_6$ is selected from:

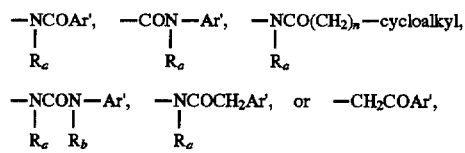

wherein
cycloalkyl is defined as $C_3$–$C_6$ cycloalkyl, cyclohexenyl or cyclopentenyl;

n is 0–2;

and wherein Ar' is selected from the moieties:

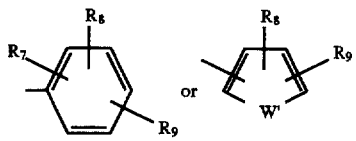

wherein $R_a$ and $R_b$ are independently selected from H, —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

W' is selected from O, S, NH, N-lower alkyl ($C_1$–$C_3$), —NCO-lower alkyl ($C_1$–$C_3$), Or $NSO_2$-lower alkyl ($C_1$–$C_3$);

or a pharmaceutically acceptable salt, ester or prodrug thereof.

Among the more preferred compounds of this invention are those selected from:

N-[4-(pyrido[2,3-b][1,5]benzoxazepin-6(5H)-ylcarbonyl)phenyl]-2-methyl-5-fluorobenzamide.

N-[4-(pyrido[2,3-b][1,5]benzoxazepin-6(5H)-ylcarbonyl)-3-chlorophenyl]-2-methyl-5-fluorobenzamide.

N-[4-(pyrido[2,3-b][1,5]benzoxazepin-6(5H)-ylcarbonyl)-3-chlorophenyl]-2-methyl-3-fluorobenzamide.

N-[4-(pyrido[2,3-b][1,5]benzoxazepin-6(5H)-ylcarbonyl)-3-chlorophenyl]-2-chloro-5-fluorobenzamide.

N-[4-(pyrido[2,3-b][1,5]benzoxazepin-6(5H)-ylcarbonyl)-3-chlorophenyl]-2-fluoro-6-chlorobenzamide.

N-[4-(pyrido[2,3-b][1,5]benzoxazepin-6(5H)-ylcarbonyl)-3-methylphenyl]-2-methyl-5-fluorobenzamide.

N-[4-(pyrido[2,3-b][1,5]benzoxazepin-6(5H)-ylcarbonyl)-3-methylphenyl]-2-methyl-3-fluorobenzamide.

N-[4-(pyrido[2,3-b][1,4]benzoxazepin-5(6H)-ylcarbonyl)-3-chlorophenyl]-2-methyl-5-fluorobenzamide.

N-[4-(pyrido[2,3-b][1,4]benzoxazepin-5(6H)-ylcarbonyl)-3-chlorophenyl]-2-methyl-3-fluorobenzamide.

N-[4-(pyrido[2,3-b][1,4]benzoxazepin-5(6H)-ylcarbonyl)-3-chlorophenyl]-2-chloro-5-fluorobenzamide.

N-[4-(pyrido[2,3-b][1,4]benzoxazepin-5(6H)-ylcarbonyl)-3-chlorophenyl]-2-fluoro-6-chlorobenzamide.

N-[4-(pyrido[2,3-b][1,4]benzoxazepin-5(6H)-ylcarbonyl)-3-chlorophenyl]-2,5-dichlorobenzamide.

N-[4-(pyrido[2,3-b][1,4]benzoxazepin-5(6H)-ylcarbonyl)-3-methylphenyl]-2-methyl-5-fluorobenzamide.

N-[4-(pyrido[2,3-b][1,4]benzoxazepin-5(6H)-ylcarbonyl)-3-methylphenyl]-2-methyl-3-fluorobenzamide.

N-[4-(pyrido[2,3-b][1,5]benzothiazepin-6(5H)-ylcarbonyl)phenyl]-2-methyl-5-fluorobenzamide.

N-[4-(pyrido[2,3-b][1,5]benzothiazepin-6(5H)-ylcarbonyl)-3-chlorophenyl]-2-methyl-5-fluorobenzamide.

N-[4-(pyrido[2,3-b][1,5]benzothiazepin-6(5H)-ylcarbonyl)-3-chlorophenyl]-2-methyl-3-fluorobenzamide.

N-[4-(pyrido[2,3-b][1,5]benzothiazepin-6(5H)-ylcarbonyl)-3-chlorophenyl]-2-chloro-5-fluorobenzamide.

N-[4-(pyrido[2,3-b][1,5]benzothiazepin-6(5H)-ylcarbonyl)-3-chlorophenyl]-2-fluoro-6-chlorobenzamide.

N-[4-(pyrido[2,3-b][1,5]benzothiazepin-6(5H)-ylcarbonyl)-3-methylphenyl]-2-methyl-5-fluorobenzamide.

N-[4-(pyrido[2,3-b][1,5]benzothiazepin-6(5H)-ylcarbonyl)-3-methylphenyl]-2-methyl-3-fluorobenzamide.

N-[4-(pyrido[2,3-b][1,4]benzothiazepin-5(6H)-ylcarbonyl)-3-chlorophenyl]-2-methyl-5-fluorobenzamide.

N-[4-(pyrido[2,3-b][1,4]benzothiazepin-5(6H)-ylcarbonyl)-3-chlorophenyl]-2-methyl-3-fluorobenzamide.

N-[4-(pyrido[2,3-b][1,4]benzothiazepin-5(6H)-ylcarbonyl)-3-chlorophenyl]-2-chloro-5-fluorobenzamide.

N-[4-(pyrido[2,3-b][1,4]benzothiazepin-5(6H)-ylcarbonyl)-3-chlorophenyl]-2-fluoro-6-chlorobenzamide.

N-[4-(pyrido[2,3-b][1,4]benzothiazepin-5(6H)-ylcarbonyl)-3-chlorophenyl]-2,5-dichlorobenzamide.

N-[4-(pyrido[2,3-b][1,4]benzothiazepin-5(6H)-ylcarbonyl)-3-methylphenyl]-2-methyl-5-fluorobenzamide.

N-[4-(pyrido[2,3-b][1,4]benzothiazepin-5(6H)-ylcarbonyl)-3-methylphenyl]-2-methyl-3-fluorobenzamide.

N-[4-[(6,11-dihydro-5H-pyrido[2,3-b][1,4]benzodiazepin-5-yl)carbonyl]-phenyl]-2-methyl-5-fluorobenzamide.

N-[4-[(6,11-dihydro-5H-pyrido[2,3-b][1,4]benzodiazepin-5-yl)carbonyl]-3-chlorophenyl]-2-methyl-5-fluorobenzamide.

N-[4-[(6,11-dihydro-5H-pyrido[2,3-b][1,4]benzodiazepin-5-yl)carbonyl]-3-chlorophenyl]-2-methyl-3-fluorobenzamide.

N-[4-[(6,11-dihydro-5H-pyrido[2,3-b][1,4]benzodiazepin-5-yl)carbonyl]-3-chlorophenyl]-2-chloro-5-fluorobenzamide.

N-[4-[(6,11-dihydro-5H-pyrido[2,3-b][1,4]benzodiazepin-5-yl)carbonyl]-3-chlorophenyl]-2-fluoro-6-chlorobenzamide.

N-[4-[(6,11-dihydro-5H-pyrido[2,3-b][1,4]benzodiazepin-5-yl)carbonyl]-3-methylphenyl]-2-methyl-5-fluorobenzamide.

N-[4-[(6,11-dihydro-5H-pyrido[2,3-b][1,4]benzodiazepin-5-yl)carbonyl]-3-methylphenyl]-2-methyl-3-fluorobenzamide.

N-[4-[(5,11-dihydro-6H-pyrido[2,3-b][1,5]benzodiazepin-6-yl)carbonyl]phenyl]-2-methyl-5-fluorobenzamide.

N-[4-[(5,11-dihydro-6H-pyrido[2,3-b][1,5]benzodiazepin-6-yl)carbonyl]-3-chlorophenyl]-2-methyl-5-fluorobenzamide.

N-[4-[(5,11-dihydro-6H-pyrido[2,3-b][1,5]benzodiazepin-6-yl)carbonyl]-3-chlorophenyl]-2-chloro-5-fluorobenzamide.

N-[4-[(5,11-dihydro-6H-pyrido[2,3-b][1,5]benzodiazepin-6-yl)carbonyl]-3-chlorophenyl]-2-methyl-3-fluorobenzamide.

N-[4-[(5,11-dihydro-6H-pyrido[2,3-b][1,5]benzodiazepin-6-yl)carbonyl]-3-chlorophenyl]-2-fluoro-6-chlorobenzamide.

N-[4-[(5,11-dihydro-6H-pyrido[2,3-b][1,5]benzodiazepin-6-yl)carbonyl]-3-methylphenyl]-2-methyl-5-fluorobenzamide.

N-[4-[(5,11-dihydro-6H-pyrido[2,3-b][1,5]benzodiazepin-6-yl)carbonyl]-3-methylphenyl]-2-methyl-3-fluorobenzamide.

The subject compounds of the present invention are tested for biological activity as follows:

Binding Assay to Rat Hepatic $V_1$ Receptors

Rat liver plasma membranes expressing the vasopressin $V_1$ receptor subtypes are isolated by sucrose density gradient according to the method described by Lesko et al., (1973). These membranes are quickly suspended in 50.0 mM Tris.HCl buffer, pH 7.4, containing 0.2% bovine serum albumin (BSA) and 0.1 mM phenylmethylsulfonylfluoride (PMSF) and kept frozen at −70° C. until used in subsequent binding experiments. For binding experiments, the following is added to the wells of a ninety-six well format microtiter plate: 100 μl of 100.0 mM Tris.HCl buffer containing 10.0 mM $MgCl_2$, 0.2% heat inactivated BSA and a mixture of protease inhibitors: leupeptin, 1.0 mg %; aprotinin, 1.0 mg %; 1,10-phenanthroline, 2.0 mg %; trypsin inhibitor, 10.0 mg % and 0.1mM PMSF, 20.0 μl of [phenylalanyl-3,4,5,-$^3$H]vasopressin (S.A. 45.1 Ci/mmole) at 0.8 nM, and the reaction initiated by the addition of 80 μl of tissue membranes containing 20 μg of tissue protein. The plates are kept undisturbed on the bench top at room temperature for 120 min. to reach equilibrium. Non-specific samples are assayed in the presence of 0.1 μM of the unlabeled antagonist phenylalanylvasopressin, added in 20.0 μl volume.

For test compounds, these are solubilized in 50% dimethylsulfoxide (DMSO) and added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for $IC_{50}$ values by the LUNDON-2 program for competition (LUNDON SOFTWARE, Ohio) and displayed in Table I.

Binding Assay to Rat Kidney Medullary $V_2$ Receptors

Medullary tissues from rat kidneys are dissected out, cut into small pieces and soaked in a 0.154 mM sodium chloride solution containing 1.0 mM EDTA with many changes of the liquid phase, until the solution is clear of blood. The tissue is homogenized in a 0.25 M sucrose solution containing 1.0 mM EDTA and 0.1 mM PMSF using a Potter-Elvehjem homogenizer with a teflon pestle. The homogenate is filtered through several layers (4 layers) of cheese cloth. The filtrate is rehomogenized using a dounce homogenizer, with a tight fitting pestle. The final homogenate is centrifuged at 1500 x g for 15 min. The nuclear pellet is discarded and the supernatant fluid recentrifuged at 40,000 x g for 30 min. The resulting pellet formed contains a dark inner part with the exterior, slightly pink. The pink outer part is suspended in a small amount of 50.0 mM Tris.HCl buffer, pH 7.4. The protein content is determined by the Lowry's method (Lowry et al., *J. Biol. Chem.*, 1953). The membrane suspension is stored at −70° C., in 50.0 mM Tris.HCl, containing 0.2% inactivated BSA and 0.1 mM PMSF in aliquots of 1.0 ml containing 10.0 mg protein per ml of suspension until use in subsequent binding experiments.

For binding experiments, the following is added in μl volume to wells of a 96 well format of a microtiter plate: 100.0 μl of 100.0 mM Tris.HCl buffer containing 0.2% heat inactivated BSA, 10.0 mM MgCl$_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1 mM PMSF, 20.0 μl of [$^3$H]Arginine$^8$, vasopressin (S.A. 75.0 Ci/mmole) at 0.8 nM and the reaction initiated by the addition of 80.0 μl of tissue membranes (200.0 μg tissue protein). The plates are left undisturbed on the bench top for 120 min to reach equilibrium. Non-specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, Ohio) and displayed in Table I.

Radioligand Binding Experiments with Human Platelet Membranes (a) platelet Membrane preparation:

Frozen platelet rich plasma (PRP), received from the Hudson Valley Blood Services, are thawed to room temperature. (Platelet Source: Hudson Valley Blood Services, Westchester Medical Center, Valhalla, N.Y.). The tubes containing the PRP are centrifuged at 16,000 x g for 10 min. at 4° C. and the supernatant fluid discarded. The platelets resuspended in an equal volume of 50.0 mM Tris.HCl, pH 7.5 containing 120 mM NaCl and 20.0 mM EDTA. The suspension is recentrifuged at 16,000 x g for 10 min. This washing step is repeated one more time. The wash discarded and the lysed pellets homogenized in low ionic strength buffer of Tris.HCl, 5.0 mM, pH 7.5 containing 5.0 mM EDTA. The homogenate is centrifuged at 39,000 x g for 10 min. The resulting pellet is resuspended in Tris.HCl buffer, 70.0 mM, pH 7.5 and recentrifuged at 39,000 x g for 10 min. The final pellet is resuspended in 50.0 mM Tris.HCl buffer pH 7.4 containing 120 mM NaCl and 5.0 mM KCl to give 1.0–2.0 mg protein per ml of suspension.

(b) Binding to Vasopressin V$_1$ receptor subtype in Human Platelet Membranes:

In wells of a 96 well format microtiter plate, add 100 μl of 50.0 mM Tris.HCl buffer containing 0.2% BSA and a mixture of protease inhibitors (aprotinin, leupeptin etc.). Then add 20 μl of [$^3$H]Ligand (Manning or Arg$^8$Vasopressin), to give final concentrations ranging from 0.01 to 10.0 nM. Initiate the binding by adding 80.0 μl of platelet suspension (approx. 100 μg protein). Mix all reagents by pipetting the mixture up and down a few times. Non specific binding is measured in the presence of 1.0 μM of unlabeled ligand (Manning or Arg$^8$Vasopressin). Let the mixture stand undisturbed at room temperature for ninety (90) min. Upon this time, rapidly filter off the incubate under vacuum suction over GF/B filters, using a Brandel Harvester. The radioactivity caught on the filter disks is determined by the addition of liquid scintillant and counting in a liquid scintillator.

Binding to Membranes of Mouse Fibroblast Cell Line (LV-2) Transfected with the cDNA Expressing the Human V$_2$ Vasopressin Receptor (a) Membrane Preparation Flasks of 175 ml capacity, containing attached cells grown to confluence, are cleared of culture medium by aspiration. The flasks containing the attached cells are rinsed with 2×5 ml of phosphate buffered saline (PBS) and the liquid aspirated off each time. Finally, 5 ml of an enzyme free dissociation Hank's based solution (Specialty Media, Inc., Lafayette, N.J.) is added and the flasks are left undisturbed for 2 min. The content of all flasks is poured into a centrifuge tube and the cells pelleted at 300 x g for 15 min. The Hank's based solution is aspirated off and the cells homogenized with a polytron at setting #6 for 10 sec in 10.0 mM Tris.HCl buffer, pH 7.4 containing 0.25 M sucrose and 1.0 mM EDTA. The homogenate is centrifuged at 1500 x g for 10 min to remove ghost membranes. The supernatant fluid is centrifuged at 100,000 x g for 60 min to pellet the receptor protein. Upon completion, the pellet is resuspended in a small volume of 50.0 mM Tris.HCl buffer, pH 7.4. The protein content is determined by the Lowry method and the receptor membranes are suspended in 50.0 mM Tris.HCl buffer containing 0.1 mM phenylmethylsulfonylfluoride (PMSF) and 0.2% bovine serum albumin (BSA) to give 2.5 mg receptor protein per ml of suspension.

(b) Receptor Binding

For binding experiments, the following is added in μl volume to wells of a 96 well format of a microtiter plate: 100.0 μl of 100.0 mM Tris.HCl buffer containing 0.2% heat inactivated BSA, 10.0 mM MgCl$_2$ and a mixture of protease inhibitors: leupeptin, 1.0 mg %; aprotinin, 1.0 mg %; 1,10-phenanthroline, 2.0 mg %; trypsin inhibitor, 10.0 mg % and 0.1mM PMSF., 20.0 μl of [$^3$H]Arginine$^8$, vasopressin (S.A. 75.0 Ci/mmole) at 0.8 nM and the reaction initiated by the addition of 80.0 μl of tissue membranes (200.0 μg tissue protein). The plates are left undisturbed on the bench top for 120 min to reach equilibrium. Non specific binding is assessed in the presence of 1.0 μM of unlabeled ligand, added in 20 μl volume. For test compounds, these are solubilized in 50% dimethylsulfoxide (DMSO) and added in 20.0 μl volume to a final incubation volume of 200 μl. Upon completion of binding, the content of each well is filtered off, using a Brandel® cell Harvester (Gaithersburg, Md.). The radioactivity trapped on the filter disk by the ligand-receptor complex is assessed by liquid scintillation counting in a Packard LS Counter, with an efficiency of 65% for tritium. The data are analyzed for IC$_{50}$ values by the LUNDON-2 program for competition (LUNDON SOFTWARE, Ohio) and the data is displayed in Table I.

TABLE I

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ μM | $V_2$ $IC_{50}$ μM |
|---|---|---|---|
| 1 | 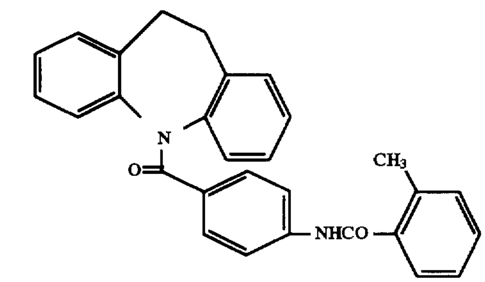 | 2.5 | 0.86 |
| 2 | 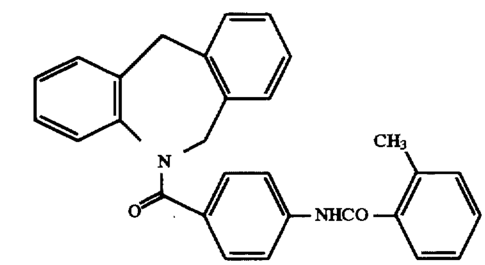 | 0.15 | 0.068 |
| 3 | 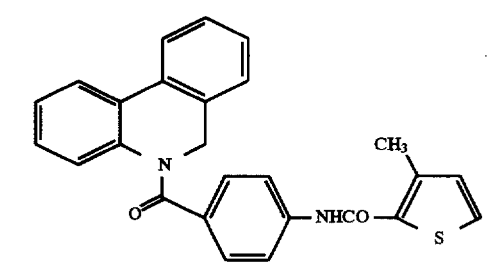 | 0.17 | 0.42 |
| 4 | 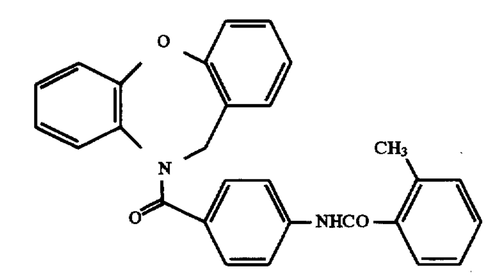 | 1.5 | 1.7 |
| 5 | 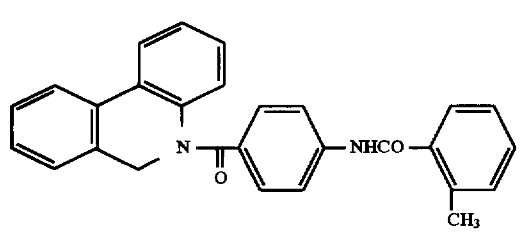 | 0.056 | 0.029 |

TABLE I-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ $IC_{50}$ μM | $V_2$ $IC_{50}$ μM |
|---|---|---|---|
| 6 | 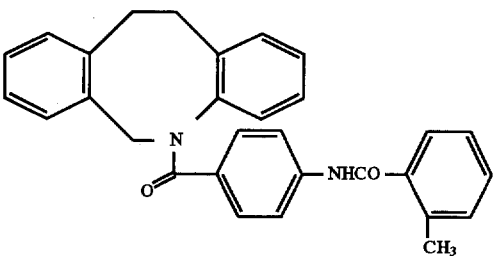 | 60% (50 μM) | 80% (50 μM) |
| 7 | 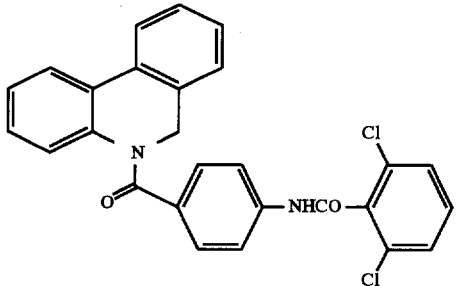 | 0.63 | 0.077 |
| 8 | 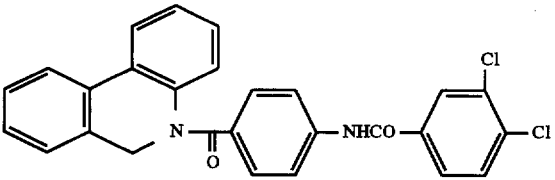 | 2.8 | 1.5 |
| 9 | 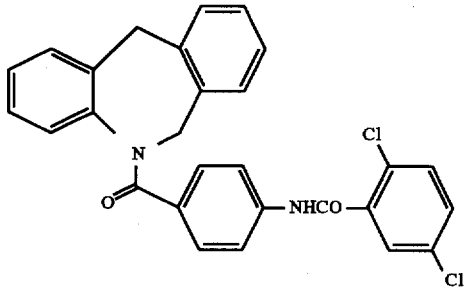 | 1.1 | 0.28 |
| 10 | 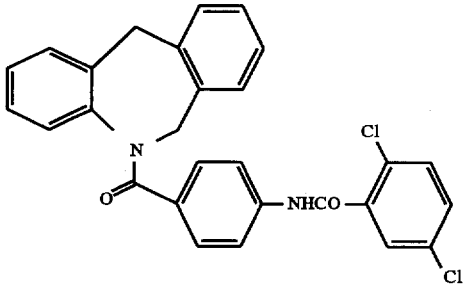 | 0.17 | 0.064 |

TABLE I-continued

Binding Assay to Rat Hepatic $V_1$ Receptors and Rat Kidney
Medullary $V_2$ Receptors or *Binding to $V_1$ Receptor Subtype in
Human Platelet and **Binding to Membranes of Mouse
Fibroblast Cell Line (LV-2) Transfected with the cDNA
Expressing the Human $V_2$ Receptor

| Ex. No. | Structure | $V_1$ $IC_{50}$ μM | $V_2$ $IC_{50}$ μM |
|---|---|---|---|
| 11 | 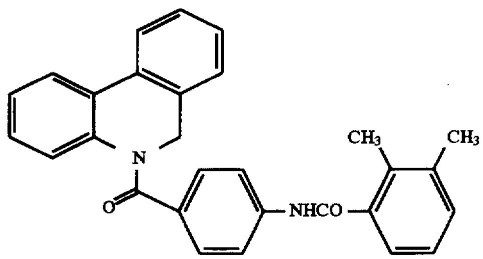 | 0.16 | 0.033 |
| 12 | 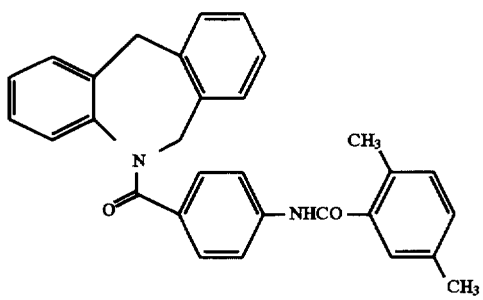 | 0.39 | 0.18 |
| 13 | 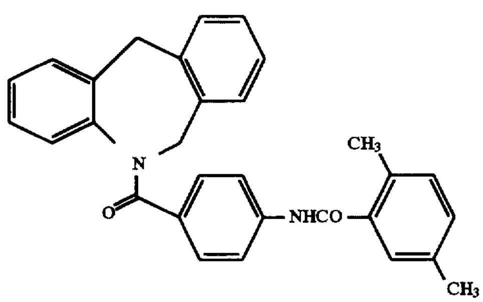 | 0.34 | 0.30 |
| 14 | 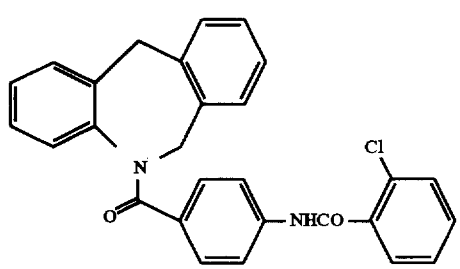 | 0.057 | 0.066 |
| 16 | 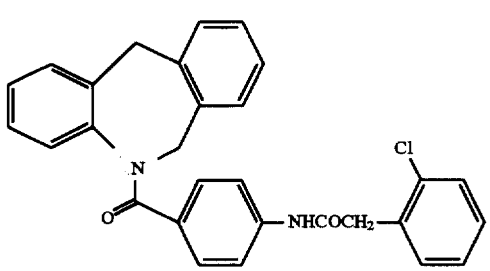 | 0.053 | 0.065 |

TABLE I-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ $IC_{50}$ μM | $V_2$ $IC_{50}$ μM |
| --- | --- | --- | --- |
| 17 | 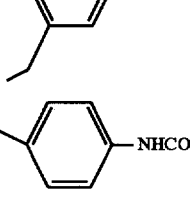 | 65% (50 μM) | 52% (50 μM) |
| 18 | 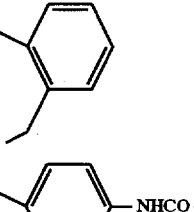 | 0.084 | 0.52 |
| 19 | 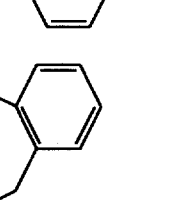 | 1.3 | 1.2 |
| 20 | 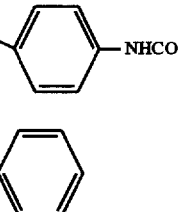 | 17% (10 μM) | 48% (10 μM) |
| 21 | 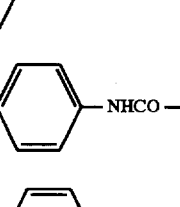 | 0.28 | 0.44 |

TABLE I-continued

Binding Assay to Rat Hepatic $V_1$ Receptors and Rat Kidney
Medullary $V_2$ Receptors or *Binding to $V_1$ Receptor Subtype in
Human Platelet and **Binding to Membranes of Mouse
Fibroblast Cell Line (LV-2) Transfected with the cDNA
Expressing the Human $V_2$ Receptor

| Ex. No. | Structure | $V_1$ IC$_{50}$ μM | $V_2$ IC$_{50}$ μM |
|---|---|---|---|
| 22 | 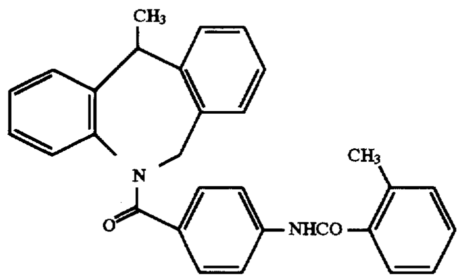 | 0.32 | 0.14 |
| 23 | 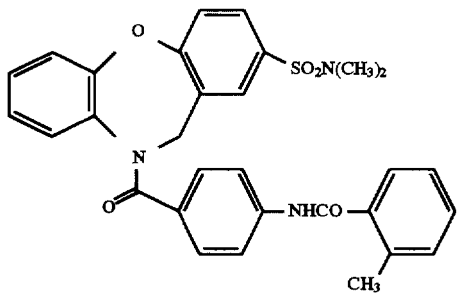 | 19% (50 μM) | 47% (50 μM) |
| 24 | 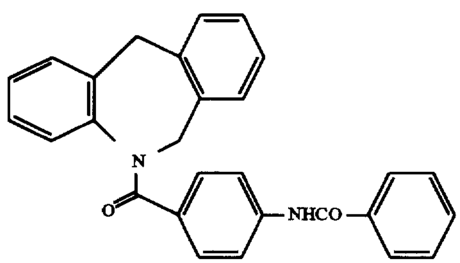 | 0.17 | 0.41 |
| 25 | 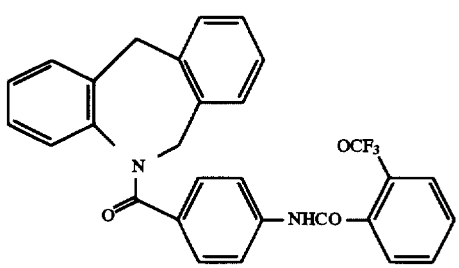 | 0.052 | 0.56 |
| 61 | 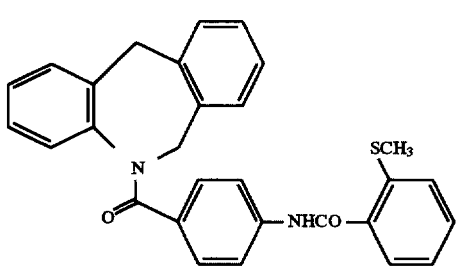 | 0.052 | 0.068 |

TABLE I-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ μM | $V_2$ $IC_{50}$ μM |
|---|---|---|---|
| 62 | 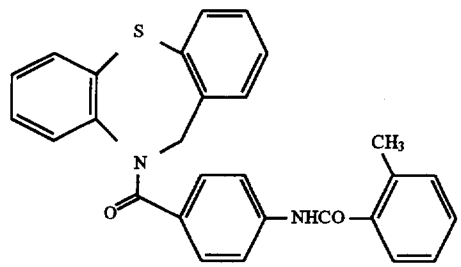 | 0.404 | 0.858 |
| 92 | 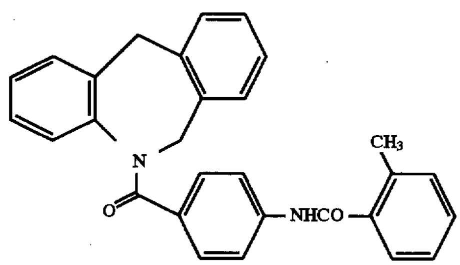 | 0.098 | 0.025 |
| 119 | 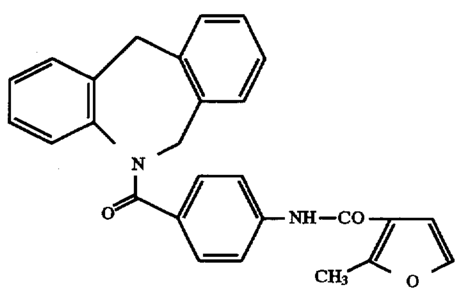 | 0.039 | 1.1 |
| 121 | 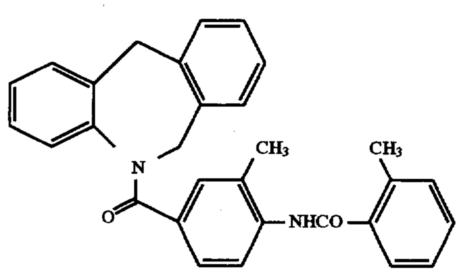 | 72% (1 μM) | 80% (1 μM) |
| 122 | 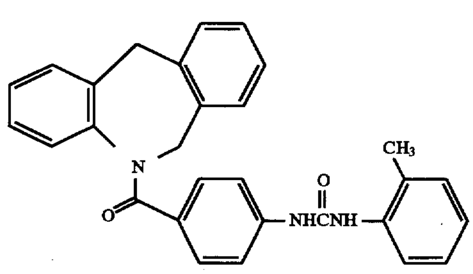 | *95% (10 μM) | *92% (10 μM) |

TABLE I-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | Structure | $V_1$ $IC_{50}$ μM | $V_2$ $IC_{50}$ μM |
|---|---|---|---|
| 123 | 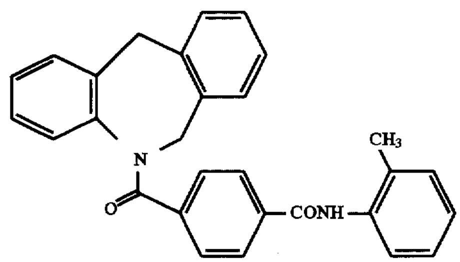 | 0.043 | 0.19 |
| 124 | 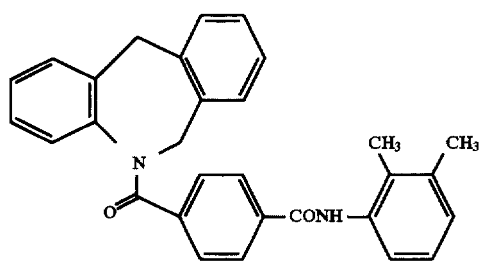 | 1.2 | 0.21 |
| 136 | 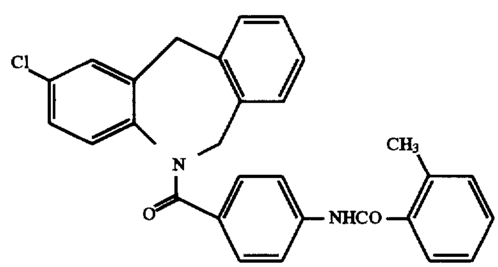 | 0.016 | 0.027 |
| 137 | 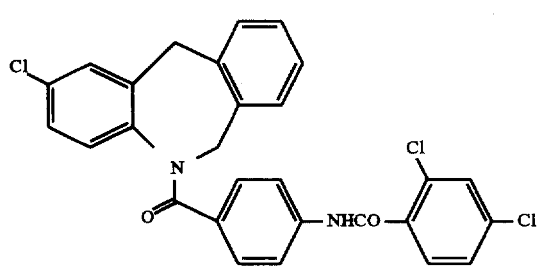 | 0.076 | 0.064 |
| 138 | 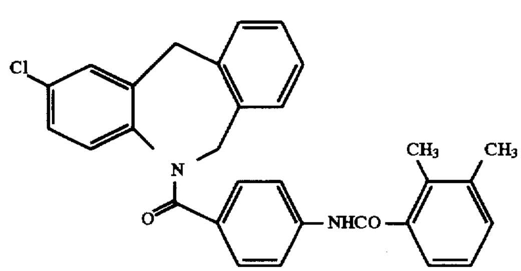 | 0.046 | 0.051 |

TABLE I-continued

Binding Assay to Rat Hepatic V₁ Receptors and Rat Kidney
Medullary V₂ Receptors or *Binding to V₁ Receptor Subtype in
Human Platelet and **Binding to Membranes of Mouse
Fibroblast Cell Line (LV-2) Transfected with the cDNA
Expressing the Human V₂ Receptor

| Ex. No. | Structure | $V_1$ $IC_{50}$ μM | $V_2$ $IC_{50}$ μM |
|---|---|---|---|
| 167 | 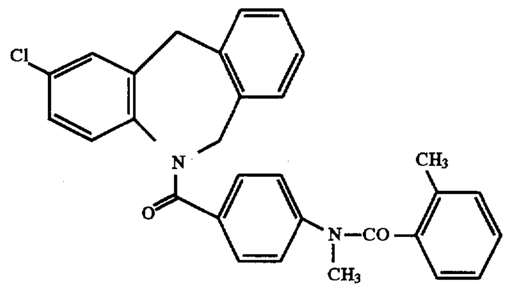 | 0.51 | 0.43 |
| 165 | 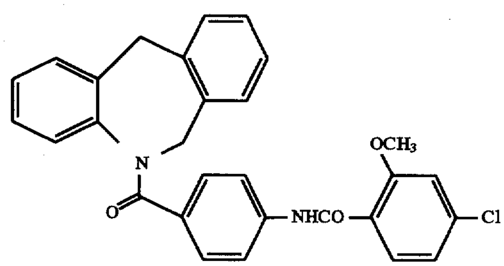 | 0.49 | 0.37 |
| 166 | 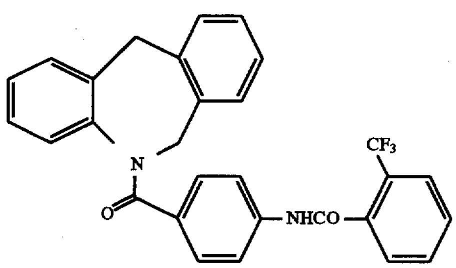 | 0.083 | 0.245 |
| 249 | 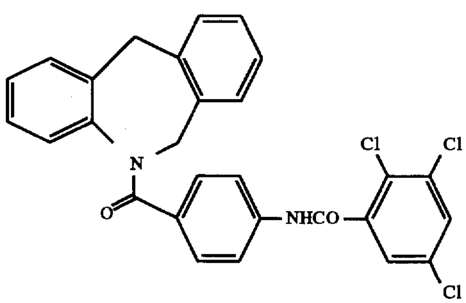 | 61% (10 μM) | 88% (10 μM) |
| 250 | 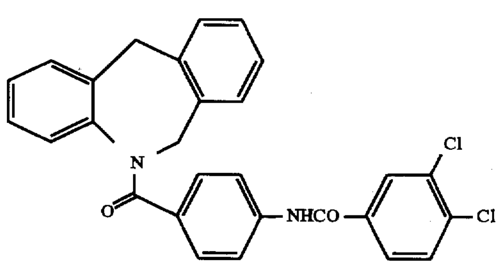 | 52% (10 μM) | 77% (10 μM) |

TABLE I-continued

Binding Assay to Rat Hepatic V₁ Receptors and Rat Kidney
Medullary V₂ Receptors or *Binding to V₁ Receptor Subtype in
Human Platelet and **Binding to Membranes of Mouse
Fibroblast Cell Line (LV-2) Transfected with the cDNA
Expressing the Human V₂ Receptor

| Ex. No. | Structure | $V_1$ $IC_{50}$ μM | $V_2$ $IC_{50}$ μM |
|---|---|---|---|
| 251 | (dibenzazepine)-C(O)-C₆H₄-NHCOCH₂-(3,5-dichlorophenyl) | 1.5 | 0.14 |
| 252 | (dibenzazepine)-C(O)-C₆H₄-NHCO-(2,6-dichlorophenyl) | 0.26 | 0.26 |
| 253 | (dibenzazepine)-C(O)-C₆H₄-NHCO-(2,3-dichlorophenyl) | 0.31 | 0.19 |
| 254 | (dibenzazepine)-C(O)-C₆H₄-NHCO-(2-CH₃-3-F-phenyl) | 0.10 | 0.037 |
| 255 | (dibenzazepine)-C(O)-C₆H₄-NHCO-(cyclohexenyl) | 0.027 | 0.039 |

TABLE I-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ μM | $V_2$ $IC_{50}$ μM |
|---|---|---|---|
| 256 | 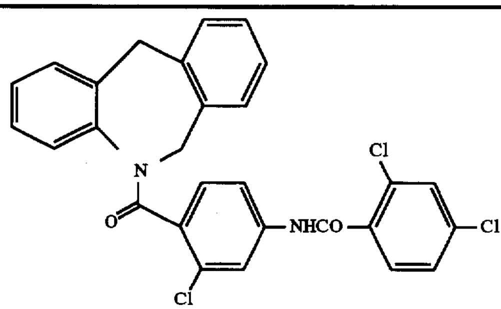 | 0.10 | 0.054 |
| 257 | 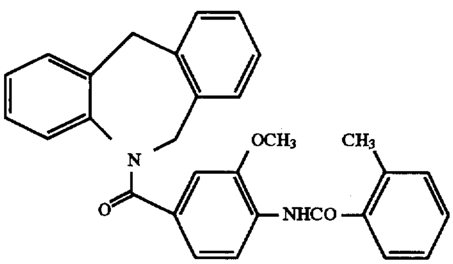 | *0.016 | **0.020 |
| 258 | 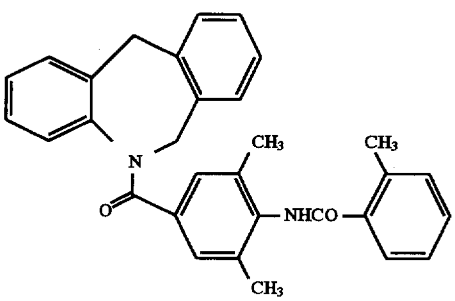 | 75% (10 μM) | 87% (10 μM) |
| 259 | 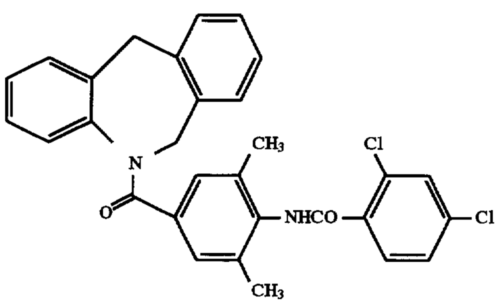 | 4.0 | 13% (10 μM) |
| 260 | 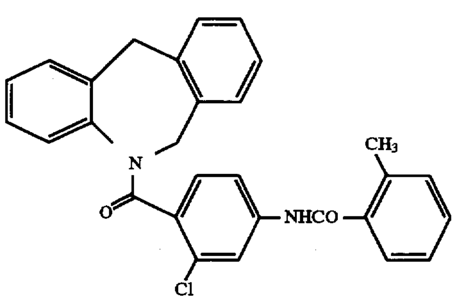 | 0.12 | 0.065 |

TABLE I-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | Structure | $V_1$ $IC_{50}$ μM | $V_2$ $IC_{50}$ μM |
|---------|-----------|-------------------|-------------------|
| 261 | 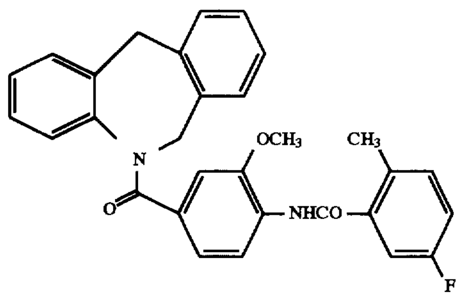 | *0.021 | **0.016 |
| 262 | 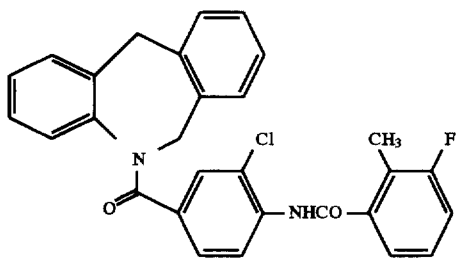 | *0.62 | **0.25 |
| 263 | 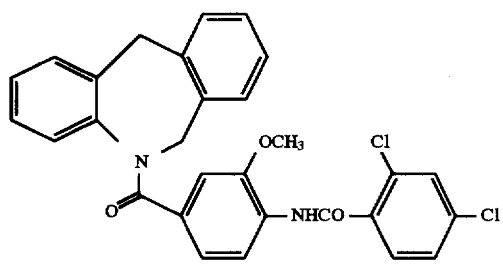 | *0.43 | **0.047 |
| 264 | 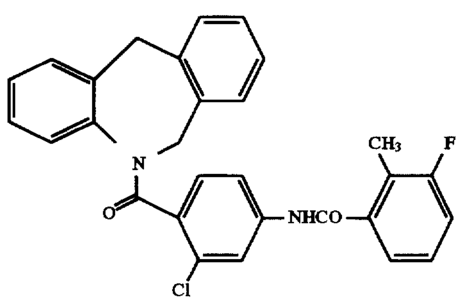 | *0.98 | **0.028 |
| 267 | 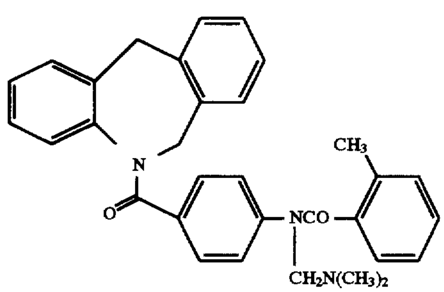 | 0.026 | 0.082 |

TABLE I-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ IC$_{50}$ μM | $V_2$ IC$_{50}$ μM |
|---|---|---|---|
| 268 | 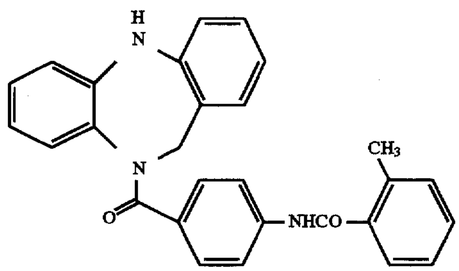 | 0.019 | 0.042 |
| 345 | 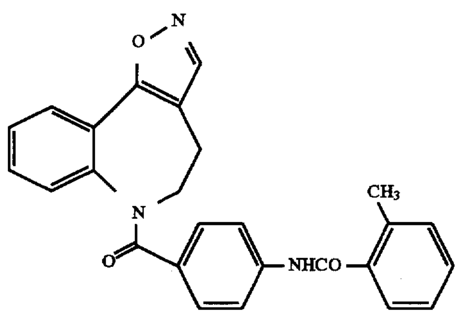 | 99% (10 μM) | 81% (10 μM) |
| 379 | 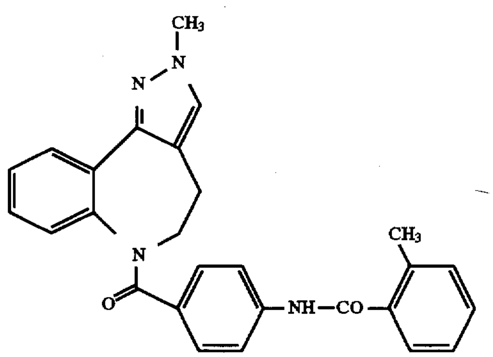 | 0.25 | 0.053 |
| 416 | 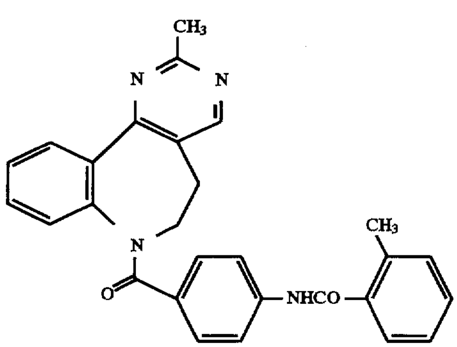 | 34.5 | 1.1 |

TABLE I-continued

Binding Assay to Rat Hepatic $V_1$ Receptors and Rat Kidney
Medullary $V_2$ Receptors or *Binding to $V_1$ Receptor Subtype in
Human Platelet and **Binding to Membranes of Mouse
Fibroblast Cell Line (LV-2) Transfected with the cDNA
Expressing the Human $V_2$ Receptor

| Ex. No. | Structure | $V_1$ IC$_{50}$ μM | $V_2$ IC$_{50}$ μM |
|---|---|---|---|
| 448 | 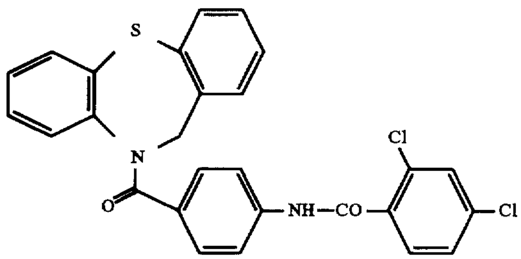 | 0.073 | 0.19 |
| 449 | 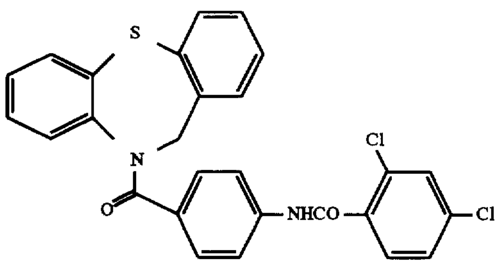 | 0.36 | 0.25 |
| 453 | 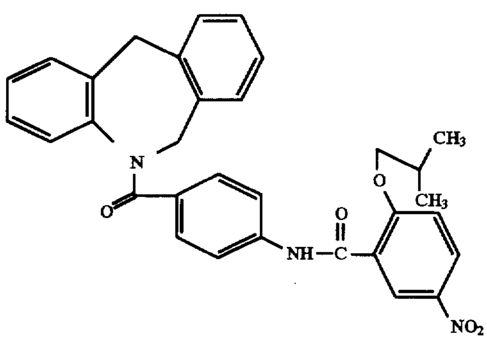 | *14% (10 μM) | 26% (10 μM) |
| 456 | 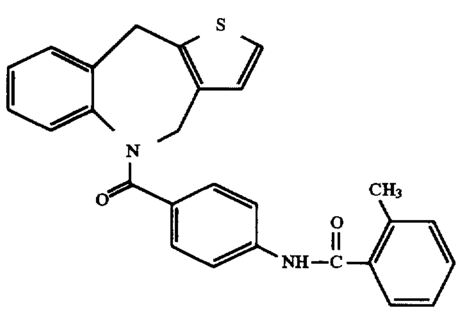 | *0.036 | **0.009 |

TABLE I-continued

Binding Assay to Rat Hepatic V₁ Receptors and Rat Kidney Medullary V₂ Receptors or *Binding to V₁ Receptor Subtype in Human Platelet and **Binding to Membranes of Mouse Fibroblast Cell Line (LV-2) Transfected with the cDNA Expressing the Human V₂ Receptor

| Ex. No. | Structure | $V_1$ IC$_{50}$ μM | $V_2$ IC$_{50}$ μM |
|---|---|---|---|
| 457 | 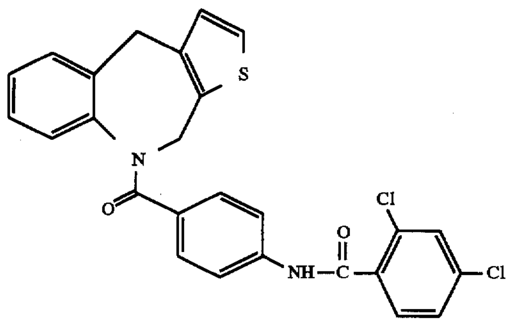 | *0.039 | **0.012 |
| 458 | 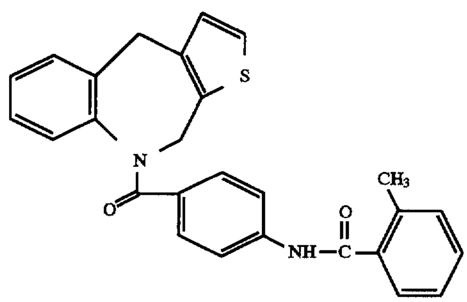 | *0.0018 | **0.00071 |
| 454 | | 64% (10 μM) | 33% (10 μM) |
| 454 | | 64% (10 μM) | 37% (10 μM) |

TABLE I-continued
Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor
| Ex. No. | Structure | $V_1$ IC$_{50}$ μM | $V_2$ IC$_{50}$ μM |
|---|---|---|---|
| 451 | 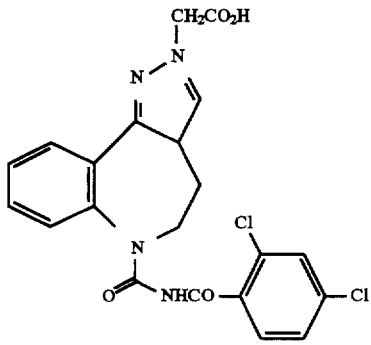 | *35% (1 μM) | **69% (1 μM) |
| 450 | 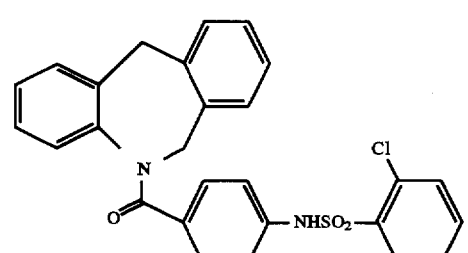 | 87% (10 μM) | 29% (10 μM) |
| 452 | 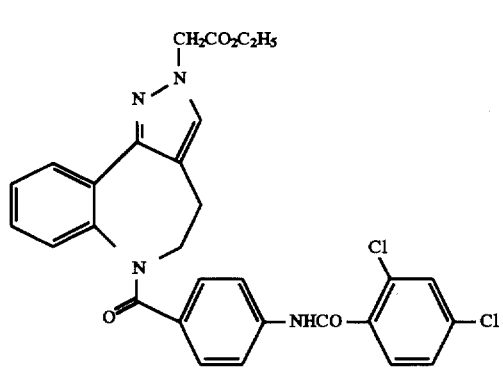 | *0.47 | **0.01 |
| 455 | 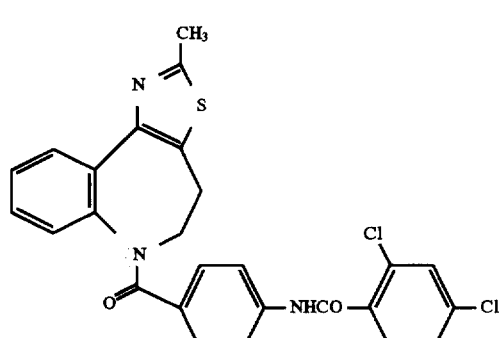 | *0.25 | **0.10 |

TABLE I-continued

Binding Assay to Rat Hepatic $V_1$ Receptors and Rat Kidney Medullary $V_2$ Receptors or *Binding to $V_1$ Receptor Subtype in Human Platelet and **Binding to Membranes of Mouse Fibroblast Cell Line (LV-2) Transfected with the cDNA Expressing the Human $V_2$ Receptor

| Ex. No. | Structure | $V_1$ $IC_{50}$ µM | $V_2$ $IC_{50}$ µM |
|---|---|---|---|
| 534 | 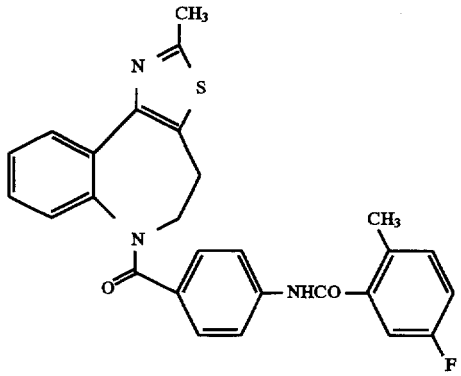 | *0.09 | **0.073 |

Vasopressin $V_2$ Antagonist Activity in Conscious Hydrated Rats:

Conscious hydrated rats are treated with compounds under study from 0.1 to 100 mg/kg orally or vehicle. Two to four rats are used for each compound. One hour later, arginine vasopressin (AVP, antidiuretic hormore, ADH) dissolved in peanut oil is administered at 0.4 µg/kg intraperitoneally. Two rats in each test would not receive arginine vasopressin but only the vehicle (peanut oil) to serve as water-loading control. Twenty minutes later each rat is given 30 mL/kg of deionized water orally by gavage and is placed individually in a metabolic cage equipped with a funnel and a graduated glass cylinder to collect urine for four hours. Urine volume is measured and osmolality analyzed by use of a Fiske One-Ten osmometer (Fiske Assoc., Norwood, Mass., USA). Urinary sodium, potassium, and chloride are analyzed by use of ion-specific electrodes in a Beckman E3 (Electrolyte 3) Analyzer. In the following results, decreased urine volume and decreased osmolality relative to AVP-control indicates activity. The results are displayed in Table II.

TABLE II

Diuretic Effect of CL Compounds ($V_2$ Antagonism) in Normal Sprague-Dawley Rats

| Ex. No. | Dose (mg/kg) | N | Urine Volume (ml/4 hrs.) | Osmolality (mOsm/kg) |
|---|---|---|---|---|
| Water-Load Control | | 78 | 13.3 ± 0.3 | 229 ± 6 |
| Water-Load Control + DMSO | | | | |
| (10%) | | 6 | 12.1 ± 1 | 497 ± 53 |
| (20%) | | 4 | 12.4 ± 0.8 | 361 ± 30 |
| AVP-Control | | 76 | 2 ± 0.2 | 1226 ± 58 |
| 2 | 30 | 6 | 18.9 ± 1.7 | 401 ± 49 |
| | 10 | 6 | 15.2 ± 2.4 | 408 ± 34 |
| | 3 | 6 | 2.9 ± 0.5 | 1235 ± 162 |
| 5 | 10 | 2 | 2 | 1137 |
| 10 | 10 | 2 | 7.1 | 1023 |
| 11 | 30 | 4 | 9.7 ± 0.6 | 1114 ± 55 |
| 14 | 30 | 2 | 13.1 | 739 |
| 16 | 30 | 2 | 7.2 | 1257 |
| 22 | 30 | 2 | 10.2 | 738 |
| 61 | 10 | 2 | 9.3 | 975 |
| 62 | 10 | 2 | 7.7 | 1034 |
| 92 | 10 | 2 | 13.5 | 679 |
| 121 | 10 | 2 | 5 | 1064 |
| 123 | 10 | 2 | 5.8 | 1125 |
| 124 | 10 | 2 | 5.5 | 1172 |
| 136 | 30 | 2 | 19 | 306 |
| 137 | 30 | 2 | 15.8 | 358 |
| 138 | 30 | 2 | 13.8 | 380 |
| 167 | 30 | 2 | 2 | 1544 |
| 250 | 30 | 2 | 6.5 | 1378 |
| 251 | 10 | 2 | 7.5 | 835 |
| 252 | 10 | 2 | 7.5 | 790 |
| 253 | 10 | 2 | 6 | 837 |
| 255 | 30 | 2 | 2.3 | 1456 |
| 257 | 10 | 2 | 11.8 | 434 |
| 259 | 10 | 2 | 6 | 1080 |
| 260 | 10 | 4 | 13.8 ± 2.1 | 498 ± 25 |
| 261 | 10 | 2 | 3.8 | 1337 |
| 262 | 10 | 2 | 6.8 | 899 |
| 264 | 10 | 2 | 12 | 682 |
| 266 | 10 | 2 | 4.3 | 1186 |
| 267 | 10 | 2 | 7.5 | 517 |
| 268 | 30 | 2 | 7.4 | 831 |
| 379 | 20 | 2 | 7 | 483 |
| 416 | 10 | 2 | 4.3 | 1156 |
| 448 | 30 | 2 | 4.8 | 1084 |
| 451 | 10 | 2 | 5.3 | 989 |
| 452 | 10 | 2 | 7.8 | 584 |
| 453 | 10 | 2 | 9.4 | 776 |
| 454 | 10 | 2 | 4 | 1255 |
| 455 | 10 | 2 | 13.5 | 420 |
| 456 | 10 | 2 | 4.8 | 1209 |
| 457 | 10 | 2 | 5.8 | 1036 |
| 458 | 10 | 2 | 13.5 | 537 |

TABLE II-continued

Diuretic Effect of CL Compounds ($V_2$ Antagonism) in Normal Sprague-Dawley Rats

| Ex. No. | Dose (mg/kg) | N | Urine Volume (ml/4 hrs.) | Osmolality (mOsm/kg) |
|---|---|---|---|---|
| 534 | 10 | 2 | 10.6 | 695 |

Vasopressin $V_1$ Antagonist Activity in Conscious Rats:

Conscious rats are restrained in a supine position with elastic tape. The area at the base of the tail is locally anesthetized by subcutaneous infiltration with 2% procaine (0.2 ml). Using aseptic technique the ventral caudal tail artery is isolated and a cannula made of PE 10 and 20 (heat-fused) tubing is passed into the lower abdominal aorta. The cannula is secured, heparinized (1000 i.u./cc), sealed and the wound closed with one or two stitches of Dexon 4-0. The caudal vein is also cannulated in the same manner for intravenous drug administration. The duration of the surgery is approximately 5 minutes. Additional local anesthesia (2% procaine or lidocaine) is provided as needed.

The animals are placed in plastic restraining cages in an upright position. The cannula is attached to a Statham P23Db pressure transducer and pulsatile blood pressure is recorded. Increase of systolic blood pressure responses to arginine vasopressin 0.01 and 0.2 international unit (I.U.) (350 I.U.=1 mg) injections are recorded prior to any drug (compound) administration, after which each rat is dosed orally with compounds under study 0.1–100 mg/kg (10 cc/kg) or intravenously 0.1–30 mg/kg (1 cc/kg). The vasopressin injections are repeated 30,60,90,120,180,240 and 300 min. later. Percentage of antagonism by the compound is calculated using the pre-drug vasopressin vasopressor response as 100%.

The results of this test on representative compounds of this invention are shown in Table III.

The results of this test on representative compounds of this invention in which the dose, the maximum % inhibition and the time in minutes, are shown in Table IV.

TABLE III

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| CONTROL | | 0.01 | 0 | 225 | 245 | 20 | 20 | |
| | | | | 205 | 225 | 20 | | |
| | | 0.02 | | 225 | 255 | 30 | 32.5 | |
| | | | | 205 | 240 | 35 | | |
| Vehicle 2% starch | 10 cc/kg p.o. | 0.01 | 30 | 215 | 240 | 25 | 25 | −25 |
| | | | | 200 | 225 | 25 | | |
| | | 0.02 | | 220 | 255 | 35 | 35 | −8 |
| | | | | 210 | 245 | 35 | | |
| | | 0.01 | 60 | 220 | 240 | 20 | 25 | −25 |
| | | | | 200 | 230 | 30 | | |
| | | 0.02 | | 225 | 260 | 35 | 35 | −8 |
| | | | | 215 | 250 | 35 | | |
| | | 0.01 | 90 | 210 | 235 | 25 | 22.5 | −13 |
| | | | | 200 | 220 | 20 | | |
| | | 0.02 | | 235 | 275 | 40 | 37.5 | −15 |
| | | | | 205 | 240 | 35 | | |
| | | 0.01 | 120 | 225 | 245 | 20 | 22.5 | −13 |
| | | | | 200 | 225 | 25 | | |
| | | 0.02 | | 225 | 250 | 25 | 35 | −8 |
| | | | | 200 | 245 | 45 | | |
| | | 0.01 | 180 | 210 | 235 | 25 | 20 | 0 |
| | | | | 195 | 210 | 15 | | |
| | | 0.02 | | 225 | 225 | 30 | 36 | −11 |
| | | | | 195 | 237 | 42 | | |
| | | 0.01 | 240 | 225 | 240 | 15 | 22.5 | −13 |
| | | | | 180 | 210 | 30 | | |
| | | 0.02 | | 225 | 250 | 25 | 35 | −8 |
| | | | | 190 | 235 | 45 | | |
| SPONTANEOUSLY HYPERTENSIVE RATS n = 2 Body weight(s): 420, 420 grams | | | | | | | | |
| CONTROL | | 0.05 | 0 | 240 | 270 | 30 | 27.5 | |
| | | | | 230 | 255 | 25 | | |
| | | 0.1 | | 230 | 285 | 55 | 45 | |
| | | | | 235 | 270 | 35 | | |
| Ex. No. 5 | 10 i.v. | 0.05 | 30 | 225 | 260 | 35 | 30 | −9 |
| | | | | 235 | 260 | 25 | | |
| | | 0.1 | | 230 | 265 | 35 | 35 | 22 |
| | | | | 225 | 260 | 35 | | |
| Ex. No. 5 | 20 i.v. | 0.05 | 60 | 245 | 250 | 5 | 10 | 64 |
| | | | | 225 | 240 | 15 | | |
| | | 0.1 | | 245 | 260 | 15 | 17.5 | 61 |
| | | | | 235 | 255 | 20 | | |
| | | 0.05 | 90 | 225 | 240 | 15 | 10 | 64 |
| | | | | 220 | 225 | 5 | | |
| | | 0.1 | | 230 | 250 | 20 | | 56 |
| | | | | 225 | 245 | 20 | | |
| | | 0.05 | 120 | 225 | 245 | 20 | 15 | 45 |
| | | | | 225 | 235 | 10 | | |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.1 | | 230 | 245 | 15 | 17.5 | 61 |
| | | | | 225 | 245 | 20 | | |
| | | 0.05 | 180 | 225 | 245 | 20 | 12.5 | 55 |
| | | | | 230 | 235 | 5 | | |
| | | 0.1 | | 225 | 255 | 30 | 20 | 56 |
| | | | | 240 | 250 | 10 | | |
| | | 0.05 | 240 | 215 | 235 | 20 | 17.5 | 36 |
| | | | | 220 | 235 | 15 | | |
| | | 0.1 | | 215 | 250 | 35 | 25 | 44 |
| | | | | 230 | 245 | 15 | | |
| | | 0.05 | 300 | 210 | 245 | 35 | 22.5 | 18 |
| | | | | 245 | 255 | 10 | | |
| | | 0.1 | | 200 | 235 | 35 | 30 | 33 |
| | | | | 235 | 260 | 25 | | |
| SPONTANEOUSLY HYPERTENSIVE RATS n = 2 Body weight(s): 400, 400 grams | | | | | | | | |
| CONTROL | | 0.01 | 0 | 130 | 170 | 40 | 30 | |
| | | | | 159 | 179 | 20 | | |
| | | 0.02 | | 136 | 192 | 56 | 51 | |
| | | | | 164 | 210 | 46 | | |
| Ex. No. 10 | 10 i.v. | 0.01 | 30 | 136 | 184 | 48 | 37.5 | −25 |
| | | | | 150 | 177 | 27 | | |
| | | 0.02 | | 136 | 197 | 61 | 64.5 | −26 |
| | | | | 150 | 218 | 68 | | |
| Ex. No. 10 | 20 i.v. | 0.01 | 60 | 141 | 156 | 15 | 14.5 | 52 |
| | | | | 150 | 164 | 14 | | |
| | | 0.02 | | 138 | 161 | 23 | 22.5 | 56 |
| | | | | 152 | 174 | 22 | | |
| | | 0.01 | 90 | 137 | 154 | 17 | 16 | 47 |
| | | | | 151 | 166 | 15 | | |
| | | 0.02 | | 135 | 161 | 26 | 23 | 55 |
| | | | | 153 | 173 | 20 | | |
| | | 0.01 | 120 | 138 | 155 | 17 | 13.5 | 55 |
| | | | | 150 | 160 | 10 | | |
| | | 0.02 | | 138 | 161 | 23 | 22 | 57 |
| | | | | 157 | 178 | 21 | | |
| | | 0.01 | 180 | 132 | 154 | 22 | 25.5 | 15 |
| | | | | 145 | 174 | 29 | | |
| | | 0.02 | | 140 | 174 | 34 | 29.5 | 42 |
| | | | | 157 | 182 | 25 | | |
| | | 0.01 | 240 | 131 | 156 | 25 | 22.5 | 25 |
| | | | | 149 | 169 | 20 | | |
| | | 0.02 | | 140 | 174 | 34 | 34.5 | 32 |
| | | | | 157 | 192 | 35 | | |
| | | 0.01 | 300 | 144 | 166 | 22 | 24.5 | 18 |
| | | | | 151 | 178 | 27 | | |
| | | 0.02 | | 135 | 170 | 35 | 34 | 33 |
| | | | | 145 | 178 | 33 | | |
| SPONTANEOUSLY HYPERTENSIVE RATS n = 2 Body weight(s): 520, 470 grams | | | | | | | | |
| CONTROL | | 0.01 | 0 | 135 | 152 | 17 | 22.5 | |
| | | | | 132 | 160 | 28 | | |
| | | 0.02 | | 149 | 216 | 67 | 52 | |
| | | | | 137 | 174 | 37 | | |
| Ex. No. 14 | 10 i.v. | 0.01 | 30 | 131 | 142 | 11 | 11 | 51 |
| | | | | 143 | 154 | 11 | | |
| | | 0.02 | | 151 | 173 | 22 | 23 | 56 |
| | | | | 136 | 160 | 24 | | |
| | | 0.01 | 60 | 151 | 163 | 12 | 12 | 47 |
| | | | | 139 | 151 | 12 | | |
| | | 0.02 | | 153 | 171 | 18 | 22 | 58 |
| | | | | 140 | 166 | 26 | | |
| | | 0.01 | 90 | 135 | 142 | 7 | 13.5 | 40 |
| | | | | 140 | 160 | 20 | | |
| | | 0.02 | | 135 | 173 | 38 | 29.5 | 43 |
| | | | | 145 | 166 | 21 | | |
| | | 0.01 | 120 | 137 | 155 | 18 | 16 | 29 |
| | | | | 137 | 151 | 14 | | |
| | | 0.02 | | 143 | 168 | 25 | 23.5 | 55 |
| | | | | 139 | 161 | 22 | | |
| | | 0.01 | 180 | 131 | 153 | 22 | 21.5 | 4 |
| | | | | 134 | 155 | 21 | | |
| | | 0.02 | | 140 | 170 | 30 | 30.5 | 41 |
| | | | | 131 | 162 | 31 | | |
| | | 0.01 | 240 | 146 | 170 | 24 | 26.5 | −18 |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 141 | 166 | 29 | | |
| | | 0.02 | | 140 | 171 | 30 | 32 | 38 |
| | | | | 141 | 175 | 34 | | |
| | | 0.01 | 300 | 138 | 160 | 22 | 24.5 | −9 |
| | | | | 142 | 169 | 27 | | |
| | | 0.02 | | 152 | 186 | 34 | 33 | 37 |
| | | | | 144 | 176 | 32 | | |
| SPONTANEOUSLY HYPERTENSIVE RATS n = 2 Body weight(s): 480, 420 grams | | | | | | | | |
| CONTROL | | 0.01 | 0 | 139 | 182 | 43 | 29.5 | |
| | | | | 128 | 144 | 16 | | |
| | | 0.02 | | 142 | 182 | 40 | 33 | |
| | | | | 162 | 188 | 26 | | |
| Ex. No. 16 | 30 p.o. | 0.01 | 30 | 133 | 166 | 33 | 25 | 15 |
| | | | | 148 | 165 | 17 | | |
| | | 0.02 | | 136 | 163 | 27 | 27.5 | 17 |
| | | | | 154 | 182 | 28 | | |
| | | 0.01 | 60 | 131 | 168 | 37 | 30.5 | −3 |
| | | | | 154 | 178 | 24 | | |
| | | 0.02 | | 134 | 163 | 29 | 29 | 12 |
| | | | | 162 | 191 | 29 | | |
| | | 0.01 | 90 | 137 | 166 | 29 | 28.5 | 3 |
| | | | | 149 | 177 | 28 | | |
| | | 0.02 | | 137 | 172 | 35 | 40.5 | −23 |
| | | | | 149 | 195 | 46 | | |
| | | 0.01 | 120 | 146 | 163 | 17 | 23.5 | 20 |
| | | | | 148 | 178 | 30 | | |
| | | 0.02 | | 142 | 166 | 24 | 29.5 | 11 |
| | | | | 161 | 196 | 35 | | |
| | | 0.01 | 180 | 142 | 169 | 27 | 30.5 | −3 |
| | | | | 140 | 174 | 34 | | |
| | | 0.02 | | 138 | 169 | 31 | 26 | 21 |
| | | | | 153 | 174 | 21 | | |
| | | 0.01 | 240 | 140 | 163 | 23 | 30 | −2 |
| | | | | 140 | 177 | 37 | | |
| | | 0.02 | | 143 | 160 | 17 | 30 | 9 |
| | | | | 157 | 200 | 43 | | |
| SPONTANEOUSLY HYPERTENSIVE RATS n = 2 Body weight(s): 420, 460 grams | | | | | | | | |
| CONTROL | | 0.01 | 0 | 147 | 169 | 22 | 21.5 | |
| | | | | 138 | 159 | 21 | | |
| | | 0.02 | | 151 | 198 | 47 | 42 | |
| | | | | 145 | 182 | 37 | | |
| Ex. No. 22 | 10 i.v. | 0.01 | 30 | 152 | 164 | 12 | 8.5 | 60 |
| | | | | 146 | 151 | 5 | | |
| | | 0.02 | | 152 | 177 | 25 | 18.5 | 56 |
| | | | | 148 | 160 | 12 | | |
| | | 0.01 | 60 | 151 | 166 | 15 | 11 | 49 |
| | | | | 144 | 151 | 7 | | |
| | | 0.02 | | 121 | 144 | 23 | 25 | 40 |
| | | | | 141 | 168 | 27 | | |
| | | 0.01 | 90 | 149 | 166 | 17 | 14 | 35 |
| | | | | 140 | 151 | 11 | | |
| | | 0.02 | | 151 | 166 | 15 | 13 | 69 |
| | | | | 140 | 151 | 11 | | |
| | | 0.01 | 120 | 138 | 155 | 17 | 17.5 | 19 |
| | | | | 129 | 147 | 18 | | |
| | | 0.02 | | 148 | 183 | 35 | 30 | 29 |
| | | | | 141 | 166 | 25 | | |
| | | 0.01 | 180 | 142 | 168 | 26 | 20 | 7 |
| | | | | 141 | 155 | 14 | | |
| | | 0.02 | | 150 | 185 | 35 | 36 | 14 |
| | | | | 132 | 169 | 37 | | |
| | | 0.01 | 240 | 134 | 169 | 35 | 28 | −30 |
| | | | | 139 | 160 | 21 | | |
| | | 0.02 | | 139 | 200 | 61 | 48 | −14 |
| | | | | 150 | 185 | 35 | | |
| | | 0.01 | 300 | 139 | 171 | 32 | 30 | −40 |
| | | | | 121 | 149 | 28 | | |
| | | 0.02 | | 140 | 210 | 70 | 52.5 | −25 |
| | | | | 150 | 185 | 35 | | |
| SPONTANEOUSLY HYPERTENSIVE RATS n = 2 Body weight(s): 450, 495 grams | | | | | | | | |
| CONTROL | | 0.01 | 0 | 161 | 191 | 30 | 28.5 | |
| | | | | 143 | 170 | 27 | | |
| | | 0.02 | | 157 | 217 | 60 | 51.5 | |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 145 | 188 | 43 | | |
| Ex. No. 61 | 10 i.v. | 0.01 | 30 | 158 | 182 | 24 | 21 | 26 |
| | | | | 146 | 164 | 18 | | |
| | | 0.02 | | 158 | 196 | 38 | 32.5 | 37 |
| | | | | 146 | 173 | 27 | | |
| Ex. No. 61 | 20 i.v. | 0.01 | 60 | 163 | 180 | 17 | 13 | 54 |
| | | | | 147 | 156 | 9 | | |
| | | 0.02 | | 159 | 179 | 20 | 14.5 | 72 |
| | | | | 146 | 155 | 9 | | |
| | | 0.01 | 90 | 153 | 165 | 12 | 8 | 72 |
| | | | | 150 | 154 | 4 | | |
| | | 0.02 | | 154 | 173 | 19 | 16.5 | 68 |
| | | | | 144 | 158 | 14 | | |
| | | 0.01 | 120 | 151 | 165 | 14 | 12 | 58 |
| | | | | 145 | 155 | 10 | | |
| | | 0.02 | | 151 | 176 | 25 | 20 | 61 |
| | | | | 143 | 158 | 15 | | |
| | | 0.01 | 180 | 142 | 165 | 23 | 15.5 | 46 |
| | | | | 143 | 151 | 8 | | |
| | | 0.02 | | 148 | 172 | 24 | 17.5 | 66 |
| | | | | 145 | 156 | 11 | | |
| | | 0.01 | 240 | 144 | 156 | 12 | 12 | 58 |
| | | | | 144 | 156 | 12 | | |
| | | 0.02 | | 150 | 179 | 29 | 23 | 55 |
| | | | | 147 | 164 | 17 | | |
| | | 0.01 | 300 | 142 | 161 | 19 | 15.5 | 46 |
| | | | | 144 | 156 | 12 | | |
| | | 0.02 | | 140 | 167 | 27 | 24 | 53 |
| | | | | 153 | 174 | 21 | | |
| SPONTANEOUSLY HYPERTENSIVE RATS n = 2 Body weight(s): 570, 460 grams | | | | | | | | |
| CONTROL | | 0.01 | 0 | 139 | 179 | 40 | 39.5 | |
| | | | | 150 | 189 | 39 | | |
| | | 0.02 | | 143 | 204 | 61 | 60.5 | |
| | | | | 156 | 216 | 60 | | |
| Ex. No. 62 | 10 i.v. | 0.01 | 30 | 144 | 196 | 52 | 57 | −44 |
| | | | | 141 | 203 | 62 | | |
| | | 0.02 | | 158 | 217 | 59 | 61.5 | −2 |
| | | | | 163 | 227 | 64 | | |
| Ex. No. 62 | 20 i.v. | 0.01 | 60 | 131 | 148 | 17 | 13 | 67 |
| | | | | 135 | 144 | 9 | | |
| | | 0.02 | | 135 | 173 | 38 | 29.5 | 51 |
| | | | | 134 | 155 | 21 | | |
| | | 0.01 | 90 | 132 | 156 | 24 | 23 | 42 |
| | | | | 127 | 149 | 22 | | |
| | | 0.02 | | 140 | 195 | 55 | 54 | 11 |
| | | | | 136 | 189 | 53 | | |
| | | 0.01 | 120 | 137 | 160 | 23 | 23.5 | 41 |
| | | | | 138 | 162 | 24 | | |
| | | 0.02 | | 143 | 189 | 46 | 50 | 17 |
| | | | | 139 | 193 | 54 | | |
| | | 0.01 | 180 | 131 | 155 | 24 | 24.5 | 38 |
| | | | | 133 | 158 | 25 | | |
| | | 0.02 | | 139 | 155 | 16 | 15 | 75 |
| | | | | 144 | 158 | 14 | | |
| | | 0.01 | 240 | 126 | 153 | 27 | 30 | 24 |
| | | | | 133 | 166 | 33 | | |
| | | 0.02 | | 134 | 167 | 33 | 40.5 | 33 |
| | | | | 142 | 190 | 48 | | |
| | | 0.01 | 300 | 128 | 152 | 24 | 25 | 37 |
| | | | | 138 | 164 | 26 | | |
| | | 0.02 | | 140 | 167 | 27 | 38 | 37 |
| | | | | 146 | 195 | 49 | | |
| SPONTANEOUSLY HYPERTENSIVE RATS n = 2 Body weight(s): 500, 450 grams | | | | | | | | |
| CONTROL | | 0.01 | 0 | 144 | 177 | 33 | 30 | |
| | | | | 128 | 155 | 27 | | |
| | | 0.02 | | 145 | 197 | 52 | 46.5 | |
| | | | | 127 | 168 | 41 | | |
| Ex. No. 92 | 10 i.v. | 0.01 | 30 | 155 | 165 | 10 | 10.5 | 65 |
| | | | | 153 | 164 | 11 | | |
| | | 0.02 | | 160 | 177 | 17 | 18.5 | 60 |
| | | | | 155 | 175 | 20 | | |
| | | 0.01 | 60 | 143 | 159 | 16 | 18 | 40 |
| | | | | 150 | 170 | 20 | | |

TABLE III-continued

VASOPRESSIN (VAS)VASOPRESSOR RESPONSE

| Dose (mg/kg) | VAS Dose i.u./kg I.V. | Min Post Dose | Control Before VAS | Response After VAS | Change | Average Change | % Inhibition |
|---|---|---|---|---|---|---|---|
| | 0.02 | | 152 | 168 | 16 | 22 | 53 |
| | | | 149 | 177 | 28 | | |
| | 0.01 | 90 | 145 | 162 | 17 | 17.5 | 42 |
| | | | 127 | 145 | 18 | | |
| | 0.02 | | 141 | 168 | 27 | 27 | 42 |
| | | | 144 | 171 | 27 | | |
| | 0.01 | 120 | 135 | 156 | 21 | 29 | 37 |
| | | | 113 | 130 | 17 | | |
| | 0.02 | | 134 | 154 | 20 | 20.5 | 56 |
| | | | 126 | 147 | 21 | | |
| | 0.01 | 180 | 137 | 159 | 22 | 18 | 40 |
| | | | 144 | 158 | 14 | | |
| | 0.02 | | 144 | 180 | 36 | 29.5 | 37 |
| | | | 142 | 165 | 23 | | |
| | 0.01 | 240 | 149 | 169 | 20 | 19 | 37 |
| | | | 137 | 155 | 18 | | |
| | 0.02 | | 149 | 169 | 20 | 18 | 61 |
| | | | 146 | 162 | 16 | | |
| | 0.01 | 300 | 151 | 171 | 20 | 17.5 | 42 |
| | | | 144 | 159 | 15 | | |
| | 0.02 | | 158 | 182 | 24 | 24 | 48 |
| | | | 139 | 163 | 24 | | |

SPONTANEOUSLY HYPERTENSIVE RATS n = 2 Body weight(s): 440, 490 grams

| | | | | | | | |
|---|---|---|---|---|---|---|---|
| CONTROL | | 0.01 | 0 | 149 | 177 | 28 | 28 |
| | | | | 149 | 177 | 28 | |
| | | 0.02 | | 155 | 196 | 41 | 41 |
| | | | | 155 | 196 | 41 | |
| Ex. No. 121 | 10 i.v. | 0.01 | 30 | 154 | 175 | 21 | 21 | 25 |
| | | | | 154 | 175 | 21 | | |
| | | 0.02 | | 154 | 190 | 36 | 36 | 12 |
| | | | | 154 | 190 | 36 | | |
| Ex. No. 121 | 20 i.v. | 0.01 | 60 | 155 | 168 | 13 | 13 | 54 |
| | | | | 155 | 168 | 13 | | |
| | | 0.02 | | 156 | 175 | 19 | 19 | 54 |
| | | | | 156 | 175 | 19 | | |
| | | 0.01 | 90 | 159 | 172 | 13 | 13 | 54 |
| | | | | 159 | 172 | 13 | | |
| | | 0.02 | | 157 | 179 | 22 | 22 | 46 |
| | | | | 157 | 179 | 22 | | |
| | | 0.01 | 120 | 159 | 164 | 5 | 5 | 82 |
| | | | | 159 | 164 | 5 | | |
| | | 0.02 | | 154 | 173 | 19 | 19 | 54 |
| | | | | 154 | 173 | 19 | | |
| | | 0.01 | 180 | 151 | 169 | 18 | 18 | 36 |
| | | | | 151 | 169 | 18 | | |
| | | 0.02 | | 159 | 173 | 14 | 14 | 66 |
| | | | | 159 | 173 | 14 | | |
| | | 0.01 | 240 | 149 | 169 | 20 | 20 | 29 |
| | | | | 149 | 169 | 20 | | |
| | | 0.02 | | 151 | 172 | 21 | 21 | 49 |
| | | | | 151 | 172 | 21 | | |
| | | 0.01 | 300 | 151 | 168 | 17 | 17 | 39 |
| | | | | 151 | 168 | 17 | | |
| | | 0.02 | | 152 | 177 | 25 | 25 | 39 |
| | | | | 152 | 177 | 25 | | |

SPONTANEOUSLY HYPERTENSIVE RATS n = 2 Body weight(s): 585, 410 grams

| | | | | | | | |
|---|---|---|---|---|---|---|---|
| CONTROL | | 0.01 | 0 | 140 | 162 | 22 | 17.5 |
| | | | | 147 | 160 | 13 | |
| | | 0.02 | | 138 | 169 | 31 | 33 |
| | | | | 141 | 176 | 35 | |
| Ex. No. 123 | 10 i.v. | 0.01 | 30 | 139 | 151 | 12 | 17.5 | 0 |
| | | | | 154 | 177 | 23 | | |
| | | 0.02 | | 139 | 177 | 38 | 20 | 39 |
| | | | | 154 | 156 | 2 | | |
| Ex. No. 123 | 20 i.v. | 0.01 | 60 | 137 | 140 | 3 | 6 | 66 |
| | | | | 147 | 156 | 9 | | |
| | | 0.02 | | 132 | 139 | 7 | 6 | 82 |
| | | | | 146 | 151 | 5 | | |
| | | 0.01 | 90 | 137 | 141 | 4 | 6 | 66 |
| | | | | 149 | 157 | 8 | | |
| | | 0.02 | | 135 | 138 | 3 | 7 | 79 |
| | | | | 149 | 160 | 11 | | |
| | | 0.01 | 120 | 136 | 139 | 3 | 5 | 71 |

TABLE III-continued

VASOPRESSIN (VAS) VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 147 | 154 | 7 | | |
| | | 0.02 | | 138 | 141 | 3 | 4.5 | 86 |
| | | | | 150 | 156 | 6 | | |
| | | 0.01 | 180 | 138 | 141 | 3 | 4 | 77 |
| | | | | 150 | 155 | 5 | | |
| | | 0.02 | | 138 | 142 | 4 | 6.5 | 80 |
| | | | | 148 | 157 | 9 | | |
| | | 0.01 | 240 | 137 | 145 | 8 | 8 | 54 |
| | | | | 146 | 154 | 8 | | |
| | | 0.02 | | 140 | 146 | 6 | 6.5 | 80 |
| | | | | 148 | 155 | 7 | | |
| | | 0.01 | 300 | 138 | 144 | 6 | 8 | 54 |
| | | | | 144 | 154 | 10 | | |
| | | 0.02 | | 140 | 148 | 8 | 8 | 76 |
| | | | | 146 | 154 | 8 | | |
| SPONTANEOUSLY HYPERTENSIVE RATS n = 2 Body weight(s): 500, 480 grams | | | | | | | | |
| CONTROL | | 0.01 | 0 | 150 | 172 | 22 | 32.5 | |
| | | | | 140 | 183 | 43 | | |
| | | 0.02 | | 147 | 187 | 40 | 35.5 | |
| | | | | 162 | 193 | 31 | | |
| Ex. No. 124 | 10 i.v. | 0.01 | 30 | 150 | 187 | 37 | 38.5 | −18 |
| | | | | 153 | 193 | 40 | | |
| | | 0.02 | | 148 | 187 | 39 | 43.5 | −23 |
| | | | | 146 | 194 | 48 | | |
| Ex. No. 124 | 20 i.v. | 0.01 | 60 | 151 | 155 | 4 | 4 | 88 |
| | | | | 148 | 152 | 4 | | |
| | | 0.02 | | 150 | 173 | 23 | 17.5 | 51 |
| | | | | 147 | 159 | 12 | | |
| | | 0.01 | 90 | 143 | 159 | 16 | 12.5 | 62 |
| | | | | 147 | 156 | 9 | | |
| | | 0.02 | | 148 | 163 | 15 | 18 | 49 |
| | | | | 144 | 165 | 21 | | |
| | | 0.01 | 120 | 144 | 157 | 13 | 12.5 | 62 |
| | | | | 147 | 159 | 12 | | |
| | | 0.02 | | 151 | 167 | 16 | 19.5 | 45 |
| | | | | 149 | 172 | 23 | | |
| | | 0.01 | 180 | 131 | 152 | 21 | 21 | 35 |
| | | | | 125 | 146 | 21 | | |
| | | 0.02 | | 143 | 165 | 22 | 21.5 | 39 |
| | | | | 143 | 164 | 21 | | |
| | | 0.01 | 240 | 144 | 163 | 19 | 18 | 45 |
| | | | | 141 | 158 | 17 | | |
| | | 0.02 | | 147 | 168 | 21 | 24.5 | 31 |
| | | | | 148 | 176 | 28 | | |
| | | 0.01 | 300 | 141 | 160 | 19 | 20 | 38 |
| | | | | 138 | 159 | 21 | | |
| | | 0.02 | | 139 | 176 | 37 | 33.5 | 6 |
| | | | | 142 | 172 | 30 | | |
| SPONTANEOUSLY HYPERTENSIVE RATS n = 2 Body weight(s): 600, 550 grams | | | | | | | | |
| CONTROL | | 0.01 | 0 | 230 | 265 | 35 | 25 | |
| | | | | 235 | 250 | 15 | | |
| | | 0.02 | | 240 | 280 | 40 | 35 | |
| | | | | 235 | 265 | 30 | | |
| Ex. No. 5 | 50 p.o. | 0.01 | 30 | 250 | 275 | 25 | 22.5 | 10 |
| | | | | 240 | 260 | 20 | | |
| | | 0.02 | | 260 | 295 | 35 | 35 | 0 |
| | | | | 235 | 270 | 35 | | |
| | | 0.01 | 60 | 240 | 275 | 35 | 30 | −20 |
| | | | | 235 | 260 | 25 | | |
| | | 0.02 | | 260 | 290 | 30 | 35.5 | 7 |
| | | | | 245 | 280 | 35 | | |
| | | 0.01 | 90 | 255 | 270 | 15 | 17.5 | 30 |
| | | | | 235 | 255 | 20 | | |
| | | 0.02 | | 260 | 290 | 30 | 32.5 | 7 |
| | | | | 245 | 280 | 35 | | |
| | | 0.01 | 120 | 245 | 285 | 40 | 30 | −20 |
| | | | | 220 | 240 | 20 | | |
| | | 0.02 | | 260 | 295 | 35 | 40 | −14 |
| | | | | 255 | 270 | 45 | | |
| | | 0.01 | 180 | 240 | 255 | 15 | 20 | 20 |
| | | | | 220 | 245 | 25 | | |
| | | 0.02 | | 240 | 270 | 30 | 37.5 | −7 |
| | | | | 250 | 295 | 45 | | |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.01 | 240 | 230 | 255 | 25 | 22.5 | 10 |
| | | | | 255 | 245 | 20 | | |
| | | 0.02 | | 260 | 290 | 30 | 38.5 | −10 |
| | | | | 233 | 280 | 47 | | |
| SPONTANEOUSLY HYPERTENSIVE RATS n = 2 Body weight(s): 410, 430 grams | | | | | | | | |
| CONTROL | | 0.05 | 0 | 240 | 270 | 30 | 27.5 | |
| | | | | 230 | 255 | 25 | | |
| | | 0.1 | | 230 | 285 | 55 | 45 | |
| | | | | 235 | 270 | 35 | | |
| Ex. No. 5 | 10 i.v. | 0.05 | 30 | 225 | 260 | 35 | 30 | −9 |
| | | | | 235 | 260 | 25 | | |
| | | 0.01 | | 230 | 265 | 35 | 35 | 22 |
| | | | | 225 | 260 | 35 | | |
| | 20 i.v. | 0.05 | 60 | 245 | 250 | 5 | 10 | 64 |
| | | | | 225 | 240 | 15 | | |
| | | 0.01 | | 245 | 260 | 15 | 17.5 | 61 |
| | | | | 235 | 255 | 20 | | |
| | | 0.05 | 90 | 225 | 240 | 15 | 10 | 64 |
| | | | | 220 | 225 | 5 | | |
| | | 0.1 | | 230 | 250 | 20 | 20 | 56 |
| | | | | 225 | 245 | 20 | | |
| | | 0.05 | 120 | 225 | 245 | 20 | 15 | 45 |
| | | | | 225 | 235 | 10 | | |
| | | 0.1 | | 230 | 245 | 15 | 17.5 | 61 |
| | | | | 225 | 245 | 20 | | |
| | | 0.05 | 180 | 225 | 245 | 20 | 12.5 | 55 |
| | | | | 230 | 235 | 5 | | |
| | | 0.1 | | 225 | 255 | 30 | 20 | 56 |
| | | | | 240 | 250 | 10 | | |
| | | 0.05 | 240 | 215 | 235 | 20 | 17.5 | 36 |
| | | | | 220 | 235 | 15 | | |
| | | 0.1 | | 215 | 250 | 35 | 25 | 44 |
| | | | | 230 | 245 | 15 | | |
| SPONTANEOUSLY HYPERTENSIVE RATS n = 2 Body weight(s): 400, 400 grams | | | | | | | | |
| | | 0.05 | 300 | 210 | 245 | 35 | 22.5 | 18 |
| | | | | 245 | 255 | 10 | | |
| | | 0.1 | | 200 | 235 | 35 | 30 | 33 |
| | | | | 235 | 260 | 25 | | |
| CONTROL | | 0.01 | 0 | 130 | 170 | 40 | 30 | |
| | | | | 159 | 179 | 20 | | |
| | | 0.02 | | 136 | 192 | 56 | 51 | |
| | | | | 164 | 210 | 46 | | |
| Ex. No. 10 | 10 i.v. | 0.01 | 30 | 136 | 184 | 48 | 37.5 | −25 |
| | | | | 150 | 177 | 27 | | |
| | | 0.02 | | 136 | 197 | 61 | 64.5 | −26 |
| | | | | 150 | 218 | 68 | | |
| | 20 i.v. | 0.01 | 60 | 141 | 156 | 15 | 14.5 | 52 |
| | | | | 150 | 164 | 14 | | |
| | | 0.02 | | 138 | 161 | 23 | 22.5 | 56 |
| | | | | 152 | 174 | 22 | | |
| | | 0.01 | 90 | 137 | 154 | 17 | 16 | 47 |
| | | | | 151 | 166 | 15 | | |
| | | 0.02 | | 135 | 161 | 26 | 23 | 55 |
| | | | | 153 | 173 | 20 | | |
| | | 0.01 | 120 | 138 | 155 | 17 | 13.5 | 55 |
| | | | | 150 | 160 | 10 | | |
| | | 0.02 | | 138 | 161 | 23 | 22 | 57 |
| | | | | 157 | 178 | 21 | | |
| | | 0.01 | 180 | 132 | 154 | 22 | 25.5 | 15 |
| | | | | 145 | 174 | 29 | | |
| | | 0.02 | | 140 | 174 | 34 | 29.5 | 42 |
| | | | | 157 | 182 | 25 | | |
| | | 0.01 | 240 | 131 | 156 | 25 | 22.5 | 25 |
| | | | | 149 | 169 | 20 | | |
| | | 0.02 | | 140 | 174 | 34 | 34.5 | 32 |
| | | | | 157 | 192 | 35 | | |
| SPONTANEOUSLY HYPERTENSIVE RATS n = 2 Body weight(s): 520, 470 grams | | | | | | | | |
| | | 0.01 | 300 | 144 | 166 | 22 | 24.5 | 18 |
| | | | | 151 | 178 | 27 | | |
| | | 0.02 | | 135 | 170 | 35 | 34 | 33 |
| | | | | 145 | 178 | 33 | | |
| CONTROL | | 0.01 | 0 | 135 | 152 | 17 | 22.5 | |
| | | | | 132 | 160 | 28 | | |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.02 | | 149 | 216 | 67 | 52 | |
| | | | | 137 | 174 | 37 | | |
| Ex. No. 14 | 10 i.v. | 0.01 | 30 | 131 | 142 | 11 | 11 | 51 |
| | | | | 143 | 154 | 11 | | |
| | | 0.02 | | 151 | 173 | 22 | 23 | 56 |
| | | | | 136 | 160 | 24 | | |
| | | 0.01 | 60 | 151 | 163 | 12 | 12 | 47 |
| | | | | 139 | 151 | 12 | | |
| | | 0.02 | | 153 | 171 | 18 | 22 | 58 |
| | | | | 140 | 166 | 26 | | |
| | | 0.01 | 90 | 135 | 142 | 7 | 13.5 | 40 |
| | | | | 140 | 160 | 20 | | |
| | | 0.02 | | 135 | 173 | 38 | 29.5 | 43 |
| | | | | 145 | 166 | 21 | | |
| | | 0.01 | 120 | 137 | 155 | 18 | 16 | 29 |
| | | | | 137 | 151 | 14 | | |
| | | 0.02 | | 143 | 168 | 25 | 23.5 | 55 |
| | | | | 139 | 161 | 22 | | |
| | | 0.01 | 180 | 131 | 153 | 22 | 21.5 | 4 |
| | | | | 134 | 155 | 21 | | |
| | | 0.02 | | 140 | 170 | 30 | 30.5 | 41 |
| | | | | 131 | 162 | 31 | | |
| | | 0.01 | 240 | 146 | 170 | 24 | 26.5 | −18 |
| | | | | 141 | 166 | 29 | | |
| | | 0.02 | | 140 | 171 | 30 | 32 | 38 |
| | | | | 141 | 175 | 34 | | |
| SPONTANEOUSLY HYPERTENSIVE RATS n = 2 Body weight(s): 480, 420 grams | | | | | | | | |
| | | 0.01 | 300 | 138 | 160 | 22 | 24.5 | −9 |
| | | | | 142 | 169 | 27 | | |
| | | 0.02 | | 152 | 186 | 34 | 33 | 37 |
| | | | | 144 | 176 | 32 | | |
| CONTROL | | 0.01 | 0 | 139 | 182 | 43 | 29.5 | |
| | | | | 128 | 144 | 16 | | |
| | | 0.02 | | 142 | 182 | 40 | 33 | |
| | | | | 162 | 188 | 26 | | |
| Ex. No. 16 | 30 p.o. | 0.01 | 30 | 133 | 166 | 33 | 25 | 15 |
| | | | | 148 | 165 | 17 | | |
| | | 0.02 | | 136 | 163 | 27 | 27.5 | 17 |
| | | | | 154 | 182 | 28 | | |
| | | 0.01 | 60 | 131 | 168 | 37 | 30.5 | −3 |
| | | | | 154 | 178 | 24 | | |
| | | 0.02 | | 134 | 163 | 29 | 29 | 12 |
| | | | | 162 | 191 | 29 | | |
| | | 0.01 | 90 | 137 | 166 | 29 | 28.5 | 3 |
| | | | | 149 | 177 | 28 | | |
| | | 0.02 | | 137 | 172 | 35 | 40.5 | −23 |
| | | | | 149 | 195 | 46 | | |
| | | 0.01 | 120 | 146 | 163 | 17 | 23.5 | 20 |
| | | | | 148 | 178 | 30 | | |
| | | 0.02 | | 142 | 166 | 24 | 29.5 | 11 |
| | | | | 161 | 196 | 35 | | |
| | | 0.01 | 180 | 142 | 169 | 27 | 30.5 | −3 |
| | | | | 140 | 174 | 34 | | |
| | | 0.02 | | 138 | 169 | 31 | 26 | 21 |
| | | | | 153 | 174 | 21 | | |
| | | 0.01 | 240 | 140 | 163 | 23 | 30 | −2 |
| | | | | 140 | 177 | 37 | | |
| | | 0.02 | | 143 | 160 | 17 | 30 | 9 |
| | | | | 157 | 200 | 43 | | |
| SPONTANEOUSLY HYPERTENSIVE RATS n = 2 Body weight(s): 420, 460 grams | | | | | | | | |
| CONTROL | | 0.01 | 0 | 147 | 169 | 22 | 21.5 | |
| | | | | 138 | 159 | 21 | | |
| | | 0.02 | | 151 | 198 | 47 | 42 | |
| | | | | 145 | 182 | 37 | | |
| Ex. No. 22 | 10 i.v. | 0.01 | 30 | 152 | 164 | 12 | 8.5 | 60 |
| | | | | 146 | 151 | 5 | | |
| | | 0.02 | | 152 | 177 | 25 | 18.5 | 56 |
| | | | | 148 | 160 | 12 | | |
| | | 0.01 | 60 | 151 | 166 | 15 | 11 | 49 |
| | | | | 144 | 151 | 7 | | |
| | | 0.02 | | 121 | 144 | 23 | 25 | 40 |
| | | | | 141 | 168 | 27 | | |
| | | 0.01 | 90 | 149 | 166 | 17 | 14 | 35 |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 140 | 151 | 11 | | |
| | | 0.02 | | 151 | 166 | 15 | 13 | 69 |
| | | | | 140 | 151 | 11 | | |
| | | 0.01 | 120 | 138 | 155 | 17 | 17.5 | 19 |
| | | | | 129 | 147 | 18 | | |
| | | 0.02 | | 148 | 183 | 35 | 30 | 29 |
| | | | | 141 | 166 | 25 | | |
| | | 0.01 | 180 | 142 | 168 | 26 | 20 | 7 |
| | | | | 141 | 155 | 14 | | |
| | | 0.02 | | 150 | 185 | 35 | 36 | 14 |
| | | | | 132 | 169 | 37 | | |
| | | 0.01 | 240 | 134 | 169 | 35 | 28 | −30 |
| | | | | 139 | 160 | 21 | | |
| | | 0.02 | | 139 | 200 | 61 | 48 | −14 |
| | | | | 150 | 185 | 35 | | |
| | | 0.01 | 300 | 139 | 171 | 32 | 30 | −40 |
| | | | | 121 | 149 | 28 | | |
| | | 0.02 | | 140 | 210 | 70 | 52.5 | −25 |
| | | | | 150 | 185 | 35 | | |
| SPONTANEOUSLY HYPERTENSIVE RATS n = 2 Body weight(s): 450, 495 grams | | | | | | | | |
| CONTROL | | 0.01 | 0 | 161 | 191 | 30 | 28.5 | |
| | | | | 143 | 170 | 27 | | |
| | | 0.02 | | 157 | 217 | 60 | 51.5 | |
| | | | | 145 | 188 | 43 | | |
| Ex. No. 61 | 10 i.v. | 0.01 | 30 | 158 | 182 | 24 | 21 | 26 |
| | | | | 146 | 164 | 18 | | |
| | | 0.02 | | 158 | 196 | 38 | 32.5 | 37 |
| | | | | 146 | 173 | 27 | | |
| | 20 i.v. | 0.01 | 60 | 163 | 180 | 17 | 13 | 54 |
| | | | | 147 | 156 | 9 | | |
| | | 0.02 | | 159 | 179 | 20 | 14.5 | 72 |
| | | | | 146 | 155 | 9 | | |
| | | 0.01 | 90 | 153 | 165 | 12 | 8 | 72 |
| | | | | 150 | 154 | 4 | | |
| | | 0.02 | | 154 | 173 | 19 | 16.5 | 68 |
| | | | | 144 | 158 | 14 | | |
| | | 0.01 | 120 | 151 | 165 | 14 | 12 | 58 |
| | | | | 145 | 155 | 10 | | |
| | | 0.02 | | 151 | 176 | 25 | 20 | 61 |
| | | | | 143 | 158 | 15 | | |
| | | 0.01 | 180 | 142 | 165 | 23 | 15.5 | 46 |
| | | | | 143 | 151 | 8 | | |
| | | 0.02 | | 148 | 172 | 24 | 17.5 | 66 |
| | | | | 145 | 156 | 11 | | |
| | | 0.01 | 240 | 144 | 156 | 12 | 12 | 58 |
| | | | | 144 | 156 | 12 | | |
| | | 0.02 | | 150 | 179 | 29 | 23 | 55 |
| | | | | 147 | 164 | 17 | | |
| | | 0.01 | 300 | 142 | 161 | 19 | 15.5 | 46 |
| | | | | 144 | 156 | 12 | | |
| | | 0.02 | | 140 | 167 | 27 | 24 | 53 |
| | | | | 153 | 174 | 21 | | |
| SPONTANEOUSLY HYPERTENSIVE RATS n = 2 Body weight(s): 570, 460 grams | | | | | | | | |
| CONTROL | | 0.01 | 0 | 139 | 179 | 40 | 39.5 | |
| | | | | 150 | 189 | 39 | | |
| | | 0.02 | | 143 | 204 | 61 | 60.5 | |
| | | | | 156 | 216 | 60 | | |
| Ex. No. 62 | 10 i.v. | 0.01 | 30 | 144 | 196 | 52 | 57 | −44 |
| | | | | 141 | 203 | 62 | | |
| | | 0.02 | | 158 | 217 | 59 | 61.5 | −2 |
| | | | | 163 | 227 | 64 | | |
| | 20 i.v. | 0.01 | 60 | 131 | 148 | 17 | 13 | 67 |
| | | | | 135 | 144 | 9 | | |
| | | 0.02 | | 135 | 173 | 38 | 29.5 | 51 |
| | | | | 134 | 155 | 21 | | |
| | | 0.01 | 90 | 132 | 156 | 24 | 23 | 42 |
| | | | | 127 | 149 | 22 | | |
| | | 0.02 | | 140 | 195 | 55 | 54 | 11 |
| | | | | 136 | 189 | 53 | | |
| | | 0.01 | 120 | 137 | 160 | 23 | 23.5 | 41 |
| | | | | 138 | 162 | 24 | | |
| | | 0.02 | | 143 | 189 | 46 | 50 | 17 |
| | | | | 139 | 193 | 54 | | |

TABLE III-continued

VASOPRESSIN (VAS)VASOPRESSOR RESPONSE

|  | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | 0.01 | 180 | 131 | 155 | 24 | 24.5 | 38 |
| | | | | 133 | 158 | 25 | | |
| | | 0.02 | | 139 | 155 | 16 | 15 | 75 |
| | | | | 144 | 158 | 14 | | |
| | | 0.01 | 240 | 126 | 153 | 27 | 30 | 24 |
| | | | | 133 | 166 | 33 | | |
| | | 0.02 | | 134 | 167 | 33 | 40.5 | 33 |
| | | | | 142 | 190 | 48 | | |
| | | 0.01 | 300 | 128 | 152 | 24 | 25 | 37 |
| | | | | 138 | 164 | 26 | | |
| | | 0.02 | | 140 | 167 | 27 | 38 | 37 |
| | | | | 146 | 195 | 49 | | |
| SPONTANEOUSLY HYPERTENSIVE RATS n = 2 Body weight(s): 500, 450 grams | | | | | | | | |
| CONTROL | | 0.01 | 0 | 144 | 177 | 33 | 30 | |
| | | | | 128 | 155 | 27 | | |
| | | 0.02 | | 145 | 197 | 52 | 46.5 | |
| | | | | 127 | 168 | 41 | | |
| Ex. No. 92 | 10 i.v. | 0.01 | 30 | 155 | 165 | 10 | 10.5 | 65 |
| | | | | 153 | 164 | 11 | | |
| | | 0.02 | | 160 | 177 | 17 | 18.5 | 60 |
| | | | | 155 | 175 | 20 | | |
| | | 0.01 | 60 | 143 | 159 | 16 | 18 | 40 |
| | | | | 150 | 170 | 20 | | |
| | | 0.02 | | 152 | 168 | 16 | 22 | 53 |
| | | | | 149 | 177 | 28 | | |
| | | 0.01 | 90 | 145 | 162 | 17 | 17.5 | 42 |
| | | | | 127 | 145 | 18 | | |
| | | 0.02 | | 141 | 168 | 27 | 27 | 42 |
| | | | | 144 | 171 | 27 | | |
| | | 0.01 | 120 | 135 | 156 | 21 | 19 | 37 |
| | | | | 113 | 130 | 17 | | |
| | | 0.02 | | 134 | 154 | 20 | 20.5 | 56 |
| | | | | 126 | 147 | 21 | | |
| | | 0.01 | 180 | 137 | 159 | 22 | 18 | 40 |
| | | | | 144 | 158 | 14 | | |
| | | 0.02 | | 144 | 180 | 36 | 29.5 | 37 |
| | | | | 142 | 165 | 23 | | |
| | | 0.01 | 240 | 149 | 169 | 20 | 19 | 37 |
| | | | | 137 | 155 | 18 | | |
| | | 0.02 | | 149 | 169 | 20 | 18 | 61 |
| | | | | 146 | 162 | 16 | | |
| | | 0.01 | 300 | 151 | 171 | 20 | 17.5 | 42 |
| | | | | 144 | 159 | 15 | | |
| | | 0.02 | | 158 | 182 | 24 | 24 | 48 |
| | | | | 139 | 163 | 24 | | |
| SPONTANEOUSLY HYPERTENSIVE RATS n = 2 Body weight(s): 440, 490 grams | | | | | | | | |
| CONTROL | | 0.01 | 0 | 149 | 177 | 28 | 28 | |
| | | | | 149 | 177 | 28 | | |
| | | 0.02 | | 155 | 196 | 41 | 41 | |
| | | | | 155 | 196 | 41 | | |
| Ex. No. 121 | 10 i.v. | 0.01 | 30 | 154 | 175 | 21 | 21 | 25 |
| | | | | 154 | 175 | 21 | | |
| | | 0.02 | | 154 | 190 | 36 | 36 | 12 |
| | | | | 154 | 190 | 36 | | |
| | 20 i.v. | 0.01 | 60 | 155 | 168 | 13 | 13 | 54 |
| | | | | 155 | 168 | 13 | | |
| | | 0.02 | | 156 | 175 | 19 | 19 | 54 |
| | | | | 156 | 175 | 19 | | |
| | | 0.01 | 90 | 159 | 172 | 13 | 13 | 54 |
| | | | | 159 | 172 | 13 | | |
| | | 0.02 | | 157 | 179 | 22 | 22 | 46 |
| | | | | 157 | 179 | 22 | | |
| | | 0.01 | 120 | 159 | 164 | 5 | 5 | 82 |
| | | | | 159 | 164 | 5 | | |
| | | 0.02 | | 154 | 173 | 19 | 19 | 54 |
| | | | | 154 | 173 | 19 | | |
| | | 0.01 | 180 | 151 | 169 | 18 | 18 | 36 |
| | | | | 151 | 169 | 18 | | |
| | | 0.02 | | 159 | 173 | 14 | 14 | 66 |
| | | | | 159 | 173 | 14 | | |
| | | 0.01 | 240 | 149 | 169 | 20 | 20 | 29 |
| | | | | 149 | 169 | 20 | | |
| | | 0.02 | | 151 | 172 | 21 | 21 | 49 |

TABLE III-continued

VASOPRESSIN (VAS)VASOPRESSOR RESPONSE

| | Dose (mg/kg) | VAS Dose i.u./kg I.V. | Min Post Dose | Control Before VAS | Response After VAS | Change | Average Change | % Inhibition |
|---|---|---|---|---|---|---|---|---|
| | | | | 151 | 172 | 21 | | |
| | | 0.01 | 300 | 151 | 168 | 17 | 17 | 39 |
| | | | | 151 | 168 | 17 | | |
| | | 0.02 | | 152 | 177 | 25 | 25 | 39 |
| | | | | 152 | 177 | 25 | | |
| SPONTANEOUSLY HYPERTENSIVE RATS n = 2 Body weight(s): 585, 410 grams | | | | | | | | |
| CONTROL | | 0.01 | 0 | 140 | 162 | 22 | 17.5 | |
| | | | | 147 | 160 | 13 | | |
| | | 0.02 | | 138 | 169 | 31 | 33 | |
| | | | | 141 | 176 | 35 | | |
| Ex. No. 123 | 10 i.v. | 0.01 | 30 | 139 | 151 | 12 | 17.5 | 0 |
| | | | | 154 | 177 | 23 | | |
| | | 0.02 | | 139 | 177 | 38 | 20 | 39 |
| | | | | 154 | 156 | 2 | | |
| | 20 i.v. | 0.01 | 60 | 137 | 140 | 3 | 6 | 66 |
| | | | | 147 | 156 | 9 | | |
| | | 0.02 | | 132 | 139 | 7 | 6 | 82 |
| | | | | 146 | 151 | 5 | | |
| | | 0.01 | 90 | 137 | 141 | 4 | 6 | 66 |
| | | | | 149 | 157 | 8 | | |
| | | 0.02 | | 135 | 138 | 3 | 7 | 79 |
| | | | | 149 | 160 | 11 | | |
| | | 0.01 | 120 | 136 | 139 | 3 | 5 | 71 |
| | | | | 147 | 154 | 7 | | |
| | | 0.02 | | 138 | 141 | 3 | 4.5 | 86 |
| | | | | 150 | 156 | 6 | | |
| | | 0.01 | 180 | 138 | 141 | 3 | 4 | 77 |
| | | | | 150 | 155 | 5 | | |
| | | 0.02 | | 138 | 142 | 4 | 6.5 | 80 |
| | | | | 148 | 157 | 9 | | |
| | | 0.01 | 240 | 137 | 145 | 8 | 8 | 54 |
| | | | | 146 | 154 | 8 | | |
| | | 0.02 | | 140 | 146 | 6 | 6.5 | 80 |
| | | | | 148 | 155 | 7 | | |
| | | 0.01 | 300 | 138 | 144 | 6 | 8 | 54 |
| | | | | 144 | 154 | 10 | | |
| | | 0.02 | | 140 | 148 | 8 | 8 | 76 |
| | | | | 146 | 154 | 8 | | |
| SPONTANEOUSLY HYPERTENSIVE RATS n = 2 Body weight(s): 500, 480 grams | | | | | | | | |
| CONTROL | | 0.01 | 0 | 150 | 172 | 22 | 32.5 | |
| | | | | 140 | 183 | 43 | | |
| | | 0.02 | | 147 | 187 | 40 | 35.5 | |
| | | | | 162 | 193 | 31 | | |
| Ex. No. 124 | 10 i.v. | 0.01 | 30 | 150 | 187 | 37 | 38.5 | −18 |
| | | | | 153 | 193 | 40 | | |
| | | 0.02 | | 148 | 187 | 39 | 43.5 | −23 |
| | | | | 146 | 194 | 48 | | |
| | 20 i.v. | 0.01 | 60 | 151 | 155 | 4 | 4 | 88 |
| | | | | 148 | 152 | 4 | | |
| | | 0.02 | | 150 | 173 | 23 | 17.5 | 51 |
| | | | | 147 | 159 | 12 | | |
| | | 0.01 | 90 | 143 | 159 | 16 | 12.5 | 62 |
| | | | | 147 | 156 | 9 | | |
| | | 0.02 | | 148 | 163 | 15 | 18 | 49 |
| | | | | 144 | 165 | 21 | | |
| | | 0.01 | 120 | 144 | 157 | 13 | 12.5 | 62 |
| | | | | 147 | 159 | 12 | | |
| | | 0.02 | | 151 | 167 | 16 | 19.5 | 45 |
| | | | | 149 | 172 | 23 | | |
| | | 0.01 | 180 | 131 | 152 | 21 | 21 | 35 |
| | | | | 125 | 146 | 21 | | |
| | | 0.02 | | 143 | 165 | 22 | 21.5 | 39 |
| | | | | 143 | 164 | 21 | | |
| | | 0.01 | 240 | 144 | 163 | 19 | 18 | 45 |
| | | | | 141 | 158 | 17 | | |
| | | 0.02 | | 147 | 168 | 21 | 24.5 | 31 |
| | | | | 148 | 176 | 28 | | |
| | | 0.01 | 300 | 141 | 160 | 19 | 20 | 38 |
| | | | | 138 | 159 | 21 | | |
| | | 0.02 | | 139 | 176 | 37 | 33.5 | 6 |
| | | | | 142 | 172 | 30 | | |

SPONTANEOUSLY HYPERTENSIVE RATS n = 2 Body weight(s): 600, 550 grams

TABLE IV

VASOPRESSIN (VAS) VASOPRESSOR RESPONSE

| Ex. No. | Dose mg/kg | MAX % Inhibition | Time (Min) |
|---|---|---|---|
| 2 | 10 p.o. | 65 | 180 |
| 136 | 10 i.v. | 81 | 30 |
| 137 | 10 i.v. | 52 | 30 |
| 138 | 10 i.v. | 88 | 60 |
| 167 | 10 i.v. | 70 | 180 |
| 251 | 30 i.v. | 41 | 60 |
| 252 | 30 i.v. | 75 | 120 |
| 253 | 30 i.v. | 57 | 180 |
| 254 | 30 i.v. | 74 | 60 |
| 255 | 10 i.v. | 65 | 60 |
| 257 | 10 i.v. | 71 | 60 |
| 258 | 30 i.v. | 61 | 60 |
| 259 | 30 i.v. | 29 | 90 |
| 260 | 30 i.v. | 79 | 120 |
| 261 | 10 i.v. | 74 | 60 |
| 263 | 10 i.v. | 55 | 90 |
| 266 | 30 i.v. | 21 | 120 |
| 267 | 10 i.v. | 74 | 120 |
| 268 | 10 i.v. | 85 | 90 |
| 379 | 10 i.v. | 75 | 300 |
| 416 | 30 i.v. | 44 | 90 |
| 448 | 30 i.v. | 60 | 90 |
| 449 | 10 i.v. | 45 | 90 |
| 455 | 30 i.v. | 46 | 120 |
| 457 | 10 i.v. | 61 | 300 |
| 458 | 10 i.v. | 77 | 180 |

Oxytocin Receptor Binding (a) Membrane preparation

Female Sprague-Dawley rats weighing approximately 200–250 g are injected intramuscularly (i.m.) with 0.3 mg/kg of body weight of diethylstilbestrol (DES). The rats are sacrificed 18 hours later under pentobarbital anesthesia. The uteri are dissected out, cleaned of fat and connective tissues and rinsed in 50 ml of normal saline. The tissue pooled from six rats is homogenized in 50 ml of 0.01 mM Tris.HCl, containing 0.5 mM dithiothreitol and 1.0 mM EDTA, adjusted to pH 7.4, using a polytron at setting 6 with three passes of 10 sec each. The homogenate is passed through two (2) layers of cheesecloth and the filtrate centrifuged at 1000× g for 10 min. The clear supernatant is removed and recentrifuged at 165,000× g for 30 min. The resulting pellet containing the oxytocin receptors is resuspended in 50.0 mM Tris.HCl containing 5.0 mM MgCl$_2$ at pH 7.4, to give a protein concentration of 2.5 mg/ml of tissue suspension. This preparation is used in subsequent binding assays with [$^3$H]Oxytocin.

(b) Radioligand Binding

Binding of 3,5-[$^3$H]Oxytocin ([$^3$H]OT) to its receptors is done in microtiter plates using [$^3$H]OT, at various concentrations, in an assay buffer of 50.0 mM Tris.HCl, pH 7.4 and containing 5.0 mM MgCl$_2$, and a mixture of protease inhibitors: BSA, 0.1 mg; aprotinin, 1.0 mg; 1,10-phenanthroline, 2.0 mg; trypsin, 10.0 mg; and PMSF, 0.3 mg per 100 ml of buffer solution. Non-specific binding is determined in the presence of 1.0 uM unlabeled OT. The binding reaction is terminated after 60 min., at 22° C., by rapid filtration through glass fiber filters using a Brandel® cell harvester (Biomedical Research and Development Laboratories, Inc., Gaithersburg, Md.). Competition experiments are conducted at equilibrium using 1.0 nM [$^3$H]OT and varying the concentration of the displacing agents. The concentrations of agent displacing 50% of [$^3$H]OT at its sites (IC$_{50}$) are calculated by a computer assisted LUNDON-2 program (LUNDON SOFTWARE INC., Ohio, USA).

The results of this assay on representative examples are shown in Table V.

TABLE V

Oxytocin

| Ex. No. | Dose (μM) | % Inhibition at 10 μM | IC$_{50}$ |
|---|---|---|---|
| 2 | 10 | 73 | 2.9 |
| 5 | 10 | 90 | 2 |
| 11 | 10 | 71 | 4.4 |
| 249 | 10 | 38 | |
| 250 | 10 | 15 | |
| 251 | 10 | 77 | |
| 253 | 10 | 77 | 3.1 |
| 254 | 10 | 95 | 1.9 |
| 255 | 10 | 99 | 0.46 |
| 256 | 10 | 47 | 6.5 |
| 257 | 10 | 97 | 0.189 |
| 258 | 10 | 18 | |
| 259 | 10 | 7 | |
| 260 | 10 | 44 | |
| 261 | 10 | 97 | 0.21 |
| 262 | 10 | 55 | 6.2 |
| 263 | 10 | 94 | 0.26 |
| 264 | 1 | 34 | |
| 266 | 10 | 15 | |
| 267 | 10 | 89 | 1.1 |
| 268 | 10 | 89 | 2.4 |
| 345 | 10 | 2 | |
| 379 | 10 | 96 | 0.81 |
| 416 | 10 | 19 | |
| 448 | 10 | 39 | |
| 450 | 10 | 33 | |
| 451 | 1 | 0 | |
| 452 | 1 | 22 | |
| 453 | 5 | 53 | 3.3 |
| 454 | 10 | 78 | 2.5 |
| 455 | 10 | 88 | 1.1 |
| 534 | 10 | 86 | 0.94 |

The compounds of the present invention can be used in the form of salts derived from pharmaceutically or physiologically acceptable acids or bases. These salts include, but are not limited to, the following: salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium or with organic bases. The compounds can also be used in the form of esters, carbamates and other conventional "pro-drug" forms, which, when administered in such form, convert to the active moiety in vivo. When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oi8ls such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

REFERENCE EXAMPLE 1

6,11-Dihydro-5H-dibenz[b,e]azepine

A mixture of 48.52 g (0.20 mol) of 2-aminobenzophenone-2'-carboxylic acid and 500 ml of xylene is refluxed for 67 hours, cooled to room temperature and filtered. The solid is washed with xylene to give 43.3 g (97.8%) of 5H-dibenz[b,e]azepine-6,11-dione as light tan crystals, m.p. 245°–248° C. To 4.46 g (0.020 mol) of the preceding compound in 25 ml of tetrahydrofuran is added 12 ml (0.12 mol) of a 10 molar solution of boron-dimethylsulfide in tetrahydrofuran. An additional 10 ml of tetrahydrofuran is added and the mixture is stirred overnight and then is refluxed (solids dissolve) for 4 hours. The solution is cooled and 15 ml of methanol added dropwise. The mixture is concentrated under vacuum, 50 ml of 2N sodium hydroxide is added and the mixture refluxed for 2 hours. The solid is filtered, washed with water, air dried and extracted with dichloromethane. The extract is dried ($Na_2SO_4$) and the solvent removed to give 3.25 g (83%) of crystals, m.p. 117°–122° C.

REFERENCE EXAMPLE 2

4-[(2-Methylbenzoyl)amino]benzoic acid

A mixture of 43.42 g (0.26 mol) of ethyl 4-aminobenzoate and 40.8 g (0.26 mol) of 2-methylbenzoyl chloride in 150 ml of dichloromethane is cooled in an ice bath and 26.56 g (0.26 mol) of triethylamine is added dropwise. After the addition, the solution is stirred at room temperature overnight. The mixture is poured into water and the organic layer separated. The organic layer is washed with water, 1N HCl, 1M $NaHCO_3$ and dried ($Na_2SO_4$). The solvent is removed and the solid slurried with ethyl acetate and filtered to give 57 g of ethyl 4-[(2-methylbenzoyl)amino]benzoate as crystals, m.p. 110°–115° C.

A mixture of 50.7 g (0.20 mol) of the preceding compound, 280 ml of ethanol and 55 ml of 10N NaOH is refluxed for 5 minutes. The mixture is cooled to room temperature, diluted with 200 ml of water and acidified with concentrated hydrochloric acid (pH 1–2). The mixture is filtered and the solid washed with water and dried to give 51 g of product as white crystals, m.p. 270°–275° C.

REFERENCE EXAMPLE 3

4-[(2-Methylbenzoyl)amino]benzoyl chloride

A mixture of 10.3 g of 4-[(2-methylbenzoyl)amino] benzoic acid and 32 ml of thionyl chloride is refluxed for 1.5 hours. The solution is concentrated under vacuum. Toluene is added and the solvent removed under vacuum. Toluene is added and the mixture chilled and filtered to give a yellow solid, m.p. 135°–141° C.

REFERENCE EXAMPLE 4

4-[(2,6-Dimethoxybenzoyl)amino]benzoic acid

A mixture of 2 g (10 mmol) of 2,6-dimethoxybenzoyl chloride, 1.65 g (10 mmol) of ethyl 4-aminobenzoate, 1.11 g of triethylamine and 61 mg of 4-dimethylaminopyridine in 10 ml of dichloromethane is refluxed for 20 hours. The mixture is diluted with water and the organic layer separate. The organic layer is washed with water, 1N HCl, 1N $Na_2CO_3$, brine and dried ($Na_2SO_4$). The solvent is removed to give a solid which is crystallized from ethyl acetate to give 1.22 g of ethyl 4-[(2,6-dimethoxybenzoyl)amino] benzoate as crystals, m.p. 183°–185° C.

A mixture of 3.88 g (11.79 mmol) of the preceding compound, 17.3 ml of 2N NaOH and 20 ml of methanol is stirred at room temperature overnight. Methanol (30 ml) and water (10 ml) are added and the solution refluxed for ½ hour. The solvents are removed under vacuum and the residual solid triturated with ether and the ether decanted. The solid is dissolved in 30 ml of water and acidified with 2N HCl (pH 3). The mixture is filtered, the solid washed with water and dried at 60° C. under vacuum to give 3.0 g of solid, m.p. 236°–240° C.

REFERENCE EXAMPLE 5

4-[(4-Pyridinylcarbonyl)amino]benzoic acid

To a cooled mixture of 1.78 g (0.01 mol) of isoniconinoyl chloride hydrochloride in 5 ml of dichloromethane is added 2.52 g (0.025 mol) of triethylamine. To the solution is added a solution of 1.65 g of ethyl 4-aminobenzoate in 5 ml of dichloromethane. After stirring at room temperature overnight, 50 mg of 4-dimethylaminopyridine is added and the mixture is refluxed for 24 hours. The mixture is poured into water and filtered to give 3.4 g of brown solid. A 0.50 g sample is triturated with ethyl acetate to give 0.37 g of ethyl 4-[(4-pyridinylcarbonyl)amino]benzoate as yellow crystals, m.p. 143°–145° C.

Anal. Calc'd for $C_{15}H_{14}N_2O_3$: C,66.7; H,5.2; N,10.4 Found: C,66.4; H,5.1; N,10.3.

A solution of 8.15 g (30 mmol) of the preceding compound and 22 ml of 2N NaOH in 60 ml of methanol is heated on a steam bath for 1 hour. The mixture is cooled and filtered to the solid in water is added 2N citric acid. Stirring and filtering gives 4.24 g of crystals, m.p. 362°–365° C.

Anal. Calc'd for $C_{13}H_{10}N_2O_3$ ½ $H_2O$ C,62.1; H,4.4; N,11.1 Found: 62.6; H,4.3; N,11.0.

REFERENCE EXAMPLE 6

4-[(3-Pyridinylcarbonyl)amino]benzoic acid

A mixture of 1.83 g (0.01 mol) of nicotinoyl chloride hydrochloride (97%), 1.65 g of (0.01 mol) of ethyl 4-aminobenzoate, 2.22 g (0.022 mol) of triethylamine and 61 mg of 4-dimethylaminopyridine in 33 ml of dichloromethane is refluxed 24 hours. The solution is washed with water, 2N citric acid and $NaHCO_3$ solution. The solvent is removed and the residue triturated with methanol to give 2.3 g of ethyl 4-[(3-pyridinylcarbonyl)amino]benzoate as yellow crystals, m.p. 125°–127° C.

A mixture of 12.0 g (0.044 mol) of ethyl 4-[(3-pyridinylcarbonyl)amino]benzoic acid, 65 ml of 2N sodium hydroxide and 120 ml of methanol is refluxed for 0.75 hour. The solvent is removed and the residue extracted with diethyl ether. The residue is diluted with water and solid citric acid is added until the pH is 4–5. The mixture is filtered and the solid washed with water and air dried to give crystals, m.p. 307°–310° C.

REFERENCE EXAMPLE 7

5,6-Dihydro-5-(4-nitrobenzoyl)phenanthridine

To a suspension of 7.5 g of 5,6-dihydrophenanthridine in 40 ml of warm pyridine under nitrogen is added 3.6 g of 4-nitrobenzoyl chloride. The mixture is stirred overnight, filtered and the solid washed twice with 5 ml of pyridine. To the filtrate is added 250 ml of 2N HCl and the mixture stirred and then filtered to give 6.6 g of solid. This solid is heated with 25 ml of ethyl acetate and filtered. The filtrate is diluted with 25 ml of hexane and filtered. The filtrate is chromatographed HPLC on a Waters-Prep 500 instrument with two silica gel columns and hexane-ethyl acetate (4:1) as solvent. Cuts containing product are combined to give 2.3 g of yellow crystals, m.p. 153° to 154° C.

Anal. Calc'd for $C_{20}H_{14}N_2O_3$: C,72.7; H,4.3; N,8.5 Found: 72.0; H,4.3; N,8.3.

REFERENCE EXAMPLE 8

5-(4-Aminobenzoyl)-5,6-dihydrophenanthridine

A solution of 2.15 g of 5,6-dihydro-5-(4-nitrobenzoyl) phenanthridine in 50 ml of ethyl acetate and 0.5 g of 10% palladium-on-carbon is hydrogenated in a Parr apparatus under an atmosphere of hydrogen for three hours. The mixture is filtered through diatomaceous earth and the solvent removed to give 1.7 g of the product as a yellow foam.

REFERENCE EXAMPLE 9

6,11-Dihydro-5-(4-nitrobenzoyl)-5H-dibenz[b,e] azepine

A mixture of 2.34 g (12 mmol) of 6,11-dihydro-5H-dibenz [b,e]azepine, 2.23 g (12 mmol) of 4-nitrobenzoyl chloride, 1.94 g (15 mmol) of diisopropylethylamine and 70.5 mg of 4-(dimethylamino)pyridine in 25 ml of dichloromethane is stirred at room temperature for 2 hours, refluxed for 3 hours and allowed to stand at room temperature for 2 days. The mixture is washed with water, 1N sodium bicarbonate, water, 1N HCl,-brine and dried ($Na_2SO_4$). The solvent is removed to give 4.0 g of solid. Trituration with ethyl acetate and filtering gives 2.85 g of off-white crystals, m.p. 185°–188° C.

Anal. Calc'd for $C_{21}H_{16}N_2O_3$ 0.5 $H_2O$: C,71.4; H,4.7; N,7.9. Found: C,71.5; H,4.5; N,7.9.

REFERENCE EXAMPLE 10

5-(4-Aminobenzoyl)-6,11-dihydro-5H-dibenz[b,e] azepine

To a solution of 4.5 g of 6,11-dihydro-5-(4-nitrobenzoyl)-5H-dibenz[b,e]azepine in 230 ml of glacial acetic acid is added 0.58 g of 10% palladium-on-carbon and the mixture under hydrogen (38 psi) shaken in a Parr hydrogenator for 6.5 hours. The mixture is filtered through diatomaceous earth and the filtrate concentrated to give 4.0 g of solid. The solid is extracted with 100 ml of dichloromethane and the extract washed with water, dried ($Na_2SO_4$). The solvent is removed to give 4.0 g of yellow crystals, m.p. 168°–175° C. A sample chromatographed on a thick layer silica gel plate with hexane-ethyl acetate (8:7) as solvent gives yellow crystals, m.p. 173°–175° C.

Anal. Calc'd for $C_{21}H_{18}N_2O$: C,80.2; H,5.8; N,8.9. Found: C,79.2; H,6.0; N,8.8.

REFERENCE EXAMPLE 11

2-Chloro-5H-dibenz[b,e]azepine-6,11-dione

Chlorine gas is bubbled into a mixture (partial suspension) of 1.0 g (450 mmol) of 5H-dibenz[b,e]azepine-6,11-dione in 50 ml of glacial acetic acid. The temperature of the mixture rises to 38° C. On standing, as the temperature of the solutions decreases, a white solid precipitates. The mixture is filtered to give 0.40 g of solid (mixture of starting material and product in ratio of 1:8). The filtrate on standing gives 0.10 g of product as crystals, m.p. 289°–293° C.

REFERENCE EXAMPLE 12

10,11-Dihydro-N,N-dimethyldibenz[b,f][1,4] oxazepine-2-sulfonamide

To 5.88 g of 10,11-dihydro-N,N-dimethyl-11-oxodibenz [b,f][1,4]oxazepine-2-sulfonamide in 5 ml of tetrahydrofuran is added 20 ml of a molar solution of borane-dimethylsulfide in tetrahydrofuran. The mixture is stirred overnight and then refluxed for 2 hours. The mixture is chilled, diluted with 10 ml of methanol and then concentrated, methanol added again and the mixture concentrated. To the mixture is added 20 ml of 2N NaOH and the mixture refluxed for 2 hours. The mixture is extracted with dichloromethane, the extract dried (MgSO$_4$) and filtered. The filtrate is passed through a thin pad of hydrous magnesium silicate and the pad washed with dichloromethane. The filtrate is concentrated to give 4.8 g of crystals, m.p. 99°–102° C. Recrystallization from diisopropylether-dichloromethane gives 3.96 g of crystals, m.p. 109°–110° C. Mass Spectrum (FAB) 305(M+H).

Anal. Calc'd for C$_{15}$H$_{16}$N$_2$O$_3$S: C,59.2; H,5.3; N,9.2; S,10.6. Found: C,57.6; H,5.2; N,8.9; S,10.1.

REFERENCE EXAMPLE 13

10,11-Dihydro-N,N-dimethyl-10-(4-nitrobenzoyl) dibenz[b,f][1,4]oxazepine-2-sulfonamide A mixture of 0.9 g of 10,11-dihydro-N,N-dimethyldibenz[b,f][1,4]oxazepine-2-sulfonamide and 0.55 g of 4-nitrobenzoyl chloride in 3 ml of pyridine is stirred for 7 hours. To the mixture is added 20 ml of 2N hydrochloric acid and the mixture is extracted with ethyl acetate. The extract is washed with 5 ml of 2N HCl and three times with 5 ml of 2N Na$_2$CO$_3$. The extract is dried (MgSO$_4$) and filtered through a thin pad of hydrous magnesium silicate. The pad is washed with ethyl acetate and the filtrate concentrated to give 1.1 g of a yellow solid. Crystallization from dichloromethane-diisopropylether gives 0.62 g of crystals, m.p. 177°–178° C.

REFERENCE EXAMPLE 14

2-Chloro-5,6-dihydrophenanthridine

To a hot (70° C.) solution of 2.62 g (17 mmol) of 6(5H)-phenanthridinone in 120 ml of acetic acid is added chlorine gas for 10 minutes. The solution is allowed to cool to room temperature and the mixture filtered. The crystals are filtered to give 1.35 g of crystals, m.p. 310°–318° C.

To the preceding compound (1.57 g) in 25 ml of tetrahydrofuran is added 12 ml of a 10 molar solution of boron-dimethylsulfide in tetrahydrofuran. The mixture is refluxed for 18 hours, cooled and 15 ml of methanol is added. The mixture is concentrated under vacuum and 50 ml of 2N sodium hydroxide added. The mixture is refluxed for 2 hours and the solid filtered off and washed with water and air dried to give the product as a solid.

REFERENCE EXAMPLE 15

9-Chloro-5H-dibenz[b,e]azepin-6,11-dione

A mixture of 11.15 g of 5H-dibenz[b,e]azepin-6,11-dione and 600 ml of glacial acetic acid is heated on a steam bath until the solid dissolves. To the solution (70° C.) is added chlorine gas chlorine is bubbled through the solution until a precipitate begins to form. The mixture is allowed to cool to room temperature and is filtered to give 7.3 g of product, m.p. 290° C. to 295° C.

REFERENCE EXAMPLE 16

9-Chloro-6,11-dihydro-5H-dibenz[b,e]azepine

To a mixture of 7.28 g of 9-chloro-5H-dibenz[b,e]azepin-6,11-dione in 25 ml of tetrahydrofuran under argon is added 8.5 ml of 10 molar boron-dimethylsulfide in tetrahydrofuran. The mixture is stirred 18 hours at room temperature, 30 ml of tetrahydrofuran added and the mixture refluxed for 3 hours (solids dissolved). The solution is cooled to room temperature and 25 ml of methanol added dropwise. The volatiles are removed under vacuum. To the residue is added 100 ml of 2N NaOH. The mixture is refluxed overnight and filtered. The solid is extracted with dichloromethane and the extract is washed with 2N citric acid, water and dried (Na$_2$SO$_4$). The solvent is removed to give 4.2 g of solid which is triturated with ethyl acetate-hexane (1:2) to give crystals, m.p. 137° C. to 141° C.

REFERENCE EXAMPLE 17

10,11-Dihydrodibenz[b,f][1,4]thiazepine

To a mixture of 3.3 g of 10,11-dihydro-11-oxodibenz[b,f][1,4]thiazepine in 25 ml of tetrahydrofuran is added 4.0 ml of 10 molar borane-dimethylsulfide in tetrahydrofuran. The mixture is stirred at room temperature for 18 hours, 50 ml of anhydrous methanol added and the solvent removed. An additional 3 ml of methanol is added and the solvent removed to give white crystals. A sample is purified by chromatography on silica gel with hexane-chloroform-ethyl acetate (2:1:1) as solvent to give white crystals, m.p. 145°–148° C.

The following compounds are prepared as described in Reference Example 17.

REFERENCE EXAMPLE 18

4-Methyl-10,11-dihydrodibenz[b,f][1,4]thiazepine

REFERENCE EXAMPLE 19

4-Chloro-10,11-dihydrodibenz[b,f][1,4]thiazepine

REFERENCE EXAMPLE 20

2-Methyl-10,11-dihydrodibenz[b,f][1,4]thiazepine

REFERENCE EXAMPLE 21

2-Chloro-10,11-dihydrodibenz[b,f][1,4]thiazepine

REFERENCE EXAMPLE 22

2-Methoxy-10,11-dihydrodibenz[b,f][1,4]thiazepine

REFERENCE EXAMPLE 23

8-Chloro-10,11-dihydrodibenz[b,f][1,4]thiazepine

REFERENCE EXAMPLE 24

4,8-Dichloro-10,11-dihydrodibenz[b,f][1,4]thiazepine

REFERENCE EXAMPLE 25

8-Chloro-4-methyl-10,11-dihydrodibenz[b,f][1,4]thiazepine

REFERENCE EXAMPLE 26

8-Methoxy-10,11-dihydrodibenz[b,f][1,4]thiazepine

REFERENCE EXAMPLE 27

7-Chloro-4-methyl-10,11-dihydrodibenz[b,f][1,4]thiazepine

The following compounds are prepared as described in Reference Example 12.

REFERENCE EXAMPLE 28

2-Chloro-10,11-dihydrodibenz[b,f][1,4]-oxazepine

REFERENCE EXAMPLE 29

2-Methyl-10,11-dihydrodibenz[b,f][1,4]-oxazepine

REFERENCE EXAMPLE 30

4-Chloro-10,11-dihydrodibenz[b,f][1,4]-oxazepine

REFERENCE EXAMPLE 31

3-Methyl-10,11-dihydrodibenz[b,f][1,4]-oxazepine

REFERENCE EXAMPLE 32

7-Chloro-10,11-dihydrodibenz[b,f][1,4]-oxazepine

REFERENCE EXAMPLE 33

8-Chloro-10,11-dihydrodibenz[b,f][1,4]-oxazepine

REFERENCE EXAMPLE 34

2,4-Dichloro-10,11-dihydrodibenz[b,f][1,4]-oxazepine

REFERENCE EXAMPLE 35

4,8-Dichloro-10,11-dihydrodibenz[b,f][1,4]-oxazepine

REFERENCE EXAMPLE 36

4-Chloro-8-methyl-10,11-dihydrodibenz[b,f][1,4]-oxazepine

REFERENCE EXAMPLE 37

4-Methyl-7-chloro-10,11-dihydrodibenz[b,f][1,4]-oxazepine

REFERENCE EXAMPLE 38

1-Chloro-4-methyl-10,11-dihydrodibenz[b,f][1,4]-oxazepine

REFERENCE EXAMPLE 39

2-Fluoro-10,11-dihydrodibenz[b,f][1,4]-oxazepine

REFERENCE EXAMPLE 40

N-(2-Iodophenyl)-2-10-iodophenylacetamide

A solution of 13.32 g (0.05 mol) of 2-iodophenylacetic acid in 75 ml thionyl chloride is refluxed for 2 hours, and the volatiles removed under vacuum. Toluene is added (3 times) and the solvent removed under vacuum after each addition to give 2-iodophenylacetyl chloride as a gum. To the preceding compound (0.05 mol) in a mixture of 100 ml of toluene-dichloromethane (1:1) is added 11 g (0.05 mol) of 2-iodoaniline and (0.10 mol) of diisopropylethylamine. The mixture is stirred at room temperature overnight and the solvent removed. The residue is dissolved in dichloromethane and the solution washed with 1N HCl, saturated sodium bicarbonate, brine and dried ($Na_2SO_4$). The solvent is removed and the residue recrystallized from methanol-ether to give 16.0 g of light brown crystals, m.p. 160°–163° C.

REFERENCE EXAMPLE 41

2-Iodo-N-(2-iodophenyl)benzeneethanamine

To a suspension of 1.39 g (3 mmol) of 2-iodo-N-(2-iodophenyl)benzeneacetamide in 30 ml of tetrahydrofuran-dichloromethane (1:1) is added 3.75 ml of 2.0 molar borane-dimethylsulfide in tetrahydrofuran. The solution is stirred 1 hr at room temperature and then refluxed for 16 hours. The mixture is cooled and water slowly added dropwise until gas evolution ceases. The volatiles are removed under vacuum and the aqueous residue made alkaline with 2N sodium hydroxide. The mixture is extracted with ether (50 ml) and the extract is washed with brine and dried ($Na_2SO_4$). The solution is filtered through a thin pad hydrous magnesium silicate and the filter pad is washed with ether and the filtrate evaporated. The residual solid is washed with isooctane to give 1.20 g of white solid. Recrystallization from diethylether/hexane gives white crystals.

REFERENCE EXAMPLE 42

N-(4-Nitrobenzoyl-N-(2-iodophenyl)-2-iodobenzeneethylamine

To a solution of 0.90 g of 2-iodo-N-(2-iodophenyl)benzeneethanamine in 4 ml of tetrahydrofuran is added 0.41 g of triethylamine, and 0.57 g of 4-nitrobenzoyl chloride. The mixture is stirred at room temperature for 2 hours and the solvent removed under vacuum. The residue is dissolved in ethyl acetate-dichloromethane (5:1) and the solution washed with 1N HCl, saturated $NaHCO_3$, brine and dried ($Na_2SO_4$). The solution is filtered through a thin pad of hydrous magnesium silicate. The filtrate is evaporated and the residual solid triturated with diethyl ether and hexane to give 1.10 g of product as a white solid.

REFERENCE EXAMPLE 43

5-(4-Nitrobenzoyl)-6,7-dihydro-5H-dibenz[b,d]azepine

To a solution of 0.90 g of N-(4-nitrobenzoyl)-N-(2-iodophenyl)-2-iodobenzeneethylamine in 10 ml of N,N-dimethylpropyleneurea (DMPU) is added 1.91 g of "activated" copper bronze. The mixture is stirred and heated at 195° for 2 days, cooled and slowly dropped into 100 ml of 0.5N HCl with stirring. The precipitate is filtered, washed with $H_2O$ and air dried (1.0 g of solid). The solid is extracted with ethyl acetate to give 0.50 g of solid. Chromatography on thick layer silica gel plates with ethyl acetate-hexane (1:2) as solvent gives 0.15 g of yellow solid.

REFERENCE EXAMPLE 44

5-(4-Aminobenzoyl)-6,7-dihydro-5H-dibenz[b,d]azepine

A solution of 0.15 g of 5-(4-nitrobenzoyl)-6,7-dihydro-5H-dibenz[b,d]azepine in 20 µl of ethanol-ethyl acetate and 10 mg of 10% palladium-on-carbon is hydrogenated under 35 pounds per square inch of hydrogen for 8 hr. The mixture is filtered through diatomaceous earth and the filtrate evaporated to give 0.13 g of product as a light yellow solid.

REFERENCE EXAMPLE 45

5-(4-Nitro-3-methylbenzoyl)-6,11-dihydro-5H-dibenz[b,e]azepine

A mixture of 1.17 g of 6,11-dihydro-5H-dibenz[b,e]azepine, 1.20 g of 3-methyl-4-nitrobenzoyl chloride, 0.80 ml of diisopropylethylamine in 25 ml of dichloromethane is stirred 18 hours at room temperature. The mixture is washed with water and dried ($Na_2SO_4$). The solution is filtered through a thin pad of hydrous magnesium silicate. The filtrate is concentrated and diluted while hot with hexane to give 1.40 g of crystals. Recrystallization from dichloromethane-hexane gives 1.26 g of crystals, m.p. 179°–180° C.

REFERENCE EXAMPLE 46

5-(4-Amino-3-methylbenzoyl)-6,11-dihydro-5H-dibenz[b,e]azepine

A mixture of 1.11 g of 5-(4-nitro-3-methylbenzoyl)-6,11-dihydro-5H-dibenz[b,e]azepine, 50 ml of ethanol, 0.30 g of anhydrous hydrazine and 0.27 g palladium-on-carbon is refluxed 1 hour, and then filtered through diatomaceous earth. The filtrate is evaporated and the residue recrystallized from dichloromethane-hexane to give 0.80 g of crystals, m.p. 203°–204° C.

REFERENCE EXAMPLE 47

4-[(6,11-Dihydro-5H-dibenz[b,e]azepin-5-yl)carbonyl]benzoic acid

A mixture of 0.975 g of 6,11-dihydro-5H-dibenz[b,e]azepine and 0.20 g of NaH (60% in oil) in 20 ml of tetrahydrofuran is stirred at room temperature for 0.5 hr. Then 1.1 g of mono-methyl terephthalyl chloride (prepared from mono-methyl terephthalate and thionyl chloride) is added and the mixture refluxed 18 hours. The mixture is cooled, poured into ice water and filtered. The solid is triturated with dichloromethane-hexane to give 1.0 g of crystals, m.p. 182°–185° C. The preceding compound, methyl 4-[(6,11-dihydro-5H-dibenz[b,e]azepin-5-yl)carbonyl]benzoate (2.11 g), 20 ml of 2N NaOH and 20 ml of methanol is stirred overnight and then heated on a steam bath for 1 hr. The solvent is removed to give a solid. The solid is extracted with ether (discarded). The solid is dissolved in water and the solution acidified with citric acid to give a solid. The solid is filtered and washed with water to give 1.84 g of crystals, m.p. 220°–225° C.

REFERENCE EXAMPLE 48

2-Methylfurane-3-carbonyl chloride

A mixture of 4.0 g of methyl-2-methylfurane-3-carboxylate, 30 ml of 2N NaOH and 15 ml methanol is refluxed for 1.5 hours. The solvent is removed under vacuum to give a solid. The solid is extracted with dichloromethane (discarded). The solid is dissolved in water and the solution acidified with 2N citric acid to give a solid. The solid is washed with water and dried to give crystals 1.05 g of crystals of 2-methylfuran-3-carboxylic acid. The preceding compound (0.95 g) and 3 ml of thionyl chloride is refluxed for 1 hr. The solvent is removed, toluene added (20 ml, three times) and the solvent removed to give the product as an oil.

REFERENCE EXAMPLE 49

2-Chloro-5-(4-nitrobenzoyl)-6,11-dihydro-5H-dibenz[b,e]azepine

A mixture of 2.05 g of 2-chloro-6,11-dihydro-5H-dibenz[b,e]azepine, 2.15 g of 4-nitrobenzoyl chloride, 1.50 g of N,N-diisopropylethylamine, 54 mg of 4-(dimethylamino)pyridine in 15 ml of dichloromethane is refluxed for 18 hours. The mixture is cooled and washed with $H_2O$, 1N HCl, 1M $NaHCO_3$, brine and dried ($Na_2SO_4$). The solution is filtered through a thin pad of hydrous magnesium silicate and the pad washed with dichloromethane. The filtrate is concentrated and the residue recrystallized from dichloromethane-hexane to give 2.33 g of crystals, m.p. 198°–201° C.

REFERENCE EXAMPLE 50

2-Chloro-5-(4-aminobenzoyl)-6,11-dihydro-5H-dibenz[b,e]azepine

A solution of 2.1 g of 2-chloro-5-(4-nitrobenzoyl)-6,11-dihydro-5H-dibenz[b,e]azepine in 400 ml of ethyl acetate-ethanol (1:1) and 0.25 g of palladium-on-carbon is hydrogenated in a Parr hydrogenator under 38 pounds per square inch of hydrogen. The mixture is filtered through diatomaceous earth and the filtrate concentrated to dryness. The solid (1.94 g) is dissolved in dichloromethane and the solution filtered through a thin pad of hydrous magnesium silicate. The filter pad is washed with dichloromethane and the filtrate concentrated. The residue is crystallized from dichloromethane-hexane to give 1.43 g of crystals, m.p. 211°–214° C.

REFERENCE EXAMPLE 51

1,2,3,4-Tetrahydro-1-(4-nitrobenzoyl)-5H-1-benzazepine

To a solution of 5.0 g of 1,2,3,4-tetrahydro-5H-1-benzazepine and 5.91 ml of triethylamine in 50 ml of dichloromethane, chilled in an ice bath, is added, dropwise, 6.32 g of 4-nitrobenzoyl chloride in 75 ml of dichloromethane. The mixture is stirred at 0° C. for 1.5 hr and then at room temperature for 18 hours. The mixture is washed with $H_2O$, 2M HCl, 1M NaOH and dried ($Na_2SO_4$). The solvent is removed and the residue recrystallized from ethanol with the aid of activated carbon to give 7.75 g of light yellow crystals, m.p. 148.5°–150.5° C.

REFERENCE EXAMPLE 52

1,2,3,4-Tetrahydro-1-(4-nitrobenzoyl)-5H-1-benzapin-5-one

A sample (3.0 g) of 1,2,3,4-tetrahydro-1-(4-nitrobenzoyl)-5H-1-benzazepine is dissolved in 200 ml of tert-butanol (with heat). To the solution is added 8 ml of $H_2O$ and 6.72 g of anhydrous $MgSO_4$ and then a solution of 3.36 g of $KMnO_4$ in 100 ml of $H_2O$ is added and the mixture heated at 65° C. for 20 hours. The mixture is filtered through diatomaceous earth and the filter pad washed with tert-butanol. The combined filtrate is concentrated (t-butanol removed) under vacuum. The solid is filtered and washed well with water to give (after drying) 2.7 g of crystals. Chromatography on silica gel with hexane-ethyl acetate

REFERENCE EXAMPLE 53

3,4-Dihydro-1H-1-benzazepine-2,5-dione

To a solution of 225 ml of glacial acid and 8.5 ml of concentrated sulfuric acid is added 49.54 g (0.30 mol) of 2'-nitroacetophenone and 47.02 g (0.50 mol) of glyoxylic acid (hydrated). The mixture is heated at 100° C. 16 hours. The mixture is cooled and poured over crushed ice. After the ice melts, the mixture is filtered and the solid washed with cold water. The solid is dried and recrystallized from dichloromethane-hexane to give 20.1 g of 3-(2-nitrobenzoyl)acrylic acid as white crystals, m.p. 153°–158° C. A solution of the preceding compound (9.0 g) in 80 ml of ethanol and 1.6 g of palladium-on-carbon is hydrogenated in a Parr hydrogenator under 30 pounds per square inch of hydrogen for 20 hours. The mixture is filtered through diatomaceous earth and the solvent is removed. The residue (7.0 g) is chromatographed on silica gel with hexane-ethyl acetate (1:1) as solvent to give 4.0 g of 3-(2-aminobenzoyl) acrylic acid as an orange solid, m.p. 103°–107° C. A 0.50 g sample of the preceding compound, 0.36 ml of triethylamine and 0.43 ml of diethoxyphosphinyl cyanide in 20 ml of dichloromethane is stirred at room temperature for 5 days. The solvent is removed, ethyl acetate is added and the mixture washed with water, 2N citric acid, 1M NaHCO$_3$, brine and dried (Na$_2$SO$_4$). The solvent is removed and the residue purified by chromatography over silica gel with ethyl acetate-hexane (1:1) as solvent to give 0.190 g of light brown crystals, m.p. 168°–170° C.

REFERENCE EXAMPLE 54

4-[(Dimethylamino)methylene]-1,2,3,4-tetrahydro-1-(4-nitrobenzoyl)-5M-1-benzazepin-5-one A mixture of 0.780 g of 1,2,3,4-tetrahydro-1-(4-nitrobenzoyl)-5H-1-benzazepin-5-one and 10 ml of tert-butoxy bis(dimethylamino)methane (Bredereck's Reagent) is heated on a steam bath while stirring for 1.5 hours (solid dissolved). Cooling gives a solid and the mixture is diluted with ethyl acetate and filtered. The solid is dissolved in dichloromethane-ethyl acetate (7:3) and the solution filtered through a thin pad of hydrous magnesium silicate. The filter pad is washed with dichloromethane-ethyl acetate (7:3) and the combined filtrate evaporated to give 0.43 g of yellow crystals, Mass Spec (CI) MH$^+$=366, m.p. 180°–183° C.

REFERENCE EXAMPLE 55

6,7-Dihydro-7-(4-nitrobenzoyl)-5H-pyrimido[5,4-d][1]benzazepine

To a solution of 0.152 g (1.89 mmol) of formamidine hydrochloride in 10 ml of methanol under argon is added 0.102 g (1.89 mmol) of sodium methoxide. After stirring 5 min., a solution of 0.46 g (1.26 mmol) of 4-[(dimethylamino)methylene]-1,2,3,4-tetrahydro-1-(4-nitrobenzoyl)-5H-1-benzazepine-5-one in 5 ml of methanol is added and the mixture stirred 18 hours. The solvent is removed, dichloromethane added, and the mixture filtered. The solid is washed with dichloromethane. The combined filtrate is concentrated to dryness to give 0.47 g of tan foam. The preceding solid is purified by chromatography on silica gel. The compound is dissolved in ethyl acetate-dichloromethane and applied to the column. The column is then eluted with ethyl acetate to give 0.25 g of product as pale yellow crystals.

REFERENCE EXAMPLE 56

4-[(Dimethylamino)methylene]-3,4-dihydro-1H-1-benzazepine-2,5-dione

A mixture of 0.250 g (1.43 mmol) of 3,4-dihydro-1H-1-benzazepine-2,5-dione and 5.5 ml (4.93 g, 41.5 mmol) of N,N-dimethylformamide, dimethylacetal is heated at 90° C. for 1.5 hour. The mixture is cooled, diluted with diethylether and filtered. The solid is washed well with diethylether and dried to give 0.26 g of tan crystals, m.p. 203°–205° C.

REFERENCE EXAMPLE 57

2-Methyl-6,7-dihydro-5H-pyrimido[5,4-d][1]benzazepine

To a solution of 0.308 g (3.26 mmol) of acetamidine hydrochloride in 15 ml of methanol under argon is added 0.176 g of (3.26 mmol) of sodium methoxide and the mixture stirred for 5 min. To the mixture is added 0.50 g (2.17 mmol) of 4-[(dimethylamino)methylene]-1,2,3,4-tetrahydro-5H-1-benzazepine-2,5-dione and the mixture stirred at room temperature overnight. The mixture (containing thick precipitate) is diluted with 3 ml of methanol, chilled and filtered. The filtrate is concentrated to dryness. The residue and original solid are combined and chloroform added. The mixture is washed with water, the organic layer is treated with activated carbon and then filtered through a thin pad of hydrous magnesium silicate. The filtrate is evaporated to give 0.41 g of crystals, m.p. 257°–258° C.

The preceding compound is heated with 5 equivalents of lithium hydride in dioxane for 24 hours to give the product as a solid.

REFERENCE EXAMPLE 58

10,11-Dihydro-10-(4-nitrobenzoyl)dibenz[b,f][1,4]thiazepine

To a solution of 1.6 g of 10,11-dihydrodibenz[b,f][1,4]thiazepine in 30 ml of dichloromethane is added 0.1 g of 4-(N,N-dimethylamino)pyridine, 4 ml of triethylamine and 1.0 g of 4-nitrobenzoyl chloride and the mixture is stirred for 16 hours. The mixture is poured into ice-water and extracted with 3×150 ml of dichloromethane. The combined organic extract is washed with water, 2N HCl, 2N Na$_2$CO$_3$, water and dried (MgSO$_4$). The solvent is removed in vacuo and the product (2.6 g) purified by chromatography on silica gel with hexane-ethyl acetate (4:1) as eluent to give 2.2 g of crystals, m.p. 147°–149° C.

REFERENCE EXAMPLE 59

10,11-Dihydro-10-(4-aminobenzoyl)dibenz[b,f][1,4]thiazepine

A mixture of 2.2 g of 10,11-dihydro-10-(4-nitrobenzoyl)dibenz[b,f][1,4]thiazepine in 150 ml of methanol is shaken in a Parr hydrogenator under 50 pounds per square inch of hydrogen for 72 hours. The mixture is filtered through diatomaceous earth and the filtrate evaporated in vacuo. The residue is recrystallized from chloroform-hexane to give 1.8 g of crystals, m.p. 52°–55° C.

REFERENCE EXAMPLE 60

4-[N-Methyl-N-(2-methylbenzoyl)amino]benzoic acid

A sample of 1.51 g of sodium hydride (60% in oil) is washed with hexane under argon to remove the oil. To the washed sodium hydride is added 5 ml of N,N-dimethylformamide. To this mixture is added dropwise a solution of 8.69 g of ethyl 4-[(2-methylbenzoyl)amino]benzoate in 20 ml of N,N-dimethylformamide. The mixture is stirred at room temperature for 0.5 hour and then 5.23 g of methyl iodide is added. The mixture is stirred at room temperature for 16 hours. The mixture is diluted with water and extracted with dichloromethane. The extract is dried ($Na_2SO_4$), concentrated to reduce the volume and the solution filtered through a thin pad of hydrous magnesium silicate. The filtrate is concentrated in vacuo to give 11 g of an oil (1:1 mixture of product and N,N-dimethylformamide). The preceding product, ethyl 4-[N-methyl-N-(2-methylbenzoyl)amino]benzoate, (11 g) is dissolved in 30 ml of methanol and 25 ml of 2N NaOH added. The mixture is refluxed for 2 hours and the solovent removed. The residue is extracted with ether (discard) and the remaining residue dissolved in 50 ml of water. The basic solution is acidified with 2N citric acid and the solid filtered off and washed with water. The product is air dried to give 6.72 g of crystals, m.p. 187°–190° C.

REFERENCE EXAMPLE 61

4-[N-Methyl-N-(2-methylbenzoylamino]benzoyl chloride

A solution of 6.72 g of 4-[N-methyl-N-(2-methylbenzoyl)amino]benzoic acid in 20 ml of thionyl chloride is refluxed for one hour. The volatiles are removed in vacuo. Toluene is added to the residue and then the toluene removed in vacuo (repeated several times) to give the 7.3 g of product as a brown oil.

As described for Reference Example 60, but substituting the appropriate ethyl 4-[(N-aroyl)amino]benzoate, the following compounds are prepared.

REFERENCE EXAMPLE 62

4-[N-Methyl-N-(2-chlorobenzoyl)amino]benzoic acid

REFERENCE EXAMPLE 63

N-[N-Methyl-N-(2,5-dichlorobenzoyl)amino] benzoic acid

REFERENCE EXAMPLE 64

N-[N-Methyl-N-(2,4-dichlorobenzoyl)amino] benzoic acid

REFERENCE EXAMPLE 65

4-[N-methyl-N-(2-chloro-4-methylbenzoyl)amino] benzoic acid

REFERENCE EXAMPLE 66

4-[N-methyl-N-(2-methyl-4-chlorobenzoyl)amino] benzoic acid

REFERENCE EXAMPLE 67

4-[N-Methyl-N-(2,4-dimethylbenzoyl)amino] benzoic acid

REFERENCE EXAMPLE 68

4-[N-Methyl-N-(2,3-dimethylbenzoyl)amino] benzoic acid

REFERENCE EXAMPLE 69

4-[N-Methyl-N-(2-methoxybenzoyl)amino]benzoic acid

REFERENCE EXAMPLE 70

4-[N-Methyl-N-(2-trifluoromethoxybenzoyl)amino] benzoic acid

REFERENCE EXAMPLE 71

4-[N-Methyl-N-(2,4-dimethoxybenzoyl)amino] benzoic acid

REFERENCE EXAMPLE 72

4-[N-Methyl-N-(2-methoxy-4-chlorobenzoyl)amino] benzoic acid

REFERENCE EXAMPLE 73

4-[N-Methyl-N-(2-methylthiobenzoyl)amino] benzoic acid

REFERENCE EXAMPLE 74

4-[N-Methyl-N-(2-methylthiophen-3-ylcarbonyl) amino]benzoic acid

REFERENCE EXAMPLE 75

4-[N-Methyl-N-(3-methylthiophene-2-ylcarbonyl) amino]benzoic acid

REFERENCE EXAMPLE 76

4-[N-Methyl-N-(2-methylfuran-3-ylcarbonyl)amino] benzoic acid

REFERENCE EXAMPLE 77

4-[N-Methyl-N-(3-methylfuran-2-ylcarbonyl]amino] benzoic acid

REFERENCE EXAMPLE 78

4-[N-Methyl-N-(phenylacetyl)amino]benzoic acid

REFERENCE EXAMPLE 79

4-[N-Methyl-N-[2-Chlorophenylacetyl)amino] benzoic acid

REFERENCE EXAMPLE 80

4-[N-Methyl-N-(2-methoxyphenylacetyl)amino] benzoic acid

REFERENCE EXAMPLE 81

4-[N-Methyl-N-(2-methylphenylacetyl)amino] benzoic acid

REFERENCE EXAMPLE 82

4-[N-Methyl-N-(cyclohexylcarbonyl)amino]benzoic acid

REFERENCE EXAMPLE 83

4-[N-Methyl-N-[3-cyclohexenecarbonyl)amino] benzoic acid

REFERENCE EXAMPLE 84

4-[N-Methyl-N-(cyclohexylacetyl)amino]benzoic acid

REFERENCE EXAMPLE 85

5,6-Dihydropyrido[2,3-b][1,4]benzothiazepine

To a suspension of 11.67 g of 2-thiobenzoic acid in a mixture of 32 ml of ethanol and 11 ml of water is added portionwise 12.72 g of solid sodium bicarbonate. After the complete addition, the mixture is stirred for 15 minutes and 10.0 g of 2-chloro-3-nitropyridine added portionwise. The mixture is refluxed for 2 hours, cooled and then concentrated in vacuo. The residual aqueous solution is diluted with 15 ml of water, acidified with 2N HCl and extracted twice with 250 ml of ethyl acetate. The extract is concentrated under vacuum to give a yellow solid residue. The residue is dissolved in a minimum of ethyl acetate by heating on a steam bath. The solution is cooled overnight and filtered. (2.5 g of starting material). The filtrate is concentrated, chilled and filtered to give 12.5 g of 2-(3-nitro-2-pyridinylthio)benzoic acid as a yellow solid. The preceding compound (5.0 g) and 0.75 g of Pd/C in 60 ml of ethanol is shaken in a Parr hydrogenator under 45 psi of hydrogen for 18 hours. The mixture is filtered through diatmoaceous earth and the filter cake washed with 200 ml of dichloromethane. The combined filtrate is evaporated in vacuo to give a solid.

The solid is triturated with ethanol and filtered to give 3.6 g of yellow solid. This solid (3.0 g) is again hydrogenated with Pd/c (0.50 g) in 50 ml of ethanol and 30 ml of acetic acid under 45 psi of hydrogen for 18 hours. The mixture is filtered through diatomaceous earth and the filter cake washed with methanol. The combined filtrate is concentrated in vacuo to give 1.6 g of solid. This solid in 25 ml of N,N-dimethylformamide is again reduced with 0.80 g of Pd/C under 45 psi of hydrogen to give 0.57 g of solid. Recrystalization from ethyl acetate gives 0.28 g of 2-(3-amino-2-pyridinylthio)benzoic acid. The preceding compound (0.20 g) is heated in 2-hydroxypyridine at 170° C. to give 5,6-dihydropyrido[2,3-b][1,4]benzothiazepine as a yellow solid. The preceding compound is reacted with borane-dimethylsulfide as described for Reference Example 17 to give the product as a solid.

REFERENCE EXAMPLE 86

5,6-Dihydro-5-(4-aminobenzoyl)pyrido[2,3-b][1,4] benzothiazepine

To a mixture of 10 mmol of 5,6-dihydropyrido[2,3-b][1,4]benzothiazepine and 11 mmol of 4-nitrobenzoyl in 25 ml of dichloromethane chilled to 0° C. is added 15 mmol of triethylamine. The mixture is stirred at room temperature for 5 hours and then diluted with 75 ml of dichloromethane. The mixture is washed with $H_2O$, 2N citric acid, $NaHCO_3$, brine and dried ($Na_2SO_4$). The solvent is removed to give 5,6-dihydro-5-(4-nitrobenzoyl)pyrido[2,3-b][1,4] benzothiazepine as a solid. A mixture of the preceding compound (5 mmol), 0.3 g of Pd/C and 3 mmol of hydrazine in 25 ml of ethanol is refluxed for 3 hours. The mixture is filtered through diatomaceous earth and the filtrate evaporated in vacuo to give a solid. The solid is purified by chromatography on silica gel with ethyl acetate-hexane as solvent to give the product as a solid.

REFERENCE EXAMPLE 87

5,11-Dihydro-6-(4-aminobenzoyl)-6H-pyrido[2,3-e] [1]-benzazepine

To a mixture of 10 mmol of 5,11-dihydro-6H-pyrido[2,3-e][1]benzazepine, and 11 mmol of 4-nitrobenzoyl chloride in 25 ml of dichloromethane, chilled to 0° C., is added 15 mmol of triethylamine. The mixture is stirred at room temperature for 5 hours and diluted with 75 ml of dichloromethane. The mixture is washed with $H_2O$, 2N citric acid, $NaHCO_3$, brine and dried ($Na_2SO_4$). The solvent is removed in vacuo to give 5,11-dihydro-6-(4-nitrobenzoyl)-6H-pyrido [3,2-e][1]benzazepine as a solid. A mixture of the preceding compound (5 mmol) 0.3 g of Pd/C and 3 mmol of hydrazine in 25 ml of ethanol is refluxed 3 hours. The mixture is filtered through diatomaceous earth and the filtrate evaporated an vacuo to a solid. The solid is purified by chromatography on silica gel to give the product as a solid.

REFERENCE EXAMPLE 88

2-Nitro-2'-carboxy-diphenylamine

A stirred solid mixture of 13.7 g of anthranilic acid, 20.2 g of o-bromonitrobenzene, 13.8 g of anhydrous potassium carbonate and 0.1 g of copper metal is heated 200° C. oil bath. The reaction mixture is heated for 2 hours, cooled and the solid washed with ether (3×100 ml). The solid is dissolved in hot water and filtered. The filtrate is acidified with 40 ml of HCl and the resulting solid is collected and dried to give 20.5 g of the desired product as a solid, m.p. 262°–265° C.

REFERENCE EXAMPLE 89

2-Amino-2'-carboxy-diphenylamine

A solution of 7.3 g of 2-nitro-2'-carboxydiphenylamine in 50 ml of methanol containing 10% palladium-on-carbon is hydrogenated under 42 pounds of pressure for 24 hours. The reaction mixture is filtered through diatomaceous earth. The filtrate is evaporated to dryness in vacuo to give 6.6 g of the desired product as a solid, m.p. 72°–75° C.

REFERENCE EXAMPLE 90

5,11-Dihydro-10H-dibenz[b,e][1,4]diazepine-11-one

A mixture of 6.6 g of 2-amino-2'-carboxydiphenylamine in 300 ml of xylene is heated at reflux for 20 hours. The xylene is evaporated in vacuo to a residue which is evaporated from 210 ml of toluene in vacuo to a residue which is evaporated from 50 ml of chloroform to give a residue. The residue is dissolved in 10 ml of tetrahydrofuran and added to 400 ml of ice-cold hexane. The resulting solid is collected, to give 4.3 g of the desired product as a solid, m.p. 121°–123° C.

REFERENCE EXAMPLE 91

5,11-Dihydro-10H-dibenz[b,e][1,4]diazepine

To a stirred solution of 4.3 g of 5,11-dihydro-10H-dibenz[b,e][1,4]diazepin-11-one in 50 ml of tetrahydrofuran, under nitrogen and cooled to 0° C. is added 4.0 ml of 10N methyl sulfide-borane complex. The ice bath is removed after 30 minutes and the reaction mixture stirred at room temperature for 18 hours. The reaction mixture is cooled in an ice bath and 30 ml of anhydrous methanol added dropwise and evaporated to dryness in vacuo. Another 30 ml of methanol is added and evaporated to a residue. The residue is quenched with 30 ml of 40% sodium hydroxide followed by heating at 110° C. for 45 minutes and cooling to room temperature. The reaction mixture is diluted with 200 ml of water and extracted with methylene chloride (3×100 ml). The combined extracts are washed with 1N HCl, water and 0.5N NaOH. The organic layer is dried and evaporated in vacuo to give 3.2 g of the desired product, m.p. 114°–116° C.

REFERENCE EXAMPLE 92

5H-Dibenz[b,e]azepine-6,11-dione

A mixture of 2.50 g of 2-aminobenzophenone-2'-carboxylic acid in 50 ml of xylene is stirred at reflux for 23 hours. The mixture is filtered to give 1.82 g of the desired product as a solid.

REFERENCE EXAMPLE 93

2-Chloro-5H-dibenz[b,e]azepine-6,11-dione

A mixture of 1.0 g of 5H-dibenz[b,e]azepine-6,11-dione in 50 ml of acetic acid is stirred while chlorine is bubbled into the reaction mixture until saturated. The temperature increases to 38° C. After standing, a precipitate forms and is filtered, washed with hexane and air dried to give 0.62 g of solid which is purified by chromatography to give the desired product as a solid, m.p. 289°–293° C.

REFERENCE EXAMPLE 94

2-Chloro-6,11-Dihydro-5H-dibenz[b,e]azepine

To a mixture of 7.28 g of 2-chloro-5H-dibenz[b,e]azepine-6,11-dione in 25 ml of anhydrous tetrahydrofuran, under argon, is added dropwise 8.5 ml of (10M) boron-dimethyl sulfide. The reaction mixture is stirred at room temperature for 18 hours. The reaction mixture is heated at reflux for 3 hours and cooled to room temperature. While stirring, 25 ml of methyl alcohol is carefully added, followed by 100 ml of 2N NaOH. The reaction mixture is heated at reflux for 24 hours and the solid collected. The solid is dissolved in methylene chloride and washed with 2N citric acid, water and dried ($Na_2SO_4$). The volatiles are evaporated in vacuo to give 4.16 g of a residue which is crystallized from ethyl acetate-hexane to give 2.05 g of the desired product as a crystalline solid, m.p. 137°–141° C.

REFERENCE EXAMPLE 95

5,6-Dihydro-6-(4-nitrobenzoyl)-4H-isoxazolo[4,5-d][1]benzazepine

A solution of 0.250 g of 1,2,3,4-tetrahydro-4-[(dimethylamino)methylene-1-(4-nitrobenzoyl)-5H-1-benzazepin-5-one and 95.2 mg of hydroxylamine hydrochloride in 8 ml of methyl alcohol is heated at reflux under argon for 4 hours. The methanol is evaporated in vacuo to a residue which is dissolved in 10% ethyl acetate in methylene chloride and the solution passed through a pad of silica gel. The filtrate is evaporated in vacuo to give the desired product as a solid. CIMS:$MH^+$=336.

REFERENCE EXAMPLE 96

5,6-Dihydro-6-(4-aminobenzoyl)-4H-isoxazolo[4,5-d][1]benzazepine

A mixture of 0.050 g of 5,6-dihydro-6-(4-nitrobenzoyl)-4H-isoxazolo[4,5-d][1]benzazepine and 0.169 g of $SnCl_2$ 2 $H_2O$ in 2 ml of ethyl alcohol is heated at reflux under argon for 1 hour. Water and 10% $NaHCO_3$ is added until basic. The volatiles are evaporated in vacuo to a residue which is stirred with 1:1 chloroform-methanol and filtered. The filtrate is evaporated in vacuo to a residue which is dissolved in methyl alcohol, treated with activated carbon, filtered through diatomaceous earth and concentrated in vacuo to give 100 mg of the desired product as a white crystalline solid. CIMS($CH_4$):$MH^+$=306.

REFERENCE EXAMPLE 97

6,7-Dihydro-2-methyl-7-(4-nitrobenzoyl)-5H-pyrimido[5,4-d][1]benzazepine

To a stirred solution of 0.233 g of acetamidine hydrochloride in 36 ml of methyl alcohol under argon is added 0.133 g of $NaOCH_3$. After 5 minutes, 0.600 g of 4-[(dimethylamino)methylene]-1,2,3,4-tetrahydro-1-(4-nitrobenzoyl)-5H-1-benzazepin-5-one is added and stirring continued for 18 hours. The volatiles are evaporated to a residue which is dissolved in ethyl acetate and passed through a pad of silica gel. The filtrate is evaporated in vacuo to give 590 mg of the desired product as tan crystals, m.p. 211°–212° C. HR FABMS: Exact mass (M+H): 361.1295.

REFERENCE EXAMPLE 98

6,7-Dihydro-2-methyl-7-(4-aminobenzoyl)-5H-pyrimido[5,4-d][1]benzazepine

A mixture of 400 mg of 6,7-dihydro-2-methyl-7-(4-nitrobenzoyl)-5H-pyrimido[5,4-d][1]benzazepine, 87 μl of anhydrous hydrazine and 40 mg of 10% Pd/C in 22 ml of ethyl alcohol is heated at reflux for 1.25 hours, filtered through diatomaceous earth and the pad washed well with methyl alcohol. The combined filtrates are evaporated in vacuo to a residue which is dissolved in ethyl acetate and filtered through a pad of hydrous magnesium silicate and the filtrate concentrated in vacuo to a residue which is dissolved in methyl alcohol and evaporated again to give 330 mg of the desired product as a yellow foam. HR FABMS: Exact mass (M+H): 331.1555.

REFERENCE EXAMPLE 99

4-[(Dimethylamino)methylene]-1,2,3,4-tetrahydro-1-(4-nitrobenzoyl)-5H-1-benzazepin-5-one A mixture of 1.35 g of 1,2,3,4-tetrahydro-1-(4-nitrobenzoyl)-5H-1-benzazepin-5-one and 15 ml of tert-butoxy-bis(dimethylamino)methane is heated for on a steam bath for 2 hours. The volatiles are evaporated in vacuo to a residue which is stirred with ether and filtered. The cake is washed with ether and the combined filtrates evaporated in vacuo to a residue which is dissolved in 30% ethyl acetate in methylene chloride and passed through a pad of hydrous magnesium silicate. The filtrate is evaporated in vacuo to a residue which is dissolved in 30% ethyl acetate in methylene chloride and passed through a pad of hydrous magnesium silicate. The filtrate is evaporated in vacuo to a residue to give 1.60 g of yellow crystalline product, m.p. 180°–183° C.

REFERENCE EXAMPLE 100

2,4,5,6-Tetrahydro-2-methyl-6-(4-nitrobenzoyl) pyrazolo[4,3-d][1]benzazepine

A solution of 0.150 g of 4-[(dimethylamino)methylene]-1,2,3,4-tetrahydro-1-(4-nitrobenzoyl)-5H-1-benzazepin-5-one and 44 μl of methylhydrazine in 5 ml of methyl alcohol is heated at reflux for 18 hours. A precipitate forms on standing. The volaties are evaporated to a residue which is purified by column chromatography on silica gel by elution with 5% ethyl acetate-methylene chloride. The product fractions are combined and the volatiles evaporated to a residue which is dissolved in chloroform-methanol, filtered through glass wool and the filtrate evaporated in vacuo to give 0.110 g of the desired product as pale yellow crystals.

REFERENCE EXAMPLE 101

2,4,5,6-Tetrahydro-2-methyl-6-(4-nitrobenzoyl) pyrazolo[4,3-d][1]benzazepine

A mixture of 0.520 g of 2,4,5,6-tetrahydro-2-methyl-6-(4-nitrobenzoyl)pyrazolo[4,3-d][1]benzazepine, 18 μl of anhydrous hydrazine and 52 mg of 10% palladium-on-carbon in 30 ml of absolute ethyl alcohol is heated at reflux for 1 hour. The reaction mixture is filtered through diatomaceous earth and the cake washed with 100 ml of methyl alcohol and 1:1 chloroform-methyl alcohol to give 430 mg of the desired product as off-white crystals. CIMS(CH$_4$) MH$^+$=319.

REFERENCE EXAMPLE 102

5-(2-Chloro-4-aminobenzoyl)-6,11-dihydro-5H-dibenz[b,e]azepine

A mixture of 1.40 g of 5-(2-chloro-4-nitrobenzoyl)-6,11-dihydro-5H-dibenz[b,e]azepine, 0.20 g of 10% palladium-on-carbon, 0.25 g of anhydrous hydrazine in 25 ml of absolute ethanol is heated at reflux for 1 hour. The mixture is filtered through diatomaceous earth and the filtrate evaporated in vacuo to a residue which is dissolved in methylene chloride and hexane added at the boil to give 0.60 g of the desired product as a crystalline solid, m.p. 158°–161° C.

REFERENCE EXAMPLE 103

2-[2-(Tributylstannyl)-3-thienyl]-1,3-dioxolane

To a stirred solution of 15.6 g (0.10 mol) of 2-(3-thienyl)-1,3-dioxolane in 100 ml of anhydrous ether, n-butyl-lithium (1.48N, in hexane, 74.3 ml) is added dropwise under nitrogen at room temperature. After being refluxed for 15 minutes, the reaction mixture is cooled to –78° C. and tri-n-butyltin chloride (34.18 g, 0.105 mol) in 100 ml of dry tetrahydrofuran is added dropwise. After the addition is complete, the mixture is warmed to room temperature and the solvent evaporated. To the oily residue 100 ml of hexane is added, and the resulting precipitate (LiCl) is filtered off. The filtrate is evaporated and the residue distilled at reduced pressure, giving 34.16 g (77%) of the desired product.

REFERENCE EXAMPLE 104

2-[2-[(2-Nitrophenyl)methyl]-3-thienyl]-1,3-dioxolane

A mixture of 2-[2-(tributylstannyl)-3-thienyl]-1,3-dioxolane (8.8 gms, 20 mmols), 2-nitrobenzyl bromide (4.5 gms, 22 mmol) and tetrakis (triphenylphosphine)-palladium (0) (200 mg) is refluxed in degassed toluene for 16 hours under nitrogen atmosphere. At the end, the reaction mixture is cooled to room temperature and filtered through diatomaceous earth. The toluene is removed by concentrating at reduced pressure and the product isolated by silica gel column chromatography by elution with 30% ethyl acetate-:hexane to give 4.5 gms. of the desired product as a viscous liquid. Mass Spectrum; M$^+$292.

REFERENCE EXAMPLE 105

4,10-Dihydro-5H-thieno[3,2-c][1]benzazepine

A stirred solution of 4 gms of 2-[2-[(2-nitrophenyl)methyl]-3-thienyl]-1,3-dioxolane in acetone (50 ml) and acetic acid (90% 50 ml) is heated to 60° C. Zinc dust (10 gms) is slowly added and after the addition, reaction mixture is stirred for 6 hours. At the end, reaction mixture is filtered and the residue washed with acetone and concentrated. The brown residue is extracted with chloroform and washed well with water. The organic layer is dried (Na$_2$SO$_4$) and filtered and concentrated. The product is isolated by silica gel column chromatography by eluting with 20% ethyl acetate-:hexane to give 2.0 g of the desired product as a pale yellow crystalline solid, m.p. 86° C. Mass Spectrum; M$^+$202.

REFERENCE EXAMPLE 106

4,5-Dihydro-4,4-dimethyl-2-[3-[(2-nitrophenyl) methyl]-2-thienyl]oxazole

To a solution of 4,5-dihydro-4,4-dimethyl-2-(2-thienyl)-oxazole (4.5 gms 25 mmol) in anhydrous ether at –70° C., n-butyl-lithium (2.5 molar solution in hexane, 11 ml) is added drop by drop under N$_2$ atmosphere. The reaction mixture is stirred at –78° C. for 45 minutes and tri-n-butyltin chloride (8.3 gms 25 mmol) in dry ether is added drop by drop. The reaction mixture is stirred at room temperature for 1 hour and quenched with water. The reaction mixture is extracted with ether, washed well with water, dried and concentrated. The product obtain is pure enough for further transformation. The oil product, 4,5-dihydro-4,4-dimethyl-2-[3-(tributylstannyl)-2-thienyl]-oxazole is mixed with 2-nitrobenzyl bromide (5.5 g 25 mmol) in toluene and refluxed in the presence of tetrakis (triphenylphosphine)-palladium (0) (200 mg) for 16 hours. At the end, reaction mixture is cooled to room temperature and filtered. Toluene is removed under reduced pressure and the product is isolated as brown oil by silica gel column chromatography by eluting it with 30% ethyl acetate:hexane to give 5.7 g of the desired product. Mass Spectrum; $M^+316$.

REFERENCE EXAMPLE 107

9,10-Dihydro-4H-thieno[3,2-c][1]benzazepin-10-one

A solution of 4,5-dihydro-4,4-dimethyl-2-[3-[(2-nitrophenyl)methyl]-2-thienyl]oxazole 5 gms is refluxed in acetone/water (3:1 100 ml) containing 1N HCl (30 ml) for 24 hours. The reaction mixture is concentrated and the residue is dissolved in glacial acetic acid (100 ml). The acetic acid is stirred at 70° C. and zinc dust (10 gm) is slowly added. Stirring is continued at 70° C. for 6 hours. At the end, the reaction mixture is cooled to room temperature and filtered. Acetic acid is removed under reduced pressure and the residue is extracted with chloroform. The chloroform layer is dried and concentrated to give 2.9 gms of the desired product as a brown solid. Mass Spectrum; $M^+215$.

REFERENCE EXAMPLE 108

9,10-Dihydro-4H-thieno[3,2-c][1]benzazepine

A stirred solution of 2.0 g of 9,10-dihydro-4H-thieno[2,3-c][1]benzazepin-10-one and lithium aluminum hydride (500 mg) in tetrahydrofuran is refluxed for 4 hours. At the end, reaction mixture is carefully quenched with ice cold water and extracted with chloroform. The organic layer is washed well with water and dried over anhydrous $Na_2SO_4$, filtered and concentrated. The product is purified by silica gel column chromatography by eluting it with 30% ethyl acetate:hexane to give 1.2 g of the desired product as a bright yellow solid. Mass Spectrum; $M^+=202$.

REFERENCE EXAMPLE 109

4-Bromo-1,2,3,4-tetrahydro-1-(4-nitrobenzoyl)-5H-1-benzazepin-5-one

A mixture of 0.200 g of 1,2,3,4-tetrahydro-1-(4-nitrobenzoyl)-5H-1-benzazepin-5-one in 2.5 ml of acetic acid is warmed until solution then allowed to cool to room temperature. While stirring, a solution of 0.103 g of bromine in 0.5 ml of acetic acid is added dropwise. After rapid decolorization, the reaction mixture is stirred for 1.5 hours and poured into water. The solid is collected, washed with water and air dried to give 220 mg of the desired product as a crystalline solid, Mass Spectrum; $MH^+=389,391$.

REFERENCE EXAMPLE 110

5,6-Dihydro-2-methyl-6-(4-nitrobenzoyl)-4H-thiazolo[5,4-d][1]benzazepine

A mixture of 1.19 g of 4-bromo-1,2,3,4-tetrahydro-1-(4-nitrobenzoyl)-5H-1-benzazepin-5-one and 0.230 g of thioacetamide in 4 ml of ethyl alcohol is refluxed under argon for 18 hours. The volatiles are evaporated in vacuo to a residue which is partitioned between $CHCl_3$ and 10% $NaHCO_3$. The organic layer is separated and washed twice with water. The organic layer is separated, dried ($MgSO_4$) and evaporated in vacuo to give 1.08 g of yellow foam which is purified by flash chromatography on silica by elution with 4% ethyl acetate in methylene chloride to give 560 mg of the desired product as pale yellow foam.

REFERENCE EXAMPLE 111

5,6-Dihydro-2-methyl-6-(4-aminobenzoyl)-4H-thiazolo[5,4-d][1]benzazepine

A mixture of 0.080 g of 5,6-dihydro-2-methyl-6-(4-aminobenzoyl)-4H-thiazolo[5,4-d][1]benzazepine and 0.248 g of $SnCl_2$ dihydrate in 3.5 ml of ethyl alcohol is refluxed under argon for 1 hour. The reaction mixture is diluted with ice water and the pH adjusted to 8 with 10% $NaHCO_3$. After stirring for 3 hours, the mixture is extracted with $CHCl_3$(3×). The combined organic layers are treated with activated carbon, filtered through a pad of $MgSO_4$ and the filtrate evaporated in vacuo to a residue. The residue is chromatographed on silica gel by elution with 30% ethyl acetate in methylene chloride to give 60 mg of the desired product as a tan solid, $CIMS(CH_4)$: $MH^+=336$.

REFERENCE EXAMPLE 112

Methyl 4-[2-(2-chlorophenyl)-2-cyano-2-(4-morpholinyl)ethyl]benzoate

A 0.876 g sample of 60% sodium hydride in oil is washed with hexane followed by the addition of 60 ml of dry N,N-dimethylformamide. The reaction mixture is stirred for 1 hour under argon at room temperature after the addition of 4.73 g of α-(2-chlorophenyl)-4-morpholineacetonitrile. To the reaction mixture is added 4.58 g of methyl 4-(bromomethyl)benzoate and stirring continued for 3 hours. Several drops of acetic acid is added to ice water and the reaction quenched. The pH is 3–4 and saturated $NaHCO_3$ added to adjust the pH to 6–7. Upon cooling a solid forms which is filtered, washed with water and dried to give 5.92 g of yellow solid. Crystallization from methylene chloride-hexane gives 2.10 g of the desired product as a crystalline solid, m.p. 116°–118° C.

REFERENCE EXAMPLE 113

Methyl 4-[2-(2-chlorophenyl)-2-oxoethyl]benzoate

A mixture of 1.0 g of methyl [4-(2-chlorophenyl)-2-cyano-2-(4-morpholinyl)ethyl]benzoate and 14 ml of acetic acid and 6 ml of water is heated at reflux for 20 minutes then poured over crushed ice. After stirring for 15 minutes the resulting solid is collected, washed with water and air dried to give 0.63 g of tan solid, m.p. 40°–42° C.

REFERENCE EXAMPLE 114

4-[2-(2-chlorophenyl]-2-oxoethyl]benzoic acid

A mixture of 18.78 g of methyl 4-[2-(2-chlorophenyl)-2-oxoethyl]benzoate in 288.8 ml of $CH_3OH$, 72.2 ml of water and 5.2 g of NaOH is refluxed for 3 hours then acidified with 2N citric acid. The reaction mixture is evaporated in vacuo to remove the $CH_3OH$. The aqueous phase is extracted with $CH_2Cl_2$ and acidified with 1N HCl. The resulting solid is collected and dried under vacuum to give 17.27 g of the desired product, m.p. 168°–172° C.

EXAMPLE 1

N-[4-[(10,11-dihydro-5H-dibenz[b,f]azepin-5-yl) carbonyl]phenyl]-2-methylbenzamide To a mixture of 1.37 g (5 mmol) of 4-[(2-methylbenzoyl) amino]benzoyl chloride and 0.061 g of 4-(dimethylamino)

pyridine in 4 ml of pyridine is added 0.975 g (5 mmol) of 10,11-dihydro-5H-dibenz[b,f]azepine. The mixture is heated at 80° C. for 18 hours and then 0.2 g of sodium hydride (60% in oil) (5 mmol) is added. The mixture is refluxed for 2 hours, diluted with dichloromethane and water and then filtered. To the filtrate is added 1N HCl and the mixture filtered. The filtrate is dried ($Na_2SO_4$) and the solvent removed to give a solid. The solid (1.1 g) is chromatographed on thick layer silica gel plates to give 70 mg of yellow solid, m.p. 112°–118° C.

Anal. Calc'd for $C_{29}H_{24}N_2O$: C,80.5; H,5.6; N,6.5. Found: C,78.7; H,5.8; N,6.7.

EXAMPLE 2

N-[4-[(6,11-Dihydro-5H-dibenz[b,e]azepin-5-yl) carbonyl]phenyl]-2-methylbenzamide To a solution of 0.27 g (1 mmol) of 4-[(2-methylbenzoyl)amino]benzoyl chloride in 2 ml of tetrahydrofuran is added 0.20 g (1 mmol) of 6,11-dihydro-5H-dibenz[b,e]azepine and 0.20 g of triethylamine. The mixture is stirred at room temperature for 3 hours and the solvent removed under vacuum. To the residue is added 1N HCl and the mixture extracted with ethyl acetate (20 ml) and the extract washed with saturated $NaHCO_3$, brine and dried ($Na_2SO_4$). The solution is filtered through a thin pad of hydrous magnesium silicate and the filtrate evaporated. The residue is triturated with ether-hexane and filtered to give 0.47 g of a white solid: Mass Spectrum; EI 433 (M+1); EI-high resolution 432.1842.

Anal. Calc'd for $C_{29}H_{24}N_2O_2$: C,80.5; H,5.6; N,6.5. Found: C,79.0; H,6.0; N,6.1.

A sample crystallized from ethyl acetate-hexane gives crystals, m.p. 198°14 203° C.

EXAMPLE 3

3-Methyl-N-[4-[(5(6H)-phenanthridinyl)carbonyl] phenyl]-2-thiophenecarboxamide To 0.193 g (1.2 mmol) of 3-methylthiophene-2-carbonyl chloride in 3 ml of dichloromethane, cooled to 0° C., is added 209 µl triethylamine. The mixture is stirred and 0.30 g (1 mmol) of 5-(4-aminobenzoyl)-5,6-dihydrophenanthridine is added. The mixture is stirred at room temperature overnight and then concentrated under vacuum. To the residue is added 30 ml of ethyl acetate and the mixture washed with 2 ml each of water, 2N citric acid, 1M sodium bicarbonate and brine. The organic layer is dried ($Na_2SO_4$) and the solvent removed to give 0.30 g of solid. The solid is chromatographed on thick layer silica gel plates with ethyl acetate-hexane (1:1) as solvent to give 150 mg of product as a yellow foam.

Anal. Calc'd for $C_{26}H_{20}N_2O_2S$: C,71.3; H,6.0; N,6.9; S,7.9. Found: C,71.0; H,5.8; N,6.8; S,7.8.

EXAMPLE 4

N-[4-[(2-Chlorodibenz[b,f][1,4]oxazepin-10(11H)-yl)carbonyl]phenyl]-2-methylbenzamide To a mixture of 0.229 g (1.0 mmol) of 2-chloro-10,11-dihydrodibenz[b,f][1,4]oxazepine in 1.0 ml of pyridine under nitrogen is added 0.30 g (1.1 mmol) of 4-[(2-methylbenzoyl)amino]benzoyl chloride. The mixture is stirred at room temperature for 1 hour, heated on a steam bath for 5 minutes and 8 ml of 2N HCl added. The mixture is extracted with ethyl acetate and the extract washed three times with 1 ml of 1N sodium bicarbonate. The organic layer is dried ($MgSO_4$) and the solvent removed. The residue is crystallized from ethyl acetate-hexane to give 0.24 g of crystals, m.p. 207°–208° C.

Anal. Calc'd for $C_{28}H_{21}N_2O_3Cl$: C,71.9; H,4.5; N,6.0; Cl,7.6. Found: C,71.6; H,4.6; N,5.9; Cl,7.4.

EXAMPLE 5

2-Methyl-N-[4-[(5(6H)-phenanthridinyl)carbonyl] phenyl]benzamide

To a solution of 0.181 g (1.0 mmol) of 5,6-dihydrophenanthridine in 2 ml of warm pyridine is added 0.273 g (1.0 mmol) of 4-[(2-methylbenzoyl)amino]benzoyl chloride. The mixture is stirred overnight at room temperature, 1.2 ml of 2NHCl added. The solid which separates is filtered and washed with water. The solid is dissolved in dichloromethane and the solution washed with 2M sodium carbonate. The organic layer is concentrated and the residue chromatographed twice on silica gel with ethyl acetate-hexane as solvent to give 79 mg of crystals, m.p. 190°–194° C. Mass Spec-FAB 419 (M+H).

Anal. Calc'd for $C_{28}H_{20}N_2O_2 \cdot H_2O$: C,77.4; H,5.1; N,6.4. Found: C,77.5; H,5.1; N,6.4.

EXAMPLE 6

N-[4-[(11,12-Dihydrodibenz[b,f]azocin-5-(6H)-yl) carbonyl]phenyl]-2-methylbenzamide To a mixture of 0.245 g (1 mmol) of 5,6,11,12-tetrahydrodibenz[b,f]azocine hydrochloride and 30 µl (2.2 mmol) of triethylamine in 2 ml of dichloromethane is added a solution of 0.281 g (1.1 mmol) of 4-[(2-methylbenzoyl)amino]benzoyl chloride in 4 ml of dichloromethane. The mixture is stirred overnight at room temperature, washed with water 2N HCl (3×2 ml) and 1N sodium bicarbonate (3×2 ml). The organic layer is dried ($MgSO_4$) and filtered through a thin pad of hydrous magnesium silicate (pad washed with 3 volumes of $CH_2Cl_2$). The filtrate is concentrated to give 200 mg of a foam; Mass Spec.-FAB 447 (M+H).

Anal. Calc'd for $C_{30}H_{26}N_2O_2$: C,80.7; H,5.9; N,6.3. Found: C,79.1; H,5.7; N,6.1.

EXAMPLE 7

2-6-Dichloro-N-[4-[(5(6H)-phenanthridinyl) carbonyl]phenyl]benzamide

A mixture of 300 mg (0.5 mmol) of 5-(4-aminobenzoyl)-5,6-dihydrophenanthridine and 230 mg of (0.55 mmol) of 2,6-dichlorobenzoyl chloride in 1.2 ml of pyridine is heated (100° C.) for 3 hr and then stirred at room temperature for 6 days. To the mixture is added 10 mg of 4-(dimethylamino) pyridine and the mixture stirred for 22 days. To the mixture is added 6 ml of 2N HCl and the solid filtered and washed with 2N HCl, 1N NaOH, $H_2O$ to give 0.57 g of solid. The solid is chromatographed on thick layer silica gel plates with hexane ethyl-acetate (1:1) to give 110 mg of solid. Recrystallization from $CH_2Cl_2$-diisopropyl ether to give 73 mg of white crystals, m.p. 230°–235° C.

Anal. Calc'd for $C_{27}H_{18}Cl_2N_2O_2 \cdot H_2O$: C,66.0; H,4.1; N,5.7; Cl,14.4. Found: C,65.5; H,4.1; N,5.6; Cl,14.6.

EXAMPLE 8

3,4-Dichloro-N-[4-[(5(6H)-phenanthridinyl) carbonyl]phenyl]benzamide

A mixture of 150 mg (0.5 mmol) of 5-(4-aminobenzoyl)-5,6-dihydrophenanthridine and 115 mg (0.55 mmol) of 3,4-dichlorobenzoyl chloride in 1 ml of pyridine is stirred at room temperature for 6 hours. To the mixture is added 6 ml of 2N HCl and the mixture stirred and filtered to give a solid. The solid is washed with water, 2N sodium carbonate and water to give 254 mg of crystals, m.p. 94°–95° C. The solid is chromatographed on thick layer silica gel plates with hexane ethyl-acetate (1:1) as solvent to give 107 mg of solid. Mass Spec (FAB) 473 (M+H).

EXAMPLE 9

N-[4-[(6,11-Dihydro-5H-dibenz[b,e]azepin-5-yl)carbonyl]phenyl]-2,5-dichlorobenzamide A mixture of 0.625 g (2 mmol) of 5-(4-aminobenzoyl)-6,11-dihydro-5H-dibenz[b,e]azepine, 0.629 g (3 mmol) of 2,5-dichlorobenzoyl chloride, 0.303 g (3 mmol) of triethylamine and 15 mg of 4-(dimethylamino)pyridine in 10 ml of dichloromethane is stirred at room temperature for 3 hours. The mixture is washed with water, 1N HCl, $H_2O$, 1M $NaHCO_3$, brine and dried ($Na_2SO_4$). The solvent is removed to give crystals. Recrystallization from hexane-$CH_2Cl_2$ gives 0.16 g of white crystals, m.p. 203°–231° C.

Anal. Calc'd for $C_{28}H_{20}Cl_2N_2O_2$: C,69.0; H,4.1; N,5.8; Cl,14.6. Found: C,69.0; H,3.8; N,5.6; Cl,14.8.

EXAMPLE 10

N-[4-[(6,11-Dihydro-5H-dibenz[b,e]azepin-5-yl)carbonyl]phenyl]-3,4-dichlorobenzamide As described for Example 9, 0.111 g (1.1 mmol) of 5-(4-aminobenzoyl)-6,11-dihydro-5H-dibenz[b,e]azepine in 8 ml of dichloromethane is reacted with 0.230 g of (1.1 mmol) of 2,4-dichlorobenzoyl chloride. The product is recrystallized from hexane-dichloromethane to give 0.24 g of crystals, m.p. 212°–215° C.

Anal. Calc'd for $C_{18}H_{20}Cl_2N_2O_2$ $H_2O$: C,66.5; H,4.4; N,5.5. Found: C,66.8; H,4.0; N,5.5.

EXAMPLE 11

N-[4-[(6,11-Dihydro-5H-dibenz[b,e]azepin-5-yl)carbonyl]phenyl]-2,3-dimethylbenzamide As described for Example 9, 0.628 g (2 mmol) of 5-(4-aminobenzoyl)-6,11-dihydro-5H-dibenz[b,e]azepine is reacted with 0.506 g (3.0 mmol) of 2,3-dimethylbenzoyl chloride in dichloromethane. The product is recrystallized from hexane-dichloromethane to give 0.12 g of crystals, m.p. 138°–142° C.

Anal. Calc'd for $C_{30}H_{26}N_2O_2$: C,80.7; H,5.9; N,6.3. Found: C,80.0; H,5.9; N,6.1.

EXAMPLE 12

N-[4-[(6,11-Dihydro-5H-dibenz[b,e]azepin-5-yl)carbonyl]phenyl]-2,5-dimethylbenzamide As described for Example 9, 0.471 g (1.5 mmol) of 5-(4-aminobenzoyl)-6,11-dihydro-5H-dibenz[b,e]azepine is reacted with 0.303 g (1.8 mmol) of 2,5-dimethylbenzoyl chloride in 10 ml of dichloromethane. The product is recrystallized from dichloromethane-hexane to give 0.43 g of crystals, m.p. 213°–216° C.

Anal. Calc'd for $C_{30}H_{26}N_2O_2$: C,80.7; H,5.9; N,6.3. Found: C,80.0; H,5.9; N,6.1.

EXAMPLE 13

N-[4-[(6,11-Dihydro-5H-dibenz[b,e]azepin-5-yl)carbonyl]phenyl]-2,4-dimethylbenzamide As described in Example 9, 0.471 g (1.5 mmol) of 5-(4-aminobenzoyl)-6,11-dihydro-5H-dibenz[b,e]azepine is reacted with 0.303 g (1.8 mmol) of 2,4-dimethylbenzoyl chloride in 10 ml of dichloromethane. The product is recrystallized from hexane-dichloromethane to give 0.38 g of crystals, m.p. 197°–199° C.

Anal. Calc'd for $C_{30}H_{26}N_2O_2$ ½ $H_2O$: C,79.1; H,6.0; N,6.2. Found: C,79.0; H,5.8; N,6.2.

EXAMPLE 14

N-[4-[(6,11)-Dihydro-5H-dibenz[b,e]azepin-5-yl)carbonyl]phenyl]-2-chlorobenzamide As described in Example 9, 0.471 g (1.5 mmol) of 5-(4-aminobenzoyl)-6,11-dihydro-5H-dibenz[b,e]azepine is reacted with 0.315 g (1.8 mmol) of 2-chlorobenzoyl chloride in dichloromethane. The product is chromatographed on thick layer silica gel plates with hexane-ethyl acetate (1:1) as solvent to give a solid. Recrystallization from hexane-dichloromethane gives 100 mg of crystals, m.p. 110°–115° C.

Anal. Calc'd for $C_{28}H_{21}ClN_2O_2$ ½ $H_2O$: C,72.8; H,4.8; N,6.1; Cl7.7. Found: C,72.6; H,4.5;N,5.8; Cl,8.7.

EXAMPLE 15

N-[4-[(6,11-Dihydro-5H-dibenz[b,e]azepin-5-yl)carbonyl]phenyl]-2-methylbenzamide As described for Example 9, 0.942 g (3 mmol) of 5-(4-aminobenzoyl)-6,11-dihydro-5H-dibenz[b,e]azpine is reacted with 0.52 g (3.3 mmol) of 2-methylbenzoyl chloride in 20 ml of dichloromethane. The product is triturated with hexane-ethyl acetate to give 1.0 g of yellow crystals, m.p. 198°–203° C.

EXAMPLE 16

2-Chloro-N-[4-[(6,11-dihydro-5H-dibenz[b,e]azepin-5-yl)carbonyl]phenyl]benzeneacetamide A mixture of 0.471 g (1.5 mmol) of 5-(4-aminobenzoyl)-6,11-dihydro-5H-dibenz[b,e]azepine, 0.340 g (1.8 mmol) of 2-chlorophenylacetyl chloride, 0.20 g of triethylamine and 9 mg of 4-(dimethylamino)pyridine in 10 ml of dichloromethane is stirred at room temperature for 48 hours. An additional 0.27 g of 2-chlorophenylacetyl chloride is added and the mixture stirred at room temperature for 2.5 hr. The mixture is washed with 1N HCl, $H_2O$, 1M $NaHCO_3$, brine and dried ($Na_2SO_4$). The solvent is removed and the solid recrystallized from dichloromethane to give 0.27 g of crystals, m.p. 191°–194° C.

Anal. Calc'd for $C_{29}H_{23}ClN_2O_2$: C,74.6; H,5.0; N,6.0; Cl,7.6. Found: C,74.4; H,4.9; N,5.9; Cl,7.8.

EXAMPLE 17

N-[4-[(6,11-Dihydro-5H-dibenz[b,e]azepin-5-yl)carbonyl]phenyl]-3-pyridinecarboxamide A mixture of 0.628 g (2 mmol) of 5-(4-aminobenzoyl)-6,11-dihydro-5H-dibenz[b,e]azepine, 0.551 g (3 mmol) of nicotinoyl chloride, hydrochloride, 0.606 g (6 mmol) of triethylamine and 15 mg of 4-(dimethylamino)pyridine in 17 ml of dichloromethane is refluxed for 7 hours. The mixture is washed with $H_2O$, 2N citric acid, $H_2O$, 1N $NaHCO_3$, brine and dried ($Na_2SO_4$). The solvent is removed and the solid recrystallized from hexane-dichloromethane to give 0.12 g of crystals, m.p. 217°–220° C.

Anal Calc'd for $C_{27}H_{21}N_3O_2$ $H_2O$: C,74.1; H,5.3; N,9.6. Found: 73.6; H,4.7; N,9.8.

EXAMPLE 18

N-[4-[(6,11-Dihydro-5H-dibenz[b,e]azepin-5-yl)carbonyl]phenyl]-3-methyl-2-thiophenecarboxamide As described for Example 9, 0.314 g (1 mmol) of 5-(4-aminobenzoyl)-6,11-dihydro-5H-dibenz[b,e]azepine is reacted with 0.177 g (1.1 mmol) of 3-methyl-2-thiophenecarbonyl chloride in 5 ml of dichloromethane and 0.111 g of triethylamine for 2 hours at room temperature to give crystals. Recrystallization from dichloromethane-hexane gives 0.235 g of crystals, m.p. 201°–204° C.

EXAMPLE 19

N-[4-[6,11-Dihydro-5H-dibenz[b,e]azepine-5-yl)carbonyl]phenyl]-3-(trifluoromethyl)benzamide As described for Example 9, 0.314 g (1 mmol) of 5-(4-aminobenzoyl)-6,11-dihydro-5H-dibenz[b,e]azepine is reacted with 0.302 g (1.4 mmol) of 3-(trifluoromethyl)benzoyl chloride in 9 ml and 0.145 g (1.4 mmol) of triethylamine for 1.5 hour at room temperature. The product is recrystallized from ethyl acetate-hexane to give 0.14 g of crystals, m.p. 190°–191° C.

EXAMPLE 20

N-[4-[(6,11-Dihydro-5H-dibenz[b,e]azepin-5-yl)carbonyl]phenyl]-4-(trifluoromethyl)benzamide As described for Example 9, 0.314 g of 5-(4-aminobenzoyl)-6,11-dihydro-5H-dibenz[b,e]azepine is reacted with 0.269 g (1.29 mmol) of 4-trifluoromethylbenzoyl chloride and 0.130 g (1.29 mmol) of triethylamine in 9 ml of dichloromethane for 1.5 hours at room temperature. The product is triturated with ethyl acetate-hexane to give 0.43 g of crystals, m.p. 205°–207° C.

EXAMPLE 21

N-[4-[(6,11-Dihydro-5H-dibenz[b,e]azepin-5-yl)carbonyl]phenyl]-2,4-difluorobenzamide As described for Example 9, 0.314 g (1.0 mmol) of 5-(4-aminobenzoyl)-6,11-dihydro-5H-dibenz[b,e]azepine is reacted with 0.194 g (1.1 mmol) of 2,4-difluorobenzoyl chloride and 0.111 g (1.1 mmol) of triethylamine in 10 ml of dichloromethane for 1.5 hours at room temperature. The product is recrystallized from ethyl acetate-hexane to give 0.37 g of crystals, m.p. 215°–217° C.

EXAMPLE 22

N-[4-[6,11-Dihydro-11-methyl-5H-dibenz[b,e]azepin-5-yl)carbonyl]phenyl]-2-methylbenzamide A sample of 6,11-dihydro-11-methyl-5H-dibenz[b,e]azepine is synthesized as described in *J. Chem. Soc.* Perkin I, 1279 (1976). A 0.210 g (1 mmol) sample is added to a stirred and cooled mixture of 0.328 g (1.2 mmol) of 4-[(2-methylbenzoyl)amino]benzoyl chloride, 279 mL (2.0 mmol) of triethylamine and 26 mg of 4-(dimethylamino)pyridine in 4 ml of dichloromethane. The solution is stirred at room temperature overnight. An additional 0.328 g of 4-[(2-methylbenzoyl)amino]benzoyl chloride and 150 µl of triethylamine is added and the mixture stirred at room temperature for 6 hours. The volatiles are removed and 30 ml of ethyl acetate is added. The mixture is washed with 12 ml each of 2N citric acid, $H_2O$, 1M $NaHCO_3$, brine and dried ($Na_2SO_4$). The solvent is removed and the residue chromatographed on thick layer silica gel plates with hexane-ethyl acetate (2:1) as solvent to give 0.13 g of product as a white solid.

Anal. Calc'd for $C_{30}H_{26}N_2O_2$ ¼ $H_2O$: C,79.9; H,5.9; N,6.2. Found: C,79.4; H,5.5; N,5.9.

EXAMPLE 23

N-[4-[[2-[(Dimethylamino)sulfonyl]dibenz[b,f][1,4]-oxazepin-10(11H)-yl]carbonyl]phenyl]-2-methylbenzamide A solution of 0.22 g of 10,11-dihydro-N,N-dimethyl-10-(4-nitrobenzoyl)dibenz[b,f][1,4]oxazepine-2-sulfonamide, 50 mg of 10% Pd/C under an atmosphere of $H_2$ is shaken in a Parr hydrogenator for 5 hours. The mixture is filtered through diatomaceous earth and the filter cake washed with ethyl acetate. The filtrate is concentrated to 5a, 6 ml and 0.83 µl of triethylamine added followed by the addition of 0.773 g of o-tolyl chloride. The mixture is stirred overnight and then washed with $H_2O$, 2N HCl, 1M $Na_2CO_3$ and brine. The filtrate is filtered through a thin pad of hydrous magnesium silicate and the pad washed with three volumes of ethyl acetate. The filtrate is concentrated under vacuum and the residual oil chromatographed on thick layer silica gel plates with hexane-ethyl acetate (1:1) to give 83 mg of a foam. Mass Spectrum (FAB) 540(M+H).

EXAMPLE 24

N-[4-[(6,11-Dihydro-5H-dibenz[b,e]azepin-5-yl)carbonyl]phenyl]benzamide

As described for Example 9, 0.314 g (1.0 mmol) of 5-(4-aminobenzoyl)-6,11-dihydro-5H-dibenz[b,e]azepine is reacted with 0.155 g (1.1 mmol) of benzoyl chloride and 0.111 g (1.1 mmol) of triethylamine in 10 ml of dichloromethane for 1.5 hours at room temperature. The product is recrystallized from dichloromethane-hexane to give 0.19 g of crystals, m.p. 219°–221° C.

Anal. Calc'd for $C_{28}H_{22}N_2O_2$: C,80.4; H,5.3; N,6.7. Found: C,79.6; H,5.5; N,6.7.

EXAMPLE 25

N-[4-[(6,11-Dihydro-5H-dibenz[b,e]azepin-5-yl)carbonyl]phenyl]-2-(trifluoromethoxy)benzamide As described for Example 9, 0.314 g (1.0 mmol) of 5-(4-aminobenzoyl)-6,11-dihydro-5H-dibenz[b,e]azepine is reacted with 0.247 g (1.1 mmol) of 2-(trifluoromethoxy)benzoyl chloride and 0.111 g (1.1 mmol) of triethylamine in 10 ml of dichloromethane at room temperature for 1.5 hours. The product is triturated with dichloromethane-hexane to give 0.35 g of crystals, m.p. 232°–235° C.

The following compounds are prepared as described for in Example 6.

EXAMPLE 26

N-[4-[(11,12-Dihydrodibenz[b,f]azocin-5(6H)-yl)carbonyl]phenyl]-2-chlorobenzamide

EXAMPLE 27

N-[4-[(11,12-Dihydrodibenz[b,f]azocin-5(6H)-yl)carbonyl]phenyl]-2-fluorobenzamide

EXAMPLE 28

N-[4-[(11,12-Dihydrodibenz[b,f]azocin-5(6H)-yl)carbonyl]phenyl]-2-methoxybenzamide

EXAMPLE 29

N-[4-[(11,12-Dihydrodibenz[b,f]azocin-5(6H)-yl)carbonyl]phenyl]-2,3-dimethylbenzamide

EXAMPLE 30

N-[4-[(11,12-Dihydrodibenz[b,f]azocin-5(6H)-yl)carbonyl]phenyl]-2,5-dimethylbenzamide

EXAMPLE 31

N-[4-[(11,12-Dihydrodibenz[b,f]azocin-5(6H)-yl)carbonyl]phenyl]-2,4-dichlorobenzamide

EXAMPLE 32

N-[4-[(11,12-Dihydrodibenz[b,f]azocin-5(6H)-yl)carbonyl]phenyl]-2,3-dichlorobenzamide

EXAMPLE 33

N-[4-[(11,12-Dihydrodibenz[b,f]azocin-5(6H)-yl)carbonyl]phenyl]-2-methyl-5-fluorobenzamide

EXAMPLE 34

N-[4-[(11,12-Dihydrodibenz[b,f]azocin-5(6H)-yl)carbonyl]phenyl]-2-chlorophenylacetamide The following compounds are prepared as described in Example 3.

EXAMPLE 35

N-[4-[(5(6H)-Phenanthridinyl)carbonyl]phenyl]-2-chlorobenzamide

EXAMPLE 36

N-[4-[(5(6H)-Phenanthridinyl)carbonyl]phenyl]-2-fluorobenzamide

EXAMPLE 37

N-[4-[(5(6H)-Phenanthridinyl)carbonyl]phenyl]-2-methoxybenzamide

EXAMPLE 38

N-[4-[(5(6H)-Phenanthridinyl)carbonyl]phenyl]-2,3-dimethylbenzamide

EXAMPLE 39

N-[4-[(5(6H)-phenanthridinyl)carbonyl]phenyl]-2,5-methylbenzamide

EXAMPLE 40

N-[4-[(5(6H)-Phenanthridinyl)carbonyl]phenyl]-2,4-dichlorobenzamide

EXAMPLE 41

N-[4-[(5(6H)-phenanthridinyl)carbonyl]phenyl]-2,3-dichlorobenzamide

EXAMPLE 42

N-[4-[(5(6H)-phenanthridinyl)carbonyl]phenyl]-2-methyl-5-fluorobenzamide

EXAMPLE 43

N-[4-[(5(6H)-Phenanthridinyl)carbonyl]phenyl]-2-chlorophenylacetamide

EXAMPLE 44

N-[4-[(5(6H)-Phenanthridinyl)carbonyl]phenyl]-2-methylphenylacetamide

EXAMPLE 45

N-[4-[(5(6H)-Phenanthridinyl)carbonyl]phenyl]-2-methyl-4-chlorobenzamide

EXAMPLE 46

N-[4-[(5(6H)-Phenanthridinyl)carbonyl]phenyl]-2-chloro-4-methylbenzamide

EXAMPLE 47

N-[4-[(5(6H)-Phenanthridinyl)carbonyl]phenyl]-2,6-dimethylbenzamide

EXAMPLE 48

N-[4-[(5(6H)-Phenanthridinyl)carbonyl]phenyl]-2-(methylthio)benzamide

EXAMPLE 49

N-[4-[(5(6H)-Phenanthridinyl)carbonyl]phenyl]-2-methyl-3-furanecarboxamide

The following compounds are prepared as described in Example 4.

EXAMPLE 50

N-[4-[(2-Chlorodibenz[b,f][1,4]oxazepin-10(11H)-yl)carbonyl]phenyl]-2-chlorobenzamide

EXAMPLE 51

N-[4-[(2-Chlorodibenz[b,f][1,4]oxazepin-10(11H)-yl)carbonyl]phenyl]-2-fluorobenzamide

EXAMPLE 52

N-[4-[(2-Chlorodibenz[b,f][1,4]oxazepin-10(11H)-yl)carbonyl]phenyl]-2-methoxybenzamide

EXAMPLE 53

N-[4-[(2-Chlorodibenz[b,f][1,4]oxazepin-10(11H)-yl)carbonyl]phenyl]-1,3-dimethylbenzamide

EXAMPLE 54

N-[4-[(2-Chlorodibenz[b,f][1,4]oxazepin-10(11H)-yl)carbonyl]phenyl]-2,5-dimethylbenzamide

EXAMPLE 55

N-[4-[(2-Chlorodibenz[b,f][1,4]oxazepin-10(11H)-yl)carbonyl]phenyl]-2,4-dichlorobenzamide

EXAMPLE 56

N-[4-[(Dibenz[b,f][1,4]oxazepin-10(11H)-yl)carbonyl]phenyl]-2,3-dichlorobenzamide

EXAMPLE 57

N-[4-[(Dibenz[b,f][1,4]oxazepin-10(11H)-yl)carbonyl]phenyl]-2-chlorophenylacetamide

EXAMPLE 58

N-[4-[(Dibenz[b,f][1,4]oxazepin-10(11H)-yl)carbonyl]phenyl]-2-methyl-3-thiophenecarboxamide

EXAMPLE 59

N-[4-[(Dibenz[b,f][1,4]oxazepin-10(11H)-yl)carbonyl]phenyl]-2-methylphenylacetamide

EXAMPLE 60

N-[4-[(Dibenz[b,f][1,4]oxazepin-10(11H)-yl)carbonyl]phenyl]-2-methyl-4-chlorobenzamide

EXAMPLE 61

N-[4-[(6,11-Dihydro-5H-dibenz[b,e]azepin-5-yl)carbonyl]phenyl]-2-(methylthio)benzamide As described for Example 9, a mixture of 0.242 g of 2-(methylthio)benzoyl chloride (m.p. 61°–64° C.), 0.134 g of triethylamine and 0.314 g of 5-(4-aminobenzoyl)-6,11-dihydro-5H-dibenz[b,e]azepine in 10 ml of dichloromethane is stirred for 2.5 hours and worked up to give a solid. Trituration with ethyl acetate-hexane gives 0.150 g of crystals, m.p. 222°–225° C.

EXAMPLE 62

N-[4-[(Dibenz[b,f][1,4]thiazepin-10(11H)yl)carbonyl]phenyl]-2-methylbenzamide

As described for in Reference Example 12, a mixture of 3.3 g of 10,11-dihydro-11-oxodibenz[b,f][1,4]thiazepine, 25 ml of tetrahydrofuran, 4.0 ml of 10 molar borane-dimethylsulfide (2.67 equivalents) in tetrahydrofuran is stirred at room temperature 18 hours to give, after work-up, 10,11-dihydrodibenz[b,f][1,4]thiazepine as white crystals, m.p. 145°–148° C. The preceding compound (3.5 g) is suspended in 25 ml of dichloromethane and a solution of 1.8 g of 4-[(2-methylbenzoyl)amino]benzoyl chloride in 50 ml of dichloromethane added. To the stirred mixture is added 4 ml of triethylamine and 0.2 g of 4-(dimethylamino) pyridine. The mixture is stirred at room temperature for 20 hours. The mixture is filtered and the filtrate concentrated. The residue is purified by chromatography on silica gel with hexane-chloroform-ethyl acetate (2:1:1) as solvent to give 2.2 g of yellow crystals. A sample (0.80 g) is further purified by thick layer chromatography on silica gel with hexane-chloroform-ethyl acetate (2:1:1) as solvent to give 0.50 g of crystals, 76°–78° C.

The following compounds are prepared as described in Example 62.

EXAMPLE 63

N-[4-[(Dibenz[b,f][1,4]thiazepin-10(11H)yl)carbonyl]phenyl]-2-chlorobenzamide, m.p. 116°–119° C.

EXAMPLE 64

N-[4-[(Dibenz[b,f][1,4]thiazepin-10(11H)yl)carbonyl]phenyl]-2,5-dichlorobenzamide

EXAMPLE 65

N-[4-[(Dibenz[b,f][1,4]thiazepin-10(11H)yl)carbonyl]phenyl]-2,4-dichlorobenzamide, m.p. 112°–115° C.

EXAMPLE 66

N-[4-[(Dibenz[b,f][1,4]thiazepin-10(11H)yl)carbonyl]phenyl]-2-fluorobenzamide

EXAMPLE 67

N-[4-[(Dibenz[b,f][1,4]thiazepin-10(11H)yl)carbonyl]phenyl]-2-chloro-4-methylbenzamide

EXAMPLE 68

N-[4-[(Dibenz[b,f][1,4]thiazepin-10(11H)yl]
carbonyl]phenyl]-2-methyl-4-chlorobenzamide

EXAMPLE 69

N-[4-[(Dibenz[b,f][1,4]thiazepin-10(11H)yl)
carbonyl]phenyl]-2,4-dimethylbenzamide

EXAMPLE 70

N-[4-[(Dibenz[b,f][1,4]thiazepin-10(11H)yl)
carbonyl]phenyl]-2,3-dimethylbenzamide

EXAMPLE 71

N-[4-[(Dibenz[b,f][1,4]thiazepin-10(11H)yl)
carbonyl]phenyl]-2-methoxybenzamide

EXAMPLE 72

N-[4-[(Dibenz[b,f][1,4]thiazepin-10(11H)yl)
carbonyl]phenyl]-2-(trifluoromethoxy)benzamide

EXAMPLE 73

N-[4-[(Dibenz[b,f][1,4]thiazepin-10(11H)yl)
carbonyl]phenyl]-2,4-dimethoxybenzamide

EXAMPLE 74

N-[4-[(Dibenz[b,f][1,4]thiazepin-10(11H)yl)
carbonyl]phenyl]-2,6-dimethoxybenzamide

EXAMPLE 75

N-[4-[Dibenz[b,f][1,4]thiazepin-10(11H)yl)
carbonyl]phenyl]-benzamide

EXAMPLE 76

N-[4-[(Dibenz[b,f][1,4]thiazepin-10(11H)yl)
carbonyl]phenyl]-2,6-dichlorobenzamide

EXAMPLE 77

N-[4-[(Dibenz[b,f][1,4]thiazepin-10(11H)yl)
carbonyl]phenyl]-2,6-dimethylbenzamide

EXAMPLE 78

N-[4-[(Dibenz[b,f][1,4]thiazepin-10(11H)yl)
carbonyl]phenyl]-2-methylthiobenzamide

EXAMPLE 79

N-[4-[(Dibenz[b,f][1,4]thiazepin-10(11H)yl)
carbonyl]phenyl]-2-methyl-3-thiophenecarboxamide

EXAMPLE 80

N-[4-[(Dibenz[b,f][1,4]thiazepin-10(11H)yl)
carbonyl]phenyl]-3-methyl-2-thiophenecarboxamide

EXAMPLE 81

N-[4-[(Dibenz[b,f][1,4]thiazepin-10(11H)yl)
carbonyl]phenyl]-2-methyl-3-furanecarboxamide

EXAMPLE 82

N-[4-[(Dibenz[b,f][1,4]thiazepin-10(11H)yl)
carbonyl]phenyl]-3-methyl-2-furanecarboxamide

EXAMPLE 83

N-[4-[(Dibenz[b,f][1,4]thiazepin-10(11H)yl)
carbonyl]phenyl]-phenylacetamide

EXAMPLE 84

N-[4-[(Dibenz[b,f][1,4]thiazepin-10(11H)yl)
carbonyl]phenyl]-2-chlorophenylacetamide

EXAMPLE 85

N-[4-[(Dibenz[b,f][1,4]thiazepin-10(11)yl)carbonyl]
phenyl]-2-methylphenylacetamide

EXAMPLE 86

N-[4-[(Dibenz[b,f][1,4]thiazepin-10(11H)yl)
carbonyl]phenyl]-2-thiopheneacetamide

EXAMPLE 87

N-[4-[(Dibenz[b,f][1,4]thiazepin-10(11H)yl)
carbonyl]phenyl]-2-furaneacetamide

EXAMPLE 88

N-[4-[(Dibenz[b,f][1,4]thiazepin-10(11H)yl)
carbonyl]phenyl]-2-methyl-3-thiopheneacetamide

EXAMPLE 89

N-[4-[(Dibenz[b,f][1,4]thiazepin-10(11H)yl)
carbonyl]-3-chlorophenyl]-2-methylbenzamide

EXAMPLE 90

N-[4-[(Dibenz[b,f][1,4]thiazepin-10(11H)yl)carbonyl]-2-methylphenyl]-2-methylbenzamide

EXAMPLE 91

N-[4-[(6,7-Dihydro-5H-dibenz[b,d]azepin-5-yl)carbonyl]phenyl]-2-methylbenzamide

As described for Example 2, 1 mmol of 4-[(2-methylbenzoyl)amino]benzoyl chloride, 1 mmol of 5H-dibenz[b,d]azepine and 2 mmol of triethylamine are stirred at room temperature for 5 hours to give the product as a pale yellow solid.

EXAMPLE 92

N-[4-[(6,7-Dihydro-5H-dibenz[b,d]azepin-5-yl]carbonyl]phenyl]-2-methylbenzamide

A mixture of 0.10 g of 5-(4-aminobenzoyl)-6,7-dihydro-5H-dibenz[b,d]azepine, 0.10 g of triethylamine in 1 ml of dichloromethane is stirred at room temperature for 6 hours. The mixture is diluted with 6 ml of ethyl acetate and the solution washed with 1N HCl, 1N NaOH, brine and dried ($Na_2SO_4$). The solvent is removed and the solid purified by chromatography on thick layer silica gel plates with the solvent ethyl acetate-hexane (1:1) to give 90 mg of a pale yellow solid.

The following compounds are prepared as described in Example 92.

EXAMPLE 93

N-[4-[(6,7-Dihydro-5H-dibenz[b,d]azepin-5-yl)carbonyl]phenyl]-3-chlorobenzamide

EXAMPLE 94

N-[4-[(6,7-Dihydro-5H-dibenz[b,d]azepin-5-yl)carbonyl]phenyl]-2,5-dichlorobenzamide

EXAMPLE 95

N-[4-[(6,7-Dihydro-5H-dibenz[b,d]azepin-5-yl)carbonyl]phenyl]-2,4-dichlorobenzamide

EXAMPLE 96

N-[4-[(6,7-Dihydro-5H-dibenz[b,d]azepin-5-yl)carbonyl]phenyl]-2-fluorobenzamide

EXAMPLE 97

N-[4-[(6,7-Dihydro-5H-dibenz[b,d]azepin-5-yl)carbonyl]phenyl]-2-chloro-4-methylbenzamide

EXAMPLE 98

N-[4-[(6,7-Dihydro-5H-dibenz[b,d]azepin-5-yl)carbonyl]phenyl]-2-methyl-4-chlorobenzamide

EXAMPLE 99

N-[4-[(6,7-Dihydro-5H-dibenz[b,d]azepin-5-yl)carbonyl]phenyl]-2,4-dimethylbenzamide

EXAMPLE 100

N-[4-[(6,7-Dihydro-5H-dibenz[b,d]azepin-5-yl)carbonyl]phenyl]-2,3-dimethylbenzamide

EXAMPLE 101

N-[4-[(6,7-Dihydro-5H-dibenz[b,d]azepin-5-yl)carbonyl]phenyl]-2-methoxybenzamide

EXAMPLE 102

N-[4-[(6,7-Dihydro-5H-dibenz[b,d]azepin-5-yl)carbonyl]phenyl]-2-(trifluoromethoxy)benzamide

EXAMPLE 103

N-[4-[(6,7-Dihydro-5H-dibenz[b,d]azepin-5-yl)carbonyl]phenyl]-2,4-dimethoxybenzamide

EXAMPLE 104

N-[4-[(6,7-Dihydro-5H-dibenz[b,d]azepin-5-yl)carbonyl]phenyl]-2,6-dimethoxybenzamide

EXAMPLE 105

N-[4-[(6,7-Dihydro-5H-dibenz[b,d]azepin-5-yl)carbonyl]phenyl]benzamide

EXAMPLE 106

N-[4-[(6,7-Dihydro-5H-dibenz[b,d]azepin-5-yl)carbonyl]phenyl]-2,6-dichlorobenzamide

EXAMPLE 107

N-[4-[(6,7-Dihydro-5H-dibenz[b,d]azepin-5-yl)carbonyl]phenyl]-2,6-dimethylbenzamide

EXAMPLE 108

N-[4-[(6,7-Dihydro-5H-dibenz[b,d]azepin-5-yl)carbonyl]phenyl]-2-methylthiobenzamide

EXAMPLE 109

N-[4-[(6,7-Dihydro-5H-dibenz[b,d]azepin-5-yl)carbonyl]phenyl]-2-methyl-3-thiophenecarboxamide

EXAMPLE 110

N-[4-[(6,7-Dihydro-5H-dibenz[b,d]azepin-5-yl)
carbonyl]phenyl]-3-methyl-2-thiophenecarboxamide

EXAMPLE 111

N-[4-[(6,7-Dihydro-5H-dibenz[b,d]azepin-5-yl)
carbonyl]phenyl]-2-methyl-3-furanecarboxamide

EXAMPLE 112

N-[4-[(6,7-Dihydro-5H-dibenz[b,d]azepin-5-yl)
carbonyl]phenyl]-3-methyl-2-furanecarboxamide

EXAMPLE 113

N-[4-[(6,7-Dihydro-5H-dibenz[b,d]azepin-5-yl)
carbonyl]phenyl]phenylacetamide

EXAMPLE 114

N-[4-[(6,7-Dihydro-5H-dibenz[b,d]azepin-5-yl)
carbonyl]phenyl]-2-chlorophenylacetamide

EXAMPLE 115

N-[4-[(6,7-Dihydro-5H-dibenz[b,d]azepin-5-yl)
carbonyl]phenyl]-2-methylphenylacetamide

EXAMPLE 116

N-[4-[(6,7-Dihydro-5H-dibenz[b,d]azepin-5-yl)
carbonyl]phenyl]thiophene-2-carboxamide

EXAMPLE 117

N-[4-[(6,7-Dihydro-5H-dibenz[b,d]azepin-5-yl)
carbonyl]phenyl]-2-methyl-3-thiopheneacetamide

EXAMPLE 118

N-[4-[(6,7-Dihydro-5H-dibenz[b,d]azepin-5-yl)
carbonyl]phenyl]-2-methyl-3-furaneacetamide

EXAMPLE 119

N-[4-[(6,11-Dihydro-5H-dibenz[b,e]azepin-5-yl)
carbonyl]phenyl]-2-methyl-3-furanecarboxamide As described for Example 9, 2-methyl-3-furanecarbonyl chloride is reacted with 5-(4-aminobenzoyl)-6,11-dihydro-5H-dibenz[b,e]azepine to give the product. Recrystallization from dichloromethane-hexane gives crystals, m.p. 202°–204° C.

EXAMPLE 120

N-[4-[(6,11-Dihydro-5H-dibenz[b,e]azepin-5-yl)
carbonyl]phenyl]-3-chlorobenzo[b]thiophene-2-
carboxamide As described for Example 9, 3-chlorobenzo[b]thiophene-2-carbonyl chloride is reacted with 5-(4-aminobenzoyl)-6,11-dihydro-5H-dibenz[b,e]azepine to give the product. Recrystallization from dichloromethane-hexane gives crystals, m.p. 252°–254° C.

N-[4-[(6,11-Dihydro-5H-dibenz[b,e]azepin-5-yl)
carbonyl]-3-methylphenyl]-2-methylbenzamide As described for Example 9, 2-methylbenzoyl chloride is reacted with 5-(4-amino-3-methylbenzoyl)-6,11-dihydro-5H-dibenz[b,e]azepine to give the product as crystals, m.p. 112°–114° C.

EXAMPLE 122

6,11-Dihydro-5-[4-[[[(2-methylphenyl)amino]
carbonyl]amino]benzoyl]-5H-dibenz[b,e]azepine A mixture of 0.314 g of 5-(4-aminobenzoyl)-6,11-dihydro-5H-dibenz[b,e]azepine and 0.173 g of o-tolylisocyanate in 15 ml of tetrahydrofuran is refluxed overnight. An additional 84 mg of o-tolylisocyanate is added and the mixture refluxed for three hours. The solvent is removed, water added to the residue and the residue extracted with dichloromethane. The extract is washed with 1N HCl, $H_2O$, 1M $NaHCO_3$, brine and dried ($Na_2SO_4$). The solution is filtered through a thin pad of hydrous magnesium silicate. The pad is washed with dichloromethane. The filtrate (140 ml) is discarded. The filter pad is washed with acetone to give 0.370 g of product. Trituration with dichloromethane-hexane gives 0.186 g of crystals, m.p. 188°–190° C.

EXAMPLE 123

4-[(6,11-Dihydro-5H-dibenz[b,e]azepin-5-yl)
carbonyl]-N-(2-methylphenyl)benzamide To a mixture of 0.362 g of 4-[(6,11-dihydro-5H-dibenz[b,e]azepin-5-yl)carbonyl]benzoyl chloride and 0.101 g of triethylamine in 5 ml of dichloromethane is added a solution of 0.129 g of 2-methylaniline in 3 ml of dichloromethane. The mixture is stirred 1.5 hr at room temperature and then washed with $H_2O$ 1N HCl, 1M $NaHCO_3$, brine and dried ($Na_2SO_4$). The solvent is removed to give a solid. The solid is dissolved in dichloromethane and filtered through a thin pad of hydrous magnesium silicate with dichloromethane as eluent to give 0.025 g of crystals, m.p. 214°–216° C.

EXAMPLE 124

4-[(6,11-Dihydro-5H-dibenz[b,e]azepin-5-yl)
carbonyl]-N-(2,3-dimethylphenyl)benzamide As described for Example 123, a mixture of 0.361 g of 4-[(6,11-dihydro-5H-dibenz[b,e]azepin-5-yl)carbonyl]benzoyl chloride, 0.101 g of triethylamine and 0.145 g of 2,3-dimethylaniline is stirred for 1.5 hr. and worked up to give 0.44 g of crystals, m.p. 248°–251° C.

The following compounds are prepared as described in Example 123.

EXAMPLE 125

4-[(6,11-Dihydro-5H-dibenz[b,e]azepin-5-yl)
carbonyl]-N-(2-chlorophenyl)benzamide

EXAMPLE 126

4-[(6,11-Dihydro-5H-dibenz[b,e]azepin-5-yl) carbonyl]-N-(2,4-dichlorophenyl)benzamide

EXAMPLE 127

N-[(6,11-Dihydro-5H-dibenz[b,e]azepin-5-yl) carbonyl]-N-(2,5-dichlorophenyl)benzamide

EXAMPLE 128

N-[(6,11-Dihydro-5H-dibenz[b,e]azepin-5-yl) carbonyl]-N-(2,4-dimethylphenyl)benzamide

EXAMPLE 129

N-[(6,11-Dihydro-5H-dibenz[b,e]azepin-5-yl) carbonyl]-N-(2,5-dimethylphenyl)benzamide

EXAMPLE 130

4-[(6,11-Dihydro-5H-dibenz[b,e]azepin-5-yl) carbonyl]-N-(2-methoxyphenyl)benzamide

EXAMPLE 131

4-[(6,11-Dihydro-5H-dibenz[b,e]azepin-5-yl) carbonyl]-N-(2,4-dimethoxyphenyl)benzamide

EXAMPLE 132

4-[(6,11-Dihydro-5H-dibenz[b,e]azepin-5-yl) carbonyl]-N-(3-chloro-4-methoxyphenyl)benzamide

EXAMPLE 133

4-[(6,11-Dihydro-5H-dibenz[b,e]azepin-5-yl) carbonyl]-N-(5-chloro-2-methoxyphenyl)benzamide

EXAMPLE 134

4-[(6,11-Dihydro-5H-dibenz[b,e]azepin-5-yl) carbonyl]-N-(3-chlorophenyl)benzamide

EXAMPLE 135

4-[(6,11-Dihydro-5H-dibenz[b,e]azepin-5-yl) carbonyl]-N-(2-chloro-5-methoxyphenyl)benzamide

EXAMPLE 136

N-[4-[(2-Chloro-6,11-dihydro-5H-dibenz[b,e] azepin-5-yl)carbonyl]phenyl-2-methylbenzamide A mixture of 0.349 g of 2-chloro-5-(4-aminobenzoyl)-6,11-dihydro-5H-dibenz[b,e]azepine, 0.131 g of triethylamine and 0.201 g of 2-methylbenzoyl chloride in 13 ml of dichloromethane is stirred at room temperature for 3 hours. The mixture is poured into water and the organic layer separated. The organic layer is washed with 1N HCl, $H_2O$, 1N $NaHCO_3$, brine and dried ($Na_2SO_4$). The solution is filtered through a thin pad of hydrous magnesium silicate and the pad washed with dichloromethane. The filtrate is concentrated and the solid crystallized from dichloromethane-hexane to give 0.32 g of crystals, m.p. 187°–189° C.

EXAMPLE 137

N-[4-[(2-Chloro-6,11-dihydro-5H-dibenz[b,e] azepin-5-yl)carbonyl]phenyl]2,4-dichlorobenzamide As described for Example 136, a mixture of 0.349 g of 2-chloro-5-(4-aminobenzoyl)-6,11-dihydro-5H-dibenz[b,e] azepine, 0.131 g of triethylamine and 0.272 g of 2,4-dichlorobenzoyl chloride in 13 ml of dichloromethane is stirred at room temperature for 3 hours. Work-up gives a solid which is crystallized from dichloromethane-hexane to give 0.43 g of crystals, m.p. 199°–201° C.

EXAMPLE 138

N-[4-[(2-Chloro-6,11-dihydro-5H-dibenz[b,e] azepin-5-yl)carbonyl]phenyl]2,3-dimethylbenzamide As described for Example 136, a mixture of 0.349 g of 2-chloro-5-(4-aminobenzoyl)-6,11-dihydro-5H-dibenz[b,e] azepine, 0.131 g of triethylamine and 0.219 g of 2,3-dimethylbenzoyl chloride in 13 ml of dichloromethane is stirred at room temperature for 18 hours. Work-up gives a solid which is recrystallized from dichloromethane-hexane to give 0.38 g of crystals 191°–193° C.

EXAMPLE 139

2-Chloro-6,11-dihydro-5-[4-[[[(2-methylphenyl) amino]carbonyl]amino]benzoyl]-5H-dibenz[b,e] azepine As described for Example 122, a mixture of 0.348 g of 2-chloro-5-(4-aminobenzoyl)-6,11-dihydro-5H-dibenz[b,e] azepine and 0.175 g of o-tolylisocyanate in 15 ml of tetrahydrofuran is refluxed overnight and worked-up to give the product as a solid.

The following compounds are prepared as described in Example 136.

EXAMPLE 140

N-[4-[(2-Chloro-6,11-dihydro-5H-dibenz[b,e] azepin-5-yl)carbonyl]phenyl]-2-chlorobenzamide

EXAMPLE 141

N-[4-[(2-Chloro-6,11-dihydro-5H-dibenz[b,e] azepin-5-yl)carbonyl]phenyl]-2,5-dichlorobenzamide

EXAMPLE 142

N-[4-[(2-Chloro-6,11-dihydro-5H-dibenz[b,e] azepin-5-yl)carbonyl]phenyl]-2-chloro-4-methylbenzamide

EXAMPLE 143

N-[4-[(2-Chloro-6,11-dihydro-5H-dibenz[b,e]azepin-5-yl)carbonyl]phenyl]-2-methyl-4-chlorobenzamide

EXAMPLE 144

N-[4-[(2-Chloro-6,11-dihydro-5H-dibenz[b,e]azepin-5-yl)carbonyl]phenyl]-2,4-dimethylbenzamide

EXAMPLE 145

N-[4-[(2-Chloro-6,11-dihydro-5H-dibenz[b,e]azepin-5-yl)carbonyl]phenyl]-2,5-dimethylbenzamide

EXAMPLE 146

N-[4-[(2-Chloro-6,11-dihydro-5H-dibenz[b,e]azepin-5-yl]carbonyl]phenyl]-2-methoxybenzamide

EXAMPLE 147

N-[4-[(2-Chloro-6,11-dihydro-5H-dibenz[b,e]azepin-5-yl)carbonyl]phenyl]-2-trifluoromethoxybenzamide

EXAMPLE 148

N-[4-[(2-Chloro-6,11-dihydro-5H-dibenz[b,e]azepin-5-yl)carbonyl]phenyl]-2,4-dimethoxybenzamide

EXAMPLE 149

N-[4-[(2-Chloro-6,11-dihydro-5H-dibenz[b,e]azepin-5-yl)carbonyl]phenyl]-2,6-dimethoxybenzamide

EXAMPLE 150

N-[4-[(2-Chloro-6,11-dihydro-5H-dibenz[b,e]azepin-5-yl)carbonyl]phenyl]-2,6-dichlorobenzamide

EXAMPLE 151

N-[4-[(2-Chloro-6,11-dihydro-5H-dibenz[b,e]azepin-5-yl)carbonyl]phenyl]-2,6-dimethylbenzamie

EXAMPLE 152

N-[4-[(2-Chloro-6,11-dihydro-5H-dibenz[b,e]azepin-5-yl)carbonyl]phenyl]-2-methylthiobenzamide

EXAMPLE 153

N-[4-[(2-Chloro-6,11-dihydro-5H-dibenz[b,e]azepin-5-yl)carbonyl]phenyl]-2-methylthiophene-3-carboxamide

EXAMPLE 154

N-[4-[(2-Chloro-6,11-dihydro-5H-dibenz[b,e]azepin-5-yl)carbonyl]phenyl]-3-methylthiophene-2-carboxamide

EXAMPLE 155

N-[4-[(2-Chloro-6,11-dihydro-5H-dibenz[b,e]azepin-5-yl)carbonyl]phenyl]-2-methylfurane-3-carboxamide

EXAMPLE 156

N-[4-[(2-Chloro-6,11-dihydro-5H-dibenz[b,e]azepin-5-yl)carbonyl]phenyl]-3-methylfurane-2-carboxamide

EXAMPLE 157

N-[4-[(2-Chloro-6,11-dihydro-5H-dibenz[b,e]azepin-5-yl)carbonyl]phenyl]-2-chlorophenylacetamide

EXAMPLE 158

N-[4-[(2-Chloro-6,11-dihydro-5H-dibenz[b,e]azepin-5-yl)carbonyl]phenyl]-2-methylphenylacetamide

EXAMPLE 159

N-[4-[(2-Chloro-6,11-dihydro-5H-dibenz[b,e]azepin-5-yl)carbonyl]phenyl]-2-methoxy-4-chlorobenzamide

EXAMPLE 160

N-[4-[(2-Chloro-6,11-dihydro-5H-dibenz[b,e]azepin-5-yl)carbonyl]phenyl]-2-trifluorobenzamide

EXAMPLE 161

N-[4-[(2-Chloro-6,11-dihydro-5H-dibenz[b,e]azepin-5-yl)carbonyl]phenyl]-2-methoxyphenylacetamide

EXAMPLE 162

N-[4-[(2-Chloro-6,11-dihydro-5H-dibenz[b,e]azepin-5-yl)carbonyl]phenyl]cyclohexylcarboxamide

EXAMPLE 163

N-[4-[(2-Chloro-6,11-dihydro-5H-dibenz[b,e]azepin-5-yl)carbonyl]phenyl]-3-cyclohexenecarboxamide

EXAMPLE 164

N-[4-[(2-Chloro-6,11-dihydro-5H-dibenz[b,e]azepin-5-yl)carbonyl]phenyl]cyclohexylacetamide

EXAMPLE 165

N-[4-[(6,11-Dihydro-5H-dibenz[b,e]azepin-5-yl)carbonyl]phenyl]-2-methoxy-4-chlorobenzamide As described for Example 9, a mixture of 0.377 g (1 mmol) of 5-(4-aminobenzoyl)-6,11-dihydro-5H-dibenz[b,e]azepine, 0.295 g of 2-methoxy-4-chlorobenzoyl chloride, and 0.15 g of triethylamine in 10 ml of dichloromethane is stirred at room temperature for 3 hours. An additional 0.148 g of 2-methoxy-4-chlorobenzoyl chloride and 75 mg of triethylamine is added and the mixture stirred overnight. The solution is worked-up as for Example 9 to give 0.38 g of product (crystallized from dichloromethane-hexane) m.p. 237°–239° C.

EXAMPLE 166

N-[4-[(6,11-Dihydro-5H-dibenz[b,e]azepin-5-yl)carbonyl]phenyl]-2-trifluoromethylbenzamide As described for Example 9, a mixture of 0.377 g (1.44 mmol) of 5-(4-aminobenzoyl)-6,11-dihydro-5H-dibenz[b,e]azepine, 0.15 g of triethylamine and 0.300 g (1.44 mmol) of 2-trifluoromethylbenzoyl chloride is stirred at room temperature for 2 hours and then washed with 1N HCl 1M NaHCO$_3$, brine and dried (Na$_2$SO$_4$). The solution is passed through a thin pad of hydrous magnesium silicate and the filtrate evaporated to give a solid. Crystallization from dichloromethane-hexane gives 0.41 g of crystals, m.p. 191°–193° C.

EXAMPLE 167

N-[4-[(6,11-Dihydro-5H-dibenz[b,e]azepin-5-yl)carbonyl]phenyl]-N-methyl-2-methylbenzamide A mixture of 0.291 g of 6,11-dihydro-5-dibenz[b,e]azepine, 0.518 g of 4-[N-methyl-N-(2-methylbenzoyl)amino]benzoyl chloride and 0.182 g of triethylamine in 10 ml of tetrahydrofuran is stirred at room temperature for 2 hours. The solvent is removed, the residue diluted with water and extracted with dichloromethane. The extract is washed with 1N HCl water, 1M NaHCO$_3$, brine and dried (Na$_2$SO$_4$). The solution is passed through a thin pad of hydrous magnesium silicate. The filtrate is concentrated and chilled to give 0.52 g of crystals, m.p. 160°–170° C.

As described for Example 167, but substituting the appropriate aroyl chloride, the following compounds are prepared.

EXAMPLE 168

N-[4-[(6,11-Dihydro-5H-dibenz[b,e]azepin-5-yl)carbonyl]phenyl]-N-methyl-2-chlorobenzamide

EXAMPLE 169

N-[4-[(6,11-Dihydro-5H-dibenz[b,e]azepin-5-yl)carbonyl]phenyl]-N-methyl-2,5-dichlorobenzamide

EXAMPLE 170

N-[4-[(6,11-Dihydro-5H-dibenz[b,e]azepin-5-yl)carbonyl]phenyl]-N-methyl-2,4-dichlorobenzamide

EXAMPLE 171

N-[4-[(6,11-Dihydro-5H-dibenz[b,e]azepin-5-yl)carbonyl]phenyl]-N-methyl-2-fluorobenzamide

EXAMPLE 172

N-[4-[(6,11-Dihydro-5H-dibenz[b,e]azepin-5-yl)carbonyl]phenyl]-N-methyl-2-chloro-4-methylbenzamide

EXAMPLE 173

N-[4-[(6,11-Dihydro-5H-dibenz[b,e]azepin-5-yl)carbonyl]phenyl]-N-methyl-2-methyl-4-chlorobenzamide

EXAMPLE 174

N-[4-[(6,11-Dihydro-5H-dibenz[b,e]azepin-5-yl)carbonyl]phenyl]-N-methyl-2,4-dimethylbenzamide

EXAMPLE 175

N-[4-[(6,11-Dihydro-5H-dibenz[b,e]azepin-5-yl)carbonyl]phenyl]-N-methyl-2,3-dimethylbenzamide

EXAMPLE 176

N-[4-[(6,11-Dihydro-5H-dibenz[b,e]azepin-5-yl)carbonyl]phenyl]-N-methyl-2-methoxybenzamide

EXAMPLE 177

N-[4-[(6,11-Dihydro-5H-dibenz[b,e]azepin-5-yl)carbonyl]phenyl]-N-methyl-3-trifluoromethoxybenzamide

EXAMPLE 178

N-[4-[(6,11-Dihydro-5H-dibenz[b,e]azepin-5-yl)carbonyl]phenyl]-N-methyl-2,4-dimethoxybenzamide

EXAMPLE 179

N-[4-[(6,11-Dihydro-5H-dibenz[b,e]azepin-5-yl)carbonyl]phenyl]-N-methyl-2-methoxy-4-chlorobenzamide

EXAMPLE 180

N-[4-[(6,11-Dihydro-5H-dibenz[b,e]azepin-5-yl)
carbonyl]phenyl]-N-methyl-2-methylthiobenzamide

EXAMPLE 181

N-[4-[(6,11-Dihydro-5H-dibenz[b,e]azepin-5-yl)
carbonyl]phenyl]-N-methyl-2-methylthiophene-3-
carboxamide

EXAMPLE 182

N-[4-[(6,11-Dihydro-5H-dibenz[b,e]azepin-5-yl)
carbonyl]phenyl]-N-methyl-3-methyl-3-thiophene-
carboxamide

EXAMPLE 183

N-[4-[(6,11-Dihydro-5H-dibenz[b,e]azepin-5-yl)
carbonyl]phenyl]-N-methyl-2-methyl-3-furane-
carboxamide

EXAMPLE 184

N-[4-[(6,11-Dihydro-5H-dibenz[b,e]azepin-5-yl)
carbonyl]phenyl]-N-methyl-3-methyl-3-furane-
carboxamide

EXAMPLE 185

N-[4-[(6,11-Dihydro-5H-dibenz[b,e]azepin-5-yl)
carbonyl]phenyl]-N-methylphenylacetamide

EXAMPLE 186

N-[4-[(6,11-Dihydro-5H-dibenz[b,e]azepin-5-yl)
carbonyl]phenyl]-N-methyl-3-
chlorophenylacetamide

EXAMPLE 187

N-[4-[(6,11-Dihydro-5H-dibenz[b,e]azepin-5-yl)
carbonyl]phenyl]-N-methyl-2-
methoxyphenylacetamide

EXAMPLE 188

N-[4-[(6,11-Dihydro-5H-dibenz[b,e]azepin-5-yl)
carbonyl]phenyl]-N-methyl-2-
methylphenylacetamide

EXAMPLE 189

N-[4-[(6,11-Dihydro-5H-dibenz[b,e]azepin-5-yl)
carbonyl]phenyl]-N-methyl-2-methyl-3-thiophene-
acetamide

EXAMPLE 190

N-[4-[(6,11-Dihydro-5H-dibenz[b,e]azepin-5-yl)
carbonyl]phenyl]-N-methyl-2-
trifluoromethylacetamide

EXAMPLE 191

N-[4-[(6,11-Dihydro-5H-dibenz[b,e]azepin-5-yl)
carbonyl]phenyl]-N-methylcyclohexanecarboxamide

EXAMPLE 192

N-[4-[(6,11-Dihydro-5H-dibenz[b,e]azepin-5-yl)
carbonyl]phenyl]-N-methyl-3-
cyclohexanecarboxamide

EXAMPLE 193

N-[4-[(5,6-Dihydro-7H-pyrimido[5,4-d][1]
benzazepin-7-yl)carbonyl]phenyl]-2-
methylbenzamide As described for Example 1, 5 mmol of 4-[(2-methylbenzoyl)amino]benzoyl chloride is reacted with 5 mmol of 5,6-dihydro-7H-pyrimido[5,4-d][1]benzazepine in pyridine to give the product as a solid.

EXAMPLE 194

N-[4-[(5,6-Dihydro-7H-pyrimido[5,4-d][1]
benzazepin-7-yl)carbonyl]phenyl]-2,4-
dichlorobenzamide As described for Example 1, 5 mmol of 4-[(2,4-dichlorobenzoyl)amino]benzoyl chloride is reacted with 5 mmol of 5,6-dihydro-7H-pyrimido[5,4-d]-[1]-benzazepine in pyridine to give the product as a solid.

EXAMPLE 195

N-[4-[(5,6-Dihydro-7H-pyrimido[5,4-d][1]
benzazepin-7-yl)carbonyl]phenyl]-2,5-
dichlorobenzamide As described for Example 1, 5 mmol of 4-[(2,5-dichlorobenzoyl)amino]benzoyl chloride is reacted with 5mmol of 5,6-dihydro-7H-pyrimido-[5,4-d][1]benzazepine in pyridine to give the product as a solid.

EXAMPLE 196

N-[4-[(5,6-Dihydro-7H-pyrimido[5,4-d][1]
benzazepin-7-yl)carbonyl]phenyl]-2-
chlorobenzamide As described for Example 1, 5 mmol of 4-[(2-chlorobenzoyl)amino]benzoyl chloride is reacted with 5 mmol of 5,6-dihydro-7H-pyrimido[5,4-d][1]benzazepine in pyridine to give the product as a solid.

EXAMPLE 197

N-[4-[(5,6-Dihydro-7H-pyrimido[5,4-d][1]
benzazepin-7-yl)carbonyl]phenyl]-2-
chlorophenylacetamide

EXAMPLE 198

N-[4-[(5,11-Dihydro-6H-pyrido[3,2-d][1]
benzazepin-6-yl)carbonyl]phenyl]-2-
methylbenzamide A mixture of 5 mmol of 5,11-dihydro-6-(4-aminobenzoyl)
-6H-pyrido[3,2-d][1]benzazepine, 5.5 mmol of 2-methylbenzoyl chloride and 10 mmol of triethylamine in 15 ml of dichloromethane is stirred at room temperature for 16 hours. The mixture is diluted with 50 ml of dichloromethane and solution washed with 20 ml each of $H_2O$, 1M citric acid, $NaHCO_3$, brine and dried $(Na_2SO_4)$. The solvent is evaporated in vacuo to give a solid. The solid is purified by chromatography on silica gel to give the product as a solid.

The following compounds are prepared as described for in Example 198.

EXAMPLE 199

N-[4-[(5,11-Dihydro-6H-pyrido[3,2-c][1]benzazepin-6-yl)carbonyl]phenyl]-2-chlorobenzamide

EXAMPLE 200

N-[4-[(5,11-Dihydro-6H-pyrido[3,2-d][1]benzazepin-6-yl)carbonyl]phenyl]-2,5-dichlorobenzamide

EXAMPLE 201

N-[4-[(5,11-Dihydro-6H-pyrido[3,2-d][1]benzazepin-6-yl)carbonyl]phenyl]-2,4-dichlorobenzamide

EXAMPLE 202

N-[4-[(5,11-Dihydro-6H-pyrido[3,2-d][1]benzazepin-6-yl)carbonyl]phenyl]-2-chloro-4-methylbenzamide

EXAMPLE 203

N-[4-[(5,11-Dihydro-6H-pyrido[3,2-e][1]benzazepin-6-yl)carbonyl]phenyl]-2-methyl-4-chlorobenzamide

EXAMPLE 204

N-[4-[(5,11-Dihydro-6H-pyrido[3,2-e][1]benzazepin-6-yl)carbonyl]phenyl]-2,4-dimethylbenzamide

EXAMPLE 205

N-[4-[(5,11-Dihydro-6H-pyrido[3,2-e][1]benzazepin-6-yl)carbonyl]phenyl]-2,3-dimethylbenzamide

EXAMPLE 206

N-[4-[(5,11-Dihydro-6H-pyrido[3,2-e][1]benzazepin-6-yl)carbonyl]phenyl]-2-methoxybenzamide

EXAMPLE 207

N-[4-[(5,11-Dihydro-6H-pyrido[3,2-e][1]benzazepin-6-yl)carbonyl]phenyl]-2-trifluoromethoxybenzamide

EXAMPLE 208

N-[4-[(5,11-Dihydro-6H-pyrido[3,2-e][1]benzazepin-6-yl)carbonyl]phenyl]-2,4-dimethoxybenzamide

EXAMPLE 209

N-[4-[(5,11-Dihydro-6H-pyrido[3,2-e][1]benzazepin-6-yl)carbonyl]phenyl]-2-methoxy-4-chlorobenzamide

EXAMPLE 210

N-[4-[(5,11-Dihydro-6H-pyrido[3,2-e][1]benzazepin-6-yl)carbonyl]-phenyl]-2-trifluoromethylbenzamide

EXAMPLE 211

N-[4-[(5,11-Dihydro-6H-pyrido[3,2-e][1]benzazepin-6-yl)carbonyl]phenyl]-2-methylthiobenzamide

EXAMPLE 212

N-[4-[(5,11-Dihydro-6H-pyrido[3,2-e][1]benzazepin-6-yl)carbonyl]phenyl]-2-methyl-3-thiophenecarboxamide

EXAMPLE 213

N-[4-[(5,11-Dihydro-6H-pyrido[3,2-e][1]benzazepin-6-yl)carbonyl]phenyl]-3-methyl-2-thiophenecarboxamide

EXAMPLE 214

N-[4-[(5,11-Dihydro-6H-pyrido[3,2-e][1]benzazepin-6-yl)carbonyl]phenyl]-2-methyl-3-furanecarboxamide

EXAMPLE 215

N-[4-[(5,11-Dihydro-6H-pyrido[3,2-e][1]benzazepin-6-yl)carbonyl]phenyl]-3-methyl-2-furanecarboxamide

EXAMPLE 216

N-[4-[(5,11-Dihydro-6H-pyrido[3,2-e][1]benzazepin-6-yl)carbonyl]phenyl]-2-methoxyphenylacetamide

EXAMPLE 217

N-[4-[(5,11-Dihydro-6H-pyrido[3,2-e][1]
benzazepin-6-yl)carbonyl]phenyl]-2-
chlorophenylacetamide

EXAMPLE 218

N-[4-[(5,11-Dihydro-6H-pyrido[3,2-e][1]
benzazepin-6-yl)carbonyl]phenyl]-2-
methylphenylacetamide

EXAMPLE 219

N-[4-[(5,11-Dihydro-6H-pyrido[3,2-e][1]
benzazepin-6-yl)carbonyl]phenyl]-2-methyl-3-
thiopheneacetamide

EXAMPLE 220

N-[4-[(5,11-Dihydro-6H-pyrido[3,2-e][1]
benzazepin-6-yl)carbonyl]phenyl]
cyclohexanecarboxamide

EXAMPLE 221

N-[4-[(5,11-Dihydro-6H-pyrido[3,2-e][1]
benzazepin-6-yl)carbonyl]phenyl]-3-
cyclohexanecarboxamide

EXAMPLE 222

N-[4-(Pyrido[2,3-e][1,4]benzothiazepin-5(6H)-
ylcarbonyl)phenyl]-2-methylbenzamide A mixture of 5 mmol of 5,6-dihydro-5-(4-aminobenzoyl) pyrido[2,3-b][1,4]benzothiazepine, 5.5 mmol of 2-methylbenzoyl chloride and 10 mmol of triethylamine in 15 ml of dichloromethane is stirred at room temperature for 16 hours. The mixture is diluted with 50 ml of dichloromethane and the solution washed with 20 ml each of $H_2O$, 1M citric acid, NaHCO3, brine and dried (Na2SO4). The solvent is removed under vacuum to give a solid. The solid is purified by chromatography on silica gel with ethyl acetate-hexane as solvent to give the product as a solid. The following compounds are prepared as described for in Example 222.

EXAMPLE 223

N-[4-(Pyrido[2,3-b][1,4]benzothiazepin-5(6H)-
ylcarbonyl)phenyl]-2-chlorobenzamide

EXAMPLE 224

N-[4-(Pyrido[2,3-b][1,4]benzothiazepin-5(6H)-
ylcarbonyl)phenyl]-2,5-dichlorobenzamide

EXAMPLE 225

N-[4-(Pyrido[2,3-b][1,4]benzothiazepin-5(6H)-
ylcarbonyl)phenyl]-2,4-dichlorobenzamide

EXAMPLE 226

N-[4-(Pyrido[2,3-b][1,4]benzothiazepin-5(6H)-
ylcarbonyl)phenyl]-2-chloro-4-methylbenzamide

EXAMPLE 227

N-[4-(Pyrido[2,3-b][1,4]benzothiazepin-5(6H)-
ylcarbonyl)phenyl]-2-methyl-4-chlorobenzamide

EXAMPLE 228

N-[4-(Pyrido[2,3-b][1,4]benzothiazepin-5(6H)-
ylcarbonyl)phenyl]-2,4-dimethylbenzamide

EXAMPLE 229

N-[4-(Pyrido[2,3-b][1,4]benzothiazepin-5(6H)-
ylcarbonyl)phenyl]-2,3-dimethylbenzamide

EXAMPLE 230

N-[4-(Pyrido[2,3-b][1,4]benzothiazepin-5(6H)-
ylcarbonyl)phenyl]-2-methoxybenzamide

EXAMPLE 231

N-[4-(Pyrido[2,3-b][1,4]benzothiazepin-5(6H)-
ylcarbonyl)phenyl]-2-trifluoromethoxybenzamide

EXAMPLE 232

N-[4-(Pyrido[2,3-b][1,4]benzothiazepin-5(6H)-
ylcarbonyl)phenyl]-2,4-dimethoxybenzamide

EXAMPLE 233

N-[4-(Pyrido[2,3-b][1,4]benzothiazepin-5(6H)-
ylcarbonyl)phenyl]-2-methoxy-4-Chlorobenzamide

EXAMPLE 234

N-[4-(Pyrido[2,3-b][1,4]benzothiazepin-5(6H)-
ylcarbonyl)phenyl]-2-trifluoromethylbenzamide

EXAMPLE 235

N-[4-(Pyrido[2,3-b][1,4]benzothiazepin-5(6H)-
ylcarbonyl)phenyl]-2-methylthiobenzamide

EXAMPLE 236

N-[4-(Pyrido[2,3-b][1,4]benzothiazepin-5(6H)-
ylcarbonyl)phenyl]-2-methyl-3-
thiophenecarboxamide

EXAMPLE 237

N-[4-(Pyrido[2,3-b][1,4]benzothiazepin-5(6H)-ylcarbonyl)phenyl]-3-methyl-2-thiophenecarboxamide

EXAMPLE 238

N-[4-(Pyrido[2,3-b][1,4]benzothiazepin-5(6H)-ylcarbonyl)phenyl]-2-methyl-3-furanecarboxamide

EXAMPLE 239

N-[4-(Pyrido[2,3-b][1,4]benzothiazepin-5(6H)-ylcarbonyl)phenyl]-3-methyl-2-furanecarboxamide

EXAMPLE 240

N-[4-(Pyrido[2,3-b][1,4]benzothiazepin-5(6H)-ylcarbonyl)phenyl]phenylacetamide

EXAMPLE 241

N-[4-(Pyrido[2,3-b][1,4]benzothiazepin-5(6H)-ylcarbonyl)phenyl]-2-chlorophenylacetamide

EXAMPLE 242

N-[4-(Pyrido[2,3-b][1,4]benzothiazepin-5(6H)-ylcarbonyl)phenyl]-2-methoxyphenylacetamide

EXAMPLE 243

N-[4-(Pyrido[2,3-b][1,4]benzothiazepin-5(6H)-ylcarbonyl)phenyl]-2-methylphenylacetamide

EXAMPLE 244

N-[4-(Pyrido[2,3-b][1,4]benzothiazepin-5(6H)-ylcarbonyl)phenyl]-2-methyl-3-thiopheneacetamide

EXAMPLE 245

N-[4-(Pyrido[2,3-b][1,4]benzothiazepin-5(6H)-ylcarbonyl)phenyl]cyclohexanecarboxamide

EXAMPLE 246

N-[4-(Pyrido[2,3-b][1,4]benzothiazepin-5(6H)-ylcarbonyl)phenyl]cyclopentanecarboxamide

EXAMPLE 247

N-[4-(Pyrido[2,3-b][1,4]benzothiazepin-5(6H)-ylcarbonyl)phenyl]cyclohexaneacetamide

EXAMPLE 248

N-[4-(Pyrido[2,3-b][1,4]benzothiazepin-5(6H)-ylcarbonyl)phenyl]-3-cyclohexenecarboxamide

EXAMPLE 249

N-[4-[(6,11-Dihydro-5H-dibenz[b,e]azepin-5-yl)carbonyl]phenyl]-2,3,5-trichlorobenzamide A mixture of 366 mg of 2,3,5-trichlorobenzoyl chloride and 151 mg of triethylamine in 2 ml of methylene chloride is stirred while 314 mg of 5-(4-aminobenzoyl)-6,11-dihydro-5H-dibenz[b,e]azepine in 5 ml of methylene chloride is added. Stirring is continued for 1.5 hours. The reaction mixture is partitioned with water and the organic layer is washed with 1N HCl, water, 0.5N NaOH and brine. The organic layer is dried with $Na_2SO_4$ and passed through a pad of hydrous magnesium silicate. Hexane is added to the filtrate at the boil to give 0.52 g of white solid residue which is purified by column chromatography on silica gel by elution with 2:1 hexane-ethyl acetate to give 120 mg of the desired product as a crystalline solid, m.p. 225°–230° C.

EXAMPLE 250

N-[4-[(6,11-Dihydro-5H-dibenz[b,e]azepin-5-yl)carbonyl]phenyl]-3,4-dichlorobenzamide A mixture of 314 mg of 3,4-dichlorobenzoyl chloride and 151 mg of triethylamine in 2 ml of methylene chloride is stirred while 314 mg of 5-(4-aminobenzoyl)-6,11-dihydro-5H-dibenz[b,e]azepine in 5 ml of methylene chloride is added. Stirring is continued for 2 hours. The reaction mixture is partitioned with water and the organic layer is washed 1N HCl, water, 0.5N NaOH and brine. The organic layer is dried with $Na_2SO_4$ and passed through a short pad of hydrous magnesium silicate. Hexane is added to the filtrate at the boil to give 0.35 g of off-white crystalline solid, m.p. 238°–241° C.

EXAMPLE 251

N-[4-[(6,11-Dihydro-5H-dibenz[b,e]azepin-5-yl)carbonyl]phenyl]-3,5-dichlorobenzamide A mixture of 301.6 mg of 3,5-dichlorobenzoyl chloride and 145 mg of triethylamine is stirred in 2 ml of methylene chloride while 314 mg of 5-(4-amino-benzoyl)-6,11-dihydro-5H-dibenz[b,e]azepine in 5 ml of methylene chloride is added. The reaction mixture is stirred at room temperature for 2 hours and 100 mg of 3,5-dichlorobenzoyl chloride added. The reactants are heated at reflux for 36 hours. The cooled reaction mixture layer washed with 1N HCl, water, 1 N NaOH, water and brine. The organic layer is dried with $Na_2SO_4$ and passed through a short pad of hydrous magnesium silicate and hexane added to the filtrate at the boil to give 242 mg of the desired product as a crystalline solid, m.p. 263°–265° C.

EXAMPLE 252

N-[4-[(6,11-Dihydro-5H-dibenz[b,e]azepin-5-yl)carbonyl]phenyl]-3,5-dichlorobenzamide A mixture of 335 mg of 2,6-dichlorobenzoyl chloride and 258 mg of N,N-diisopropylethylamine is stirred in 2 ml of xylene while 314 mg of 5-(4-amino-benzoyl)-6,11-dihydro-5H-dibenz[b,e]azepine is added. The reactants are refluxed in an oil bath at 110° C. for 8 hours. The xylene is evaporated in vacuo to a residue which is partitioned between methylene chloride and water. The organic layer is separated, washed with 1N HCl, 1M NaHCO₃, and brine. The organic layer is dried with Na₂SO₄ and passed through a pad of hydrous magnesium silicate. Hexane is added to the filtrate at the boil to give 370 mg of the desired product as a crystalline solid, m.p. 257°–259° C.

EXAMPLE 153

N-[4-[(6,11-Dihydro-5H-dibenz[b,e]azepin-5-yl)-carbonyl]phenyl]-2,3-dichlorobenzamide A mixture of 301.6 mg of 2,3-dichlorobenzoyl chloride and 145 mg of triethylamine is stirred while 314 mg of 5-(4-aminobenzoyl)-6,11-dihydro-5H-dibenz-[b,e]azepine is added. Stirring is continued for 2 hours. Water is added and the organic layer washed with 1 N HCl, water, 1 M NaHCO₃ and water then dried over Na₂SO₄. The organic layer is passed through a pad of hydrous magnesium silicate and hexane added to the filtrate at the boil to give 0.32 g of the desired product as a crystalline solid, m.p. 225°–230° C.

EXAMPLE 254

N-[4-[(6,11-Dihydro-5H-dibenz[b,e]azepin-5-yl)-carbonyl]phenyl]-2-methyl-5-fluorobenzamide A mixture of 248.5 mg of 1-methyl-2-fluoro-benzoyl chloride and 145 mg of triethylamine is stirred while 376.8 mg of 5-(4-aminobenzoyl)-6,11-dihydro-5H-dibenz[b,e]azepine is added. Stirring is continued for 3 hours. Water is added and the organic layer washed with 1N HCl, water, 1M NaHCO₃ and water then dried over Na₂SO₄. The organic layer is passed through a pad of hydrous magnesium silicate. The desired product crystallizes from methylene chloride to give 0.417 g of the desired product, m.p. 167°–170° C.

EXAMPLE 255

N-[4-[(6,11-Dihydro-5H-dibenz[b,e]azepin-5-yl)-carbonyl]phenyl]-3-cyclohexene-1-carboxamide A mixture of 208 mg of 3-cyclohexene-1-carbonyl chloride (prepared from 3-cyclohexene-1-carboxylic acid and thionyl chloride) and 145 mg of triethylamine in 3 ml of methylene chloride is added to a solution of 377 mg of 5-(4-aminobenzoyl)-6,11-dihydro-5H-dibenz[b,e]azepine in 7 ml of methylene chloride. The mixture is stirred for 18 hours, washed with water, 1N HCl, water, 1M NaHCO₃ and brine then dried with Na₂SO₄. The organic layer is passed through a short column of hydrous magnesium silicate and hexane added to the filtrate at the boil to give 340 mg of the desired product as a crystalline solid, m.p. 234°–236° C.

EXAMPLE 156

N-[4-[(6,11-Dihydro-5H-dibenz[b,e]azepin-5-yl)-carbonyl]-3-chlorophenyl]-2,4-dichlorobenzamide A mixture of 0.50 g of 5-(2-chloro-4-amino-benzoyl)-6,11-dihydro-5H-dibenz[b,e]azepine, 0.28 g of N,N-diisopropylethylamine and 0.45 g of 2,4-dichlorobenzoyl chloride in 25 ml of methylene chloride is stirred at room temperature for 18 hours. The reaction mixture is washed with water, saturated NaHCO₃, dried (Na₂SO₄) and passed through a short pad of hydrous magnesium silicate. The filtrate is evaporated in vacuo to give the desired product as a solid residue, m.p., 150°–165° C.

EXAMPLE 257

N-[4-[(6,11-Dihydro-5H-dibenz[b,e]azepin-5-yl)-carbonyl]-2-methoxyphenyl]-1-methylbenzamide A mixture of 1.0 g of 5-(3-methoxy-4-amino-benzoyl)-6,11-dihydro-5H-dibenz[b,e]azepine, 0.47 g of N,N-diisopropylethylamine and 0.56 g of 2-methylbenzoyl chloride in 25 ml of methylene chloride is stirred at room temperature for 18 hours. The reaction mixture is washed with water and saturated NaHCO₃, dried (Na₂SO₄) and passed through a short pad of hydrous magnesium silicate. Hexane is added at the boil to give 1.27 g of the desired product as a crystalline solid, m.p. 209°–210° C.

EXAMPLE 258

N-[4-[(6,11-Dihydro-5H-dibenz[b,e]azepin-5-yl)-carbonyl]-2,6-dimethylphenyl]-2-methylbenzamide A mixture of 1.42 g of 4-[(benzoyl)amino]-3,5-dimethylbenzoic acid in 20 ml of thionyl chloride is heated on a steam bath under argon for 1 hour. The volatiles are evaporated and the residue evaporated in vacuo from toluene to give 1.40 g of the desired product as a residue which is dissolved in 50 ml of methylene chloride and treated with 0.75 g of N,N-diisopropylethylamine and 0.88 g of 10,11-dihydro-5H-dibenz[b,e]azepine. The reactants are stirred at room temperature for 18 hours and washed with water, saturated NaHCO₃, dried (Na₂SO₄), passed through a pad of hydrous magnesium silicate and hexane added to the filtrate at the boil to give 0.90 g of the desired product as a glass.

EXAMPLE 259

N-[4-[(6,11-Dihydro-5H-dibenz[b,e]azepin-5-yl)-carbonyl]-2,6-dimethylphenyl]-2,4-dichlorobenzamide A mixture of 1.69 g of 4-[(2,4-dichlorobenzoyl)amino]-3,5-dimethylbenzoic acid in 2.0 ml of thionyl chloride is heated on a steam bath under argon for i hour. The volatiles are evaporated and the residue evaporated in vacuo from toluene to give a residue. A solution of the residue in 25 ml of methylene chloride is treated with 0.75 g of N,N-diisopropylethylamine and 0.98 g of 10,11-dihydro-5H-dibenz[b,e]azepine is stirred at room temperature for 18 hours. The reaction mixture is washed with saturated NaHCO₃, dried (Na₂SO₄) and passed through a pad of hydrous magnesium silicate. The filtrate is evaporated to a glass which is dissolved in methylene chloride dried (Na₂SO₄) and passed through a short pad of hydrous magnesium silicate. The filtrate is evaporated to give 1.89 g of the desired product as an amorphorous solid.

EXAMPLE 260

N-[4-[(6,11-Dihydro-5H-dibenz[b,e]azepin-5-yl)-carbonyl]-3-chlorophenyl]-2-methylbenzamide A mixture of 0.31 g of 5-(2-chloro-4-amino-benzoyl)-6,11-dihydro-5H-dibenz[b,e]azepine and 0.15 g of N,N-diisopropylethylamine in 10 ml of methylene chloride is cooled in an ice bath while 0.18 g of 2-methylbenzoyl chloride is added. The bath is removed and the reactants stirred at room temperature for 18 hours. The mixture is washed with water, 1N HCl, water, 1M NaHCO₃, brine and dried (Na₂SO₄). The methylene chloride is removed in vacuo to give 0.34 g of the desired product as crystalline solid, m.p. 138°–150° C. M⁺=467.

EXAMPLE 261

N-[4-[(6,11-Dihydro-5H-dibenz[b,e]azepin-5-yl)-carbonyl]-2-methoxyphenyl]-2-methyl-5-fluorobenzamide A mixture of 0.79 g of 5-(3-methoxy-4-amino-benzoyl)-6,11-dihydro-5H-dibenz[b,e]azepine, 0.40 g of N,N- diisopropylethylamine and 0.55 g of 2-methyl-5-fluorobenzoyl chloride in 25 ml of methylene chloride is stirred at room temperature for 18 hours. The reaction mixture is washed with water and saturated NaHCO$_3$, dried (Na$_2$SO$_4$) and passed through a short pad of hydrous magnesium silicate. Hexane is added at the boil to the filtrate to give 1.05 g of the desired product as a solid.

EXAMPLE 262

N-[4-[(6,11-Dihydro-5H-dibenz[b,e]azepin-5-yl)-carbonyl]-2-chlorophenyl]-2-methyl-3-fluorobenzamide A mixture of 1.0 g of 6,11-dihydro-5H-dibenz-[b,e]azepine, 0.80 g of N,N-diisopropylethylamine and 2.01 g of 4-[(2-methyl-3-fluorobenzoyl)amino]-3-chloro-benzoyl chloride in 100 ml of methylene chloride is stirred at room temperature for 18 hours. The reaction mixture is washed with water, saturated NaHCO$_3$, dried (Na$_2$SO$_4$) and passed through a pad of hydrous magnesium silicate. Hexane is added to the filtrate at the boil to give 1.79 g of the desired product as a crystalline solid, m.p. 254°–256° C.

EXAMPLE 163

N-[4-[(6,11-Dihydro-5H-dibenz[b,e]azepin-5-yl)-carbonyl]-2-methoxyphenyl]-2,4-dichlorobenzamide A mixture of 1.0 g of 5-(3-methoxy-4-amino-benzoyl)-6,11-dihydro-5H-dibenz[b,e]azepine, 0.47 g of N,N-diisopropylethylamine and 0.76 g of 2,4-dichlorobenzoyl chloride in 25 ml of methylene chloride is stirred at room temperature for 18 hours. The reaction mixture is washed with water and saturated NaHCO$_3$, dried (Na$_2$SO$_4$) and passed through a short pad of hydrous magnesium silicate. Hexane is added at the boil to give 1.39 g of the desired product as a crystalline solid, m.p. 212°–214° C.

EXAMPLE 264

N-[4-[(6,11-Dihydro-5H-dibenz[b,e]azepin-5-yl)-carbonyl]-3-chlorophenyl]-2-methyl-3-fluorobenzamide A mixture of 1.85 g of 4-[(2-methyl-3-fluoro-benzoyl)amino]-2-chlorobenzoic acid in 30 ml of thionyl chloride under argon is heated at reflux for 1 hour. The thionyl chloride is evaporated in vacuo to a residue which is stirred with hexane and collected to give 1.94 g of 4-[(2-methyl-3-fluorobenzoyl)amino]-2-chlorobenzoyl chloride which is dissolved in 25 ml of methylene chloride and 0.49 g of N,N-diisopropylethylamine added, followed by 0.65 g of 6,11-dihydro-5H-dibenz[b,e]azepine. The reactants are stirred at room temperature for 18 hours and washed with water, saturated NaHCO3, dried (Na$_2$SO$_4$) and passed through a short pad of hydrous magnesium silicate to give 1.19 g of the desired product as a glass.

EXAMPLE 265

N-[4-[(6,11-Dihydro-11-oxo-5H-dibenz[b,e]azepin-5-yl)-carbonyl]phenyl]-2-methylbenzamide A mixture of 1.08 g of N-[4-[(6,11-dihydro-5H-dibenz[b,e]azepin-5-yl)carbonyl]phenyl]-2-methylbenzamide in 50 ml of t-butanol is heated, 2 ml of water is added followed by 1.18 g of MgSO$_4$, and 2.6 g of KMnO$_4$. An additional 0.84 g of KMnO$_4$ in 25 ml of water is added followed by heating at 65° C. for 18 hours. The reaction mixture is filtered and the filtrate evaporated in vacuo to give 1.2 g of a residue which is purified by column chromatography on silica gel by elution with ethyl acetate and 9:1 ethyl acetate-methanol to give 160 mg of the desired product as a solid, m.p. 115°–119° C.

EXAMPLE 266

(2-Methylphenyl)methyl 4-[(6,11-dihydro-5H-dibenz[b,e]azepin-5-yl)carbonyl)benzoate To a mixture of 248 mg of 2-methylbenzyl alcohol in 4 ml of anhydrous tetrahydrofuran is added 80 mg of sodium hydride (60% in mineral oil) and the mixture stirred for I hour. To the mixture is added 430 mg of 4-[(6,11-dihydro-5H-dibenz[b,e]azepin-5-yl)-carbonyl]benzoyl chloride and the mixture is stirred for 18 hours. The tetrahydrofuran is evaporated in vacuo to a residue which is partitioned between methylene chloride and water. The organic layer is separated and washed with 1N HCl, water, 1M NaHCO$_3$, and brine. The organic layer is dried (Na$_2$SO$_4$) and passed through a short pad of hydrous magnesium silicate and hexane added at the boil to give 170 mg of the desired product, m.p. 140°–142° C.

EXAMPLE 267

N-[4-[(6,11-Dihydro-5H-dibenz[b,e]azepin-5-yl)-carbonyl]phenyl]-N-[(dimethylamino)methyl]-2-methylbenzamide To a suspension of 14 mg of 60% sodium hydride in oil, in 2 ml of tetrahydrofuran is added 0.13 g of N-[4-[(6,11-dihydro-5H-dibenz[b,e]azepin-5-yl)carbonyl]phenyl]-2-methylbenzamide. The reactants are stirred for I hour and 62 mg of N,N-dimethylmethylene ammonium iodide added followed by stirring for 2 hours. The mixture is diluted with 10 ml of ether and filtered. The filtrate is evaporated in vacuo to a residue which is stirred with hexanes to give 0.13 g of the desired product as a white solid, m.p. 131°–133° C.

EXAMPLE 268

N-[4-[(5,11-dihydro-10H-dibenz[b,e][1,4]diazepin-5-yl)carbonyl]phenyl]-2-methylbenzamide A mixture of 1.0 g of 5,11-dihydro-10H-dibenz [b,e][1,4]diazepine 1.9 g of 4-[(2-methylbenzoyl) amino]benzoyl chloride, 4 ml of triethylamine and 0.2 g of 4-(dimethylamino)pyridine in 60 ml of methylene chloride is stirred at room temperature for 18 hours. The reaction mixture is poured into ice water and the separated organic layer washed with 50 ml each of water, 2N HCl, water, saturated NaHCO$_3$ and water. The organic layer is dried (Na$_2$SO$_4$) and the solvent removed to give a residue. The residue is chromatographed on a silica gel column using 1:4 ethyl acetate-hexane to give 1.8 g of the desired product as a solid, m.p. 68°–71° C.

The following compounds are prepared as described for Example 268.

EXAMPLE 269

N-[4-[(5,11-Dihydro-10H-dibenz[b,e][1,4]diazepin-5-yl)carbonyl]phenyl]-2-chlorobenzamide

EXAMPLE 270

N-[4-[(5,11-Dihydro-10H-dibenz[b,e][1,4]diazepin-5-yl)carbonyl]phenyl]-2,4-dichlorobenzamide

EXAMPLE 271

N-[4-[(5,11-Dihydro-10H-dibenz[b,e][1,4]diazepin-5-yl)carbonyl]phenyl]-2,5-dichlorobenzamide

EXAMPLE 272

N-[4-[(5,11-Dihydro-10H-dibenz[b,e][1,4]diazepin-5-yl)carbonyl]phenyl]-3,5-dichlorobenzamide

EXAMPLE 273

N-[4-[(5,11-Dihydro-10H-dibenz[b,e][1,4]diazepin-5-yl)carbonyl]phenyl]-2-fluorobenzamide

EXAMPLE 274

N-[4-[(5,11-Dihydro-10H-dibenz[b,e][1,4]diazepin-5-yl]carbonyl]carbonyl3-3-fluorobenzamide

EXAMPLE 275

N-[4-[(5,11-Dihydro-10H-dibenz[b,e][1,4]diazepin-5-yl)carbonyl]phenyl]-2-methyl-4-chlorobenzamide

EXAMPLE 276

N-[4-[(5,11-Dihydro-10H-dibenz[b,e][1,4]diazepin-5-yl)carbonyl]phenyl]-2,3-dimethylbenzamide

EXAMPLE 277

N-[4-[(5,11-Dihydro-10H-dibenz[b,e][1,4]diazepin-5-yl)carbonyl]phenyl]-2-methoxybenzamide

EXAMPLE 278

N-[4-[(5,11-Dihydro-10H-dibenz[b,e][1,4]diazepin-5-yl)carbonyl]phenyl]-2-(trifluoromethoxy)benzamide

EXAMPLE 279

N-[4-[(5,11-Dihydro-10H-dibenz[b,e][1,4]diazepin-5-yl)carbonyl]phenyl]-2,4-dimethoxybenzamide

EXAMPLE 280

N-[4-[(5,11-Dihydro-10H-dibenz[b,e][1,4]diazepin-5-yl)carbonyl]phenyl]-2,6-dimethoxybenzamide

EXAMPLE 281

N-[4-[(5,11-Dihydro-10H-dibenz[b,e][1,4]diazepin-5-yl)carbonyl]phenyl]-2-methoxy-4-chlorobenzamide

EXAMPLE 282

N-[4-[(5,11-Dihydro-10H-dibenz[b,e][1,4]diazepin-5-yl)carbonyl]phenyl]-2-(trifluoromethyl)benzamide

EXAMPLE 283

N-[4-[(5,11-Dihydro-10H-dibenz[b,e][1,4]diazepin-5-yl)carbonyl]phenyl]-3-(trifluoromethyl)benzamide

EXAMPLE 284

N-[4-[(5,11-Dihydro-10H-dibenz[b,e][1,4]diazepin-5-yl)carbonyl]phenyl]-2,6-dichlorobenzamide

EXAMPLE 285

N-[4-[(5,11-Dihydro-10H-dibenz[b,e][1,4]diazepin-5-yl)carbonyl]phenyl]-2-(methylthio)benzamide

EXAMPLE 286

N-[4-[(5,11-Dihydro-10H-dibenz[b,e][1,4]diazepin-5-yl)carbonyl]phenyl]-4-fluoro-2-(trifluoromethyl)benzamide

EXAMPLE 287

N-[4-[(5,11-Dihydro-10H-dibenz[b,e][1,4]diazepin-5-yl)carbonyl]phenyl]-4-fluoro-3-(trifluoromethyl)benzamide

EXAMPLE 288

N-[4-[(5,11-Dihydro-10H-dibenz[b,e][1,4]diazepin-5-yl)carbonyl]phenyl]-2-fluoro-3-(trifluoromethyl)benzamide

EXAMPLE 289

N-[4-[(5,11-Dihydro-10H-dibenz[b,e][1,4]diazepin-5-5yl)carbonyl]phenyl]-3,5-dimethylbenzamide

EXAMPLE 290

N-[4-[(5,11-Dihydro-10H-dibenz[b,e][1,4]diazepin-5-yl)carbonyl]phenyl]-2,3,5-trichlorobenzamide

EXAMPLE 300

N-[4-[(5,11-Dihydro-10H-dibenz[b,e][1,4]diazepin-5-yl)carbonyl]phenyl]-2,5-difluorobenzamide

EXAMPLE 301

N-[4-[(5,11-Dihydro-10H-dibenz[b,e][1,4]diazepin-5-yl)carbonyl]phenyl]-3-fluoro-2-methylbenzamide

EXAMPLE 302

N-[4-[(5,11-Dihydro-10H-dibenz[b,e][1,4]diazepin-5-yl)carbonyl]phenyl]-2,3-dichlorobenzamide

EXAMPLE 303

N-[4-[(5,11-Dihydro-10H-dibenz[b,e][1,4]diazepin-5-yl)carbonyl]phenyl]-4-fluoro-2-methylbenzamide

EXAMPLE 304

N-[4-[(5,11-Dihydro-10H-dibenz[b,e][1,4]diazepin-5-yl)carbonyl]phenyl]-5-fluoro-2-methylbenzamide

EXAMPLE 305

N-[4-[(5,11-Dihydro-10H-dibenz[b,e][1,4]diazepin-5-yl)carbonyl]phenyl]-2-fluoro-5-(trifluoromethyl)benzamide

EXAMPLE 306

N-[4-[(5,11-Dihydro-10H-dibenz[b,e][1,4]diazepin-5-yl)carbonyl]phenyl]-2-fluoro-6-(trifluoromethyl)benzamide

EXAMPLE 307

N-[4-[(5,11-Dihydro-10H-dibenz[b,e][1,4]diazepin-5-yl)carbonyl]phenyl]-3-fluoro-5-(trifluoromethyl)benzamide

EXAMPLE 308

N-[4-[(5,11-Dihydro-10H-dibenz[b,e][1,4]diazepin-5-yl)carbonyl]phenyl]-2-methyl-3-thiophenecarboxamide

EXAMPLE 309

N-[4-[(5,11-Dihydro-10H-dibenz[b,e][1,4]diazepin-5-yl)carbonyl]phenyl]-3-methyl-2-thiophenecarboxamide

EXAMPLE 310

N-[4-[(5,11-Dihydro-10H-dibenz[b,e][1,4]diazepin-5-yl)carbonyl]phenyl]-2-methyl-3-furanecarboxamide

EXAMPLE 311

N-[4-[(5,11-Dihydro-10H-dibenz[b,e][1,4]diazepin-5-yl)carbonyl]phenyl]-3-methyl-2-furanecarboxamide

EXAMPLE 312

N-[4-[(5,11-Dihydro-10H-dibenz[b,e][1,4]diazepin-5-yl)carbonyl]phenyl]-2-chlorobenzeneacetamide

EXAMPLE 313

N-[4-[(5,11-Dihydro-10H-dibenz[b,e][1,4]diazepin-5-yl)carbonyl]phenyl]-2-methylbenzeneacetamide

EXAMPLE 314

N-[4-[(5,11-Dihydro-10H-dibenz[b,e][1,4]diazepin-5-yl)carbonyl]phenyl]-2-methoxybenzeneacetamide

EXAMPLE 315

N-[4-[(5,11-Dihydro-10H-dibenz[b,e][1,4]diazepin-5-yl)carbonyl]phenyl]-2-methyl-3-thiopheneacetamide

EXAMPLE 316

N-[4-[(5,11-Dihydro-10H-dibenz[b,e][1,4]diazepin-5-yl)carbonyl]phenyl]-3-methyl-2-thiobeneacetamide

EXAMPLE 317

N-[4-[(5,11-Dihydro-10H-dibenz[b,e][1,4]diazepin-5-yl)carbonyl]phenyl]-2-methyl-3-furaneacetamide

EXAMPLE 318

N-[4-[(5,11-Dihydro-10H-dibenz[b,e][1,4]diazepin-5-yl)carbonyl]-2-methoxyphenyl]-3-fluoro-3-methylbenzamide

EXAMPLE 319

N-[4-[(5,11-Dihydro-10H-dibenz[b,e][1,4]diazepin-5-yl)carbonyl]-5-methoxyphenyl]-5-fluoro-2-methylbenzamide

EXAMPLE 320

M-[4-[(5,11-Dihydro-10H-dibenz[b,e][1,4]diazepin-5-yl)carbonyl]-2-methoxyphenyl]-2-chloro-4-fluorobenzamide

EXAMPLE 321

N-[4-[(5,11-Dihydro-10H-dibenz[b,e][1,4]diazepin-5-yl)carbonyl]-2-methoxyphenyl]-2,6-dichlorobenzamide

EXAMPLE 322

M-[4-[(5,11-Dihydro-10H-dibenz[b,e][1,4]diazepin-5-yl)carbonyl]-2-methoxyphenyl]-2-methylbenzamide

EXAMPLE 323

N-[4-[(5,11-Dihydro-10H-dibenz[b,e][1,4]diazepin-5-yl)carbonyl]-2-methoxyphenyl]-2,5-dichlorobenzamide

EXAMPLE 324

N-[4-[(5,11-Dihydro-10H-dibenz[b,e][1,4]diazepin-5-yl)carbonyl]-3-chlorophenyl]-2-methylbenzamide

EXAMPLE 325

N-[4-[(5,11-Dihydro-10H-dibenz[b,e][1,4]diazepin-5-yl)carbonyl]-3-chlorophenyl]-2-chlorobenzamide

EXAMPLE 326

N-[4-[(5,11-Dihydro-10H-dibenz[b,e][1,4]diazepin-5-yl)carbonyl]-3-chlorophenyl]-2,3-dimethylbenzamide

EXAMPLE 327

N-[4-[(5,11-Dihydro-10H-dibenz[b,e][1,4]diazepin-5-yl)carbonyl]-3-chlorophenyl]-2,3-dichlorobenzamide

EXAMPLE 328

N-[4-[(5,11-Dihydro-10H-dibenz[b,e][1,4]diazepin-5-yl)carbonyl]-3-chlorophenyl]-2-chloro-4-fluorobenzamide

EXAMPLE 329

N-[4-[(5,11-Dihydro-10H-dibenz[b,e][1,4]diazepin-5-yl)carbonyl]-3-chlorophenyl]-3-fluoro-2-methylbenzamide

EXAMPLE 330

N-[4-[(5,11-Dihydro-10H-dibenz[b,e][1,4]diazepin-5-yl)carbonyl]-3-chlorophenyl]-5-fluoro-2-methylbenzamide

EXAMPLE 331

N-[4-[(5,11-Dihydro-10H-dibenz[b,e][1,4]diazepin-5-yl)carbonyl]-3-chlorophenyl]-2,4-dichlorobenzamide

EXAMPLE 332

N-[4-[(5,11-Dihydro-10H-dibenz[b,e][1,4]diazepin-5-yl)carbonyl]-3-chlorophenyl]-4-fluoro-2-(trifluoromethyl)benzamide

EXAMPLE 333

N-[4-[(5,11-Dihydro-10H-dibenz[b,e][1,4]diazepin-5-yl)carbonyl]-3-chlorophenyl]-2-(methylthio)benzamide

EXAMPLE 334

N-[4-[(5,11-Dihydro-10H-dibenz[b,e][1,4]diazepin-5-yl)carbonyl]-3-chlorophenyl]-2-(trifluoromethoxy)benzamide

EXAMPLE 335

N-[4-[(5,11-Dihydro-10H-dibenz[b,e][1,4]diazepin-5-yl)carbonyl]-3-chlorophenyl]-2,6-dichlorobenzamide

EXAMPLE 336

N-[4-[(5,11-Dihydro-10H-dibenz[b,e][1,4]diazepin-5-yl)carbonyl]-3-chlorophenyl]-2-fluoro-6-(trifluoromethyl) benzamide

EXAMPLE 337

N-[4-[(5,11-Dihydro-10H-dibenz[b,e][1,4]diazepin-5-yl)carbonyl]-3-methylphenyl]-2,6-dichlorobenzamide

EXAMPLE 338

N-[4-[(5,11-Dihydro-10H-dibenz[b,e][1,4]diazepin-5-yl)carbonyl]-3-methylphenyl]-2-fluoro-6-(trifluoro-ethyl)benzamide

EXAMPLE 339

N-[4-[(5,11-Dihydro-10H-dibenz[b,e][1,4]diazepin-5-yl)carbonyl]-3-methylphenyl]-5-fluoro-2-methylbenzamide

EXAMPLE 340

N-[4-[(5,11-Dihydro-10H-dibenz[b,e][1,4]diazepin-5-yl)carbonyl]-3-methylphenyl]-2,4-dichlorobenzamide

EXAMPLE 341

N-[4-[(5,11-Dihydro-10H-dibenz[b,e][1,4]diazepin-5-yl)carbonyl]-3-methylphenyl]-4-fluoro-3-chlorobenzamide

EXAMPLE 342

N-[4-[(5,11-Dihydro-10H-dibenz[b,e][1,4]diazepin-
5-yl)carbonyl]-3-methylphenyl]-3-fluoro-2-
methylbenzamide

EXAMPLE 343

N-[4-[(5,11-Dihydro-10H-dibenz[b,e][1,4]diazepin-
5-yl)carbonyl]-3-methylphenyl]-2,3-
dimethylbenzamide

EXAMPLE 344

N-[4-[(5,11-Dihydro-10H-dibenz[b,e][1,4]diazepin-
5-yl)carbonyl]-5-methylphenyl]-2-methylbenzamide

EXAMPLE 345

N-[4-[(4,5-Dihydro-6H-isoxazolo[4,5-d][1]
benzazepin-6-yl)carbonyl]phenyl]-2-
methylbenzamide A partial solution of 0.250 g of 5,6-dihydro-6-(4-aminobenzoyl)-4H-isoxazolo[4,5-d][1]benzazepine in 4 ml of tetrahydrofuran-dioxane (1:3) under argon is treated with 160 µl of 2-methylbenzoyl chloride in 1.5 ml of dioxane followed by 114 µl of triethylamine and stirring continued for 4.5 hours at room temperature. The volatiles are evaporated in vacuo to a residue which is dissolved in methylene chloride containing methanol, washed with 10% NaHCO$_3$ and brine, then treated with activated carbon. The mixture is filtered through MgSO$_4$ and the filtrate filtered through silica gel with 15% ethylacetate in methylene chloride. The filtrate is evaporated in vacuo to a residue which is dissolved in methylene chloride, filtered through glass wool, evaporated to a residue which is dissolved in ethyl acetate by warming to give 0.25 g of the desired product as tan crystals, m.p. 257-260° C. HR FABMS: (M+H)=424.1657.

The following compounds are prepared as described in Example 345.

EXAMPLE 346

N-[4-[(4,5-Dihydro-6H-isoxazolo[4,5-d][1]
benzazepin-6-yl)carbonyl]phenyl]-2-methyl-4-
chlorobenzamide

EXAMPLE 347

N-[4-[(4,5-Dihydro-6H-isoxazolo[4,5-d][1]
benzazepin-6-yl)carbonyl]phenyl]-2,3-
dimethylbenzamide

EXAMPLE 348

N-[4-[(4,5-Dihydro-6H-isoxazolo[4,5-d][1]
benzazepin-6-yl)carbonyl]phenyl]-2-
methoxybenzamide

EXAMPLE 349

N-[4-[(4,5-Dihydro-6H-isoxazolo[4,5-d][1]
benzazepin-6-yl)carbonyl]phenyl]-2-
(trifluoromethoxy)benzamide

EXAMPLE 350

N-[4-[(4,5-Dihydro-6H-isoxazolo[4,5-d][1]
benzazepin-6-yl)carbonyl]phenyl]-2-
(trifluoromethyl)benzamide

EXAMPLE 351

N-[4-[(4,5-Dihydro-6H-isoxazolo[4,5-d][1]
benzazepin-6-yl)carbonyl]phenyl]-2-(methylthio)
benzamide

EXAMPLE 352

N-[4-[(4,5-Dihydro-6H-isoxazolo[4,5-d][1]
benzazepin-6-yl)carbonyl]phenyl]-2,3,
dichlorobenzamide

EXAMPLE 353

N-[4-[(4,5-Dihydro-6H-isoxazolo[4,5-d][1]
benzazepin-6-yl)carbonyl]phenyl]-3-fluoro-2-
methylbenzamide

EXAMPLE 354

N-[4-[(4,5-Dihydro-6H-isoxazolo[4,5-d][1]
benzazepin-6-yl)carbonyl]phenyl]-5-fluoro-2-
methylbenzamide

EXAMPLE 355

N-[4-[(4,5-Dihydro-6H-isoxazolo[4,5-d][1]
benzazepin-6-yl)carbonyl]phenyl]-2-chloro-4-
fluorobenzamide

EXAMPLE 356

N-[4-[(4,5-Dihydro-6H-isoxazolo[4,5-d][1]
benzazepin-6-yl)carbonyl]phenyl]-4-fluoro-2-
(trifluoromethyl)benzamide

EXAMPLE 357

N-[4-[(4,5-Dihydro-6H-isoxazolo[4,5-d][1]
benzazepin-6-yl)carbonyl]phenyl]-4-fluoro-3-
(trifluoromethyl) benzamide

EXAMPLE 358

N-[4-[(4,5-Dihydro-6H-isoxazolo[4,5-d][1]
benzazepin-6-yl)carbonyl]phenyl]-4-fluoro-2-
methylbenzamide

EXAMPLE 359

N-[4-[(4,5-Dihydro-6H-isoxazolo[4,5-d][1]
benzazepin-6-yl)carbonyl]phenyl]-2-fluoro-5-
(trifluoromethyl)benzamide

EXAMPLE 360

N-[4-[(4,5-Dihydro-6H-isoxazolo[4,5-d][1]
benzazepin-6-yl)carbonyl]phenyl]-2-fluoro-6-
(trifluoromethyl)benzamide

EXAMPLE 361

N-[4-[(4,5-Dihydro-6H-isoxazolo[4,5-d][1]
benzazepin-6-yl)carbonyl]-3-chlorophenyl]-3-fluoro-
2-methyl-benzamide

EXAMPLE 362

N-[4-[(4,5-Dihydro-6H-isoxazolo[4,5-d][1]
benzazepin-6-yl)carbonyl]-3-chlorophenyl]-2-
methylbenzamide

EXAMPLE 363

N-[4-[(4,5-Dihydro-6H-isoxazolo[4,5-d][1]
benzazepin-6-yl)carbonyl]-3-chlorophenyl]-2,3-
dimethylbenzamide

EXAMPLE 366

N-[4-[(4,5-Dihydro-6H-isoxazolo[4,5-d][1]
benzazepin-6-yl)carbonyl]-3-chlorophenyl]-5-fluoro-
2-methylbenzamide

EXAMPLE 365

N-[4-[(4,5-Dihydro-6H-isoxazolo[4,5-d][1]
benzazepin-6-yl)carbonyl]-3-chlorophenyl]-2-
chloro-4-fluoro-benzamide

EXAMPLE 366

N-[4-[(4,5-Dihydro-6H-isoxazolo[4,5-d][1]
benzazepin-6-yl)carbonyl]-3-chlorophenyl]-2,3-
dichlorobenzamide

EXAMPLE 367

N-[4-[(4,5-Dihydro-6H-isoxazolo[4,5-d][1]
benzazepin-6-yl)carbonyl]-3-methylphenyl]-2-
methylbenzamide

EXAMPLE 368

N-[4-[(4,5-Dihydro-6H-isoxazolo[4,5-d][1]
benzazepin-6-yl)carbonyl]-3-methylphenyl]-2,3-
dimethylbenzamide

EXAMPLE 369

N-[4-[(4,5-Dihydro-6H-isoxazolo[4,5-d][1]
benzazepin-6-yl)carbonyl]-3-methylphenyl]-3-
fluoro-2-methylbenzamide

EXAMPLE 370

N-[4-[(4,5-Dihydro-6H-isoxazolo[4,5-d][1]
benzazepin-6-yl)carbonyl]-3-methylphenyl]-5-
fluoro-3-methyl-benzamide

EXAMPLE 371

N-[4-[(4,5-Dihydro-6H-isoxazolo[4,5-d][1]
benzazepin-6-yl)carbonyl]-3-methylphenyl]-4-
fluoro-2-methylbenzamide

EXAMPLE 372

N-[4-[(4,5-Dihydro-6H-isoxazolo[4,5-d][1]
benzazepin-6-yl)carbonyl]-3-methylphenyl]-2-
methylthiobenzamide

EXAMPLE 373

N-[4-[(4,5-Dihydro-6H-isoxazolo[4,5-d][1]
benzazepin-6-yl)carbonyl]-3-methylphenyl]-2-
(trifluoromethoxy)benzamide

EXAMPLE 374

N-[4-[(4,5-Dihydro-6H-isoxazolo[4,5-d][1]
benzazepin-6-yl)carbonyl]-3-methylphenyl]-3-
fluoro-2-methylbenzamide

EXAMPLE 375

N-[4-[(4,5-Dihydro-6H-isoxazolo[4,5-d][1]
benzazepin-6-yl)carbonyl]-3-methoxyphenyl]-5-
fluoro-2-methylbenzamide

EXAMPLE 376

N-[4-[(4,5-Dihydro-6H-isoxazolo[4,5-d][1]
benzazepin-6-yl)carbonyl]-3-methoxyphenyl]-2-
methylbenzamide

EXAMPLE 377

N-[4-[(4,5-Dihydro-6H-isoxazolo[4,5-d][1]
benzazepin-6-yl)carbonyl]-3-methoxyphenyl]-2-
chloro-4-fluoro-benzamide

EXAMPLE 378

N-[4-[(4,5-Dihydro-6H-isoxazolo[4,5-d][1]
benzazepin-6-yl)carbonyl]-3-methoxyphenyl]-2,3-
dichlorobenzamide

EXAMPLE 379

N-[4-[(4,5-Dihydro-2-methylpyrazolo[4,3-d][1]-
benzazepin-6(2H)-yl)carbonyl]phenyl]-2-
methylbenzamide To a mixture of 0.420 g of 2,4,5,6-tetra-hydro-2-methyl-
6-(4-aminobenzoyl)pyrazolo[4,3-d][1]-benzazepine and 275 μl of triethylamine in 6 ml of methylene chloride and 2 ml of dioxane is added a solution of 215 μl of 2-methylbenzoyl chloride in 1.5 ml of dioxane. The reactants are stirred under argon for 4.5 hours. The volatiles are evaporated in vacuo to a residue which is dissolved in methylene chloride and washed with 10% NaHCO$_3$ and brine. The organic layer is treated with activated carbon, dried with MgSO$_4$ and evaporated in vacuo to give 660 mg of a tan foam residue. The residue is purified by column chromatography on silica gel by elution with 30% ethyl acetate-methylene chloride to give 590 mg of the desired product as white crystalline solid, m.p. 246°–248° C; HR FABMS: (M+H)=437.1972.

The following examples are prepared as described for Example 379.

EXAMPLE 380

N-[4-[(4,5-Dihydro-2-methylpyrazolo[4,3-d][1]-benzazepin-6(2H)-yl)carbonyl]phenyl]-2-chlorobenzamide

EXAMPLE 381

N-[4-[(4,5-Dihydro-2-methylpyrazolo[4,3-d][1]-benzazepin-6(2H)-yl)carbonyl]phenyl]-2,4-dichlorobenzamide

EXAMPLE 382

N-[4-[(4,5-Dihydro-2-methylpyrazolo[4,3-d][1]-benzazepin-6(2H)-yl)carbonyl]phenyl]-2,3-dichlorobenzamide

EXAMPLE 383

N-[4-[(4,5-Dihydro-2-methylpyrazolo[4,3-d][1]-benzazepin-6(2H)-yl)carbonyl]phenyl]-2-methyl-4-chlorobenzamide

EXAMPLE 384

N-[4-[(4,5-Dihydro-2-methylpyrazolo[4,3-d][1]-benzazepin-6(2H)-yl)carbonyl]phenyl]-2,3-dimethylbenzamide

EXAMPLE 385

N-[4-[(4,5-Dihydro-2-methylpyrazolo[4,3-d][1]-benzazepin-6(2H)-yl)carbonyl]phenyl]-2-methoxybenzamide

EXAMPLE 386

N-[4-[(4,5-Dihydro-2-methylpyrazolo[4,3-d][1]-benzazepin-6(2H)-yl)carbonyl]phenyl]-2-(trifluoromethoxy)benzamide

EXAMPLE 387

N-[4-[(4,5-Dihydro-2-methylpyrazolo[4,3-d][1]-benzazepin-6(2H)-yl)carbonyl]phenyl]-2,4-dimethoxybenzamide

EXAMPLE 388

N-[4-[(4,5-Dihydro-2-methylpyrazolo[4,3-d][1]-benzazepin-6(2H)-yl)carbonyl]phenyl]-2-methoxy-4-chlorobenzamide

EXAMPLE 389

N-[4-[(4,5-Dihydro-2-methylpyrazolo[4,3-d][1]-benzazepin-6(2H)-yl)carbonyl]phenyl]-2-(trifluoromethyl)benzamide

EXAMPLE 390

N-[4-[(4,5-Dihydro-2-methylpyrazolo[4,3-d][1]-benzazepin-6(2H)-yl)carbonyl]phenyl]-3-(trifluoromethyl)benzamide

EXAMPLE 391

N-[4-[(4,5-Dihydro-2-methylpyrazolo[4,3-d][1]-benzazepin-6(2H)-yl)carbonyl]phenyl]-2-(methylthio)-benzamide

EXAMPLE 392

N-[4-[(4,5-Dihydro-2-methylpyrazolo[4,3-d][1]-benzazepin-6(2H)-yl)carbonyl]phenyl]-4-fluoro-2-(trifluoromethyl)benzamide

EXAMPLE 393

N-[4-[(4,5-Dihydro-2-methylpyrazolo[4,3-d][1]-benzazepin-6(2H)-yl)carbonyl]phenyl]-2-fluoro-3-(trifluoromethyl)benzamide

EXAMPLE 394

N-[4-[(4,5-Dihydro-2-methylpyrazolo[4,3-d][1]-benzazepin-6(2H)-yl)carbonyl]phenyl]-2-chloro-4-fluorobenzamide

EXAMPLE 395

N-[4-[(4,5-Dihydro-2-methylpyrazolo[4,3-d][1]-benzazepin-6(2H)-yl)carbonyl]phenyl]-3-fluoro-2-methylbenzamide

EXAMPLE 396

N-[4-[(4,5-Dihydro-2-methylpyrazolo[4,3-d][1]-benzazepin-6(2H)-yl)carbonyl]phenyl]-5-fluoro-2-methylbenzamide

EXAMPLE 397

N-[4-[(4,5-Dihydro-2-methylpyrazolo[4,3-d][1]-benzazepin-6(2H)-yl)carbonyl]phenyl]-3-fluoro-5-(trifluoromethyl)benzamide

EXAMPLE 398

N-[4-[(4,5-Dihydro-2-methylpyrazolo[4,3-d][1]-benzazepin-6(2H)-yl)carbonyl]phenyl]-2-chloro-5-(methylthiobenzamide

EXAMPLE 399

N-[4-[(4,5-Dihydro-2-methylpyrazolo[4,3-d][1]-benzazepin-6(2H)-yl)carbonyl]phenyl]-2-methyl-3-thiophenecarboxamide

EXAMPLE 400

N-[4-[(4,5-Dihydro-2-methylpyrazolo[4,3-d][1]-benzazepin-6(2M) -yl)carbonyl]phenyl]-2-methyl-3-furanecarboxamide

EXAMPLE 401

N-[4-[(4,5-Dihydro-2-methylpyrazolo[4,3-d][1]-benzazepin-6(2H)-yl)carbonyl]phenyl]-2-chlorobenzeneacetamide

EXAMPLE 402

N-[4-[(4,5-Dihydro-2-methylpyrazolo[4,3-d][1]-benzazepin-6(2H)-yl)carbonyl]phenyl]-2-methylbenzeneacetamide

EXAMPLE 403

N-[4-[(4,5-Dihydro-2-methylpyrazolo[4,3-d][1]-benzazepin-6(2H)-yl)carbonyl]-3-chlorophenyl]-2-methylbenzamlde

EXAMPLE 404

N-[4-[(4,5-Dihydro-2-methylpyrazolo[4,3-d][1]-benzazepin-6(2H)-yl)carbonyl]-3-chlorophenyl]-2,3-dimethylbenzamide

EXAMPLE 405

N-[4-[(4,5-Dihydro-2-methylpyrazolo[4,3-d][1]-benzazepin-6(2H)-yl)carbonyl]-3-chlorophenyl]-2,3-dichlorobenzamide

EXAMPLE 406

N-[4-[(4,5-Dihydro-2-methylpyrazolo[4,3-d][1]-benzazepin-6(2H)-yl)carbonyl]-3-chlorophenyl]-2,4-dichlorobenzamide

EXAMPLE 407

N-[4-[(4,5-Dihydro-2-methylpyrazolo[4,3-d][1]-benzazepin-6(2H)-yl)carbonyl]-3-chlorophenyl]-3-fluoro-2-methylbenzamide

EXAMPLE 408

N-[4-[(4,5-Dihydro-2-methylpyrazolo[4,3-d][1]-benzazepin-6(2H)-yl)carbonyl]-3-chlorophenyl]-5-fluoro-2-methylbenzamide

EXAMPLE 409

N-[4,[(4,5-Dihydro-2-methylpyrazolo[4,3-d][1]-benzazepin-6(2H)-yl)carbonyl]-3-chlorophenyl]-2-chloro-4-fluorobenzamide

EXAMPLE 410

N-[4-[(4,5-Dihydro-2-methylpyrazolo[4,3-d][1]-benzazepin-6(2H)-yl)carbonyl]-3-methylphenyl]-2-methylbenzamide

EXAMPLE 411

N-[4-[(4,5-Dihydro-2-methylpyrazolo[4,3-d][1]-benzazepin-6(2H)-yl)carbonyl]-3-methylphenyl]-2,3-dimethylbenzamide

EXAMPLE 412

N-[4-[(4,5-Dihydro-2-methylpyrazolo[4,3-d][1]-benzazepin-6(2H)-yl)carbonyl]-3-methylphenyl]-2-chloro-4-fluorobenzamide

EXAMPLE 413

N-[4-[(4,5-Dihydro-2-methylpyrazolo[4,3-d][1]-benzazepin-6(2H)-yl)carbonyl]-3-methylphenyl]-3-fluoro-2-methylbenzamide

EXAMPLE 414

N-[4-[(4,5-Dihydro-2-methylpyrazolo[4,3-d][1]-benzazepin-6(2H)-yl)carbonyl]-3-methylphenyl]-5-fluoro-2-methylbenzamide

EXAMPLE 415

N-[4-[(4,5-Dihydro-2-methylpyrazolo[4,3-d][1]-benzazepin-6(2H)-yl)carbonyl]-3-methylphenyl]-2,4-dichlorobenzamide

EXAMPLE 416

N-[4-[(6,7-Dihydro-2-methyl-5H-pyrimido[5,4-d][1]-benzazepin-7-yl)carbonyl]phenyl]-2-methylbenzamide To a solution of 0.216 mg of 6,7-dihydro-2-methyl-7-(4-aminobenzoyl)-5H-pyrimido[5,4-d][1]benzazepine in 6 ml of methylene chloride under argon is added 100 μl of triethylamine followed by a solution of 94 μl of 2-methylbenzoyl chloride in 1.5 ml of methylene chloride. The reaction mixture is stirred at room temperature for 18 hours, washed with water, saturated NaHCO$_3$ and the separated organic layer treated with activated carbon and filtered through MgSO$_4$. The filtrate is evaporated to a residue which is dissolved in ethyl acetate and evaporated in vacuo to give 300 mg of the desired product as a pale yellow foam. HR FABMS: Exact Mass (M+H):449.1974.

The following compounds are prepared as described in Example 416.

EXAMPLE 417

N-[4-[(6,7-Dihydro-2-methyl-5H-pyrimido[5,4-d][1]-benzazepin-7-yl)carbonyl]phenyl]-2,3-dimethylbenzamide

EXAMPLE 418

N-[4-[(6,7-Dihydro-.2-methyl-5H-pyrimido[5,4-d][1]-benzazepin-7-yl)carbonyl]phenyl]-2-chloro-4-fluorobenzamide

EXAMPLE 419

N-[4-[(6,7-Dihydro-2-methyl-5H-pyrimido[5,4-d][1]-benzazepin-7-yl)carbonyl]phenyl]-2,4-dichlorobenzamide

EXAMPLE 420

N-[4-[(6,7-Dihydro-2-methyl-5H-pyrimido[5,4-d][1]-benzazepin-7-yl)carbonyl]phenyl]-2,3-dichlorobenzamide

EXAMPLE 421

N-[4-[(6,7-Dihydro-2-methyl-5H-pyrimido[5,4-d][1]-benzazepin-7-yl)carbonyl]phenyl]-3-fluoro-2-methylbenzamide

EXAMPLE 422

N-[4-[(6,7-Dihydro-2-methyl-5H-pyrimido[5,4-d][1]-benzazepin-7-yl)carbonyl]phenyl]-2-methoxybenzamide

EXAMPLE 423

N-[4-[(6,7-Dihydro-2-methyl-5H-pyrimido[5,4-d][1]-benzazepin-7-yl)carbonyl]phenyl]-2-fluoro-2-methylbenzamide

EXAMPLE 424

N-[4-[(6,7-Dihydro-2-methyl-5H-pyrimido[5,4-d][1]-benzazepin-7-yl)carbonyl]phenyl]-2-[trifluoromethoxy]benzamide

EXAMPLE 425

N-[4-[(6,7-Dihydro-2-methyl-5H-pyrimido[5,4-d][1]-benzazepin-7-yl)carbonyl]phenyl]-2-methoxy-4-chlorobenzamide

EXAMPLE 426

N-[4-[(6,7-Dihydro-2-methyl-5H-pyrimido[5,4-d][1]-benzazepin-7-yl)carbonyl]phenyl]-2-chloro-5-fluorobenzamide

EXAMPLE 427

N-[4-[(6,7-Dihydro-2-methyl-5H-pyrimido[5,4-d][1]-benzazepin-7-yl)carbonyl]phenyl]-2-(trifluoromethyl)-benzamide

EXAMPLE 428

N-[4-[(6,7-Dihydro-2-methyl-5H-pyrimido[5,4-d][1]-benzazepin-7-yl)carbonyl]phenyl]-2-(methylthio)-benzamide

EXAMPLE 429

N-[4-[(6,7-Dihydro-2-methyl-5H-pyrimido[5,4-d][1]-benzazepin-7-yl)carbonyl]phenyl]-4-fluoro-2-methylbenzamide

EXAMPLE 430

N-[4-[(6,7-Dihydro-2-methyl-5H-pyrimido[5,4-d][1]-benzazepin-7-yl)carbonyl]-3-chlorophenyl]-2-methylbenzamide

EXAMPLE 431

N-[4-[(6,7-Dihydro-2-methyl-5H-pyrimido[5,4-d][1]-benzazepin-7-yl)carbonyl]-3-chlorophenyl]-2,3-dimethylbenzamide

EXAMPLE 432

N-[4-[(6,7-Dihydro-2-methyl-5H-pyrimido[5,4-d][1]-benzazepin-7-yl)carbonyl]-3-chlorophenyl]-3-fluoro-2-methylbenzamide

EXAMPLE 433

N-[4-[(6,7-Dihydro-2-methyl-5H-pyrimido[5,4-d][1]-benzazepin-7-yl)carbonyl]-3-chlorophenyl]-5-fluoro-2-methylbenzamide

EXAMPLE 434

N-[4-[(6,7-Dihydro-2-methyl-5H-pyrimido[5,4-d][1]-benzazepin-7-yl)carbonyl]-3-chlorophenyl]-2-chloro-4-fluorobenzamide

EXAMPLE 435

N-[4-[(6,7-Dihydro-2-methyl-5H-pyrimido[5,4-d][1]-benzazepin-7-yl)carbonyl]-3-chlorophenyl]-2-chloro-5-fluorobenzamide

EXAMPLE 436

N-[4-[(6,7-Dihydro-2-methyl-5H-pyrimido[5,4-d][1]-benzazepin-7-yl)carbonyl]-3-chlorophenyl]-3,3-dichlorobenzamide

EXAMPLE 437

N-[4-[(6,7-Dihydro-2-methyl-5H-pyrimido[5,4-d][1]-benzazepin-7-yl)carbonyl]-3-chlorophenyl]-2-(trifluoromethoxy)benzamide

EXAMPLE 438

N-[4-[(6,7-Dihydro-2-methyl-5H-pyrimido[5,4-d][1]-benzazepin-7-yl)carbonyl]-3-methoxyphenyl]-3-fluoro-2-methylbenzamide

EXAMPLE 439

N-[4-[(6,7-Dihydro-2-methyl-5H-pyrimido[5,4-d][1]-benzazepin-7-yl)carbonyl]-3-methoxyphenyl]-5-fluoro-2-methylbenzamide

EXAMPLE 440

N-[4-[(6,7-Dihydro-2-methyl-5H-pyrimido[5,4-d][1]-benzazepin-7-yl)carbonyl]-3-methylphenyl]-3-fluoro-2-methylbenzamide

EXAMPLE 441

N-[4-[(6,7-Dihydro-2-methyl-5H-pyrimido[5,4-d][1]-benzazepin-7-yl)carbonyl]-3-methylphenyl]-5-fluoro-2-methylbenzamide

EXAMPLE 442

N-[4-[(6,7-Dihydro-2-methyl-5H-pyrimido[5,4-d][1]-benzazepin-7-yl)carbonyl]-3-methylphenyl]-2,3-dichlorobenzamide

EXAMPLE 443

N-[4-[(6,7-Dihydro-2-methyl-5H-pyrimido[5,4-d][1]-benzazepin-7-yl)carbonyl]-3-methylphenyl]-2-chloro-5-fluorobenzamide

EXAMPLE 444

N-[4-[(6,7-Dihydro-2-methyl-5H-pyrimido[5,4-d][1]-benzazepin-7-yl)carbonyl]-2-methylphenyl]-2-chloro-4-fluorobenzamide

EXAMPLE 445

N-[4-[(6,7-Dihydro-2-methyl-5H-pyrimido[5,4-d][1]-benzazepin-7-yl)carbonyl]-3-methylphenyl]-2,3-dimethylbenzamide

EXAMPLE 446

N-[4-[(6,7-Dihydro-2-methyl-5H-pyrimido[5,4-d][1]-benzazepin-7-yl)carbonyl]-3-methylphenyl]-2-(trifluoromethyl)benzamide

EXAMPLE 447

N-[4-[(6,7-Dihydro-2-methyl-5H-pyrimido[5,4-d][1]-benzazepin-7-yl)carbonyl]-3-methylphenyl]-2-(trifluoromethoxy)benzamide

EXAMPLE 448

N-[4-[(Dibenz[b,f][1,4]thiazepin-10(11H)yl)-carbonyl]phenyl]-2-chlorobenzamide

To a solution of 385 mg of 2-chloro-benzoyl chloride in 6 ml of methylene chloride at 0° C. is added 0.6 g of 10-(4-aminobenzoyl)-10,11-dihydrodibenz[b,f]-[1,4]thiazepine followed by 0.375 ml of triethylamine. The reaction mixture is stirred at room temperature for 18 hours. The reaction mixture is washed with 20 ml of water, 1N HCl, 1N $Na_2CO_3$, water and dried over $MgSO_4$. The filtrate is evaporated in vacuo to give 0.7 g of yellowish solid which is purified by silica gel chromatography on thick layer plates by elution with 1:1 ethyl acetate-hexane to give 0.3 g of the desired product, m.p. 116°–119° C.

EXAMPLE 449

N-[4-[(Dibenz[b,f][1,4]thiazepin-10(11H)-yl)-carbonyl]phenyl]-2,4-dichlorobenzamide To a solution of 452 mg of 2,4-dichlorobenzoyl chloride in 6 ml of methylene chloride is added 0.6 g of 10-(4-aminobenzoyl)-10,11-dihydrodibenz[b,f]-[1,4]thiazepine followed by 0.375 ml of triethylamine. The reaction mixture is stirred at room temperature for 18 hours. The reaction mixture is washed with 20 ml of water, 1 N HCl, 1N $Na_2CO_3$, water and dried over $MgSO_4$. The filtrate is evaporated in vacuo to give 0.72 g of yellowish solid which is purified by silica gel chromatography on thick layer plates by elution with 1:1 ethyl acetate-hexane to give 0.254 g of the desired product as ivory crystals, m.p. 112°–115° C.

EXAMPLE 450

5-[4-[[(2-Chlorophenyl)sulfonyl]amino]benzoyl]-6,11-dihydro-5H-dibenz[b,e]azepine A mixture of 0.13 g of 5-(4-aminobenzoyl)-6,11-dihydro-5H-dibenz[b,e]azepine, 0.21 g of 2-chlorobenzenesulfonyl chloride, 0.12 g of triethylamine and 5 mg of N,N-dimethylaminopyridine in 2 ml of methylene chloride is stirred at room temperature for 18 hours. The mixture is partitioned between 1 N NaOH and ethyl acetate. The organic layer is washed with 50% $NH_4Cl$ and brine, dried over $Na_2SO_4$ and evaporated to give 0.26 g of the desired product as a yellow solid. MS(CI):663(M+H; $C^{35}$).

A solution of 0.22 g of the preceding compound in 5 ml of tetrahydrofuran is treated with 2 ml of 1N NaOH and 2 ml of methanol and stirred at room temperature for 1 hour. The organic solvents are removed in vacuo and the residue diluted with 15 ml of ethyl acetate and 5 ml of water. The organic extract is washed with 5 ml of 1N NaOH, brine and dried ($Na_2SO_4$) and evaporated in Vacuo to give 0.19 g of yellow solid which is washed with diethyletherisopropyl ether to give 0.17 g of beige solid. MS(CI):489(M+H, $Cl^{35}$).

EXAMPLE 451

6-[4-[(2,4-Dichlorobenzoyl)amino]benzoyl]-5,6-dihydropyrazolo[4,3-d][1]benzazepine-2(4H)-acetic acid To a stirred slurry of 0.477 g of 6-[4-[(2,4-dichlorobenzoyl)amino]benzoyl]-5,6-dihydropyrazolo-[4,3-d][1]benzazepine-2(4H)-acetic acid, ethyl ester in 15 ml of ethyl alcohol is added 5 ml of tetrahydrofuran followed by 1.30 ml of 1M NaOH. The reaction mixture is stirred at room temperature for 6 hours followed by the addition of 0.750 ml of 2M HCl. The acidic reaction mixture is evaporated in vacuo, triturated with $CHCl_3$, combined, treated with activated carbon, filtered through $MgSO_4$ and evaporated an yacuo to give 0.380 mg of the desired product as a clear foam.

EXAMPLE 452

Ethyl 6-[4-[(2,4-dichlorobenzoyl)amino]benzoyl]-5,6-dihydropyrazolo[4,3-d][1]benzazpeine-2(4H)-acetate To a stirred solution of 0.940 g of ethyl 6-(4-aminobenzoyl)-5,6-dihydropyrazolo[4,3-d][1]benzazepine-2(4H)-acetate in 25 ml of methylene chloride is added 369 µl of triethylamine followed by the dropwise addition of 373 µl of 2,4-dichlorobenzoyl chloride in 3.5 ml of methylene chloride. The reaction mixture is stirred at room temperature for 18 hours, washed with water, saturated $NaHCO_3$, brine and the organic layer treated with activated carbon, and filtered through $MgSO_4$. The filtrate is concentrated in vacuo to a residue which is purified by flash chromatography on silica gel using 25% ethyl acetate in methylene chloride to give 380 mg of the desired product as white crystals, m.p. 164°–167° C. The mother liquors are combined, evaporated in vacuo to a residue which is dissolved in 25% ethyl acetate in chloroform to give 535 mg of off-white solid, m.p. 160°–163.5° C.

EXAMPLE 453

N-[4-[(6,11-Dihydro-5H-dibenz[b,e]azepin-5-yl)-carbonyl]phenyl]-2-(2-methylpropoxy)benzamide To a mixture of 0.62 g of 2-chloro-5-nitrobenzoic acid and 0.61 g of triethylamine in 5 ml of methylene chloride is added 0.42 g of isobutylchloroformate at 0° C. The mixture is warmed to room temperature for 30 minutes. A solution of 0.31 g of 5-(4-aminobenzoyl)-6,7-dihydro-5H-dibenz[b,d]azepine in 1 ml of methylene chloride is added followed by 10 mg of N,N-dimethylaminopyridine and 1.0 ml of toluene is added. The mixture is heated at 100° C. for 48 hours. The room temperature reaction mixture is diluted with 15 ml of ethyl acetate and washed with 1N HCl, 1N NaOH, brine and dried ($Na_2SO_4$) and evaporated in vacuo to a residue. The residue is purified by column chromatography on silica gel by elution with 1:2 ethyl acetate-hexane to give 0.28 g of the desired product as a yellow solid. MS(CI):536(M+H).

EXAMPLE 454

N-[4-[(6,11-Dihydro-5H-dibenz[b,e]azepin-5-yl)-carbonyl]phenyl]-2-(dimethylamino)acetamide To a solution of 0.31 g of 5-(4-aminobenzoyl)-6,7-dihydro-5H-dibenz[b,e]azepine in 5 ml of methylene chloride is added 0.53 g of $Na_2CO_3$ followed by 0.31 g of N,N-dimethylglycyl chloride. The mixture is stirred at room temperature for 20 hours. The mixture is quenched with water, extracted with ethyl acetate and the organic layer dried ($Na_2SO_4$) and concentrated vacuo to give 0.39 g of yellow foam. The yellow foam is treated with 15 ml of hydrochloric acid and the suspension washed with ethyl acetate. The aqueous suspension is made alkaline with 5N NaOH and extracted with 30 ml of ethyl acetate. The organic layer is washed with brine, dried ($Na_2SO_4$) and evaporated to give 0.32 g of the desired product as an off-white solid. MS(CI): 400(M+H). A sample is treated with anhydrous HCl to give the hydrochloride salt. MS(CI): 400(M+H-HCl).

EXAMPLE 455

N-[4-(4,5-Dihydro-2-methyl-6H-thiazolo[5,4-d][1]-benzazepin-6-yl)carbonyl]phenyl]-2,4-dichlorobenzamide To a stirred solution of 0.235 g of 5,6-dihydro-2-methyl-6-(4-aminobenzoyl)-4H-thiazolo[5,4-d]-[1]benzazepine in 6 ml of methylene chloride under argon is added 107 µl of triethylamine followed by the dropwise addition of 109 µl of 2,4-dichlorobenzoyl chloride in 1 ml of methylene chloride. Stirring is continued at room temperature for 18 hours. The reaction mixture is washed with $H_2O$, saturated $NaHCO_3$ and brine. The organic layer is treated with activated carbon, filtered through $MgSO_4$ and the filtrate evaporated in vacuo to a residue which is chromatographed on silica gel by elution with 15% ehtyl acetate in methylene chloride to give 330 mg of the desired product as a tan glass.

EXAMPLE 456

N-[4-[(4,10-Dihydro-5H-thieno[3,2-d][1]benzazepin-5-yl)carbonyl]phenyl]-2-methylbenzamide A mixture of 400 mg of 4,10-dihydro-5H-thieno[3,2-d][1]benzazepine and 700 mg of 4-[(2-methylbenzoyl)amino]benzoyl chloride is stirred in 30 ml of methylene chloride in the presence of 3 ml of triethylamine for 8 hours. The volatiles are removed in vacuo to give a residue which is partitioned between chloroform and water. The organic layer is dried ($Na_2SO_4$) and the filtrate evaporated in vacuo to give a residue which is purified by column chromatography on silica gel by elution with 30% ethyl acetate-hexane to give 543 mg of the desired product. M+1=439.

EXAMPLE 457

N-[4-[(4,10-Dihydro-9H-thieno[2,3-d][1]benzazepin-9-yl)carbonyl]phenyl]-2,3-dichlorobenzamide A mixture of 200 mg of 9,10-dihydro-4H-thieno[2,3-c][1] and 350 mg of 4-[(2-methylbenzoyl)amino]benzoyl chloride is stirred in 30 ml of methylene chloride in the presence of 2 ml of triethylamine for 8 hours. The volatiles are removed in vacuo to give a residue which is partitioned between water and chloroform. The organic layer is dried ($Na_2SO_4$) and the filtrate evaporated in vacuo to give a residue which is purified by column chromatography on silica gel by elution with 30% ethyl acetate-hexane to give 266 mg of the desired product. M+1=494.

EXAMPLE 458

N-[4-[(4,10-Dihydro-9H-thieno[2,3-d][1]benzazepin-9-yl)carbonyl]phenyl]-2-methylbenzamide A mixture of 400 mg of 9,10-dihydro-4H-thieno[2,3-d][1]benzazepine and 600 mg of 4-[(2-methylbenzoyl)amino]

benzoyl chloride is stirred in 30 ml of methylene chloride in the presence of 3 ml of triethylamine for 8 hours. The volatiles are removed in vacuo to give a residue which is partitioned between water and chloroform. The organic layer is dried (Na$_2$SO$_4$) and the filtrate evaporated in vacuo to give a residue which is purified by column chromatography on silica gel by elution with 30% ethyl acetate-hexane to give 518 mg of the desired product. M+1=439.

The following examples are prepared using conditions of Example 456.

EXAMPLE 459

N-[4-[(4,10-Dihydro-5H-thieno[3,2-c][1]benzazepin-5-yl)carboxyl]-3-chlorophenyl]-2,3-dimethylbenzamide

EXAMPLE 460

N-[4-[(4,10-Dihydro-5H-thieno[3,2-c][1]benzazepin-5-yl)carbonyl]-3-chlorophenyl]-2,5-dimethylbenzamide

EXAMPLE 461

N-[4-[(4,10-Dihydro-5H-thieno[3,2-c][1]benzazepin-5-yl)carbonyl]-3,chlorophenyl]-2-methoxybenzamide

EXAMPLE 462

N-[4-[(4,10-Dihydro-5H-thieno[3,2-c][1]benzazepin-5-yl)carbonyl]-3-chlorophenyl]-2-(trifluoromethoxy)-benzamide

EXAMPLE 463

N-[4-[(4,10-Dihydro-5H-thieno[3,2-c][1]benzazepin-5-yl)carbonyl]-3-chlorophenyl]-2-methoxy-4-chlorobenzamide

EXAMPLE 464

N-[4-[(4,10-Dihydro-5H-thieno[3,2-c][1]benzazepin-5-yl)carbonyl]-3-chlorophenyl]-2-(methylthio)-benzamide

EXAMPLE 465

B-[4-[(4,10-Dihydro-5H-thieno[3,2-c][1]benzazepin-5-yl)carbonyl]-3-chlorophenyl]-2,3-dichlorobenzamide

EXAMPLE 466

N-[4-[(4,10-Dihydro-5H-thieno[3,2-c][1]benzazepin-5-yl)carbonyl]-3-chlorophenyl]-2-methyl-3-thiophenecarboxamide

EXAMPLE 467

N-[4-[(4,10-Dihydro-5H-thieno[3,2-c][1]benzazepin-5-yl)carbonyl]-3-chlorophenyl]-3-methyl-2-thiophene-carboxamide

EXAMPLE 468

N-[4-[(4,10-Dihydro-5H-thieno[3,2-c][1]benzazepin-5-yl)carbonyl]-3-chlorophenyl]-2-chlorobenzeneacetamide

EXAMPLE 469

N-[4-[(4,10-Dihydro-5H-thieno[3,2-c][1]benzazepin-5-yl)carbonyl]-3,chlorophenyl]-3-fluoro-2-methylbenzamide

EXAMPLE 470

N-[4-[(4,10-Dihydro-5H-thieno[3,2-c][1]benzazepin-5-yl)carbonyl]-3-chlorophenyl]-5-fluoro-2-methylbenzamide

EXAMPLE 471

N-[4-[(4,10-Dihydro-5H-thieno[3,2-c][1]benzazepin-5-yl)carbonyl]-3-chlorophenyl]-2,3-difluorobenzamide

EXAMPLE 472

N-[4-[(4,10-Dihydro-5H-thieno[3,2-c][1]benzazepin-5-yl)carbonyl]-3-chlorophenyl]-4-fluoro-2-methylbenzamide

EXAMPLE 475

N-[4-[(4,10-Dihydro-5H-thieno[3,2-c][1]benzazepin-5-yl)carbonyl]-3-chlorophenyl]-2,3,5-trichlorobenzamide

EXAMPLE 474

N-[4-[(4,10-Dihydro-5H-thieno[3,2-c][1]benzazepin-5-yl)carbonyl]-3-chlorophenyl]-2-fluoro-5-(trifluoromethyl)benzamide

EXAMPLE 475

N-[4-[(4,10-Dihydro-5H-thieno[3,2-c][1]benzazepin-5-yl)carbonyl]-3-chlorophenyl]-2-fluoro-6-(trifluoro-methyl)benzamide

EXAMPLE 476

N-[4-[(4,10-Dihydro-5H-thieno[3,2-c][1]benzazepin-5-yl)carbonyl]-3-chlorophenyl]-3-fluoro-5-(trifluoromethyl)benzamide

EXAMPLE 477

N-[4-[(4,10-Dihydro-5H-thieno[3,2-c][1]
benzazepin-5-yl)carbonyl]-3-chlorophenyl]-2,6-
dichlorobenzamide

EXAMPLE 478

N-[4-[(4,10-Dihydro-5H-thieno[3,2-c][1]
benzazepin-5-yl)carbonyl]-3-chlorophenyl]-2-
(trifluoromethyl)-benzamide

EXAMPLE 479

N-[4-[(4,10-Dihydro-5H-thieno[3,2-c][1]
benzazepin-5-yl)carbonyl]-3-chlorophenyl]-2-
chloro-4-fluorobenzamide

EXAMPLE 480

N-[4-[(4,10-Dihydro-5H-thieno[3,2-c][1]
benzazepin-5-yl)carbonyl]-3-chlorophenyl]-2-
chloro-5-fluoro-benzamide

EXAMPLE 481

N-[4-[(4,10-Dihydro-5H-thieno[3,2-c][1]
benzazepin-5-yl)carbonyl]-3-fluorophenyl]-3-fluoro-
2-methylbenzamide

EXAMPLE 482

N-[4-[(4,10-Dihydro-5H-thieno[3,2-c][1]
benzazepin-5-yl)carbonyl]-3-fluorophenyl]-5-fluoro-
2-methyl-benzamide

EXAMPLE 483

N-[4-[(4,10-Dihydro-5H-thieno[3,2-c][1]
benzazepin-5-yl)carbonyl]-3-fluorophenyl]-2-
Chloro-4-fluorobenzamide

EXAMPLE 484

N-[4-[(4,10-Dihydro-5H-thieno[3,2-c][1]
benzazepin-5-yl)carbonyl]-5-methylphenyl]-2-
methylbenzamide

EXAMPLE 485

N-[4-[(4,10-Dihydro-5H-thieno[3,2-c][1]
benzazepin-5-yl)carbonyl]-3-methylphenyl]-3-
fluoro-2-methylbenzamide

EXAMPLE 486

N-[4-[(4,10-Dihydro-5=-thieno[3,2-c][1]benzazepin-
5-yl)carbonyl]-3-methylphenyl]-5-fluoro-2-
methylbenzamide

EXAMPLE 487

N-[4-[(4,10-Dihydro-5H-thieno[3,2-c][1]
benzazepin-5-yl)carbonyl]-3-methylphenyl]-2-
chloro-4-fluorobenzamide

EXAMPLE 488

N-[4-[(4,10-Dihydro-5H-thieno[3,2-c][1]
benzazepin-5-yl)carbonyl]-3-methylphenyl]-2-
chloro-5-fluorobenzamide

EXAMPLE 489

N-[4-[(4,10-Dihydro-5H-thieno[3,2-c][1]
benzazepin-5-yl)carbonyl]-3-methylphenyl]-2,3-
dichlorobenzamide

EXAMPLE 490

N-[4-[(4,10-Dihydro-5H-thieno[3,2-c][1]
benzazepin-5-yl)carbonyl]-3-methylphenyl]-2-
chloro-4-fluorobenzamide

EXAMPLE 491

N-[4-[(4,10-Dihydro-5H-thieno[3,2-c][1]
benzazepin-5-yl)carbonyl]-3-methylphenyl]-2,3-
dimethylbenzamide

EXAMPLE 492

N-[4-[(4,10-Dihydro-5H-thieno[3,2-c][1]
benzazepin-5-yl)carbonyl]-3-methylphenyl]-2,4-
dichlorobenzamide

EXAMPLE 493

N-[4-[(4,10-Dihydro-5H-thieno[3,2-c][1]
benzazepin-5-yl)carbonyl]-3-methylphenyl]-2-
(methylthio)benzamide The following examples are prepared using conditions of Example 458.

EXAMPLE 494

N-[4-[(4,10-Dihydro-9H-thieno[2,3-c][1]
benzazepin-9-yl)carbonyl]-3-chlorophenyl]-2-
chlorobenzamide

EXAMPLE 495

N-[4-[(4,10-Dihydro-9H-thieno[2,3-c][1]
benzazepin-9-yl)carbonyl]-3-Chlorophenyl]-2-
methylbenzamide

EXAMPLE 496

N-[4-[(4,10-Dihydro-9H-thieno[2,3-c][1]
benzazepin-9-yl)carbonyl]-3-chlorophenyl]-2,3-
dichlorobenzamide

EXAMPLE 497

N-[4-[(4,10-Dihydro-9H-thieno[2,3-c][1]
benzazepin-9-yl)carbonyl]-3-chlorophenyl]-2,3-
dimethylbenzamide

EXAMPLE 498

N-[4-[(4,10-Dihydro-9H-thieno[2,3-c][1]
benzazepin-9-yl)carbonyl]-3-chlorophenyl]-2,4-
dichlorobenzamide

EXAMPLE 499

N-[4-[(4,10-Dihydro-9H-thieno[2,3-c][1]
benzazepin-9-yl)carbonyl]-3-chlorophenyl]-2-
methoxybenzamide

EXAMPLE 500

N-[4-[(4,10-Dihydro-9H-thieno[2,3-c][1]
benzazepin-9-yl)carbonyl]-3-chlorophenyl]-2-
(trifluoromethoxy)benzamide

EXAMPLE 501

N-[4-[(4,10-Dihydro-9H-thieno[2,3-c][1]
benzazepin-9-yl)carbonyl]-3-chlorophenyl]-2-
methoxy)-4-chlorobenzamide

EXAMPLE 502

N-[4-[(4,10-Dihydro-9H-thieno[2,3-c][1]
benzazepin-9-yl)carbonyl]-3-chlorophenyl]-2,6-
dichlorobenzamide

EXAMPLE 503

N-[4-[(4,10-Dihydro-9H-thieno[2,3-c][1]
benzazepin-9-yl)carbonyl]-3-chlorophenyl]-2-
(trifluoromethyl)benzamide

EXAMPLE 504

N-[4-[(4,10-Dihydro-9H-thieno[2,3-c][1]
benzazepin-9-yl)carbonyl]-3-chlorophenyl]-2-
(methylthio)-benzamide

EXAMPLE 505

N-[4-[(4,10-Dihydro-9H-thieno[2,3-c][1]
benzazepin-9-yl)carbonyl]-3-chlorophenyl]-3-
methyl-2-thiophene-carboxamide

EXAMPLE 506

N-[4-[(4,10-Dihydro-9H-thieno[2,3-c][1]
benzazepin-9-yl)carbonyl]-3-chlorophenyl]-2-
methyl-3-thiophene-carboxamide

EXAMPLE 507

N-[4-[(4,10-Dihydro-9H-thieno[2,3-c][1]
benzazepin-9-yl)carbonyl]-3-chlorophenyl]-2-
methylbenzeneacetamide

EXAMPLE 508

N-[4-[(4,10-Dihydro-9H-thieno[2,3-c][1]
benzazepin-9-yl)carbonyl]-3-chlorophenyl]-2-
(trifluoromethyl)-4-fluorobenzamide

EXAMPLE 509

N-[4-[(4,10-Dihydro-9H-thieno[2,3-c][1]
benzazepin-9-yl)carbonyl]-3-chlorophenyl]-2,5-
dimethylbenzamide

EXAMPLE 510

N-[4-[(4,10-Dihydro-9H-thieno[2,3-c][1]
benzazepin-9-yl)carbonyl]-3-chlorophenyl]-3-fluoro-
2-methylbenzamide

EXAMPLE 511

N-[4-[(4,10-Dihydro-9H-thieno[2,3-c][1]
benzazepin-9-yl)carbonyl]-3-chlorophenyl]-5-fluoro-
2-methylbenzamide

EXAMPLE 512

N-[4-[(4,10-Dihydro-9H-thieno[2,3-c][1]
benzazepin-9-yl)carbonyl]-3-chlorophenyl]-2-
chloro-4-fluorobenzamide

EXAMPLE 513

N-[4-[(4,10-Dihydro-9H-thieno[2,3-c][1]
benzazepin-9-yl)carbonyl]-3-chlorophenyl]-2-
chloro-5-fluorobenzamide

EXAMPLE 514

N-[4-[(4,10-Dihydro-9H-thieno[2,3-c][1]
benzazepin-9-yl)carbonyl]-3-chlorophenyl]-2-fluoro-
5-(trifluoromethyl)benzamide

EXAMPLE 515

N-[4-[(4,10-Dihydro-9H-thieno[2,3-c][1]
benzazepin-9-yl)carbonyl]-3-chlorophenyl]-3-fluoro-
5-[trifluoromethyl]benzamide

EXAMPLE 516

N-[4-[(4,10-Dihydro-9H-thieno[2,3-c][1]benzazepin-9-yl)carbonyl]-3-fluorophenyl]-2-methylbenzamide

EXAMPLE 517

N-[4-[(4,10-Dihydro-9=-thieno[2,3-c][1]benzazepin-9-yl)carbonyl]-3-fluorophenyl]-3-fluoro-2-methylbenzamide

EXAMPLE 518

N-[4-[(4,10-Dihydro-9H-thieno[2,3-c][1]benzazepin-9-yl)-carbonyl]-3-fluorophenyl]-3-fluoro-2-methylbenzamide

EXAMPLE 519

N-[4-[(4,10-Dihydro-9H-thieno[2,3-c][1]benzazepin-9-yl)carbonyl]-3-methylphenyl]-2-methylbenzamide

EXAMPLE 520

N-[4-[(4,10-Dihydro-9H-thieno[2,3-c][1]benzazepin-9-yl)carbonyl]-3-methylphenyl]-2,3-dimethylbenzamide

EXAMPLE 521

N-[4-[(4,10-Dihydro-9H-thieno[2,3-c][1]benzazepin-9-yl)carbonyl]-3-methylphenyl]-2,5-dimethylbenzamide

EXAMPLE 522

N-[4-[(4,10-Dihydro-9H-thieno[2,3-c][1]benzazepin-9-yl)carbonyl]-3-methylphenyl]-3-fluoro-2-methylbenzamide

EXAMPLE 523

N-[4-[(4,10-Dihydro-9H-thieno[2,3-c][1]benzazepin-9-yl)carbonyl]-3-methylphenyl]-5-fluoro-2-methylbenzamide

EXAMPLE 524

N-[4-[(4,10-Dihydro-9H-thieno[2,3-c][1]benzazepin-9-yl)carbonyl]-3-methylphenyl]-2,3-dichlorobenzamide

EXAMPLE 525

N-[4-[(4,10-Dihydro-9H-thieno[2,3-c][1]benzazepin-9-yl)carbonyl]-3-methylphenyl]-2,4-dichlorobenzamide

EXAMPLE 526

N-[4-[(4,10-Dihydro-9H-thieno[2,3-c][1]benzazepin-9-yl)carbonyl]-3-methylphenyl]-2-chloro-4-fluorobenzamide

EXAMPLE 527

N-[4-[(4,10-Dihydro-9H-thieno[2,3-c][1]benzazepin-9-yl)carbonyl]-3-methylphenyl]-2-chloro-5-fluorobenzamide

EXAMPLE 528

N-[4-[(4,10-Dihydro-9H-thieno[2,3-c][1]benzazepin-9-yl)carbonyl]-3-methylphenyl]-2-fluoro-5-(trifluoromethyl)benzamide

EXAMPLE 529

N-[4-[(4,10-Dihydro-9H-thieno[2,3-c][1]benzazepin-9-yl)carbonyl]-3-methylphenyl]-2-methyl-4-chlorobenzamide

EXAMPLE 530

N-[4-[(4,10-Dihydro-9H-thieno[2,3-c][1]benzazepin-9-yl)carbonyl]-3-methylphenyl]-2-methoxybenzamide

EXAMPLE 531

N-[4-[(4,10-Dihydro-9H-thieno[2,3-c][1]benzazepin-9-yl)carbonyl]-3-methylphenyl]-2-(trifluoromethoxy)benzamide

EXAMPLE 532

N-[4-[(4,10-Dihydro-9H-thieno[2,3-c][1]benzazepin-9-yl)carbonyl]-3-methylphenyl]-2-(trifluoromethyl)-benzamide

EXAMPLE 533

N-[4-[(4,10-Dihydro-9H-thieno[2,3-c][1]benzazepin-9-yl)carbonyl]-3-methylphenyl]-2-(thiomethyl)-benzamide

EXAMPLE 534

N-[4-[(4,5-Dihydro-2-methyl-6H-thiazolo[5,4-c][1]-benzazepin-6-yl)carbonyl]phenyl]-5-fluoro-2-methylbenzamide To a stirred solution of 0.235 g of 5,6-dihydro-2-methyl-6-(4-aminobenzoyl)4H-thiazolo[5,4-d][1]-benzazepine in 6 ml of methylene chloride under argon is added 107 μl of triethylamine followed by the dropwise addition of 2-methyl-5-fluorobenzoyl chloride in 1 ml of methylene chloride. Stirring is continued at room temperature for 18 hours. The reaction mixture is washed with H20, saturated NaHCO$_3$ and brine. The organic layer is treated with activated carbon, filtered through MgSO$_4$ and the filtrate evaporated in vacuo to a residue which is chromatographed on silica gel by elution with 15% ethyl acetate in methylene chloride to give 300 mg of the desired product as a white solid; Anal. Calc'd for C$_{27}$H$_{22}$FN$_3$O$_2$S: C,68.8; H,4.7; N,8.9; F,4.0; S,6.8 Found: C,67.7; H,4.6; N,8.5; F,3.7; S,6.4.

The following examples are prepared using the conditions of Example 534 with the appropriately substituted aroyl chloride.

EXAMPLE 535

N-[4-[(4,5-Dihydro-2-methyl-6H-thiazolo[5,4-d][1]-benzazepin-6-yl)carbonyl]-3-chlorophenyl]-2,3-dichlorobenzamide

EXAMPLE 536

N-[4-[(4,5-Dihydro-2-methyl-6H-thiazolo[5,4-d][1]-benzazepin-6-yl)carbonyl]-3-chlorophenyl]-2-methyl-4-chlorobenzamide

EXAMPLE 537

N-[4-[(4,5-Dihydro-2-methyl-6H-thiazolo[5,4-d][1]-benzazepin-6-yl)carbonyl]-3-chlorophenyl]-2-methoxybenzamide

EXAMPLE 538

N-[4-[(4,5-Dihydro-2-methyl-6H-thiazolo[5,4-d][1]-benzazepin-6-yl)carbonyl]-3-chlorophenyl]-2-methoxy-4-chlorobenzamide

EXAMPLE 539

N-[4-[(4,5-Dihydro-2-methyl-6H-thiazolo[5,4-d][1]-benzazepin-6-yl)carbonyl]-3-chlorophenyl]-2-(trifluoromethoxy)benzamide

EXAMPLE 540

N-[4-[(4,5-Dihydro-2-methyl-6H-thiazolo[5,4-d][1]-benzazepin-6-yl)carbonyl]-3-chlorophenyl]-2-(trifluoromethyl)benzamide

EXAMPLE 541

N-[4-[(4,5-Dihydro-2-methyl-6H-thiazolo[5,4-d][1]-benzazepin-6-yl)carbonyl]-3-chlorophenyl]-2,6-dichlorobenzamide

EXAMPLE 542

N-[4-[(4,5-Dihydro-2-methyl-6H-thiazolo[5,4-d][1]-benzazepin-6-yl)carbonyl]-3-chlorophenyl]-2,3-dimethylbenzamide

EXAMPLE 543

N-[4-[(4,5-Dihydro-2-methyl-6H-thiazolo[5,4-d][1]-benzazepin-6-yl)carbonyl]-2-chlorophenyl]-2,5-dimethylbenzamide

EXAMPLE 544

N-[4-[(4,5-Dihydro-2-methyl-6H-thiazolo[5,4-d][1]-benzazepin-6-yl)carbonyl]-3-chlorophenyl]-3-(trifluoromethyl)benzamide

EXAMPLE 545

N-[4-[(4,5-Dihydro-2-methyl-6H-thiazolo[5,4-d][1]-benzazepin-6-yl)carbonyl]-2-chlorophenyl]-2-(methylthio)benzamide

EXAMPLE 546

N-[4-[(4,5-Dihydro-2-methyl-6H-thiazolo[5,4-d][1]-benzazepin-6-yl)carbonyl]-3-chlorophenyl]-2-methyl-3-thiophenecarboxamide

EXAMPLE 547

N-[4-[(4,5-Dihydro-2-methyl-6H-thiazolo[5,4-d][1]-benzazepin-6-yl)carbonyl]-3-chlorophenyl]-3-methyl-2-thiophenecarboxamide

EXAMPLE 548

N-[4-[(4,5-Dihydro-2-methyl-6H-thiazolo[5,4-d][1]-benzazepin-6-yl)carbonyl]-3-chlorophenyl]-3-methyl-3-furanecarboxamide

EXAMPLE 549

N-[4-[(4,5-Dihydro-2-methyl-6H-thiazolo[5,4-d][1]-benzazepin-6-yl)carbonyl]-3-chlorophenyl]T2-methylbenzeneacetamide

EXAMPLE 550

N-[4-[(4,5-Dihydro-2-methyl-6H-thiazolo[5,4-d][1]-benzazepin-6-yl)carbonyl]-3-chlorophenyl]-3-fluoro-2-methylbenzamide

EXAMPLE 551

N-[4-[(4,5-Dihydro-2-methyl-6H-thiazolo[5,4-d][1]-benzazepin-6-yl)carbonyl]-3-chlorophenyl]-5-fluoro-2-methylbenzamide

EXAMPLE 552

N-[4-[(4,5-Dihydro-2-methyl-6H-thiazolo[5,4-d][1]-benzazepin-6-yl)carbonyl]-3-chlorophenyl]-4-fluoro-2-methylbenzamide

EXAMPLE 553

N-[4-[(4,5-Dihydro-2-methyl-6H-thiazolo[5,4-d][1]-benzazepin-6-yl)carbonyl]-3-chlorophenyl]-3-fluoro-4-(trifluoromethyl)benzamide

EXAMPLE 554

N-[4-[(4,5-Dihydro-2-methyl-6H-thiazolo[5,4-d][1]-benzazepin-6-yl)carbonyl]-$,chlorophenyl]-3-fluoro-5-(trifluoromethyl)benzamide

EXAMPLE 555

N-[4-[(4,5-Dihydro-2-methyl-6H-thiazolo[5,4-d][1]-benzazepin-6-yl)carbonyl]-3-chlorophenyl]-2-chloro-4-fluorobenzamide

EXAMPLE 556

N-[4-[(4,5-Dihydro-2-methyl-6H-thiazolo[5,4-d][1]-benzazepin-6-yl)carbonyl]-3-chlorophenyl]-2-chloro-5-fluorobenzamide

EXAMPLE 557

N-[4-[(4,5-Dihydro-2-methyl-6H-thiazolo[5,4-d][1]-benzazepin-6-yl)carbonyl]-3-chlorophenyl]-4-fluoro-2-(trifluoromethyl)benzamide

EXAMPLE 558

N-[4-[(4,5-Dihydro-2-methyl-6H-thiazolo[5,4-d][1]-benzazepin-6-yl)carbonyl]-3-fluorophenyl]-2-chloro-4-fluorobenzamide

EXAMPLE 559

N-[4-[(4,5-Dihydro-2-methyl-6H-thiazolo[5,4-d][1]-benzazepin-6-yl)carbonyl]-3-fluorophenyl]-3-fluoro-2-methylbenzamide

EXAMPLE 560

N-[4-[(4,5-Dihydro-2-methyl-6H-thiazolo[5,4-d][1]-benzazepin-6-yl)carbonyl]-3-fluorophenyl]-5-fluoro-2-methylbenzamide

EXAMPLE 561

N-[4-[(4,5-Dihydro-2-methyl-6H-thiazolo[5,4-d][1]-benzazepin-6-yl)carbonyl]-3-fluorophenyl]-2-chloro-4-fluorobenzamide

EXAMPLE 562

N-[4-[(4,5-Dihydro-2-methyl-6H-thiazolo[5,4-d][1]-benzazepin-6-yl)carbonyl]-3-methylphenyl]-3-fluoro-2-methylbenzamide

EXAMPLE 563

N-[4-[(4,5-Dihydro-2-methyl-6H-thiazolo[5,4-d][1]-benzazepin-6-yl)carbonyl]-3-methylphenyl]-2-methylbenzamide

EXAMPLE 564

N-[4-[(4,5-Dihydro-2-methyl-6H-thiazolo[5,4-d][1]-benzazepin-6-yl)carbonyl]-3-methylphenyl]-5-fluoro-2-methylbenzamide

EXAMPLE 565

N-[4-[(4,5-Dihydro-2-methyl-6H-thiazolo[5,4-d][1]-benzazepin-6-yl)carbonyl]-3-methylphenyl]-2-chloro-5-fluorobenzamide

EXAMPLE 566

N-[4-[(4,5-Dihydro-2-methyl-6H-thiazolo[5,4-d][1]-benzazepin-6-yl)carbonyl]-3-methylphenyl]-2,3-dimethylbenzamide

EXAMPLE 567

N-[4-[(4,S-Dihydro-2-methyl-6H-thiazolo[5,4-d][1]-benzazepin-6-yl)carbonyl]-3-methylphenyl]-2,5-dimethylbenzamide

EXAMPLE 568

N-[4-[(4,5-Dihydro-2-methyl-6H-thiazolo[5,4-d][1]-benzazepin-6-yl)carbonyl]-3-methylphenyl]-2,4-dichlorobenzamide

EXAMPLE 569

N-[4-[(4,5-Dihydro-2-methyl-6H-thiazolo[5,4-d][1]-benzazepin-6-yl)carbonyl]-3-methylphenyl]-2-methoxy-4-chlorobenzamide

EXAMPLE 570

N-[4-[(4,5-Dihydro-2-methyl-6H-thiazolo[5,4-d][1]-benzazepin-6-yl)carbonyl]-3-methylphenyl]-2-(trifluoromethoxy)benzamide

EXAMPLE 571

N-[4-[(4,5-Dihydro-2-methyl-6H-thiazolo[5,4-d][1]-benzazepin-6-yl)carbonyl]-3-methylphenyl]-2-(methylthio)benzamide

EXAMPLE 572

N-[4-[(4,5-Dihydro-2-methyl-6H-thiazolo[5,4-d][1]-benzazepin-6-yl)carbonyl]-3-methoxyphenyl]-2-methylbenzamide

EXAMPLE 573

N-[4-[(4,5-Dihydro-2-methyl-6H-thiazolo[5,4-d][1]-benzazepin-6-yl)carbonyl]-3-methoxyphenyl]-2,4-dichlorobenzamide

EXAMPLE 574

N-[4-[(4,5-Dihydro-2-methyl-6H-thiazolo[5,4-d][1]-benzazepin-3-yl)carbonyl]-3-methoxyphenyl]-2-chloro-4-fluorobenzamide

EXAMPLE 575

N-[4-[(4,5-Dihydro-2-methyl-6H-thiazolo[5,4-d][1]-benzazepin-6-yl)carbonyl]-3-methoxyphenyl]-3-fluoro-2-methylbenzamide

EXAMPLE 576

N-[4-[(4,5-Dihydro-2-methyl-6H-thiazolo[5,4-d][1]-benzazepin-6-yl)carbonyl]-3-methoxyphenyl]-5-fluoro-2-methylbenzamide

EXAMPLE 577

N-[4-[(4,5-Dihydro-2-methyl-6H-thiazolo[5,4-d][1]-benzazepin-6-yl)carbonyl]-3-methoxyphenyl]-2,3-dimethylbenzamide

EXAMPLE 578

N-[4-[(4,5-Dihydro-2-methyl-6H-thiazolo[5,4-d][1]-benzazepin-6-yl)carbonyl]-3-methoxyphenyl]-2-methylbenzeneacetamide

EXAMPLE 579

N-[4-[(4,5-Dihydro-2-methyl-6H-thiazolo[5,4-d][1]-benzazepin-6-yl)carbonyl]-3-methoxyphenyl]-2-chlorobenzeneacetamide

EXAMPLE 580

6,11-Dihydro-5-[4-[(3-methylbutanoyl)amino]benzoyl]-5H-dibenz[b,e]azepine

To a stirred solution of 0.16 g of 6,11-di-hydro-5-(4-aminobenzoyl)-5H-dibenz[b,e]azepine in 2 ml of methylene chloride is added 0.10 g of triethylamine followed by 0.09 g of iso-valeryl chloride. After stirring at room temperature for 2 hours, the reaction mixture is evaporated in vacuo to a residue. The residue is extracted with ethyl acetate-methylene chloride, washed with brine, dried ($Na_2SO_4$), filtered through hydrous magnesium silicate and evaporated in vacuo to a residue which is stirred with ether-hexanes to give 0.21 g of light yellow solid. MS(CI): 399(M+H).

We claim:

1. A compound selected from Formula I:

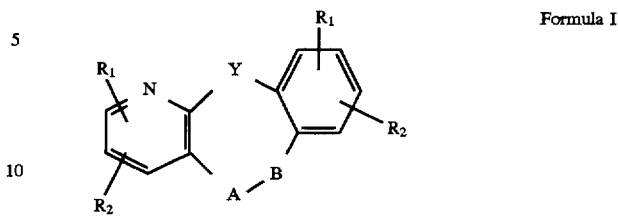

Formula I wherein;

Y is O or S;

A-B is

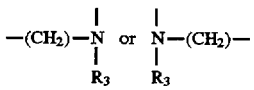

$R_1$ is H, halogen (chlorine, fluorine, bromine, iodine), OH, —S-lower alkyl ($C_1$-$C_3$), —SH, —SO lower alkyl ($C_1$-$C_3$), —$SO_2$ lower alkyl ($C_1$-$C_3$), —CO lower alkyl ($C_1$-$C_3$), —$CF_3$, lower alkyl ($C_1$-$C_3$), —O lower alkyl ($C_1$-$C_3$), —$NO_2$, —$NH_2$, —NHCO lower alkyl ($C_1$-$C_3$), —N-[lower alkyl ($C_1$-$C_3$)]$_2$, $SO_2NH_2$, —$SO_2$NH lower alkyl ($C_1$-$C_3$), or —$SO_2$N [lower alkyl ($C_1$-$C_3$)]$_2$;

$R_2$ is H, Cl, Br, I, F, —OH, lower alkyl ($C_1$-$C_3$), —O lower alkyl ($C_1$-$C_3$); or $R_1$ and $R_2$ taken together are methylenedioxy or ethylenedioxy;

$R_3$ is the moiety

wherein Ar is a moiety selected from the group

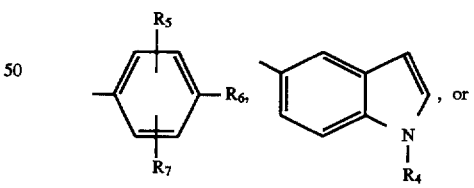
, or

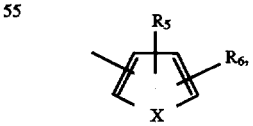

and X is selected from O, S, —$NCH_3$, or —N—$COCH_3$;

$R_4$ is selected from H, lower alkyl ($C_1$-$C_3$), —CO-lower alkyl ($C_1$-$C_3$), $SO_2$ lower alkyl ($C_1$-$C_3$), and the moieties of the formulae:

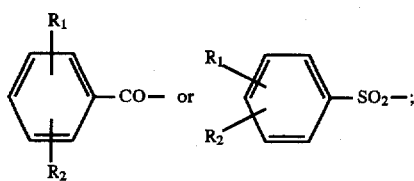

$R_5$ is H, —$CH_3$, —$C_2H_5$, Cl, Br, F, —O—$CH_3$, or O—$C_2H_5$;

$R_6$ is selected from:
(a) moieties of the formula:

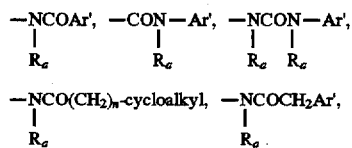

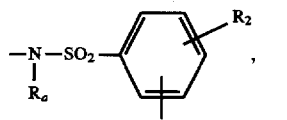

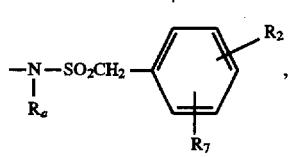

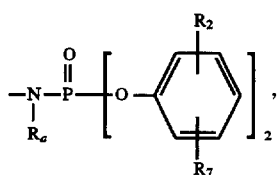

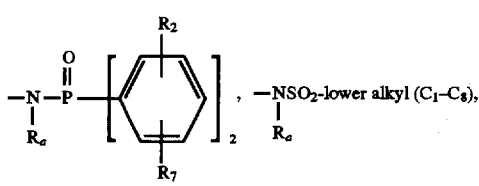

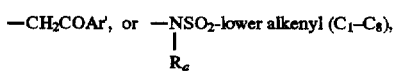

wherein cycloalkyl is defined as $C_3$–$C_6$ cycloalkyl, cyclohexenyl or cyclopentenyl;

$R_2$ is as hereinbefore defined;

n is 0–2;

$R_7$ is H, —$CH_3$, —$CH_2H_5$, Cl, Br, F, —$OCH_3$, —$OC_2H_5$, or —$CF_3$;

$R_a$ is hydrogen, $CH_3$, $C_2H_5$, moieties of the formulae:

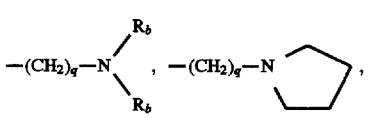

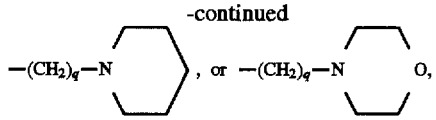

—$(CH_2)_2$-O-lower alkyl ($C_1$–$C_3$) or —$CH_2CH_2OH$;

q is one or two;

$R_b$ is hydrogen, —$CH_3$ or —$C_2H_5$;

Ar' is selected from the group:

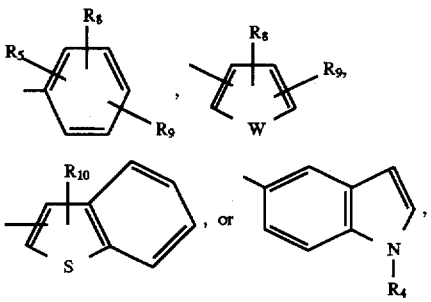

wherein $R_4$, $R_5$ are as hereinbefore defined;

$R_8$ and $R_9$ are independently hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

$R_{10}$ is selected from halogen, hydrogen, or lower alkyl ($C_1$–$C_3$);

W' is selected from O, S, NH, N-lower alkyl ($C_1$–$C_3$), —NCO-lower alkyl ($C_1$–$C_3$), or $NSO_2$-lower alkyl ($C_1$–$C_3$);

(b) a moiety of the formula:

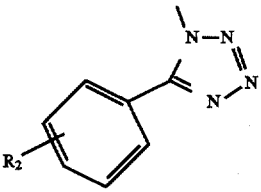

where $R_2$ is as hereinbefore defined;

(c) a moiety of the formula:

wherein J is $R_a$, lower alkyl ($C_1$–$C_8$) branched or unbranched, lower alkenyl ($C_2$–$C_8$) branched or unbranched, —O-lower alkyl ($C_1$–$C_8$) branched or unbranched, —O-lower alkenyl ($C_2$–$C_8$) branched or unbranched, tetrahydrofuran, tetrahydrothiophene, or —$CH_2$-K wherein K is halogen, —OH, tetrahydrofuran, tetrahydrothiophene or the heterocyclic ring moiety:

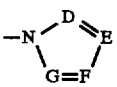

wherein D, E, F and G are selected from carbon or nitrogen and wherein the carbon atoms may be optionally substituted with halogen, (C₁–C₃)lower alkyl, hydroxy, —CO-lower alkyl (C₁–C₃), CHO, (C₁–C₃)lower alkoxy, or —CO₂-lower alkyl (C₁–C₃), and R$_a$ and R$_b$ are as hereinbefore defined; and (d) a moiety selected from those of the formulae:

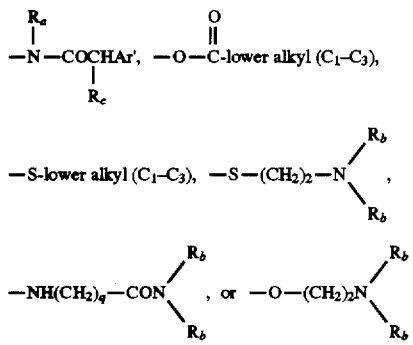

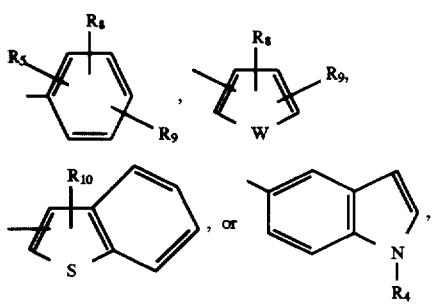

wherein

R$_c$ is selected from halogen, (C₁–C₃) lower alkyl, —O-lower alkyl (C₁–C₃) or OH;

R$_a$, Rb R$_8$, R$_9$, R$_{10}$, and W' are as hereinbefore defined; q is 1 or 2;

wherein Ar' is selected from the group:

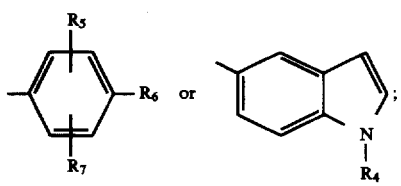

or a pharmaceutically acceptable salt, ester or prodrug thereof.

2. A compound according to claim 1 wherein R³ is the moiety

—CAr wherein Ar is a moiety selected from the group

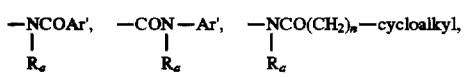

R$_6$ is selected from the group

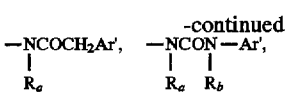

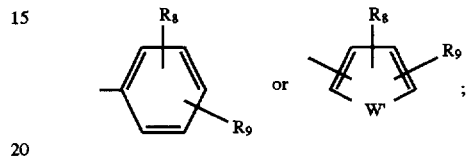

or —CH₂COAr';

wherein n is 0–2;

Ar' is

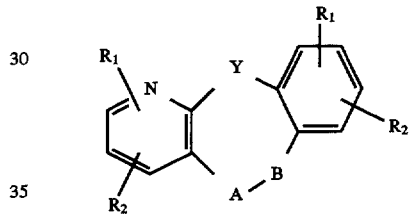

W' is O or S;

A-B, R$_a$, R$_b$, R₁, R₂, R₄, R₅, R₇, R₈, R₉, and cycloalkyl are as defined in claim 1; or a pharmaceutically acceptable salt, ester or prodrug thereof.

3. A compound of the formula:

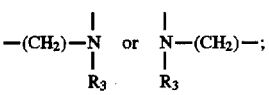

wherein;

Y is O or S;

A-B is

—(CH₂)—N   or   N—(CH₂)—;
         |            |
         R₃           R₃

R₁ is H, halogen (Cl, F, Br, I), OH, —S—lower alkyl (C₁–C₃), —SH, —SO lower alkyl (C₁–C₃), —SO₂ lower alkyl (C₁–C₃), —CO lower alkyl (C₁–C₃), —CF₃, lower alkyl (C₁–C₃), —O lower alkyl (C₁–C₃), —NO₂, —NH₂, —NHCO lower alkyl (C₁–C₃), —N—[lower alkyl (C₁–C₃)]₂, SO₂NH₂, —SO₂NH lower alkyl (C₁–C₃), or —SO₂N [lower alkyl (C₁–C₃)]₂;

R₂ is selected from H, Cl, Br, I, F, —OH, lower alkyl (C₁–C₃), or —O lower alkyl (C₁–C₃); or R₁ and R₂ taken together are methylenedioxy or ethylenedioxy;

R₃ is the moiety

—CAr wherein Ar is a moiety selected from the group

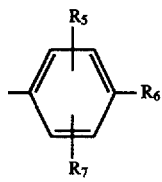

$R_5$ is H, —$CH_3$, —$C_2H_5$, Cl, Br, F, —O—$CH_3$, or —O—$C_2H_5$;

$R_6$ is selected from:

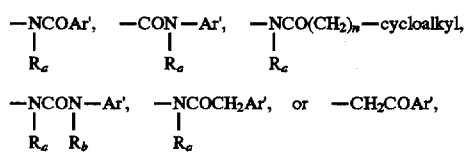

wherein cycloalkyl is defined as $C_3$-$C_6$ cycloalkyl, cyclohexenyl or cyclopentenyl;

n is 0–2;

and wherein Ar' is selected from the moieties:

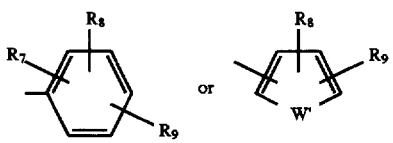

wherein $R_a$ and $R_b$ are independently selected from H, —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$-$C_3$), O-lower alkyl ($C_1$-$C_3$), S-lower alkyl ($C_1$-$C_3$), —$CF_3$, —CN, —OH, —$SCF_3$, —$OCF_3$, halogen, $NO_2$, amino, or —NH-lower alkyl ($C_1$-$C_3$);

W' is selected from O, S, NH, N-lower alkyl ($C_1$-$C_3$), —NCO-lower alkyl ($C_1$-$C_3$), or $NSO_2$-lower alkyl ($C_1$-$C_3$); or a pharmaceutically acceptable salt, ester or prodrug thereof.

4. A compound of the formula:

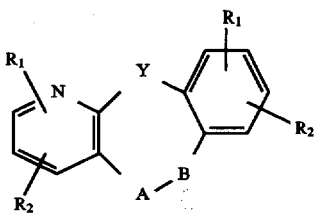

wherein;

Y is O;

A-B is

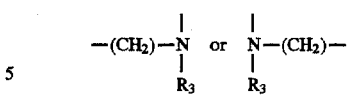

$R_1$ is H, halogen (Cl, F, Br, I), OH, —S-lower alkyl ($C_1$-$C_3$), —SH, —SO lower alkyl ($C_1$-$C_3$), —$SO_2$ lower alkyl ($C_1$-$C_3$), —CO lower alkyl ($C_1$-$C_3$), —$CF_3$, lower alkyl ($C_1$-$C_3$), —O lower alkyl ($C_1$-$C_3$), —$NO_2$, —$NH_2$, —NHCO lower alkyl ($C_1$-$C_3$), —N-[lower alkyl ($C_1$-$C_3$)]$_2$, $SO_2NH_2$, —$SO_2$NH lower alkyl ($C_1$-$C_3$), or —$SO_2$N [lower alkyl ($C_1$-$C_3$)]$_2$;

$R_2$ is selected from H, Cl, Br, I, F, —OH, lower alkyl ($C_1$-$C_3$), or —O lower alkyl ($C_1$-$C_3$); or $R_1$ and $R_2$ taken together are methylenedioxy or ethylenedioxy;

$R_3$ is the moiety

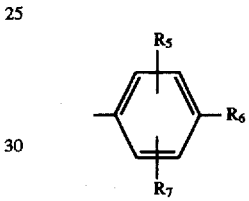

wherein Ar is a moiety selected from the group

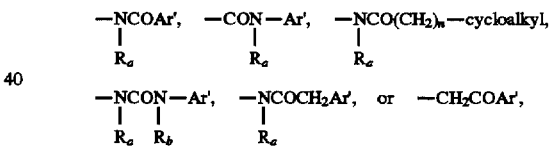

$R_5$ is H, —$CH_3$, —$C_2H_5$, Cl, Br, F, —O—$CH_3$, or —O—$C_2H_5$;

$R_6$ is selected from:

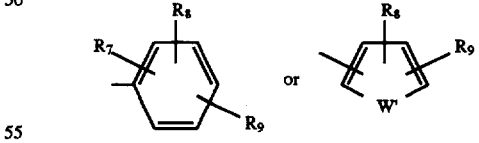

wherein cycloalkyl is defined as $C_3$-$C_6$ cycloalkyl, cyclohexenyl or cyclopentenyl;

n is 0–2;

and wherein Ar' is selected from the moieties:

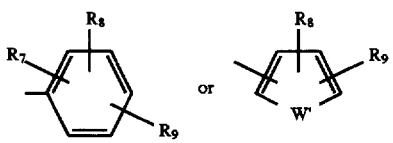

wherein $R_a$ and $R_b$ are independently selected from H, —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$-$C_3$), O-lower alkyl ($C_1$-$C_3$), S-lower alkyl ($C_1$-$C_3$), —$CF_3$, —CN, —OH, —$SCF_3$, —$OCF_3$, halogen, $NO_2$, amino, or —NH-lower alkyl ($C_1$-$C_3$);

W' is selected from O, S, NH, N-lower alkyl ($C_1$-$C_3$ ), —NCO-lower alkyl ($C_1$-$C_3$), or $NSO_2$-lower alkyl ($C_1$-$C_3$);

or a pharmaceutically acceptable salt, ester or prodrug thereof.

5. A compound of the formula:

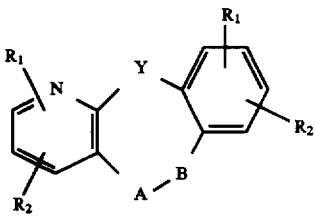

wherein;

Y is S;

A-B is

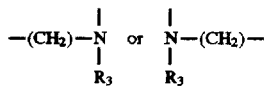

$R_1$ is H, halogen (Cl, F, Br, I), OH, —S-lower alkyl ($C_1$–$C_3$), —SH, —SO lower alkyl ($C_1$–$C_3$), —$SO_2$ lower alkyl ($C_1$–$C_3$), —CO lower alkyl ($C_1$–$C_3$), —$CF_3$, lower alkyl ($C_1$–$C_3$), —O lower alkyl ($C_1$–$C_3$), —$NO_2$, —$NH_2$, —NHCO lower alkyl ($C_1$–$C_3$), —N-[lower alkyl ($C_1$–$C_3$)]$_2$, $SO_2NH_2$, —$SO_2NH$ lower alkyl ($C_1$–$C_3$), or —$SO_2N$ [lower alkyl ($C_1$–$C_3$)]$_2$;

$R_2$ is selected from H, Cl, Br, I, F, —OH, lower alkyl ($C_1$–$C_3$), or —O lower alkyl ($C_1$–$C_3$); or $R_1$ and $R_2$ taken together are methylenedioxy or ethylenedioxy;

$R_3$ is the moiety

wherein Ar is a moiety selected from the group

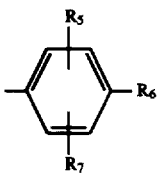

$R_5$ is H, —$CH_3$, —$C_2H_5$, Cl, Br, F, —O—$CH_3$, or —O—$C_2H_5$;

$R_6$ is selected from:

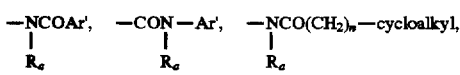

-continued

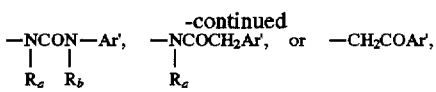

wherein cycloalkyl is defined as $C_3$–$C_6$ cycloalkyl, cyclohexenyl or cyclopentenyl;

n is 0–2;

and wherein Ar' is selected from the moieties:

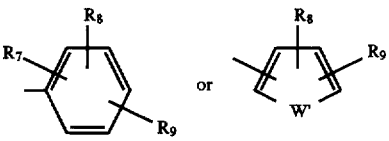

wherein $R_a$ and $R_b$ are independently selected from H, —$CH_3$, or —$C_2H_5$;

$R_7$ is H, —$CH_3$, —$C_2H_5$, Cl, Br, F, —O—$CH_3$, —O—$C_2H_5$ or —$CF_3$;

$R_8$ and $R_9$ are independently selected from hydrogen, lower alkyl ($C_1$–$C_3$), O-lower alkyl ($C_1$–$C_3$), S-lower alkyl ($C_1$–$C_3$), —$CF_3$, —CN, —OH, —$SCF_3$, —$OCF_3$, halogen, $NO_2$, amino, or —NH-lower alkyl ($C_1$–$C_3$);

W' is selected from O, S, NH, N-lower alkyl ($C_1$–$C_3$), —NCO-lower alkyl ($C_1$–$C_3$), or $NSO_2$-lower alkyl ($C_1$–$C_3$);

or a pharmaceutically acceptable salt, ester or prodrug thereof.

6. A pharmaceutical composition useful for treating disease in a mammal characterized by excess renal reabsorption of water, the pharmaceutical composition comprising an effective amount of a compound of claim 1, or a pharmaceutically acceptable salt, ester or prodrug form thereof, and a suitable pharmaceutical carrier.

7. The pharmaceutical composition of claim 6 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

8. A method for treating disease in a mammal characterized by excess renal reabsorption of water, the method comprising administering to a mammal in need thereof an effective amount of a compound of claim 1, or a pharmaceutically acceptable salt, ester or prodrug form thereof, and a suitable pharmaceutical carrier.

9. The method of claim 8 wherein the disease in a mammal characterized by excess renal reabsorption of water is congestive heart failure, nephrotic syndrome, hyponatremia, coronary vasospasm, cardiac ischemia, renal vasospasm, liver cirrhosis, brain edema, cerebral ischemia, or cerebral hemorrhage-stroke.

* * * * *